US007862807B2

(12) United States Patent
Goodman et al.

(10) Patent No.: US 7,862,807 B2
(45) Date of Patent: Jan. 4, 2011

(54) DENDRIMERS AS MOLECULAR TRANSLOCATORS

(75) Inventors: Murray Goodman, La Jolla, CA (US); Churl Min Seong, San Diego, CA (US); Guido Harms, Wittmund (DE)

(73) Assignee: University of California, San Diego, La Jolla, CA (US)

( * ) Notice: Subject to any disclaimer, the term of this patent is extended or adjusted under 35 U.S.C. 154(b) by 1281 days.

(21) Appl. No.: 10/522,128

(22) PCT Filed: Jul. 18, 2003

(86) PCT No.: PCT/US03/22771

§ 371 (c)(1),
(2), (4) Date: Feb. 27, 2006

(87) PCT Pub. No.: WO2004/009665

PCT Pub. Date: Jan. 29, 2004

(65) Prior Publication Data

US 2006/0216265 A1 Sep. 28, 2006

Related U.S. Application Data

(60) Provisional application No. 60/397,319, filed on Jul. 19, 2002.

(51) Int. Cl.
*A61K 31/74* (2006.01)
(52) U.S. Cl. .................................. 424/78.17
(58) Field of Classification Search ....................... None
See application file for complete search history.

(56) References Cited

U.S. PATENT DOCUMENTS

| 4,694,064 A | 9/1987 | Tomalia et al. |
| 4,857,599 A | 8/1989 | Tomalia et al. |
| 5,387,617 A | 2/1995 | Hedstrand et al. |
| 6,020,457 A | 2/2000 | Klimash et al. |
| 6,177,414 B1 | 1/2001 | Tomalia et al. |
| 6,190,650 B1 | 2/2001 | Matthews et al. |
| 6,306,993 B1 | 10/2001 | Rothbard et al. |
| 6,395,867 B1 | 5/2002 | Maignan |
| 6,485,718 B1 | 11/2002 | Parthasarathy et al. |

FOREIGN PATENT DOCUMENTS

| WO | WO 91/09958 | 7/1991 |
| WO | WO 94/04686 | 3/1994 |
| WO | WO 98/52614 | 11/1998 |

OTHER PUBLICATIONS

Kasai et al 12 Bioorganic & Medicinal Chemistry Letters 951 (Mar. 25, 2002).*
Liu et al 2 Pharmaceutical Sciences & Technology Today 393 (Oct. 1, 1999).*
Buschle, M. et al., Transloading of tumor antigen-derived peptides into antigen-presenting cells. Proc. Natl. Acad. Sci. USA., 94, p. 3256-3261 (1997).
Emi, N. et al., Gene Transfer Mediated by Polyarginine Requires a Formation of Big Carrier-Complex of DNA Aggregate, Biophys. Res. Commun., 231, p. 421-424 (1997).
Feichtinger, L. et al., Triurethane-Protected Guanidines and Triflydiurethane-Protected Guanidines: New Reagents for Guanidinylation Reactions, J. Org. Chem., 63, p. 8432 (1998).
Leonetti, J. -P. et al., Biological Activity of Oligonucleotide-Poly (L -lysine) Conjugates: Mechanism of Cell Uptake, Bioconjugate Chem., 1, p. 149-153 (1990).
Mitchell, D.J. et al., Polyargine enters cells more efficiently than other polycationic homopolymers, J. Peptide Res., 55 p. 318-325 (2000).
Murphy, J.E. et al., A combinatorial approach to the discovery of efficient cationic peptoid reagents for gene delivery, Proc. Natl. Acad. Sci. USA., 95, p. 1517-1522 (1998).
Pepinsky, R.B. et al., Specific Inhibition of a Human Papillomavirus E2 *Trans*-Activator by Intracellular Delivery of Its Repressor, DNA Cell Biol., 13, p. 1011-1019 (1994).
Ryser, H.J.-P., A Membrane Effect of Basic Polymers dependent on Molecular Size, Nature (London), 215, p. 934-936 (1967).
Ryser, N. J. -P. et al., Conjugation of methotrexate to poly(L-lysine) increases drug transport and overcomes drug resistance in cultured cells, Proc. Nat. Acad. Sci. USA., 75, p. 3867-3870 (1978).
Schwarze, S.R. et al., In Vivo Protein Transduction: Delivery of a Biologically Active Protein into the Mouse, Science, 285, p. 1569-1572 (1999).
Shen, W., et al., Conjugation of poly-L-lysine to albumin and horseradish peroxides:. A novel method of enhancing the cellular uptake of proteins, Proc. Nat. Acad. Sci. USA., 75, p. 1872-1876 (1978).
Vocero-Akbani, A.M. et al., Killing HIV-infected cells by transduction with an HIV protease-activated caspase-3 protein, Nat. Med., 5, p. 29-33 (1999).
Wender, P.A. et al., The design, synthesis, and evaluation of molecules that enable or enhance cellular uptake: Peptoid molecular transporters, Proc. Natl. Acad. Sci. USA., 97, p. 13003-13008 (2000).
Supplementary European Search Report, pp. 6, Jul. 26, 2007.

(Continued)

*Primary Examiner* — Michael G Hartley
*Assistant Examiner* — Paul Dickinson
(74) *Attorney, Agent, or Firm* — Foley & Lardner LLP; Stephen E. Reiter

(57) ABSTRACT

Transport molecules include a dendrimer and a biologically active molecule. The dendrimer of such transport molecules includes at least one guanidine group, at least one protonated guanidine group, at least one protected guanidine group, at least one amidine group, at least one protonated amidine group, at least one protected amidine group, at least one ureido group, at least one protonated ureido group, at least one protected ureido group, at least one thioureido group, at least one protonated thioureido group, or at least one protected thioureido group. The biologically active molecule is bonded to the dendrimer. A method of increasing the bioavailability of a drug includes bonding the drug to a dendrimer of the invention.

12 Claims, 55 Drawing Sheets

OTHER PUBLICATIONS

Mitchell, D. J. et al., "Polyarginine Enters Cells More Efficiently Than Other Polycationic Homopolymers", Journal of Peptide Research, vol. 56, No. 5, pp. 318-325, Nov. 2000 (2000-11), Abstract.

Ranganathan, D. et al., "Design and Synthesis of AB3-Type (A=1, 3, 5-Benzenetricarbonyl Unit", *Biopolymers*, vol. 54, No. 4, pp. 289-295, 2000, Abstract.

Rothbard, J. B. et al., "Conjugation of Arginine Oligomers to Cyclosporin a facilitates Topical Delivery and Inhibition of Inflammation", *Nature Medicine*, vol. 6, No. 11, pp. 1253-1257, Nov. 2000 (2000-11), Abstract.

Scott, D. A. et al, "Bis(1, 3-dihydroxy-isopropyl)amine (BDI) as an AB4 Dendritic Building Block: Rapid Synthesis of a Second Generation Dendrimer", Tetrahedron Letters, vol. 41, No. 20, pp. 3959-3962, May 2000 (2000-05), Abstract.

Futaki et al., Translocation of Branched-Chain Arginine Peptides through Cell Membranes: Flexibility in the Spatial Disposition of Positive Charges in Membrane-Permeable Peptides, Biochemistry, 41: 7925-7930, (2002).

International Search Report dated Apr. 16, 2004 for PCT Application No. PCT/US03/22772.

International Search Report dated Apr. 23, 2004 for PCT Application No. PCT/US03/22771.

* cited by examiner

6

7

8

9

10, (3G)

11, (6G)

13, (12G)

Tat$_{49-57}$ (RKKRRPPRR)

R9 (9-mer of L-Arg))

Figure 16M
Figure 16N
Figure 17A
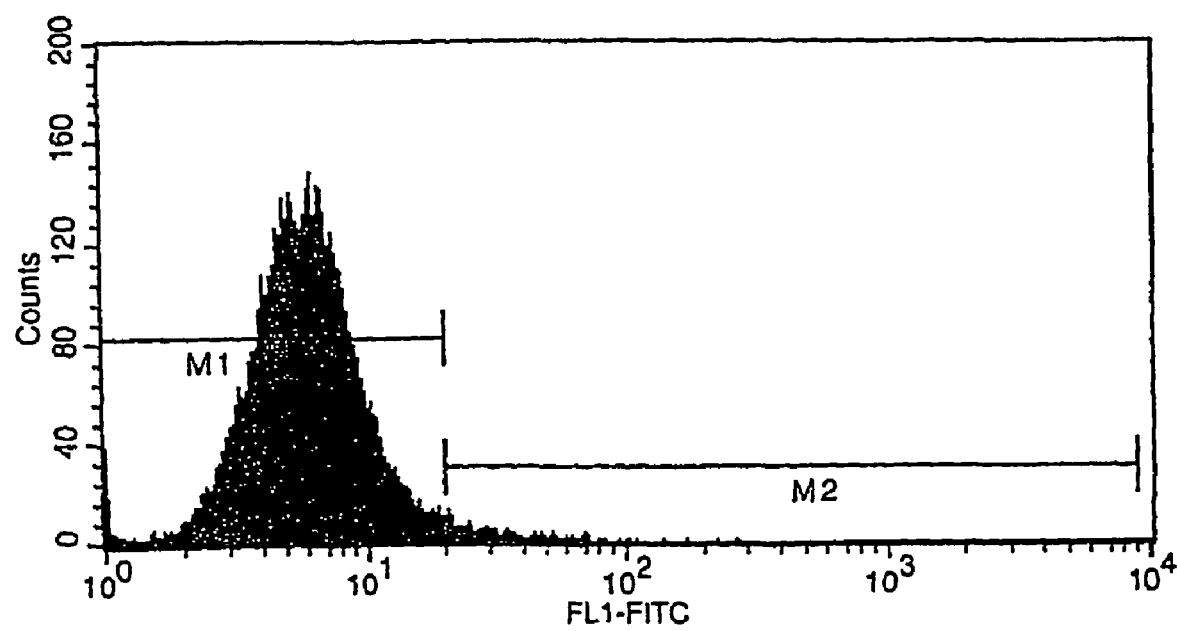

48

↓ 1, HOBt, EDC

50

58

65

59

58

↓ 1, HOBt, EDC

60

62

65

63

62

↓ 1, HOBt, EDC

64

68: R = H  ←(2N HCl)—  67: R = Boc

DENDRIMERS AS MOLECULAR TRANSLOCATORS

FIELD OF TEE INVENTION

The present invention relates to dendrimers and transport molecules, to methods of synthesizing dendrimers and transport molecules, and to methods for using dendrimers and transport molecules. In some embodiments, the transport molecules may be used to transport biologically active molecules. In other embodiments, the transport molecules may be used to transport detector molecules. The present invention further relates to pharmaceutical formulations that include dendrimers in combination with one or more biologically active molecules.

BACKGROUND OF THE INVENTION

A continuously challenging goal in the development of therapeutically useful drugs is to synthesize biologically active compounds that penetrate cells. Although a large number of drug candidates have been synthesized for the treatment of various diseases during the past few decades, many of these candidates have failed in clinical application because of low bioavailability. Therefore, significant efforts have been undertaken to improve the bioavailability of drugs and to increase their concentration in the bloodstream. The bioavailability of drugs depends significantly on the efficiency of transport into cells, which involves three concurrent steps including administration, membrane penetration, and distribution. To gain high bioavailability, drugs should be sufficiently polar for administration and distribution while sufficiently nonpolar for passive diffusion through the lipid bilayer of cell membranes. As a result, most drugs are limited to a narrow range of physical properties which be effective for the drug delivery process. Many highly promising and important drug candidates often fail to advance clinically because they fall out of this range and cannot achieve the desirable balance of water solubility and passive membrane translocation.

Recently, several efforts have been disclosed with respect to improving the cellular uptake of drug candidates into cells. See (1) WO 79/00515; (2) WO 94/04686; (3) WO 91/09958; (4) WO 98/52614; (5) Pepinsky, R. B. et al. *DNA Cell Biol.*, 13, p. 1011-1019 (1994); (6) Vocero-Akbani, A. M. et al. *Nat. Med.*, 5, p. 29-33 (1999); (7) Schwarze, S. R. et al. *Science*, 285, p. 1569-1572 (1999); (8) Ryser, H. J.-P. *Nature* (London), 215, 934-936 (1967); (9) Emi, N. et al. *Biophys. Res. Commun.*, 231, p 421-424 (1997); (10) Ryser, H. J.-P. et al. *Proc. Natl. Acad. Sci. USA.*, 75, p. 1872-1876 and 3867-3870 (1978); (11) Leonetti, J.-P. et al. *Bioconjugate Chem.*, 1, p. 149-153 (1990); (12) Murphy, J. E. et al. *Proc. Natl. Acad. Sci. U.S.A.*, 95, p. 1517-1522 (1998); (13) Buschle, M. et al. *Proc. Natl. Acad. Sci. USA.*, 94, p. 3256-3261 (1997); (14) Mitchell. D. J. et al. *J. Peptide Res.*, 55, p. 318-325 (2000); and (15) Wender. P. A. et al. *Proc. Natl. Acad. Sci. U.S.A.*, 97, p. 13003 (2000). It has been disclosed that certain naturally occurring macromolecules including the HIV-1 protein Tat enter cells through an active transport mechanism. See references (5)-(7). It has also been reported that arginine-rich fragments of HIV-1 Tat are efficiently internalized by cultured cells. See references (2) and (3). Conjugation of oligoarginine to small molecules or macromolecules has been disclosed as facilitating the delivery of the attached molecules into cells. See references (14) and (15). References (14) and (15) disclose that peptides containing 6 to 15 contiguous arginine residues can increase cellular uptake of conjugated molecules. These references also disclose that the peptoid analogs of 6 to 9 arginine residue peptides display even higher cellular uptake properties. Additionally, these references report that the chirality of the oligomers is not significant with respect to intracellular translocation and that the distance between the backbone and the guanidine head group of these materials is important in transport activity.

Despite the apparent success in the use of peptide-based molecule transporters, including peptides and peptoids derived from arginine, lysine (see reference (8)), and ornithine (see reference (9)), such molecules are limited by their toxicity, availability, and cost. Furthermore, peptide-based molecule transporters may not be sufficiently stable toward intracellular and extracellular protease activity. Upon degradation, such molecules lose their efficacy as molecular transporters. In addition, peptide-based molecules also suffer from the drawback that such molecules may trigger antigenic responses and may thus be unsuitable for long term use in a patient. Therefore, a need remains for compounds and methods for transporting biologically active molecules such as drugs into cells which exhibit improved efficacy, stability, and which are not cost-prohibitive.

SUMMARY OF THE INVENTION

Generally, the invention provides dendrimers, transport molecules, methods for making dendrimers and transport molecules, pharmaceutical formulations and medicaments that include the dendrimers and transport molecules, methods of and uses for increasing the effectiveness of a drug, methods of and uses for increasing transport of a biologically active compound across a biological membrane, methods for and uses in measuring the uptake of a dendrimer in a cell, methods for administering pharmaceutical agents to a subject, methods for and uses in increasing the bioavailability of a drug, kits that include dendrimers and/or transport molecules, and libraries of dendrimers and transport molecules.

In one aspect, the invention provides a dendrimer that includes at least two branch groups and two or more guanidine groups, protonated guanidine groups, or protected guanidine groups; two or more amidine groups, protonated amidine groups, or protected amidine groups; ureido groups, protonated ureido groups, or protected ureido groups; or thioureido groups, protonated thioureido groups, or protected thioureido groups. In such dendrimers, at least two of the two or more guanidine groups, protonated guanidine groups, or protected guanidine groups; two or more amidine groups, protonated amidine groups, or protected amidine groups; ureido groups, protonated ureido groups, or protected ureido groups; or thioureido groups, protonated thioureido groups, or protected thioureido groups are borne at the end of the at least two branch groups. In some such embodiments, the invention provides a dendrimer that includes at least three branch groups and three or more guanidine groups, protonated guanidine groups, or protected guanidine groups; two or more amidine groups, protonated amidine groups, or protected amidine groups; ureido groups, protonated ureido groups, or protected ureido groups; or thioureido groups, protonated thioureido groups, or protected ureido groups. In such dendrimers, at least three of the three or more guanidine groups, protonated guanidine groups, or protected guanidine groups; two or more amidine groups, protonated amidine groups, or protected amidine groups; ureido groups, protonated ureido groups, or protected ureido groups; or thioureido groups, protonated thioureido groups, or protected thioureido groups are borne at the end of the at least three branch groups.

In some embodiments, the dendrimer includes at least one tetravalent atom bonded to at least two branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In some such embodiments, the dendrimer includes at least one tetravalent atom that is bonded to at least three branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In other embodiments, the invention provides dendrimers that include a first tetravalent atom and a second tetravalent atom, and the first tetravalent atom and the second tetravalent atom are each bonded to at least three branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In still other embodiments, the invention provides dendrimers that include a first tetravalent atom, a second tetravalent atom, and a third tetravalent atom, and the first tetravalent atom, the second tetravalent atom, and the third tetravalent atom are each bonded to at least three branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In yet other embodiments, the invention provides dendrimers that include a first tetravalent atom, a second tetravalent atom, a third tetravalent atom, and a fourth tetravalent atom, and the first tetravalent atom, the second tetravalent atom, the third tetravalent atom, and the fourth tetravalent atom are each bonded to at least three branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups.

In some embodiments, the invention provides dendrimers which possess a degree of symmetry such that each of the guanidine groups, protonated guanidine groups, or protected guanidine groups; each of the amidine groups, protonated amidine groups, or protected amidine groups; or each of the ureido groups, protonated ureido groups, or protected ureido groups; or thioureido groups, protonated thioureido groups, or protected thioureido groups is in an identical chemical environment when each of the guanidine groups, protonated guanidine groups, or protected guanidine groups; each of the amidine groups, protonated amidine groups, or protected amidine groups; or each of the ureido groups, protonated ureido groups, or protected ureido groups; or thioureido groups, protonated thioureido groups, or protected thioureido groups is either neutrally charged or is protonated.

In other embodiments, the invention provides dendrimers that include amide bonds but do not include any peptide linkages. In still other embodiments, the invention provides a dendrimer that includes 3, 6, 9, or 12 guanidine groups, protonated guanidine groups, protected guanidine groups, amidine groups, protonated amidine groups, protected amidine groups, ureido groups, protonated ureido groups, protected ureido groups, thioureido groups, protonated thioureido groups, or protected thioureido groups.

In other embodiments, the invention provides a dendrimer that includes at least one residue of tris(hydroxymethyl)aminomethane, and the dendrimer includes at least one group of formula I.

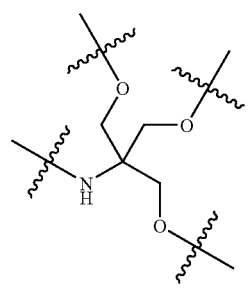

I

In some such embodiments, the dendrimer includes one, two, three, or four groups of formula I.

In other embodiments, the invention provides dendrimers that include at least one group of formula II or a protonated or protected form of the group of formula II.

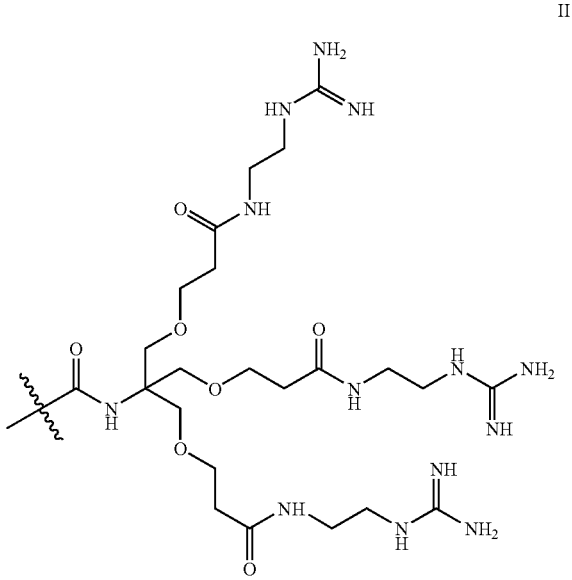

II

In some such embodiments, the dendrimer includes one, two, three, or four groups of formula II or protonated or protected forms of the group of formula II.

In other embodiments, the invention provides dendrimers that include at least one group having a structure analogous to that of formula II wherein the guanidine groups are replaced with amidine, ureido, or thioureido groups. In some such embodiments, the dendrimer includes one, two, three, or four groups having a structure analogous to that of formula II wherein the guanidine groups are replaced with amidine, ureido, or thioureido groups.

In other embodiments, the invention provides dendrimers that include at least one group having the formula III.

In other embodiments, the invention provides dendrimers that include at least one group having the formula IV.

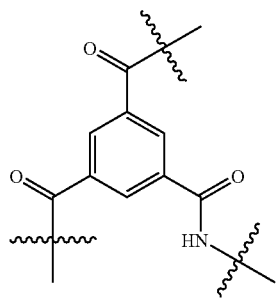

III

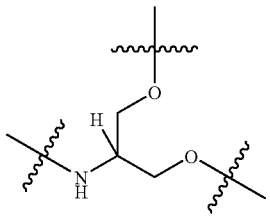

IV

In other embodiments, the invention provides dendrimers that include a group of formula V or a protonated or protected form of the group of formula V.

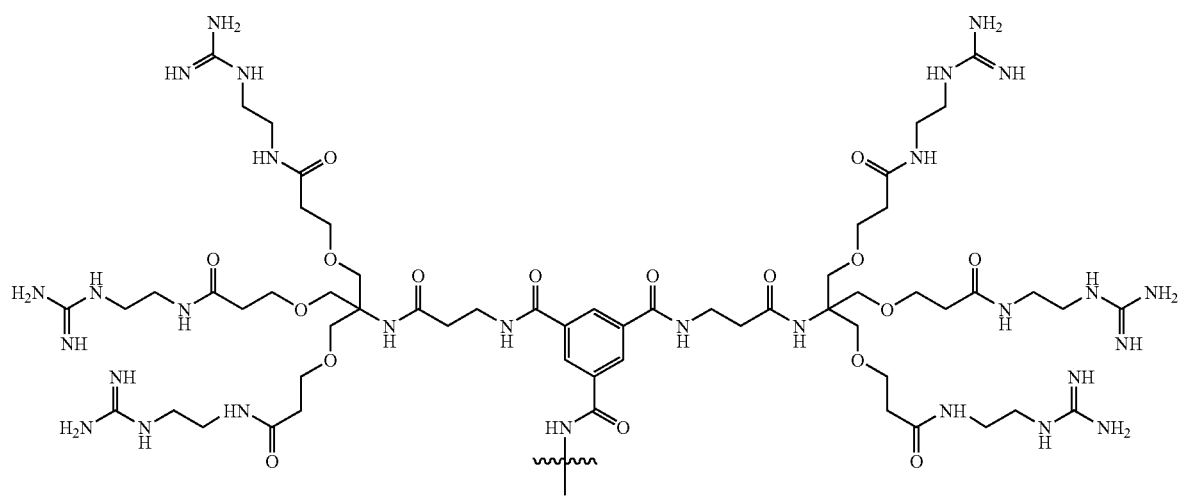

V

In other embodiments, the invention provides dendrimers that include at least one group having a structure analogous to that of formula V wherein the guanidine groups are replaced with amidine, ureido, or thioureido groups.

In other embodiments, the invention provides dendrimers that include a group of formula VI or a protonated or protected form of the group of formula VI.

VI
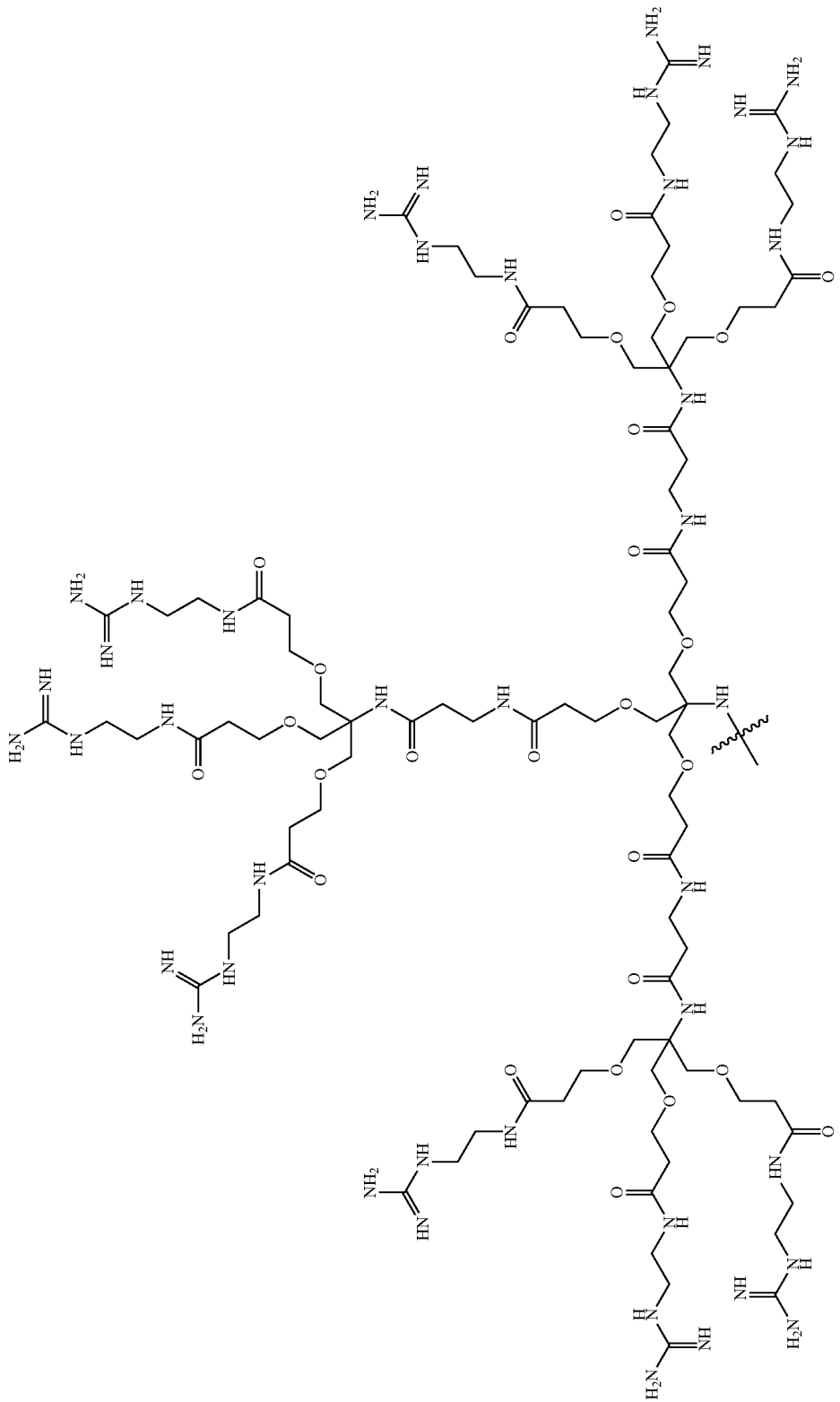

In other embodiments, the invention provides dendrimers that include at least one group having a structure analogous to that of formula VI wherein the guanidine groups are replaced with amidine, ureido, or thioureido groups.

In other embodiments, the invention provides dendrimers that include a group of formula VI or a protonated or protected form of the group of formula VII.

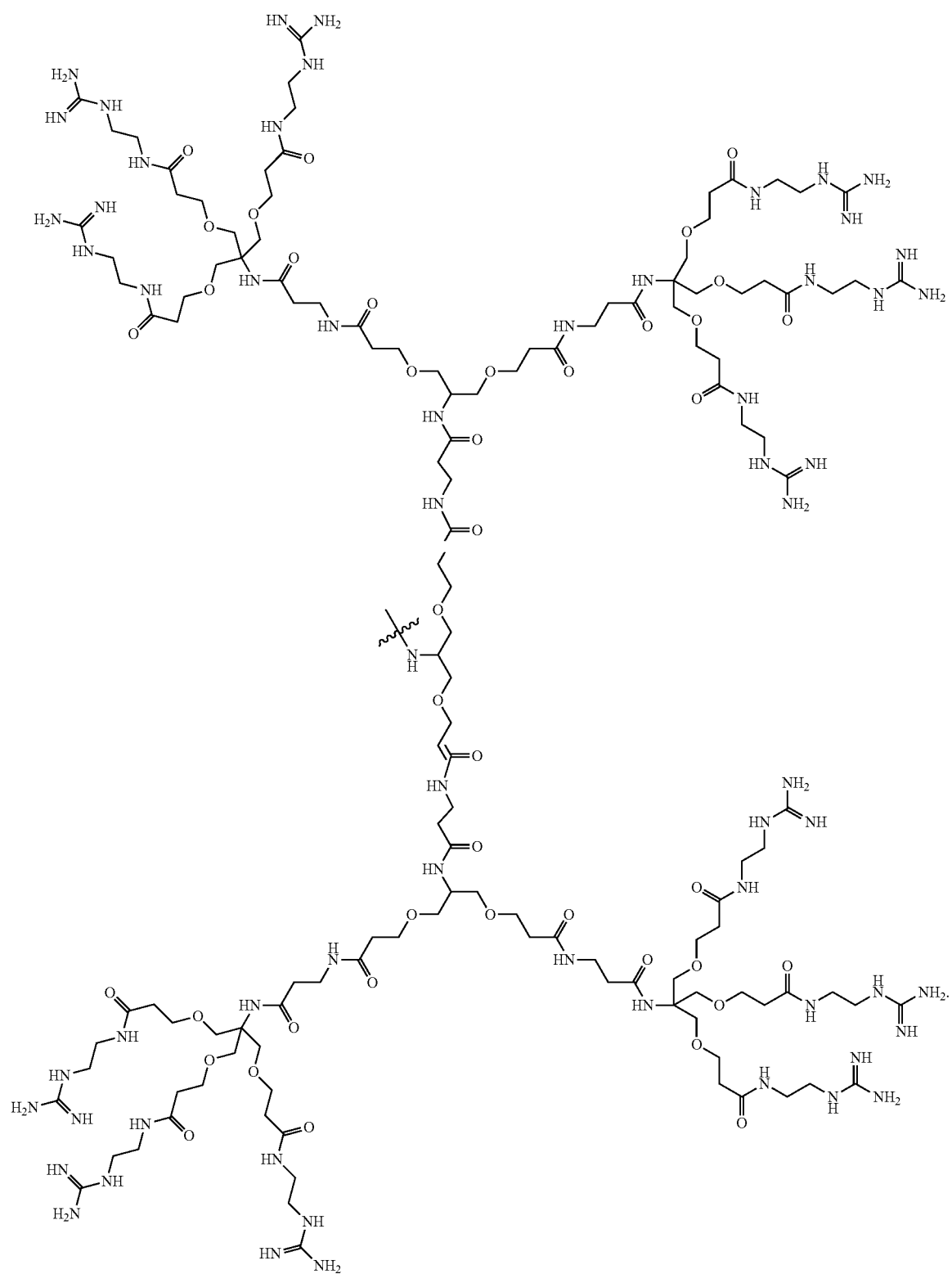

VII

In other embodiments, the invention provides dendrimers that include at least one group having a structure analogous to that of formula VII wherein the guanidine groups are replaced with amidine, ureido, or thioureido groups.

In other embodiments, the invention provides dendrimers that include a group of formula VIII or a protonated or protected form of the group of formula VIII.

port molecule includes at least one tetravalent atom bonded to at least three groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal

VIII

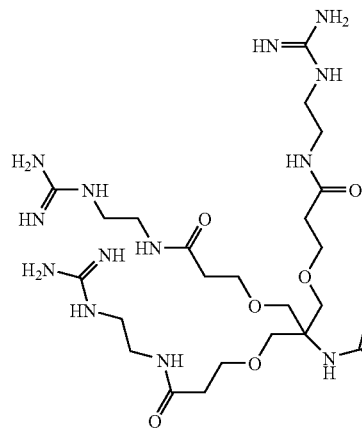
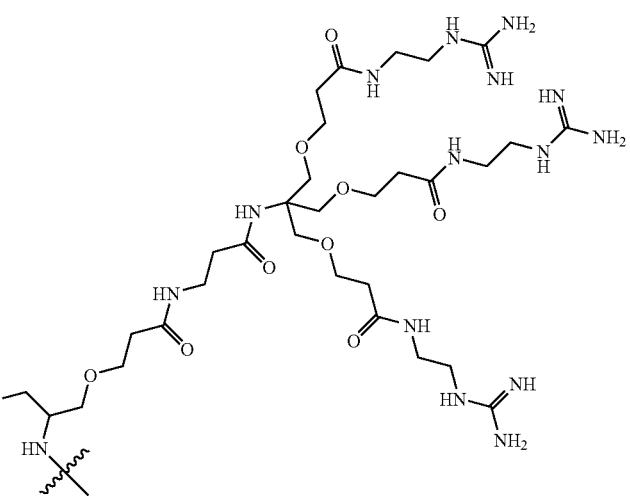

In other embodiments, the invention provides dendrimers that include at least one group having a structure analogous to that of formula VIII wherein the guanidine groups are replaced with amidine, ureido, or thioureido groups.

In other embodiments, the invention provides dendrimers that include a detection molecule bonded to the dendrimer. In some such embodiments, the detection molecule is fluorescein. In other such embodiments, the detection molecule is Green Fluorescent Protein (GFP). A method of measuring the uptake of a dendrimer in a cell is also provided. The method includes administering to a human, an animal, or a plant a dendrimer that includes a detection molecule that is bonded to the dendrimer.

The invention also provides a transport molecule. The transport molecule includes a dendrimer and a biologically active molecule. The dendrimer includes at least one guanidine group, at least one protonated guanidine group, at least one protected guanidine group, at least one amidine group, at least one protonated amidine group, at least one protected amidine group, at least one ureido group, at least one protonated ureido group, at least one protected ureido group, at least one thiorueido group, at least one protonated thioureido group, or at least one protected thioureido group, and the biologically active molecule is bonded to the dendrimer.

In some embodiments, the dendrimer of the transport molecule includes at least one tetravalent atom bonded to at least two groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In other embodiments, the dendrimer of the trans-protonated thioureido groups, or terminal protected thioureido groups. In still other embodiments, the dendrimer of the transport molecule includes a first tetravalent atom and a second tetravalent atom, wherein the first tetravalent atom and the second tetravalent atom are each bonded to at least three groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In yet other embodiments, the dendrimer of the transport molecule includes a first tetravalent atom, a second tetravalent atom, and a third tetravalent atom, wherein the first tetravalent atom, the second tetravalent atom, and the third tetravalent atom are each bonded to at least three groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In still other embodiments, the dendrimer of the transport molecule includes a first tetravalent atom, a second tetravalent atom, a third tetravalent atom, and a fourth tetravalent atom, wherein the first tetravalent atom, the second tetravalent atom, the third tetravalent atom, and the fourth tetravalent atom are each bonded to at least three groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups.

In still other embodiments, the dendrimer of the transport molecule includes at least two guanidine groups, protonated guanidine groups, protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups, and the transport molecule possesses a degree of symmetry such that the at least two guanidine groups, protonated guanidine groups, protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups are in identical chemical environments when all the guanidine groups, protonated guanidine groups, protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups of the dendrimer are either neutrally charged or are protonated. In still other embodiments, the dendrimer of the transport molecule includes three or more guanidine groups, protonated guanidine groups, protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups, and the transport molecule possesses a degree of symmetry such that each of the three or more guanidine groups, protonated guanidine groups, protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups is in an identical chemical environment when each of the three or more guanidine groups, protonated guanidine groups, protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups is either neutrally charged or is protonated. In still other embodiments, the dendrimer possesses $C_{2V}$ symmetry whereas in other embodiments, the dendrimer possesses $C_{3V}$ symmetry.

In still other embodiments, the dendrimers includes 3, 6, 9, or 12 guanidine groups, protonated guanidine groups, or protected guanidine groups; amidine groups, protonated amidine groups, or protected amidine groups; ureido groups, protonated ureido groups, or protected ureido groups; or thioureido groups, protonated thioureido groups, or protected thioureido groups.

In still other embodiments, the dendrimer of the transport molecule does not include arginine or lysine units or residues.

In still other embodiments, the dendrimer of the transport molecule includes amide bonds but does not include any peptide linkages.

In yet other embodiments, the dendrimer of the transport molecule includes a group of formula I, a group of formula II or a protonated or protected form of the group of formula II a group of formula III a group of formula IV, a group of formula V or a protonated or protected form of the group of formula V, a group of formula VI or a protonated or protected form of the group of formula VI, a group of formula VII or a protonated or a protected form of the group of formula VII, or a group of formula VIII or a protonated or protected form of the group of formula VIII. In some embodiments, the dendrimer of the transport molecule includes one, two, three, or four groups of formula I or formula II or protonated or protected forms of the group of formula II.

In other embodiments, the invention provides dendrimers that include at least one group having a structure analogous to that of formula II, formula V, formula VI, formula VII, or formula VIII, wherein the guanidine groups are replaced with amidine, ureido, or thioureido or with protonated or protected forms of such groups. This includes embodiments wherein the dendrimer includes one, two, three, or four groups having a structure analogous to that of formula II wherein the guanidine groups are replaced with amidine, ureido, or thioureido groups or protonated or protected forms of such groups.

In other embodiments, the transport molecule includes a disulfide linkage, an ether linkage, or a thioether linkage, and the biologically active molecule is bonded to the dendrimer through the disulfide linkage, the ether linkage, or the thioether linkage.

In other embodiments, the biologically active molecule is bonded to the dendrimer through an amide or ester linkage.

In other embodiments, the biologically active molecule is bonded to the dendrimer through a thiourea group.

In yet other embodiments, the biologically active molecule is bonded to the dendrimer by reaction of a maleimide on the dendrimer with a reactive group on the biologically active molecule.

In still other embodiments, the biologically active molecule is bonded to the dendrimer through a covalent bond which is in some embodiments through a carbon-carbon single bond.

In still other embodiments, the biologically active molecule bonded to the dendrimer is a drug. In some embodiments, the biologically active molecule bonded to the dendrimer is a protein. In some such embodiments, the protein has a size of less than 10 kDaltons. In other such embodiments, the protein has a size of more than 10 kDaltons. In some such embodiments, the protein has a size of 20-40 kDaltons. In some embodiments, the protein has a size of about 40-100 kDalton. In some embodiments, a protein such as Green Fluorescent Protein (GFP) is bonded to the dendrimer.

In still other embodiments, the biologically active molecule bonded to the dendrimer is a drug for the treatment of a mammalian condition.

The invention further provides pharmaceutical formulations that include any of the transport molecules of the present invention in combination with a pharmaceutically acceptable carrier.

The invention further provides a method of increasing the effectiveness of a drug. The method includes administering a pharmaceutical formulation of the invention to a human or an animal.

The invention also provides a method of increasing transport of a biologically active compound across a biological membrane. The method includes contacting a biological membrane with any transport molecule of the present invention. The transport molecule that includes the biologically active compound is transported across the biological membrane at a rate greater than the biologically active compound is transported across the biological membrane when the biologically active compound is not bonded to the dendrimer of the transport molecule.

The invention further provides a method of administering a pharmaceutical agent to a subject that includes coadministering the pharmaceutical agent and any of the dendrimers of the present invention to the subject. In some such embodiments, the dendrimer is bonded to the pharmaceutical agent. In some such embodiments, the subject is a human. In other such embodiments, the subject is a cell.

The invention also provides a method for increasing the bioavailability of a drug. The method includes bonding the drug to any of the dendrimers of the present invention. In some such embodiments, the dendrimer is bonded to the dendrimer through reaction with a peptide linking group on the dendrimer whereas in other such embodiments, the drug is bonded to the dendrimer through reaction with a non-peptide linking group on the dendrimer.

The invention further provides various methods of synthesizing dendrimers and transport molecules.

The invention further provides a transport molecule produced by any of the methods for synthesizing a transport molecule and a dendrimer molecule produced by any of the methods for synthesizing a dendrimer.

The invention further provides kits that include at least two of any of the dendrimers of the present invention or at least one dendrimer of the present invention and a linking molecule. In some embodiments, the kit includes at least two dendrimers and a linking molecule for linking the dendrimer to a biologically active molecule or a detection molecule. In still other embodiments, the kit includes instructions for attaching a biologically active molecule to the dendrimer.

The invention further provides a library that includes a plurality of dendrimers or a library that includes a plurality of transport molecules. In some embodiments, the library includes a plurality of both dendrimers and transport molecules.

Further objects, features and advantages of the invention will be apparent from the following detailed description.

BRIEF DESCRIPTION OF THE DRAWINGS

FIGS. 16A-16N are scanned in images taken through a microscope showing the cellular uptake of fluorescein-labeled compounds 10, 11, 12, 13, and 41 by HeLa S3 epithelioid cervical carcinoma cells. In preparation for these experiments, the cells were washed in a PBS buffer solution between three and five times. In each pair of images shown in FIGS. 16A through 16N, the image on the left (e.g. FIG. 16A in the first pair of images) provides an image of the cells prior to the uptake of the fluorescein-labeled compound, while the image on the right (e.g. FIGS. 16A and 16B show cellular uptake of compound 41 at a concentration of 10 μM. FIGS. 16K-16N show cellular uptake of compound 12 at a concentration of 50 μM and at higher magnification.

FIGS. 17A-17C depict graphs relating to control experiments for cellular uptake by HeLa S3 human epithelioid cervical carcinoma cell experiments in the absence of any fluorescein-labeled compound.

FIG. 37A shows typical purification processes after GFP conjugation with compound 71 containing nine guanidinium groups. The conjugation reaction (71-conjugated) and flow-through (FT) or eluted samples (Elut) are shown in (16% SDS-PAGE) gel. G9 at the bottom side of the gel represents compound 71.

FIG. 37B shows the G3, G6, and G9 conjugated with GFP (top) and transduction efficiency of the GFP-conjugated guanidinium groups into cells (bottom). These synthetic transporters or non-conjugated GFP (4 μM each) were treated to HeLa cells for 4 hrs at 37° C. without serum. The transduction efficiency was measured in FACS analysis by the fluorescence intensity of GFP inside of the cells. Average values from three independent experiments are shown.

FIGS. 38A and 38B correspond to the untreated control cells. FIGS. 38C and 38D correspond to the cells treated with GFP (4 M. FIGS. 38E and 38F correspond to the cells treated with $Tat_{49-57}$-GFP (4 μM). FIGS. 38E and 38F correspond to the cells treated with 71-GFP (4 μM. FIGS. 38B, 38D, 38F, and 38H represent the fluorescence images and FIGS. 38A, 38C, 38E, and 38G are the contrast images.

FIG. 40A is the control image using untreated HeLa cells. HeLa cells were treated with 8 μM each of $Tat_{49-57}$-GFP (FIG. 40B) or 71-GFP (FIG. 40C) for 4 hours at 37° C. without serum. After treatment, the fluorescent images were obtained using a confocal microscope.

DETAILED DESCRIPTION OF THE INVENTION

Figure 1:
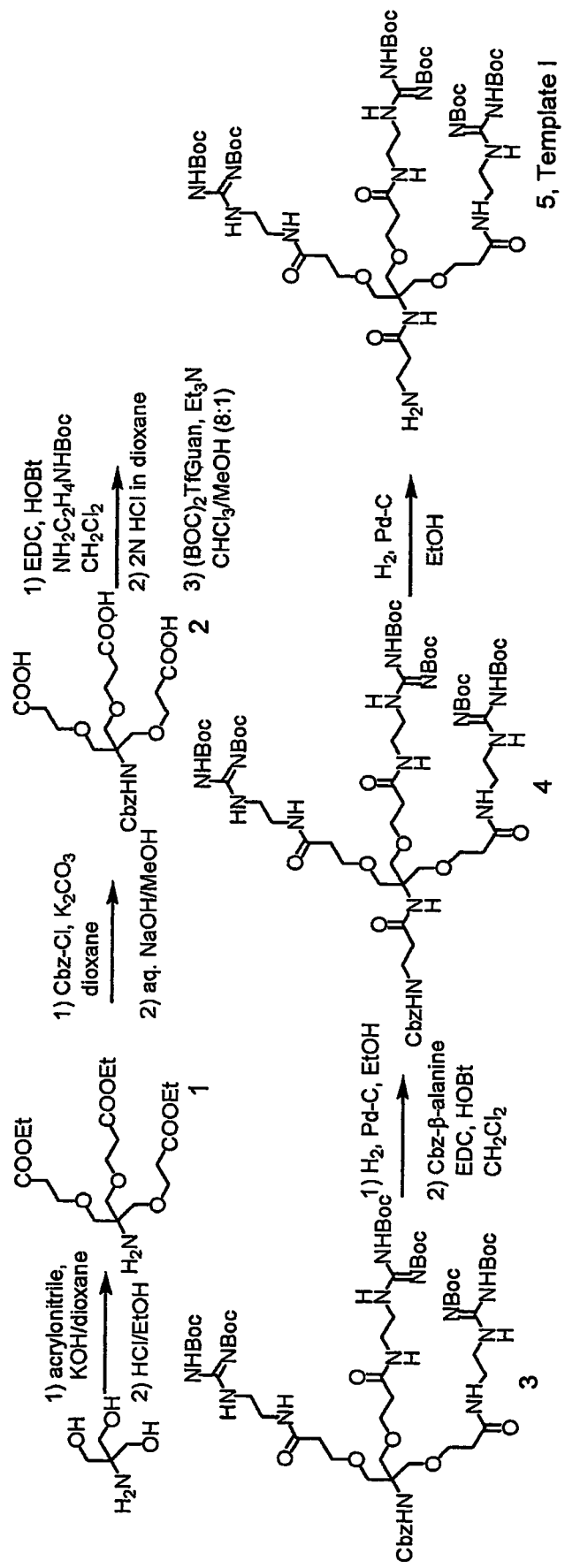
FIG. 1 depicts a reaction scheme for the synthesis of Boc-protected dendritic oligo-guanidines having three guanidine groups in identical chemical environments.
Figure 2A:
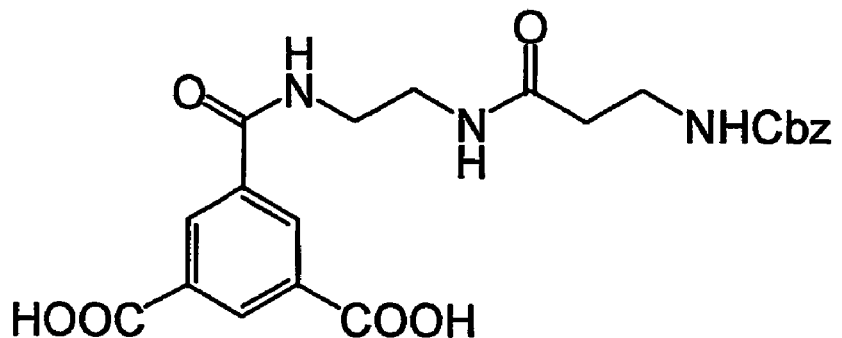
FIGS. 2A-2D depict various molecules that may act as core molecules in the synthesis of dendritic oligo-guanidines.
Figure 2B:
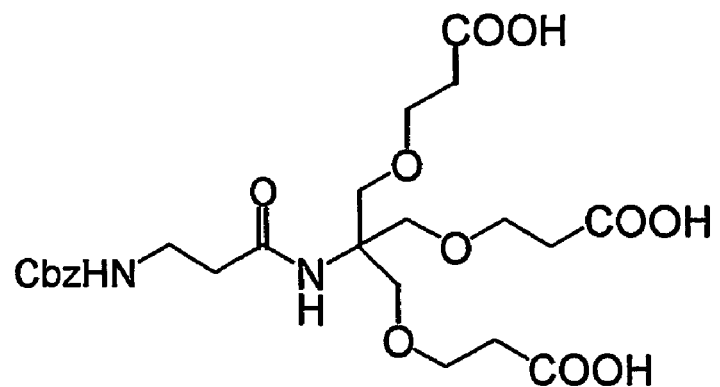
Figure 2C:
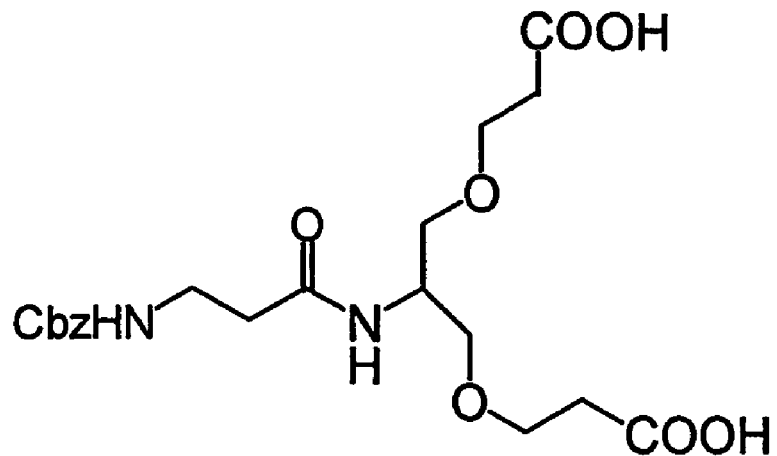
Figure 2D:
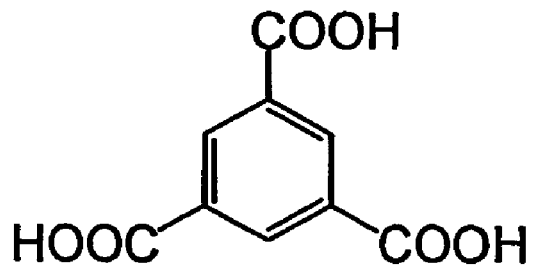
Figure 3A:
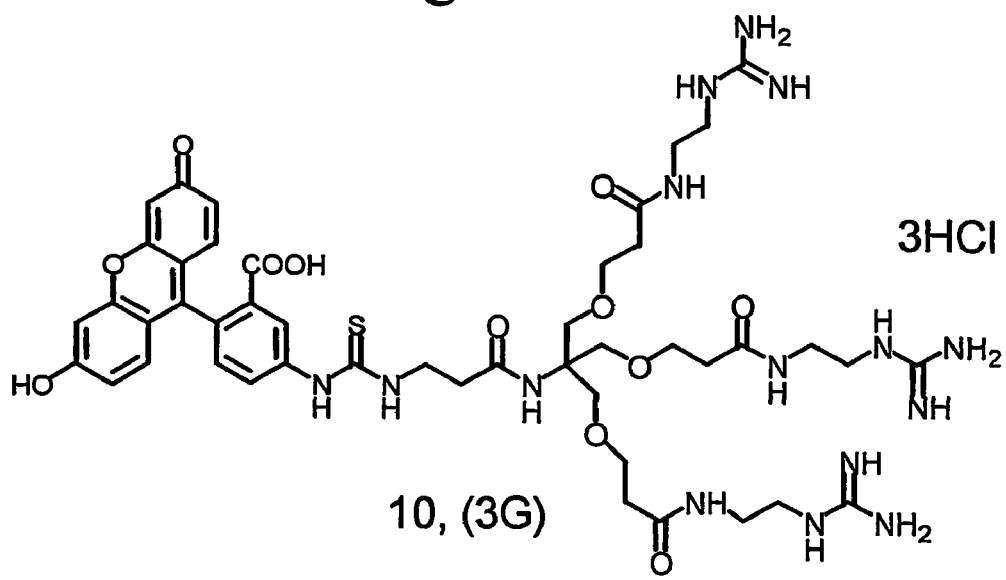
FIGS. 3A-3D depict various dendritic oligo-guanidines that include 3, 6, 9, and 12 guanidine groups and a fluorescein detection molecule linked to the dendrimer by a thiourea group.
Figure 3B:
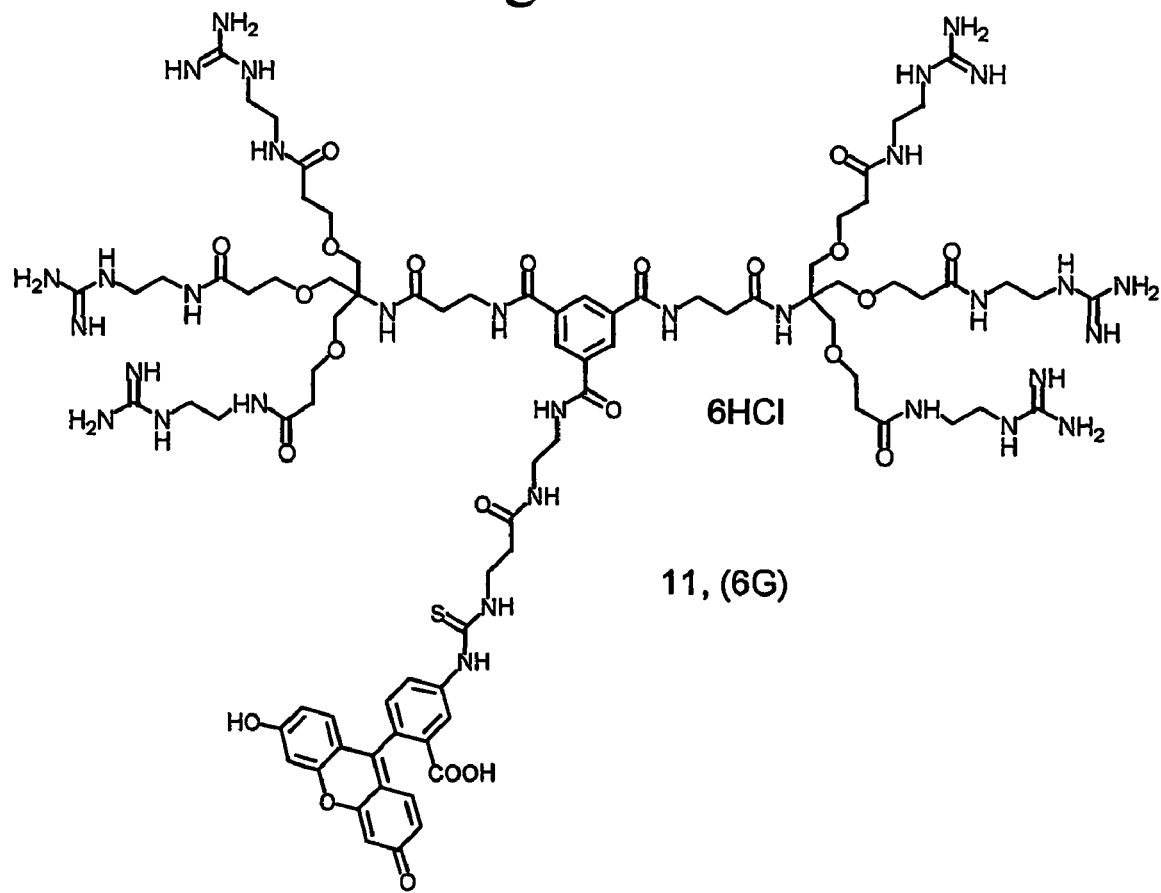
Figure 3C:
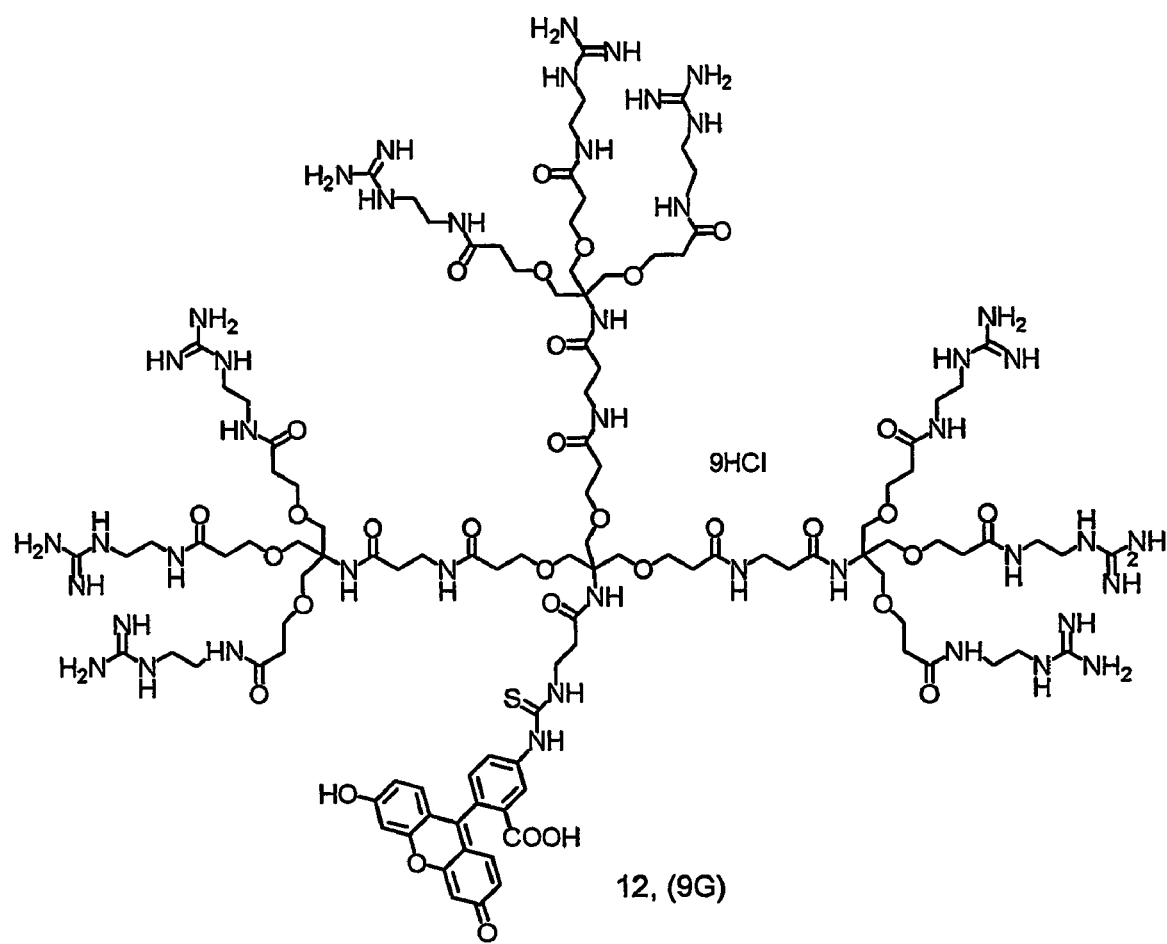
Figure 3D:
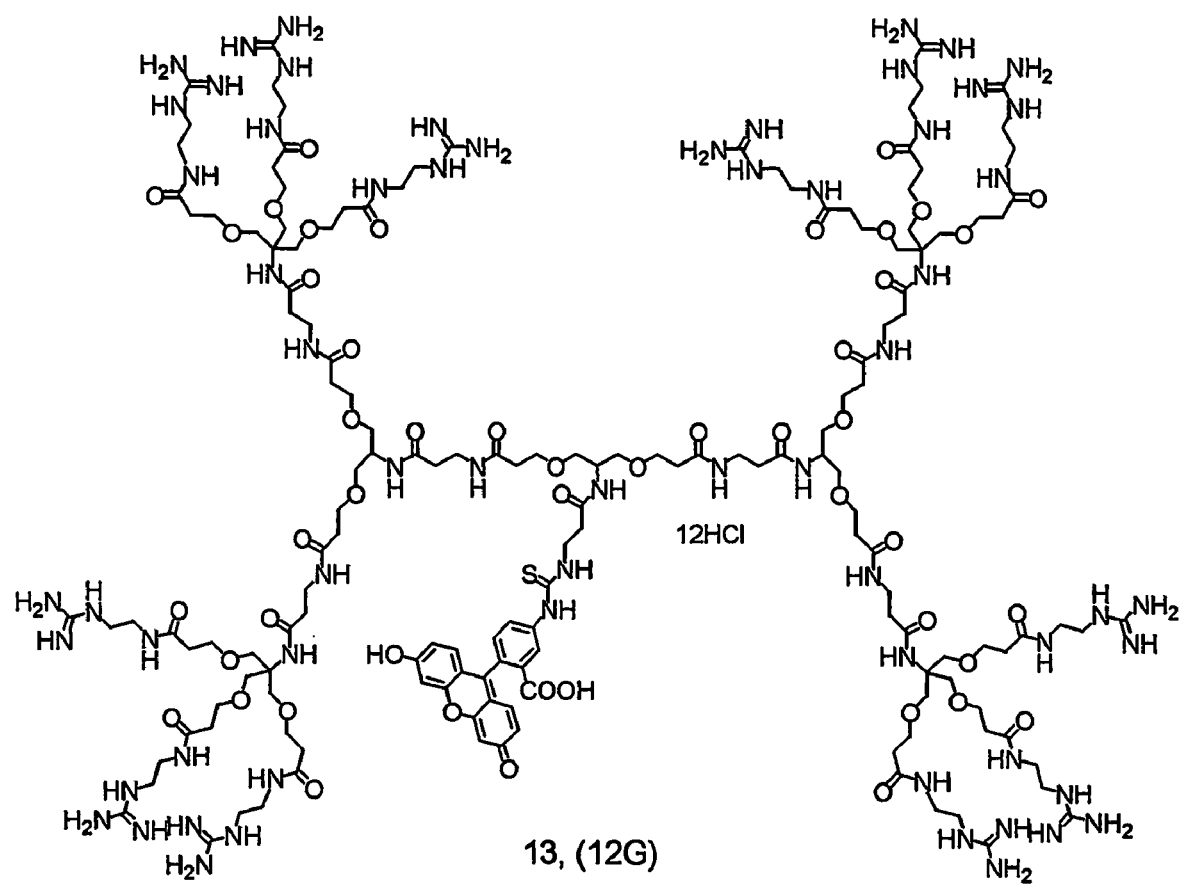
Figure 4A:
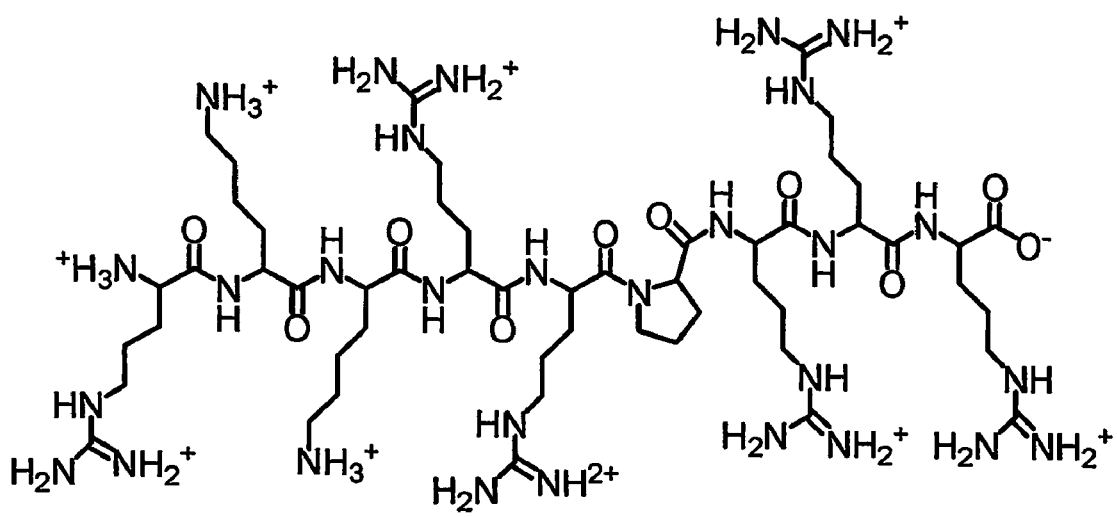
FIGS. 4A and 4B depict two oligo-guanidine peptides composed of α amino acids.
Figure 4B:
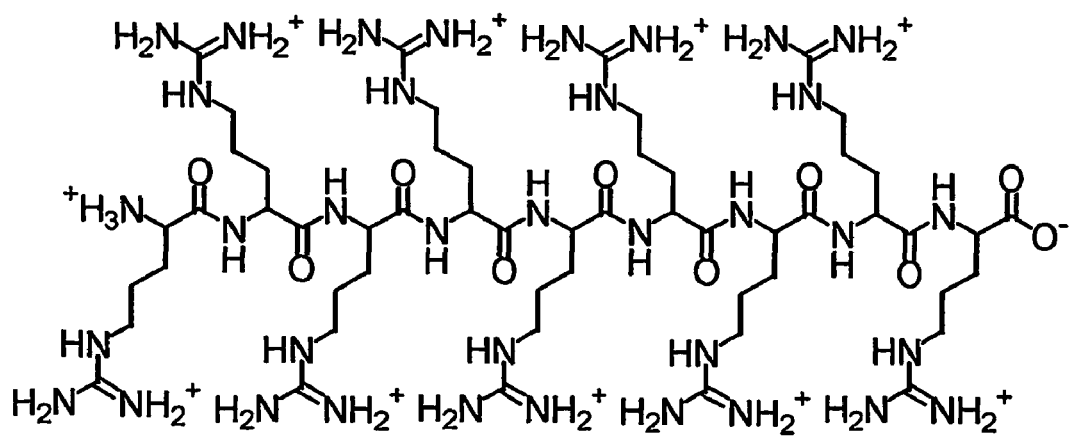

As employed herein, "peptide" refers to an organic compound that includes at least one peptide linkage. As employed herein a peptide linkage is an amide bond formed by the reaction of an amino group on a first α-amino acid with a carboxylic acid group on a second α-amino acid. An α-amino acid is an organic compound that bears both a carboxylic acid group and an amine group. The amine group of α-amino acids is bonded to the same carbon atom (the α-carbon) that is bonded to the carboxylic acid group. Examples of α-amino acids with the one letter symbols used to commonly refer to them include alanine (A), arginine (R), asparagine (N), aspartic acid (D), cysteine (C), glutamine (Q), glutamic acid (E), glycine (G), histidine (H), isolecuine (I), leucine (L), lysine (K), methionine (M), phenylalanine (F), proline (P), serine (S), threonine (T), tryptophan (W), tyrosine (Y), and valine (V).

As employed herein, "dendrimer" refers to an organic compound that has at least one branched tree-like structure originating from at least one core atom or at least one core portion of a molecule. In some embodiments, at least two of the branches of a "dendrimer" will be structurally similar to one another. In other embodiments, at least two of the branches of a "dendrimer" will be structurally identical such that molecule has a high degree of symmetry. In other embodiments, a "dendrimer" includes at least three branches that originate from at least one core atom or at least one portion of a core molecule. In still other embodiments, a "dendrimer" includes three branches that originate from at least one core atom or at least one portion of a core molecule and each of the three branches is structurally identical. In some embodiments a "dendrimer" often includes several branched tree-like structures where each branched tree-like structure originates from a core atom such as, but not limited to a tetravalent atom, or a portion of a core molecule.

As employed herein, the phrase "is in an identical chemical environment" when used with respect to two or more chemical groups such as guanidine groups, protonated guanidine groups, or protected guanidine groups in a molecule means that the molecule possesses a degree of symmetry such that the groups, while separate and distinct, are identical to one another in the way that they are arranged in the molecule. For example, methane is a tetrahedral molecule with four hydrogen atoms bonded to a central carbon atom. While separate and distinct, each hydrogen atom is in "an identical chemical environment" due to the symmetry of the molecule. As a further example, in chloroform, $CHCl_3$, each of the three chlorine atoms "is in an identical chemical environment." Groups that are "in an identical chemical environment" will have identical chemical reactivity. Additionally, if such groups include hydrogen atoms, then each of the hydrogen atoms will have the same chemical shift in the $^1$H NMR spectrum. For the purposes of this application, prochiral groups are considered to be "in an identical chemical environment." Because guanidine groups may be protonated with acids such as trifluoroacetic acid and hydrochloric acid, a molecule with more than one guanidine group in which the guanidine groups are "in an identical chemical environment" may be only partially protonated e.g. one guanidine group in a molecule with five other guanidine groups may be in a protonated form whereas the other five are not. Protonation of the single guanidine group would result in a molecule in which the protonated guanidine group is not "in an identical chemical environment" to the others. Furthermore, the protonation of the guanidine group in such a molecule may also mean that the other guanidine groups are not "in an identical chemical environment" to each of the others because the protonation of the one guanidine group has reduced the symmetry of the molecule. For this reason, when a molecule that includes a number of unprotected guanidine groups is referred to as having guanidine groups that are "in an identical chemical environment," the statement that the molecule is either neutrally charged or that each of the guanidines is protonated is used. This indicates that in order to determine whether a molecule that includes guanidine groups has guanidine groups that are "in an identical chemical environment", the molecule must be considered when all the guanidine groups are either all neutrally charged are all protonated with the same acid. For determination of whether a molecule has groups where each "is in an identical chemical environment", the effect of isotopes on the symmetry will not be considered. For example, a molecule that has three guanidine groups where each "is in an identical chemical environment" when each is neutrally charged or is fully protonated will not be converted to one where each is not "in an identical chemical environment" because one of the guanidine groups include a D atom rather than a H or includes a different isotope of N or C, or because one of the guanidine groups is bonded to a group that includes a different isotope of O or some other element. In other words, the O atoms in a compound such as $H_2NC(CH_2OH)_3$ will be considered to be "in an identical chemical environment" even if one of the H atoms of one or two of the hydroxyl groups is replaced with a D. The above discussion also applies to amidines, ureido groups, and thioureido groups in a manner analogous to guanidines.

As employed herein, a "tetravalent atom" refers to an atom that is bonded to four different groups. Examples of "tetravalent atoms" include, but are not limited to, the carbon atom in methane, chloroform, methylene chloride, chloromethane, and carbon tetrachloride; the underlined carbon atoms in compounds of structure $H_2N\underline{C}(CH_2OH)_3$, $H_2N\underline{C}H(CH_2OH)_2$, and other organic compounds; the silicon atom in compounds such as tetramethylsilane; the phosphorus atom in compounds such as triphenylphosphine oxide, alkyltriphenylphosphonium halides, and the like.

As employed herein, "alkane" refers to an organic compound that includes carbon atoms and hydrogen atoms, and includes C—H bonds and additionally includes C—C single bonds in alkanes other than methane. The term "alkane" includes straight-chain alkanes such as alkanes having from 1 to 20 carbon atoms. In some embodiments, alkanes include straight-chain alkanes such as alkanes having from 1 to 8 carbon atoms such as methane, ethane, propane, butane, pentane, hexane, heptane, and octane. The term "alkane" also includes branched-chain alkanes such as, but not limited to branched chain alkanes having from 1 to 20, and in some embodiments from 1 to 8 carbon atoms such as, but not limited to, 2-methylpropane, 2,2-dimethylpropane, 2-methylbutane, 2,3-dimethylbutane, 2,2-dimethylbutane, 2-methylpentane, 3-methylpentane, 2,3-dimethylpentane, 2,4-dimethylpentane, 2,2-dimethylpentane, 3,3-dimethylpentane, 2-methylhexane, 3-methylhexane, 2,2-dimethylhexane, 2,3-dimethylhexane, 2,4-dimethylhexane, 2,5-dimethylhexane, 3,3-dimethylhexane, 3,4-dimethylhexane, 2-methylheptane, 3-methylheptane, 4-methylheptane, 3-ethylpentane, 3-ethyl-2-methylpentane, 3-ethylhexane, and the like. A C—C or a C—H bond of an alkane may be replaced with a bond to another group such as a hydroxyl group, a halogen such as Cl, Br, F, or I, a sulfhydryl group, or an amine group. Alkanes replaced with such groups may respectively be named as hydroxyalkanes, haloalkanes such as chloroalkanes, bromoalkanes, fluoroalkanes, iodoalkanes, mercaptoalkanes, and aminoalkanes.

As employed herein, "alkyl" refers to groups that include straight chain and branched alkyl groups having 1 to about 20 carbon atoms, and in some embodiments from 1 to 8 carbon atoms. Examples of straight chain alkyl groups include methyl, ethyl, propyl, butyl, pentyl, hexyl, heptyl, and octyl groups. Examples of branched alkyl groups, include, those listed above with respect to "alkane" and include groups such as, but not limited to, isopropyl, sec-butyl t-butyl, and isopentyl groups. Representative substituted alkyl groups may be substituted one or more times with, for example, amino, sulfhydryl, alkoxy, hydroxy, or halogen groups such as F, Cl, Br, I groups, and the like.

As employed herein, "cycloalkane" refers to an organic compound that includes a ring having from 3 to 8 members formed from C atoms bonded to one another with single bonds. Examples of unsubstituted cycloalkanes include cyclopropane, cyclobutane, cyclopentane, cyclohexane, cycloheptane, and cyclooctane. Cycloalkanes may be substituted with groups, such as, but not limited to, one or more alkyl groups such as alkyl groups having from 1 to 8 carbon atoms; halogen groups such as F, Cl, Br, and I; amine groups; hydroxyl groups; sulfhydryl (SH) groups; and the like.

As employed herein, "alkene" refers to straight and branched chain groups such as those described with respect to alkanes as defined above, except that at least one double bond exists between two carbon atoms. Examples include, but are not limited to, ethylene, propylene, cis and trans, where applicable, 1-butene, 2-butene, 1-pentene, 2-pentene, 1-hexene, 2-hexene, 3-hexene, 1-heptene, 2-heptene, 3-heptene, 1-octene, 2-octene, 3-octene, 4-octene, 2-methyl-1-butene, and 2-methyl-1-pentene. The phrase "alkenyl" refers to straight and branched chain groups such as those described with respect to alkyl groups as defined above, except that at least one double bond exists between two carbon atoms. Examples include, but are not limited to vinyl, —CH═C(H)(CH$_3$), —CH═C(CH$_3$)$_2$, —C(CH$_3$═C(H)$_2$, —C(CH$_3$)═C(H)(CH$_3$), —C(CH$_2$CH$_3$)═CH$_2$, and the like. A C—C or a C—H bond of an alkene or alkenyl group may be replaced with a bond to another group such as a hydroxyl group, a halogen such as Cl, Br, F, or I, a sulfhydryl group, an amine group, or the like.

As employed herein, "cycloalkene" refers to an organic compound that includes a ring having from 3 to 8 members formed from C atoms bonded to one another with single bonds but which includes at least one carbon carbon double bond. Examples of unsubstituted cycloalkenes include cyclopropene, cyclobutene, cyclopentene, cyclohexene, cycloheptene, and cyclooctene. Cycloalkenes may be substituted with groups, such as, but not limited to, one or more alkyl groups such as alkyl groups having from 1 to 8 carbon atoms; halogen groups such as F, Cl, Br, and I; amine groups; hydroxyl groups; sulfhydryl (SH) groups; and the like.

As employed herein, "diaminoalkane" refers to an alkane in which two H atoms of the alkane are replaced by NH$_2$ groups. Examples of diaminoalkanes include, but are not limited to, such compounds as 1,2-diaminoethane, 1,3-diaminopropane, 1,4-diaminobutane, 1,5-diaminopentane, 1,6-diaminohexane, 1,7-diaminoheptane, 1,8-diaminooctane, 1,2-diaminopropane, 1,2-diaminobutane, 1,2-diaminopentane, 1,2-diaminohexane, 1,2-diaminoheptane, 1,2-diaminooctane, 1,3-diaminobutane, 1,3-diaminopentane, 1,3-diaminohexane, 1,3-diaminoheptane, 1,3-diaminooctane, 1,4-diaminopentane, 1,4-diaminohexane, 1,4-diaminoheptane, 1,4-diaminooctane, 1,5-diaminohexane, 1,5-diaminoheptane, 1,5-diaminooctane, 1,6-diaminoheptane, 1,6-diaminooctane, 1,7-diaminooctane, 2,3-diaminobutane, 2,3-diaminopentane, 2,3-diaminohexane, 2,3-diaminoheptane, 2,3-diaminooctane, 3,4-diaminohexane, 3,4-diaminoheptane, 3,4-diaminooctane, 4,5-diaminooctane, 1,5-diamino-3-methylpentane, and 1,6-diamino-3,4-dimethylhexane.

As employed herein, "diaminocycloalkane" refers to cycloalkane groups in which two H atoms of the cycloalkane are replaced by NH$_2$ groups. Examples of diaminocycloalkanes include, but are not limited to, cis and trams 1,2-diaminocyclopropane, 1,2-diaminocyclobutane, 1,2-diaminocyclopentane, 1,2-diaminocyclohexane, 1,2-diaminocycloheptane, 1,2-diaminocyclooctane, 1,3-diaminocyclobutane, 1,3-diaminocyclopentane, 1,3-diaminocyclohexane, 1,3-diaminocycloheptane, 1,3-diaminocyclooctane, 1,4-diaminocyclohexane, 1,4-diaminocycloheptane, 1,4-diaminocyclooctane, 1,5-cyclooctane, and 1,4-diamino-2-methylcyclohexane.

As employed herein, "diaminoalkene" refers to alkene groups in which two H atoms of the alkene are replaced by NH$_2$ groups. Examples of diaminoalkenes include, but are not limited to, 1,6-diamino-3-hexene, 1,7-diamino-3-heptene, 1,8-diamino-3-octene, and 1,8-diamino-4-octene.

As employed herein, "diaminocycloalkene" refers to cycloalkene groups in which two H atoms of the cycloalkene are replaced by NH$_2$ groups. Examples of diaminocycloalkenes include, but are not limited to, cis and trans 4,5-diaminocyclohex-1-ene, 4,5-diaminocyclohept-1-ene, and 4,6-diamino-cyclohept-1-ene.

As employed herein, a "hydroxyaminoalkane" refers to a diaminoalkane as defined above in which one of the amino groups is replaced by a hydroxy group.

As employed herein, a "hydroxyaminoalkene" refers to a diaminoalkene as defined above in which one of the amino groups is replaced by a hydroxy group.

As employed herein, a "hydroxyaminocycloalkane" refers to a diaminocycloalkane as defined above in which one of the amino groups is replaced by a hydroxy group.

As employed herein, a "hydroxyaminocycloalkene" refers to a diaminocycloalkene as defined above in which one of the amino groups is replaced by a hydroxy group.

As employed herein, "tris(hydroxyalkyl)aminoalkane" refers to an alkane in which one H atom is replaced with an NH$_2$ group and in which three H atoms are replaced by hydroxyalkyl groups. The hydroxyalkyl groups need not replace H atoms attached to the same carbon atom of the alkane, however, in some embodiments, two or three H atoms bonded to the same carbon atom of an alkane are replaced by hydroxyalkyl groups. Further the alkyl group of the hydroxyalkyl groups need not be the same in each of the hydroxyalkyl groups. The NH$_2$ group need not replace a H atom bonded to a carbon atom bearing one of the hydroxymethyl groups. Examples of tris(hydroxyalkyl)aminoalkanes include compounds of formula A

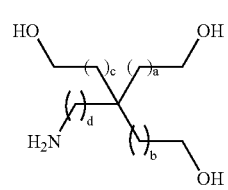

A where, with respect to compounds of structure A, a, b, c, and d are independently selected from 0, 1, 2, 3, 4, 5, 6, 7, or 8. Examples of compounds of formula A include, but are not limited to, tris(hydroxymethyl)aminomethane, 2,2,2-tris(hydroxymethyl)-1-aminoethane, 3,3,3-tris(hydroxyethyl)-1-aminopropane, 3-(hydroxyethyl)-3-(hydroxymethyl)-3-(hydroxypentyl)-1-aminopropane, and 3,3,3-tris(hydroxymethyl)-1aminopropane. Further examples of tris (hydroxyalkyl)aminoalkanes include, but are not limited to, 2-amino-1,5-dihydroxy-3-(hydroxymethyl)pentane, and 1-amino-5,6-dihydroxy-(2-hydroxymethyl)hexane.

As employed herein, "tris(hydroxyalkyl)aminomethane" refers to a compound of formula B

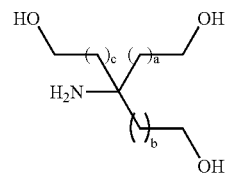

B where, with respect to compounds of formula B, a is selected from 0, 1, 2, 3, 4, 5, 6, 7, or 8, b is selected from 0, 1, 2, 3, 4, 5, 6, 7, or 8, and c is selected from 0, 1, 2, 3, 4, 5, 6, 7, or 8. In some embodiments, a, b, and c have the same value whereas in other embodiments a and b have different values and c has a value similar to a or b. In other embodiments a, b, and c each have different values. In some embodiments, a, b, and c are each independently selected from 0, 1, 2, or 3. Examples of unsubstituted tris(hydroxyalkyl)aminomethanes include, but are not limited to, tris(hydroxymethyl)aminomethane, tris(hydroxyethyl)aminomethane, tris(hydroxypropyl)-aminomethane, tris(hydroxybutyl)aminomethane [bis(hydroxymethyl)](hydroxyethyl)-aminoethane, [bis(hydroxymethyl)](hydroxypropyl)aminoethane, [bis(hydroxymethyl)](hydroxybutyl)aminoethane, [bis(hydroxyethyl)](hydroxypropyl)-aminoethane, [bis(hydroxyethyl)](hydroxybutyl)aminoethane, [bis(hydroxypropyl)](hydroxybutyl)aminoethane, (hydroxyethyl)(hydroxymethyl)-(hydroxypropyl)aminomethane, and (hydroxybutyl)(hydroxyethyl)(hydroxymethyl)-aminomethane. Tris(hydroxyalkyl)aminomethanes of formula B may also be substituted with alkyl groups and groups such as fluorine, chlorine, bromine, and iodine. A nonlimiting example of a substituted tris(hydroxyalkyl)aminomethane is tris(6-hydroxy-3,3-dimethylhexyl)aminomethane. Tris(hydroxyalkyl)aminomethanes are a type of tris(hydroxyalkyl)aminoalkane.

As employed herein, "bis(hydroxyalkyl)aminoalkane" refers to an alkane in which one H atom is replaced with an $NH_2$ group and in which two H atoms are replaced by hydroxyalkyl groups. The hydroxyalkyl groups need not replace H atoms attached to the same carbon atom of the alkane, however, in some embodiments, two H atoms bonded to the same carbon atom of an alkane are replaced by hydroxyalkyl groups. The $NH_2$ group need not replace a H atom bonded to a carbon atom bearing one of the hydroxyalkyl groups. Further the alkyl group of the hydroxyalkyl groups need not be the same for each of the two hydroxyalkyl groups. Examples of bis(hydroxyalkyl)aminoalkanes include compounds of formula C

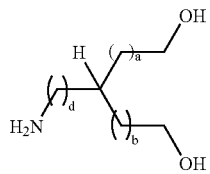

C where, with respect to compounds of structure C, a, b, and d are independently selected from 0, 1, 2, 3, 4, 5, 6, 7, or 8. Examples of compounds of formula C include, but are not limited to, bis(hydroxymethyl)aminomethane, 2,2-bis(hydroxymethyl)-1-aminoethane, 3,3-bis(hydroxyethyl)-1-aminopropane, 3-(hydroxyethyl)-3-(hydroxymethyl)-1-aminopropane, and 3,3-bis(hydroxymethyl)-1aminopropane. Further examples of bis(hydroxyalkyl)aminoalkanes include, but are not limited to, 1-amino-6-hydroxy-4-(hydroxymethyl)heptane, and 1-amino-1,1-bis(hydroxymethyl)pentane.

As employed herein, "bis(hydroxyaklyl)aminomethane" refers to a compound of formula D

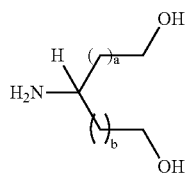

D where, with respect to compounds of formula D, a is selected from 0, 1, 2, 3, 4, 5, 6, 7, or 8 and b is selected from 0, 1, 2, 3, 4, 5, 6, 7, or 8. In some embodiments, a and b have the same value whereas in other embodiments a and b have different values. In some embodiments, a and b are independently selected from 0, 1, 2, or 3. Examples of unsubstituted bis(hydroxyalkyl)aminomethanes include, but are not limited to, bis(hydroxymethyl)aminomethane, bis(hydroxyethyl)aminomethane, bis(hydroxypropyl)-aminomethane, bis(hydroxybutyl)aminomethane (hydroxyethyl)(hydroxymethyl)aminoethane, (hydroxymethyl)(hydroxypropyl)aminoethane, (hydroxybutyl)(hydroxymethyl)aminoethane, (hydroxyethyl)(hydroxypropyl)aminoethane, (hydroxybutyl)(hydroxyethyl)aminoethane, and (hydroxybutyl)(hydroxypropyl)aminoethane. Bis(hydroxyalkyl)aminomethanes of formula D may also be substituted with alkyl groups and groups such as fluorine, chlorine, bromine, and iodine. A nonlimiting example of a substituted bis(hydroxyalkyl)aminomethane is bis(6-hydroxy-3,3dimethyl)aminomethane. Bis(hydroxyalkyl)aminomethanes are a class of bis(hydroxyalkyl)aminoalkanes.

The term "protected" with respect to hydroxyl groups, amine groups, guanidine groups, amidine groups, ureido groups, thioureido groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. A specific example of a protecting group for amines is benzyloxycarbonyl (Cbz) group. Examples of protected sulfhydryl groups include, but are not limited to, thioethers such as S-benzyl thioether, and S-4-picolyl thioether; substituted S-methyl derivatives such as hemithio, dithio and aminothio acetals; and others. Examples of protected guanidine groups include those protected with the t-butoxycarbonyl (Boc) group.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonium. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid. The pharmaceutical formulations of the present invention may include pharmaceutically acceptable salts of a pharmaceutical agent or a biologically active molecule or a pharmaceutically acceptable salt of a transport molecule.

As employed herein "guanidine group" refers to a group of formula —$NR^1$—$C(=NR^2)$—$NR^3R^4$ where $R^1$ through $R^4$ are independently selected from H, alkyl groups, or protecting groups. In many embodiments, $R^1$, $R^2$, $R^3$, and $R^4$ are all H.

As employed herein "protonated guanidine group" refers to a guanidine group as defined above which is the product of an acid-base reaction with any acid that protonates the guanidine group. Examples of suitable acids include, but are not limited to, HCl, HBr, HI. HF, and trifluoroacetic acid.

As employed herein "protected guanidine group" refers to a guanidine group as defined above in which the guanidine group is protected with any of several protecting groups. In some embodiments, $R^1$ is H, $R^2$ is a protecting group, one of $R^3$ or $R^4$ is H, and the other of $R^3$ or $R^4$ is a protecting group. An example of such a "protected guanidine group" includes, but is not limited to —NH—C(=NBoc)—NHBoc.

As employed herein "guanidinylating" refers to any reaction wherein a guanidine group is formed.

As employed herein "amidine group" refers to a group of formula —$C(=NR^2)$—$NR^3R^4$ where, with respect to this formula, $R^2$ through $R^4$ are independently selected from H, alkyl groups, and protecting groups. In many embodiments, $R^2$, $R^3$, and $R^4$ are all H.

As employed herein "protonated amidine group" refers to a amidine group as defined above which is the product of an acid-base reaction with any acid that protonates the amidine group. Examples of suitable acids include, but are not limited to HCl, HBr, HI. HF, and trifluoroacetic acid.

As employed herein "protected amidine group" refers to a amidine group as defined above in which the amidine group is protected with any of several protecting groups. In some embodiments, $R^2$ is a protecting group, one of $R^3$ or $R^4$ is H, and the other of $R^3$ or $R^4$ is a protecting group. An example of such a "protected amidine group" includes, but is not limited to —C(=NBoc)—NHBoc.

As employed herein "amidinylating" refers to any chemical reaction in which an amidine group is formed.

As employed herein "ureido group" refers to a group of formula —$NR^1$—$C(=O)$—$NR^3R^4$ where $R^1$, $R^3$, and $R^4$ are independently selected from H, alkyl groups, and protecting groups. In many embodiments, $R^1$, $R^3$, and $R^4$ are all H.

As employed herein "protonated ureido group" refers to a ureido group as defined above which is the product of an acid-base reaction with any acid that protonates the ureido group. Examples of suitable acids include, but are not limited to HCl, HBr, HI. HF, and trifluoroacetic acid.

As employed herein "protected ureido group" refers to a ureido group as defined above in which the ureido group is protected with any of several protecting groups. In some embodiments, one of $R^3$ or $R^4$ is H, and the other of $R^3$ or $R^4$ is a protecting group. An example of such a "protected thioureido group" includes, but is not limited to —NH—C(=S)—NHBoc.

As employed herein "ureidolating" refers to any chemical reaction in which a thioureido group is formed.

As employed herein "thioureido group" refers to a group of formula —$NR^1C(=S)$—$NR^3R^4$ where, with respect to this formula $R^1$, $R^3$, and $R^4$ are independently selected from H, alkyl groups, and protecting groups. In many embodiments $R^1$, $R^3$, and $R^4$ are all H.

As employed herein "protonated thioureido group" refers to a thioureido group as defined above which is the product of an acid-base reaction with any acid that protonates the thioureido group. Examples of suitable acids include, but are not limited to HCl, HBr, HI. HF, and trifluoroacetic acid.

As employed herein "protected thioureido group" refers to a thioureido group as defined above in which the thioureido group is protected with any of several protecting groups. In some embodiments, one of $R^3$ or $R^4$ is H, and the other of $R^3$ or $R^4$ is a protecting group. An example of such a "protected thioureido group" includes, but is not limited to —NH—C(=S)—NHBoc.

As employed herein "thioureidolating" refers to any chemical reaction in which a thioureido group is formed.

Generally, the invention provides dendrimers, transport molecules, methods for making dendrimers and transport molecules, pharmaceutical formulations that include the dendrimers and transport molecules, methods of increasing the effectiveness of a drug, methods of increasing transport of a biologically active compound across a biological membrane, methods for measuring the uptake of a dendrimer in a cell, methods for administering pharmaceutical agents to a subject, methods for increasing the bioavailability of a drug, kits that include dendrimers and/or transport molecules, and libraries of dendrimers and transport molecules.

In one aspect, the invention provides a dendrimer that includes at least two branch groups and two or more guanidine groups, salts or protonated forms thereof or protected forms thereof; two or more amidine groups, salts or protonated forms thereof or protected forms thereof; or two or more ureido groups, salts or protonated forms thereof, or protected forms thereof; or two or more thioureido groups, salts or protonated forms thereof or protected forms thereof. In such dendrimers, at least two of the two or more guanidine groups, salts or protonated forms thereof, or protected forms thereof; amidine groups, salts or protonated forms thereof or protected forms thereof; ureido groups, salts or protonated forms thereof, or protected forms thereof; or thioureido groups, salts or protonated forms thereof, or protected forms thereof are borne at the end of the at least two branch groups. By way of example, such dendrimers, include, but are not limited to compounds 3, 4, 5, 10, 11, 12, 13, 14, 15, 16, 17, 21, 22, 24, 25, 26, 30, 31, 32, 33, 34, 42, 43, 44, 45, 46, 47, 48, 49, 50, 56, 57, 58, 59, 60, 61, 62, 63, 64, 67, 68, 69, and 71 shown in FIGS. 1, 3A-3D, 5, 6, 7, 8, 9, 10, 11, 13A, 13B, 14, 27A, 27B, 27C, 28B, 28C, 29, 30, 31, 32, 33, 34, 35, and 36, and the transporters shown in FIG. 15. In some such embodiments, the dendrimer includes at least three branch groups and three or more guanidine groups, salts thereof, or protected forms thereof; amidine groups, salts thereof, or protected forms thereof; ureido groups, salts thereof, or protected forms thereof; or thioureido groups, salts thereof, or protected forms thereof. In such dendrimers, at least three of the three or more guanidine groups, salts thereof, or protected forms thereof; amidine groups, salts thereof, or protected forms thereof; ureido groups, salts thereof, or protected forms thereof; or thioureido groups, salts thereof, or protected forms thereof are borne at the end of the at least three branch groups. By way of example, dendrimers with at least three such branch groups and three or more guanidine groups, salts thereof, or protected forms thereof; amidine groups, salts thereof, or protected forms thereof; ureido groups, salts thereof, or protected forms thereof; or thioureido groups, salts thereof, or protected forms thereof include, but are not limited to, compounds 3, 4, 5, 10, 11, 12, 13, 14, 15, 16, 17, 21, 22, 24, 25, 26, 30, 31, 32, 33, 34, 42, 43, 44, 45, 46, 47, 48, 49, 50, 56, 57, 58, 59, 60, 61, 62, 63, 64, 67, 68, 69, and 71 shown in FIGS. 1, 3A-3D, 5, 6, 7, 8, 9, 10, 11, 13A, 13B, 14, 27A, 27B, 27C, 28B, 28C, 29, 30, 31, 32, 33, 34, 35, and 36, and the Transporters shown in FIG. 15.

In some embodiments, the dendrimer includes at least one tetravalent atom bonded to at least two branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. By way of example, such dendrimers include, but are not limited to, dendrimers with a tetravalent carbon atom that is bonded to two branch groups such as compounds 13, 30, 31, 32, 33, and 34 shown in FIGS. 3D, 10, and 11. For example compounds 13, 30, 31, 32, 33, and 34 each include a tetravalent carbon atom which is the "methane" of a bis(hydroxymethyl) aminomethane residue in the molecule, a structural unit that is quite useful for constructing dendrimers of the invention that include an even number of guanidine units, amidine units, ureido or thioureido units. For this reason, many of the dendrimers of the present invention include a group of formula IV or a similar structural unit.

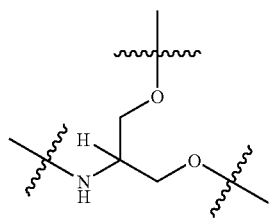

IV

Figure 13A:
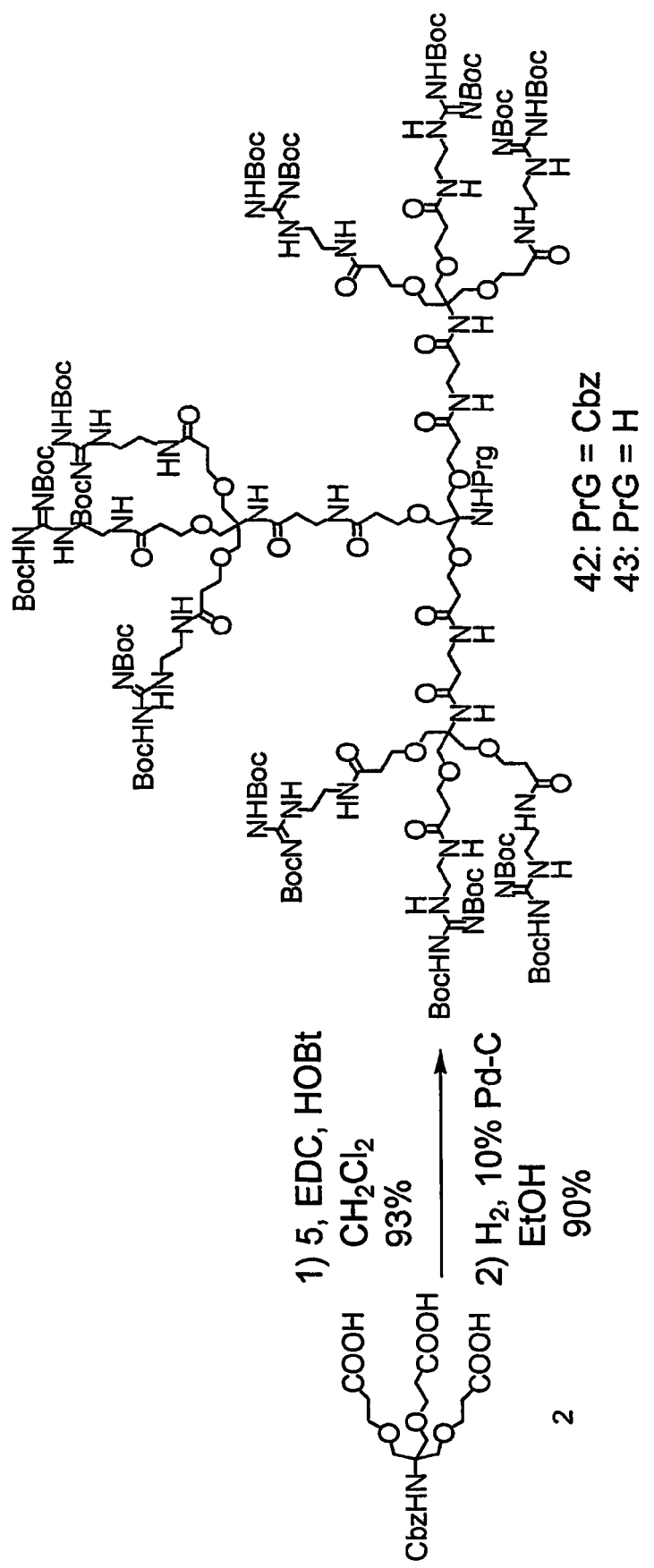
FIGS. 13A-13B depict a reaction scheme for the synthesis of dendritic oligo-guanidines that include nine Boc-protected guanidine groups in identical chemical environments and dendrimers that include a maleimide reactive group for attachment to a biologically active molecule.
Figure 14:
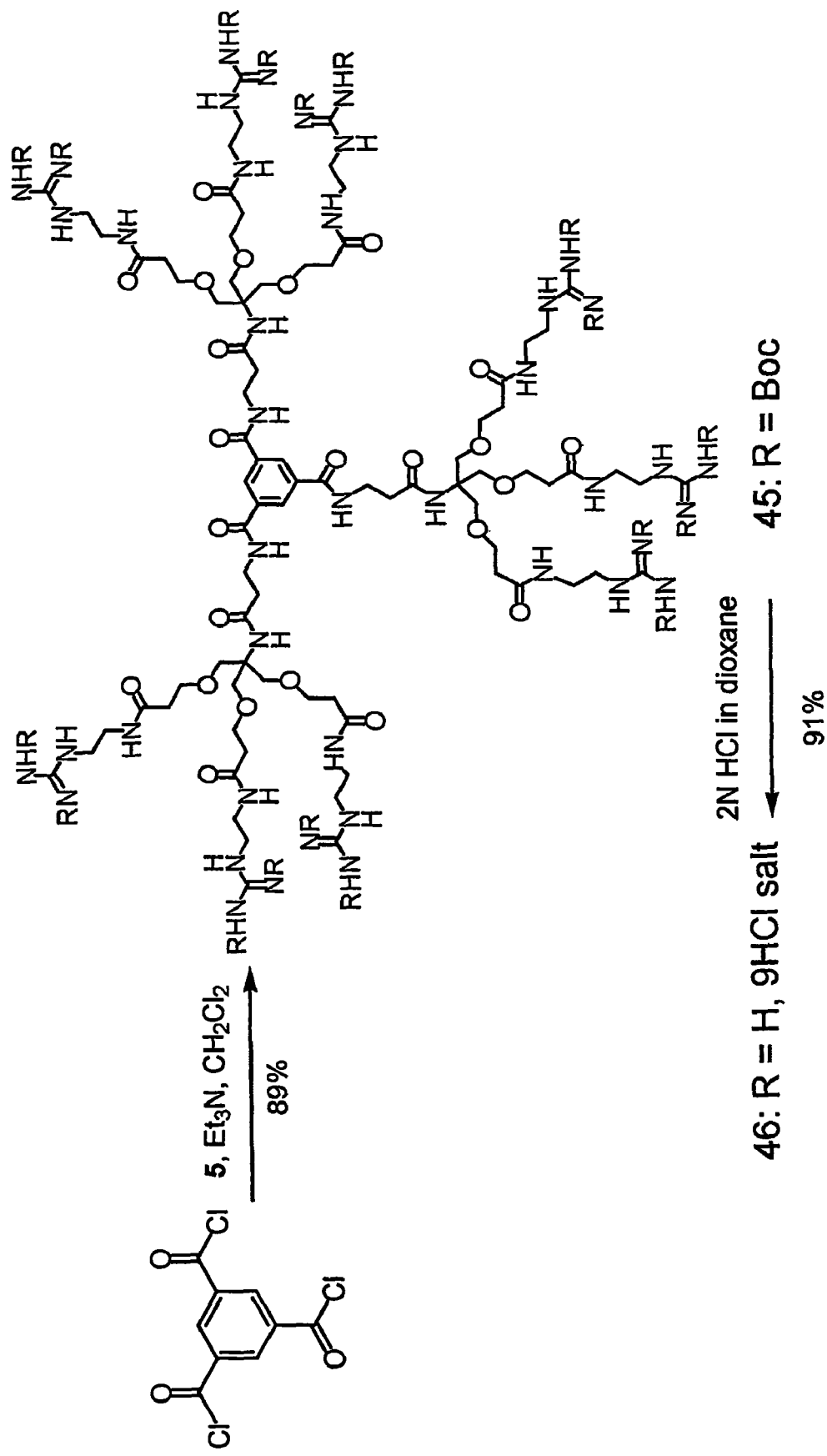
FIG. 14 depicts a reaction scheme for the synthesis of dendritic oligo-guanidines that include nine guanidine groups in identical chemical environments.
Figure 15:
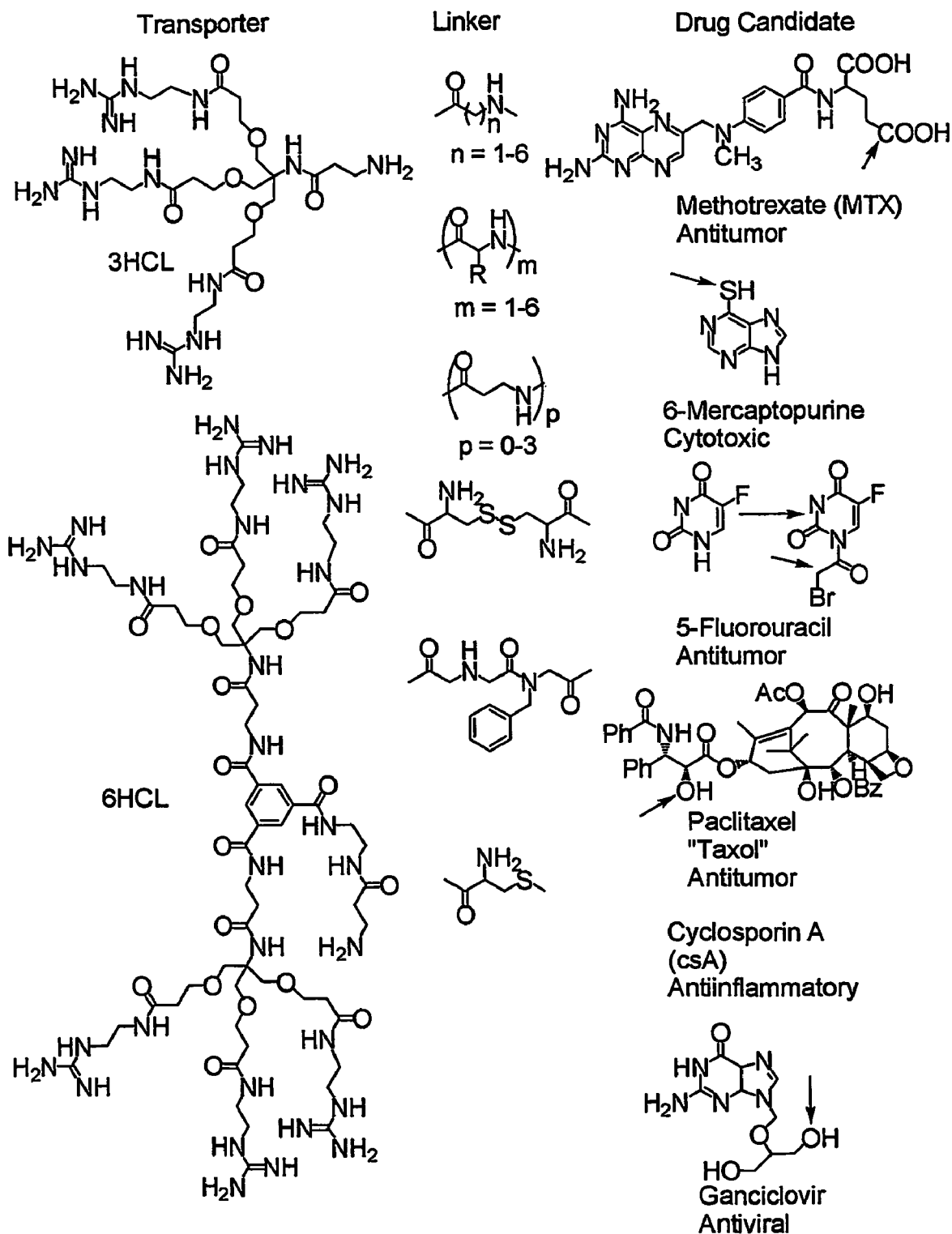
FIG. 15 depicts nonlimiting examples of various dendritic oligo-guanidine transporters, nonlimiting examples of various drugs; and nonlimiting examples of various linkers that may be used to link dendritic oligo-guanidine transporters to drugs. The arrows pointing at positions on the drug candidate structures indicate potential points of attachment where a drug may be linked to a dendritic oligo-guanidine.
Figure 16A:
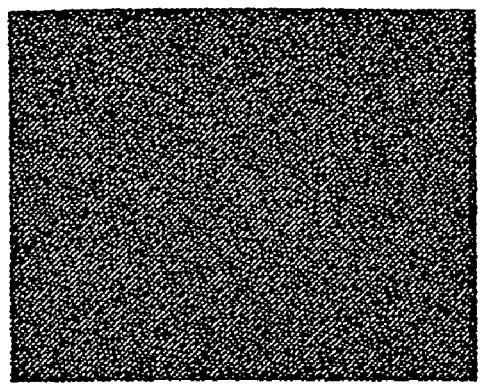
Figure 16B:
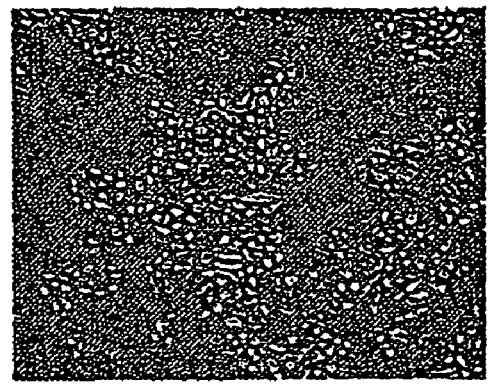
FIG. 16B in the first pair of images) provides an image of the cells after the uptake of the fluorescein-labeled compound.
Figure 16C:
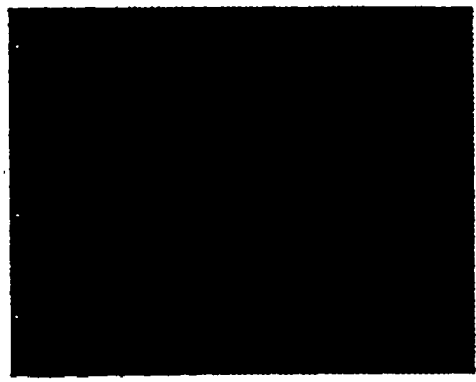
FIGS. 16C and 16D show cellular uptake of compound 10 at a concentration of 10 μM
Figure 16D:
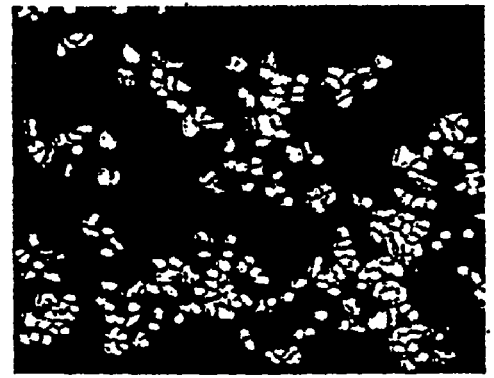
Figure 16E:
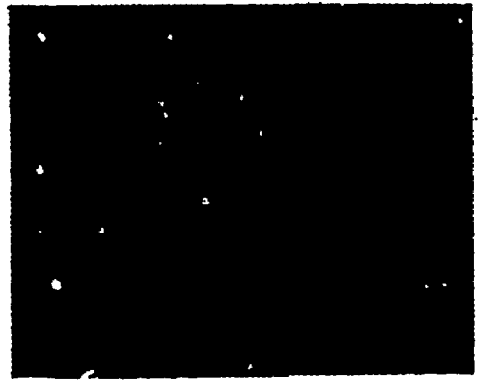
FIGS. 16E and 16F show cellular uptake of compound 11 at a concentration of 10 μM.
Figure 16F:
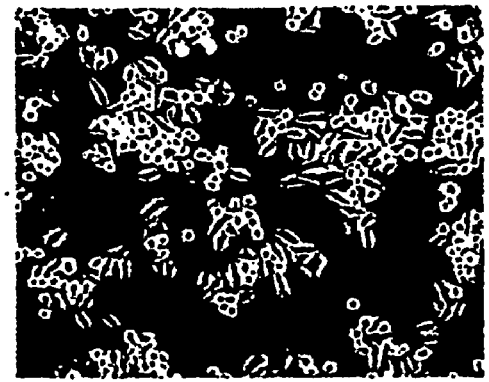
Figure 16G:
FIGS. 16G and 16H show cellular uptake of compound 12 at a concentration of 10 μM.
Figure 16H:
Figure 16I:
FIGS. 16I and 16J show cellular uptake of compound 13 at a concentration of 10 μM.
Figure 16J:
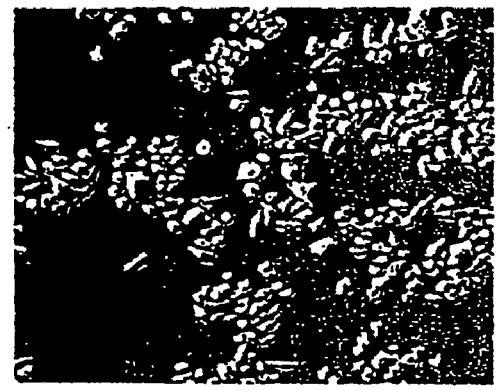
Figure 16K:
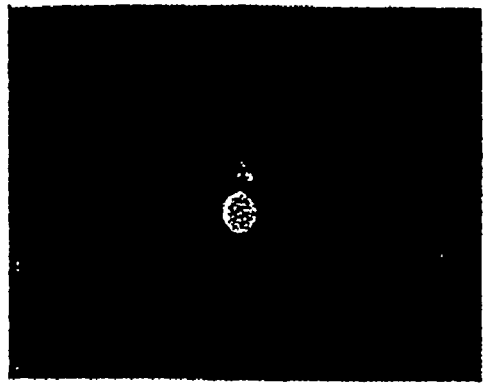
Figure 16L:
Figure 17B:
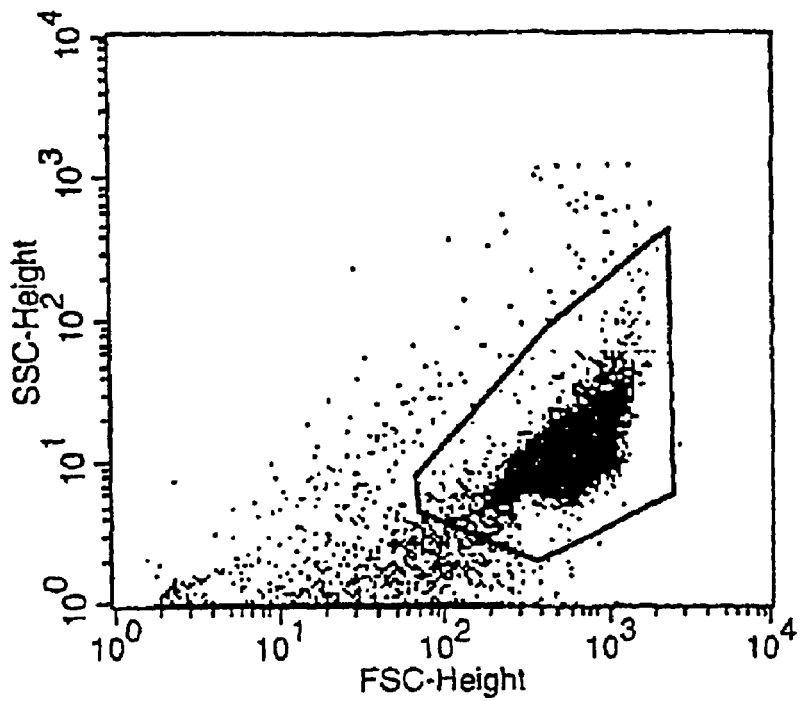
Figure 17C:
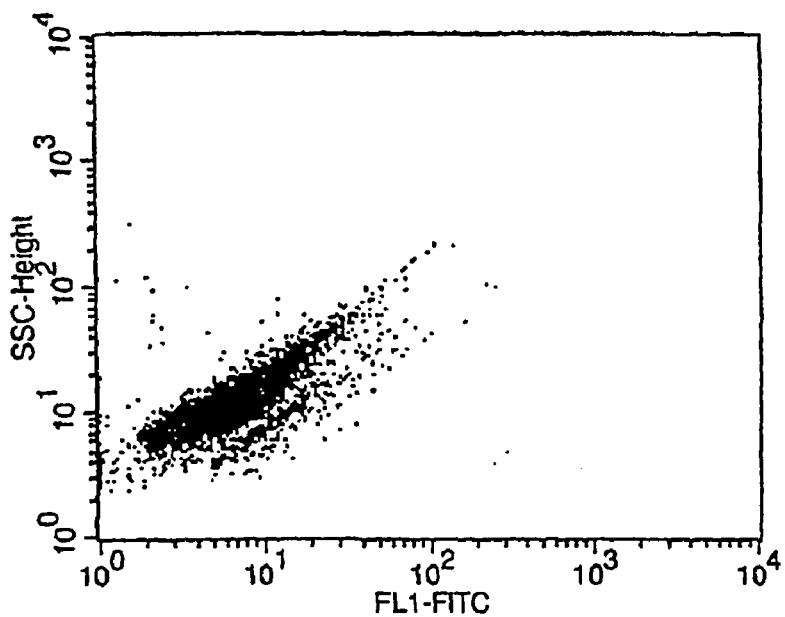
Figure 18A:
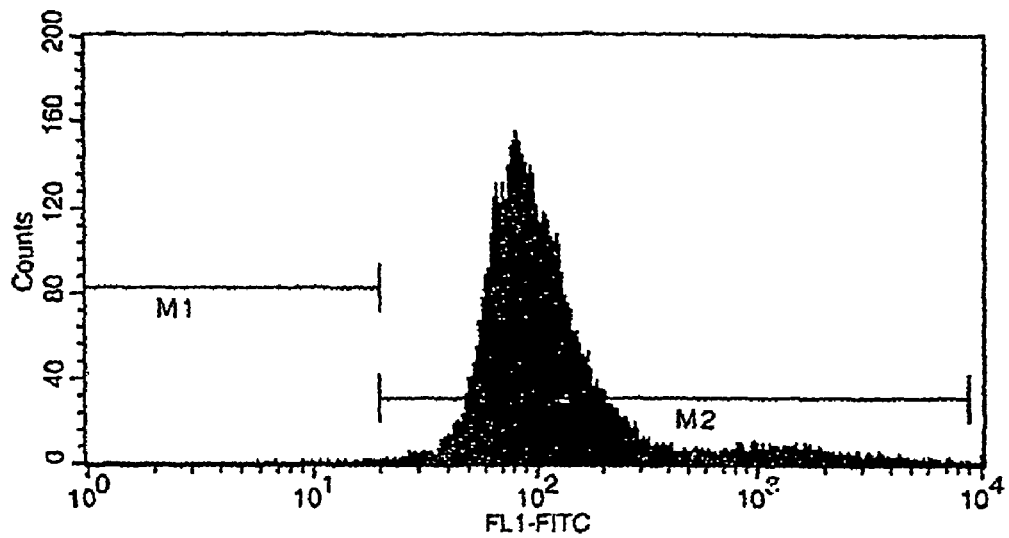
FIGS. 18A-18C depict graphs relating to the cellular uptake of fluorescein-labeled compound (12) at a concentration of 25 μM by HeLa S3 human epithelioid cervical carcinoma cells.
Figure 18B:
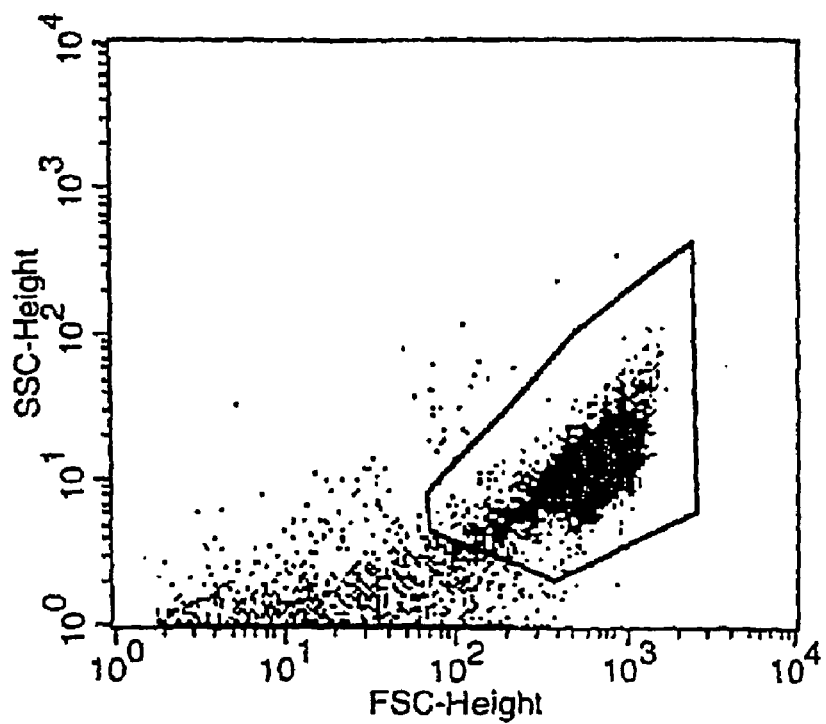
Figure 18C:
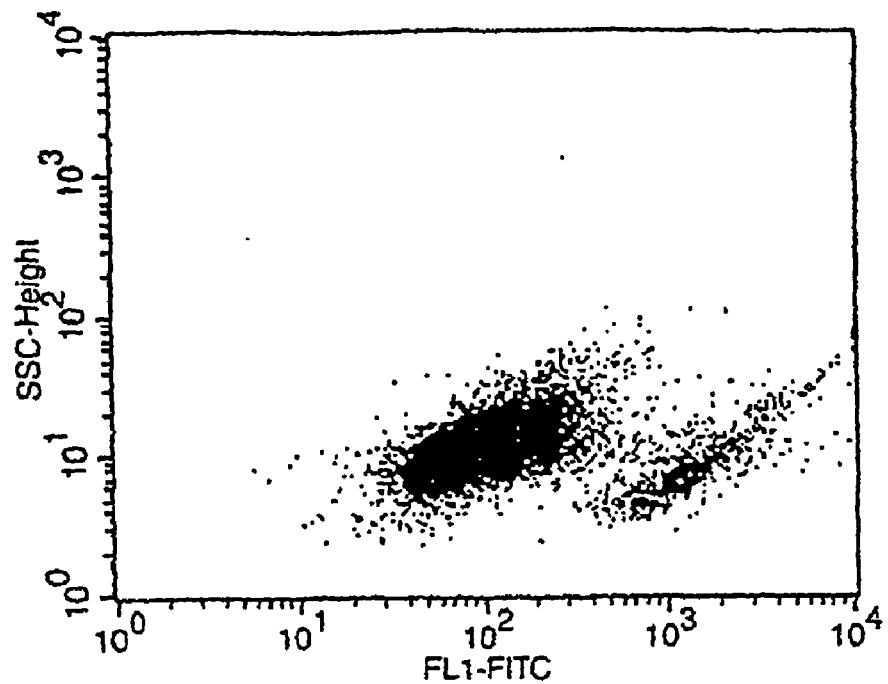
Figure 19A:
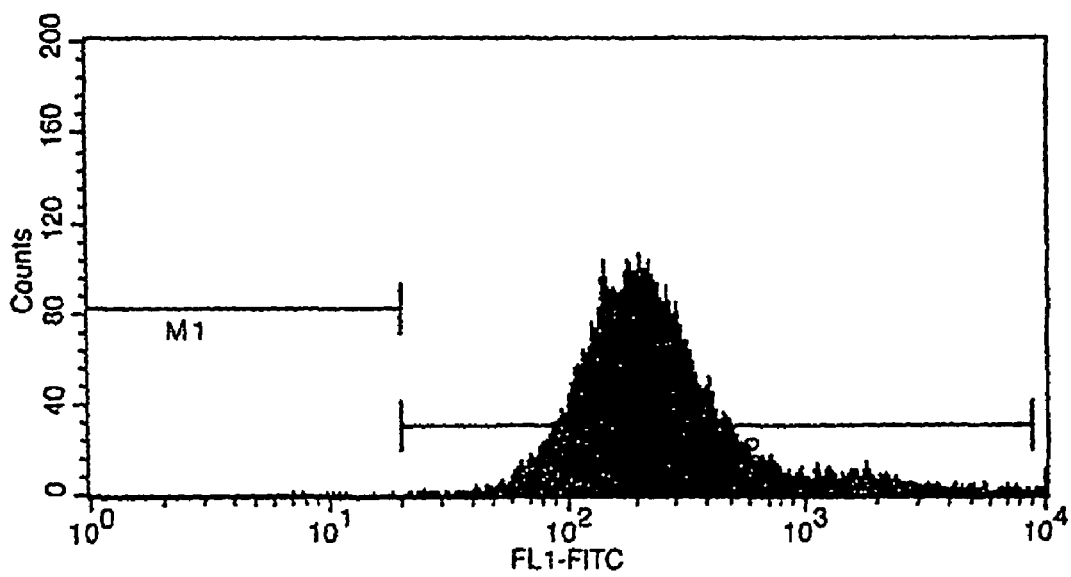
FIGS. 19A-19C depict graphs relating to the cellular uptake of fluorescein-labeled compound (12) at a concentration of 50 μM by HeLa S3 human epithelioid cervical carcinoma cells.
Figure 19B:
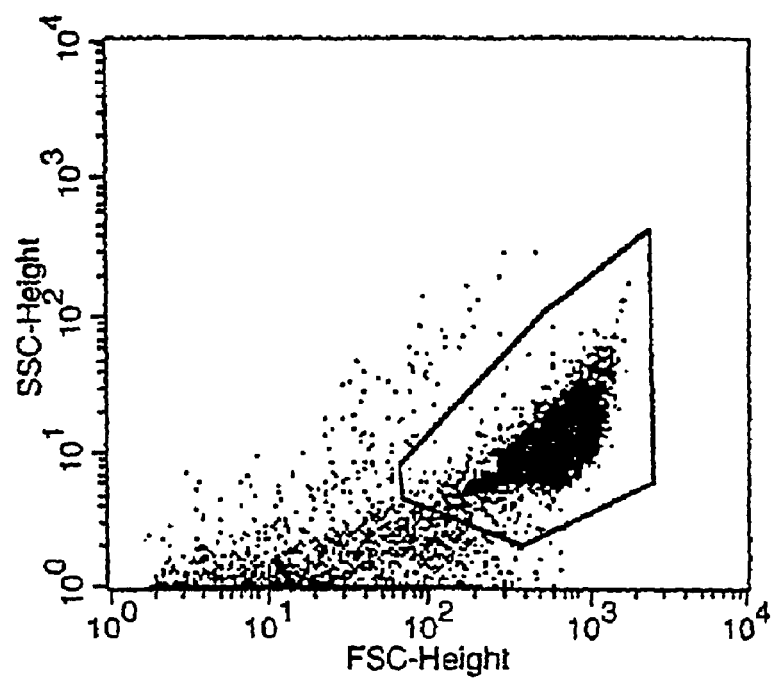
Figure 19C:
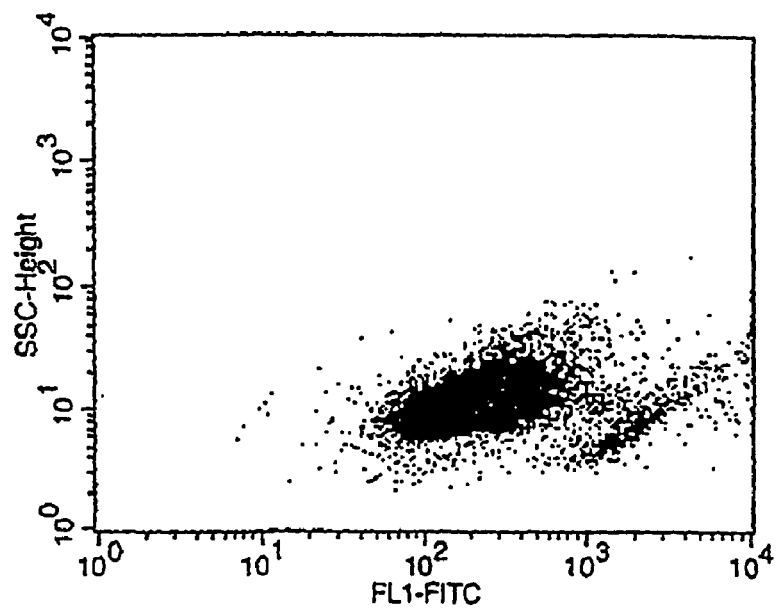

By way of example, dendrimers that include at least one tetravalent atom bonded to at least three branch groups include compounds 3, 4, 5, 10, 11, 12, 13, 14, 15, 16, 17, 21, 22, 24, 25, 26, 30, 31, 32, 33, 34, 42, 43, 44, 45, 46, 47, 48, 49, 50, 56, 57, 58, 59, 60, 61, 62, 63, 64, 67, 68, 69; and 71 shown in FIGS. 1, 3A-3D, 5, 6, 7, 8, 9, 10, 11, 13A, 13A, 14, and 27-36, and the Transporters shown in FIG. 15. For example, compounds 3, 4, and 5 (see FIG. 1) each include a tetravalent carbon atom which is the "methane" of a tris(hydroxymethyl)-aminomethane residue in the molecule, a structural unit that is quite useful in constructing dendrimers of the present invention. For this reason, many of the dendrimers of the present invention include a group of formula I or a similar structural unit.

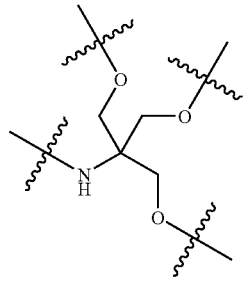

I

Notably, some dendrimers include at least one tetravalent atom that is bonded to at least two branch groups that bear terminal guanidine groups, terminal protonated guanidine groups, or terminal protected guanidine groups and at least one tetravalent atom that is bonded to at least three branch groups that bear terminal guanidine groups, terminal protonated guanidine groups, or terminal protected guanidine groups. Examples of such dendrimers, include, but are not limited to, compounds 13, 30, 31, 32, 33, and 34. In some embodiments, the dendrimer includes one, two, three, or four groups of formula I. By way of example, dendrimers with one group of formula I include, but are not limited to, 3, 4, 5, 10, 17, 47, 48, 56, 57, 58, 61, 62, and the top Transporter shown in FIG. 15. By way of example, dendrimers with two groups of formula I include, but are not limited to, compounds 11, 14, 15, 16, 21, 22, 30, 31, 49, 59, 63, 67, and 68, and the bottom Transporter shown in FIG. 15. By way of example, dendrimers with three groups of formula I include, but are not limited to, compounds 45, and 46. By way of example, dendrimers with four groups of formula I include, but are not limited to, compound 12, 13, 24, 25, 26, 32, 33, 34, 42, 43, 44, 50, 60, 64 69, and 71.

As will be apparent from the above discussion, in some embodiments the invention provides dendrimers that include at least one tetravalent atom that is bonded to at least three branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. As will also be apparent from the above discussion, in other embodiments, the invention provides dendrimers that include a first tetravalent atom and a second tetravalent atom, and the first tetravalent atom and the second tetravalent atom are each bonded to at least three branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. As will yet further be apparent from the above discussion, in still other embodiments, the invention provides dendrimers that include a first tetravalent atom, a second tetravalent atom, and a third tetravalent atom, and the first tetravalent atom, the second tetravalent atom, and the third tetravalent atom are each bonded to at least three branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. As will also be apparent from the above discussion, in yet other embodiments, the invention provides dendrimers that include a first tetravalent atom, a second tetravalent atom, a third tetravalent atom, and a fourth tetravalent atom, and the first tetravalent atom, the second tetravalent atom, the third tetravalent atom, and the fourth tetravalent atom are each bonded to at least three branch groups that bear terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups.

As noted above, dendrimers of the invention may include a group of formula I. Such dendrimers may include groups of formula II or a protonated or protected form of the group of formula II. The group of formula I has been found to be particularly useful as a structural group and scaffold for preparing dendrimers of the present invention. Notably, the group of formula II is itself a dendrimer.

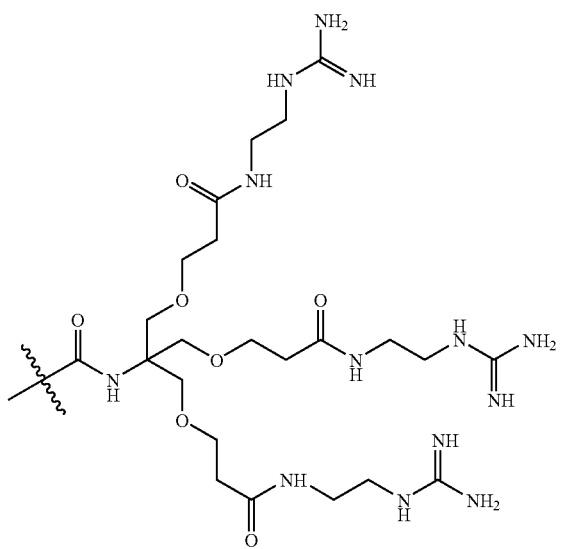

II

In some embodiments, dendrimers include one, two, three, or four groups of formula II. By way of example, dendrimers that include one group of formula II or protonated or protected forms thereof include, but are not limited to, compounds 3, 4, 5, 10, 17, and the top Transporter of FIG. 15. By way of example, dendrimers that include two groups of formula II or protonated or protected forms thereof include, but are not limited to, compounds 11, 14, 15, 16, 21, 22, 30, 31, 67, and 68 and the bottom Transporter of FIG. 15. By way of example, dendrimers that include three groups of formula II or protonated or protected forms thereof include, but are not limited to, compounds 12, 24, 25, 26, 42, 43, 44, 45, 46, 69, and 71. By way of example, dendrimers that include four groups of formula II or protonated or protected forms thereof include, but are not limited to, compounds 13, 32, 33, and 34.

In other embodiments, the invention provides dendrimers that include at least one group having a structure analogous to that of formula II wherein the guanidine groups are replaced with amidine, ureido, or thioureido groups. Such dendrimers may also include protonated or protected forms of such groups. In some embodiments, the dendrimer includes one, two, three, or four groups having a structure analogous to that of formula II wherein the guanidine groups are replaced with amidine, ureido, or thioureido groups. By way of example, dendrimers that include one group analogous to that of formula II wherein the guanidine groups have been replaced with amidine, ureido, or thioureido groups, or protonated or protected forms of such groups, include but are not limited to, compounds 48, 58, and 62. By way of example, dendrimers that include two group analogous to that of formula II wherein the guanidine groups have been replaced with amidine, ureido, or thioureido groups, or protonated or protected forms of such groups, include but are not limited to, compounds 49, 59, and 63. By way of example, dendrimers that include three group analogous to that of formula II wherein the guanidine groups have been replaced with amidine, ureido, or thioureido groups, or protonated or protected forms of such groups, include but are not limited to, compounds 50, 60, and 64.

Another structural unit that has been found useful in preparing dendrimers includes a group of formula III. Therefore, in some embodiments, the invention provides dendrimers that include at least one group having the formula III.

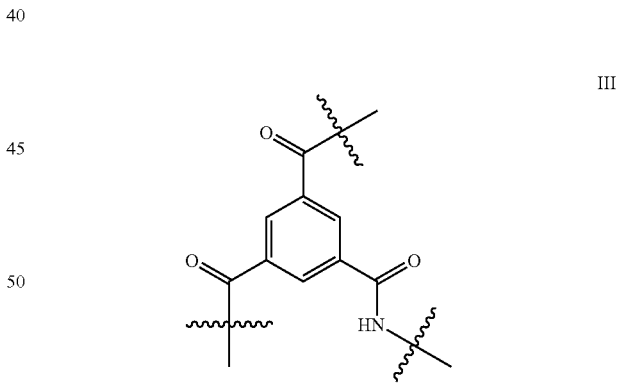

III

By way of example, dendrimers that include at least one group of formula III include, but are not limited to, compounds 11, 14, 15, 16, 21, 22, 45, 46, 49, 59, 63, 67, 68 and the bottom Transporter of FIG. 15.

Another structural unit that has been found useful in preparing dendrimers includes a group of formula V or a protonated or protected form of the group of formula V. Therefore, in some embodiments, the invention provides dendrimers that include at least one group having the formula V or a protonated or protected form of the group of formula V.

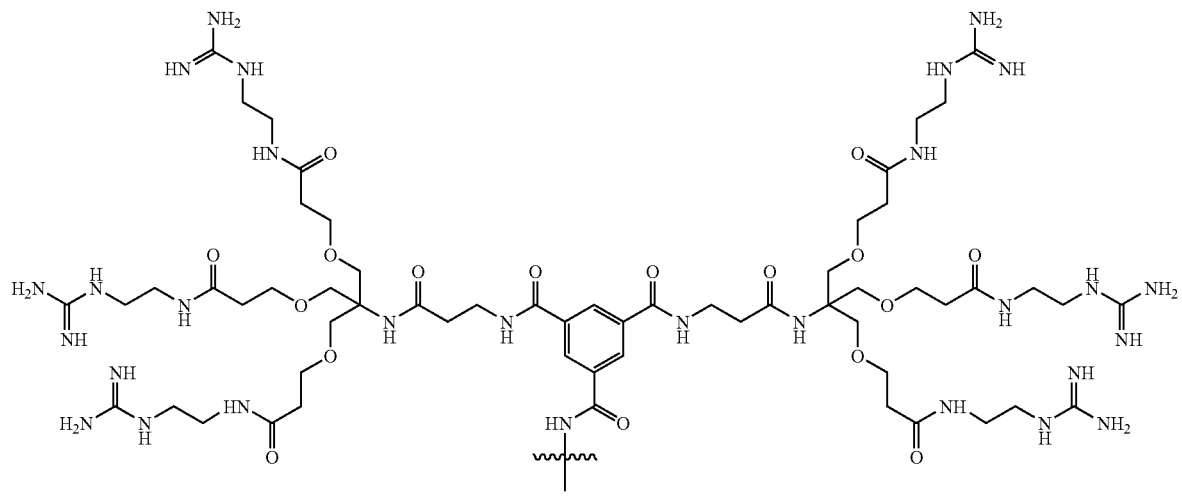

V

25

By way of example, dendrimers that include at least one group of formula V or protonated or protected forms thereof include, but are not limited to, compounds 11, 14, 15, 16, 21, 22, 45, 46, 67, 68 and the bottom Transporter of FIG. 15.

In other embodiments, the invention provides dendrimers that include at least one group having a structure analogous to that of formula V wherein the guanidine groups are replaced with amidine, ureido, or thioureido groups. Such dendrimers may also include protonated or protected forms of such groups. By way of example, dendrimers that include one group analogous to that of formula V wherein the guanidine groups have been replaced with amidine, ureido, or thioureido groups, or protonated or protected forms of such groups, include but are not limited to, compounds 49, 59, and 63.

Another structural unit that has been found useful in preparing dendrimers includes a group of formula VI or a protonated or protected form of the group of formula VI. Therefore, in some embodiments, the invention provides dendrimers that include at least one group having the formula VI or a protonated or protected form of the group of formula VI.

VI
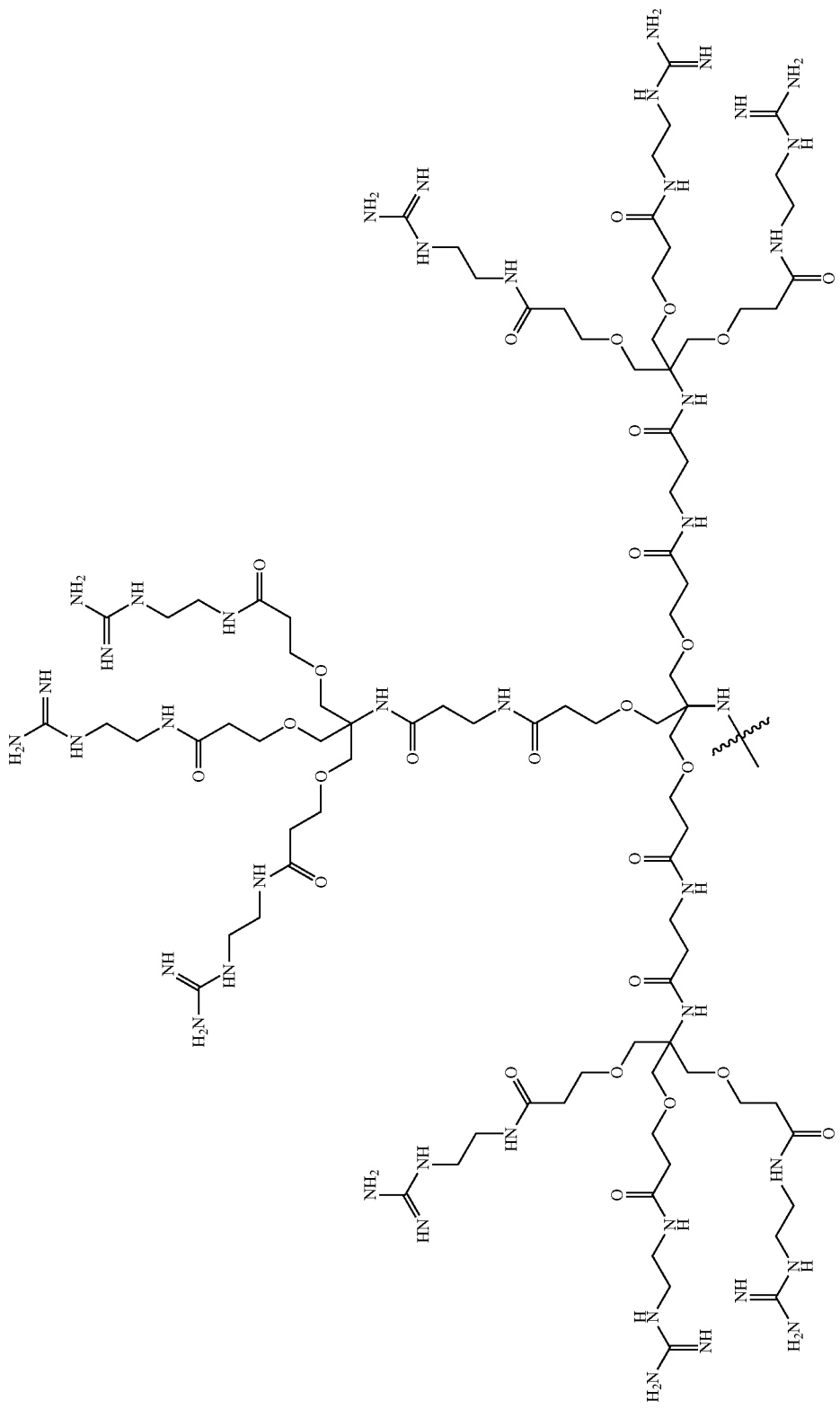

By way of example, dendrimers that include at least one group of formula VI or protonated or protected forms thereof include, but are not limited to, compounds 12, 24, 25, 26, 42, 43, 44, 69, and 71.

In other embodiments, the invention provides dendrimers that include at least one group having a structure analogous to that of formula VI wherein the guanidine groups are replaced with amidine, ureido, or thioureido groups. Such dendrimers may also include protonated or protected forms of such groups. By way of example, dendrimers that include one group analogous to that of formula VI wherein the guanidine groups have been replaced with amidine, ureido, or thioureido groups, or protonated or protected forms of such groups, include but are not limited to, compounds 50, 60, and 64.

Another structural unit that has been found useful in preparing dendrimers includes a group of formula VII or a protonated or protected form of the group of formula VII. Therefore, in some embodiments, the invention provides dendrimers that include at least one group having the formula VII or a protonated or protected form of the group of formula VII.

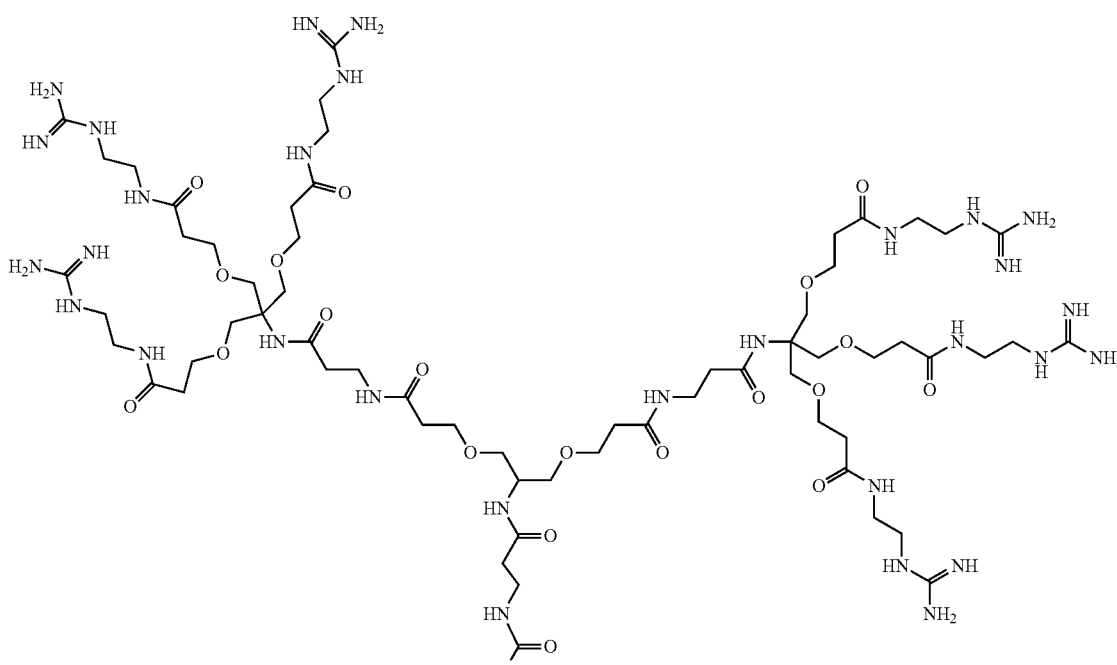

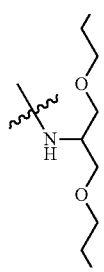

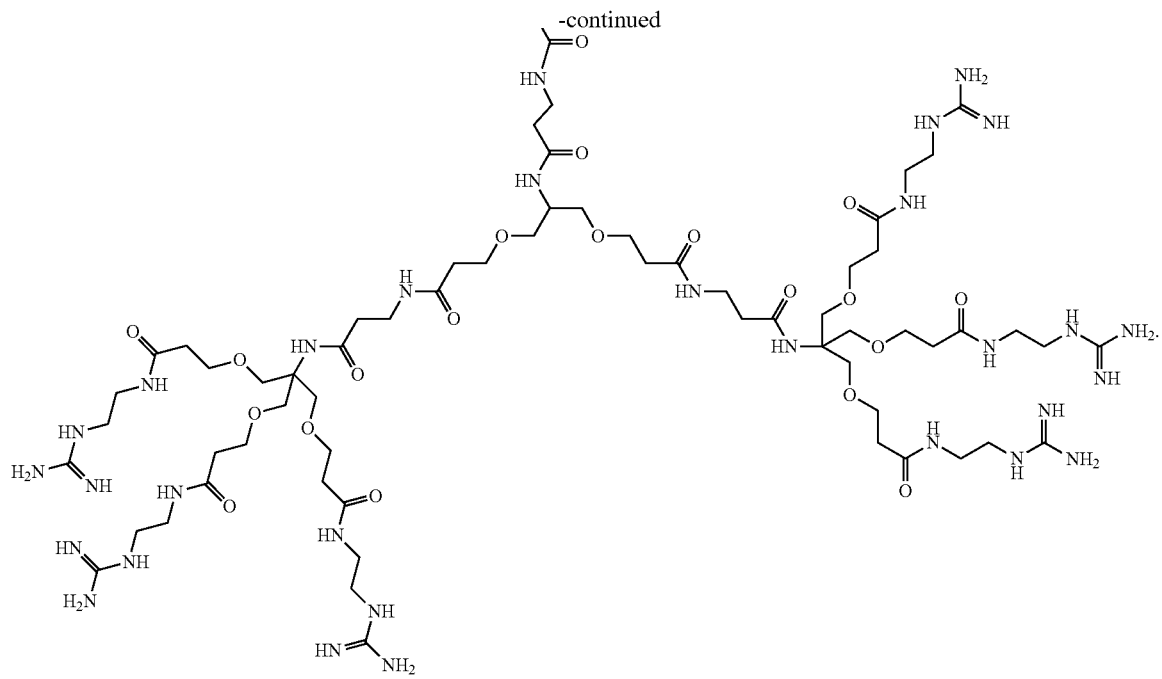

By way of example, dendrimers that include at least one group of formula VII or protonated or protected forms thereof include, but are not limited to, compounds 513, 32, 33, and 34.

In other embodiments, the invention provides dendrimers that include at least one group having a structure analogous to that of formula VII wherein the guanidine groups are replaced with amidine, ureido, or thioureido groups. Such dendrimers may also include protonated or protected forms of such groups.

Another structural unit that has been found useful in preparing dendrimers includes a group of formula VIII or a protonated or protected form of the group of formula VIII. Therefore, in some embodiments, the invention provides dendrimers that include at least one group having the formula VIII or a protonated or protected form of the group of formula VIII.

VIII

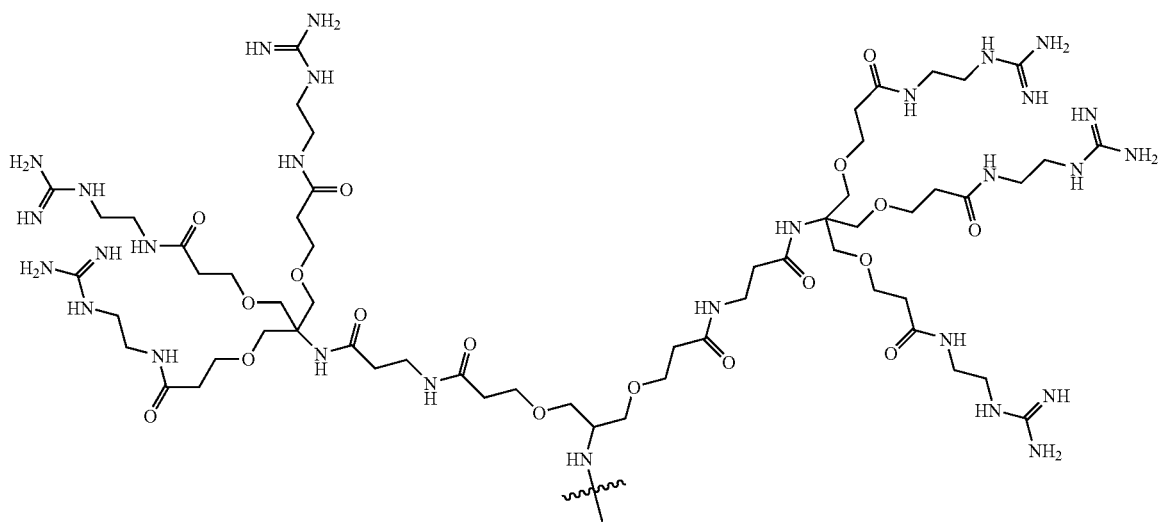

By way of example, dendrimers that include at least one group of formula VIII or protonated or protected forms thereof include, but are not limited to, compounds 13, 30, 31, 32, 33, and 34.

In other embodiments, the invention provides dendrimers that include at least one group having a structure analogous to that of formula VIII wherein the guanidine groups are replaced with amidine, ureido, or thioureido groups. Such dendrimers may also include protonated or protected forms of such groups.

One skilled in the art will recognize that many of the dendrimers of the present invention possess a high degree of symmetry although this is not required or critical to the invention because the dendrimers of the invention may be synthesized from unsymmetrical materials such as unsymmetrical tris(hydroxyalkyl)alkanes and unsymmetrical bis(hydroxyalkyl)alkanes. Formation of dendrimers using a convergent synthesis from symmetrical starting materials such as tris(hydroxymethyl)aminomethane, bis(hydroxymethyl)aminomethane, 2,2,2-tris(hydroxyethyl)-1-aminoethane, 3,3-bis(hydroxyethyl)-1-aminopropane, 1,3,5-trisubstituted benzene compounds, 1,2-disubstituted benzenes, 1,3-disubstituted benzenes, 1,4-disubstituted benzenes, and the like can produce dendrimers with high degrees of symmetry. Convergent synthesis employing symmetrical starting materials also simplifies the synthesis and characterization of such dendrimers and thereby reduces the cost of such dendrimers. In some embodiments, the invention provides dendrimers which possess a degree of symmetry such that each of the guanidine groups, salts thereof, or protected forms thereof; each of the amidine groups, salts thereof or protected forms thereof; each of the ureido groups, salts thereof or protected forms thereof or each of the thioureido groups, salts thereof or protected forms thereof is in an identical chemical environment when each of the guanidine group, salts thereof or protected forms thereof; each of the amidine groups, salts thereof, or protected forms thereof each of the ureido groups, salts thereof, or protected forms thereof or each of the thioureido groups, salts thereof, or protected forms thereof is either neutrally charged or is protonated. Although it is not required or critical to the invention, in some embodiments, the dendrimer possesses $C_{2V}$ symmetry whereas in other embodiments, the dendrimer possesses $C_{3V}$ symmetry. Symmetrical dendrimers may possess symmetry represented by other symmetry groups. By way of nonlimiting example, each of the three guanidine groups, protonated guanidine groups or protected guanidine groups in dendrimers 3, 4, 5, 10, 17, and the top Transporter shown in FIG. 15 are in identical chemical environments. By way of further nonlimiting example, each of the 6 guanidine groups, protonated guanidine groups or protected guanidine groups in dendrimers 11, 14, 15, 16, 21, 22, 30, 31, 67, 68, and the bottom Transporter shown in FIG. 15 are in identical chemical environments. By way of still further nonlimiting example, each of the 9 guanidine groups, protonated guanidine groups, or protected guanidine groups in dendrimers 12, 24, 25, 26, 42, 43, 44, 45, 46, 69, and 71 are in identical chemical environments. By way of still further nonlimiting example, each of the 12 guanidine groups, protonated guanidine groups, or protected guanidine groups in dendrimers 13, 32, 33, and 34 are in identical chemical environments.

One skilled in the art will readily recognize that the methods of the invention include the synthesis of dendrimers that include at least one group of formula IX or a protonated or a protected form of the group of formula IX

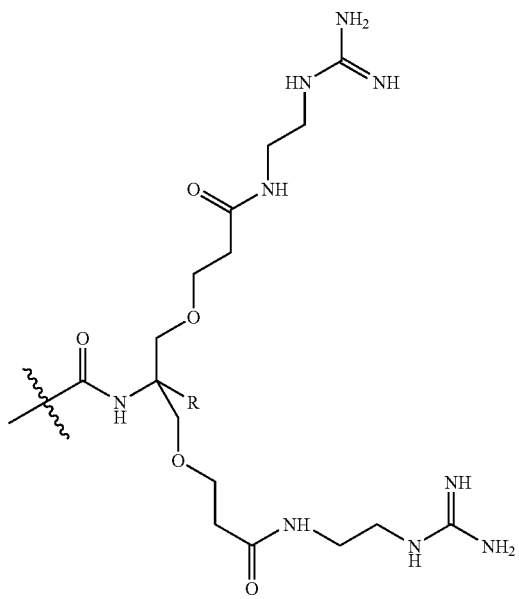

IX where, in groups of formula IX, R is H, a straight chain alkyl group having 1, 2, 3, 4, 5, 6, 7, or 8 carbon atoms, or a symmetrical branched alkyl group. Dendrimers that include groups of formula IX or protonated or protected forms thereof include two guanidines or protected guanidines that are in identical chemical environments and may be used to prepare larger dendrimers that include 4, 6, or more guanidine groups. The synthesis of dendrimers that include a group of formula IX or a protonated or protected form thereof may be readily accomplished using the methods of the present invention. For example, the synthesis of dendrimers 3, 4, and 5 shown in FIG. 1 may be applied to prepare the bis-guanidine analogs by starting with bis(hydroxymethyl)aminomethane in place of tris(hydroxymethyl)aminomethane by simply adjusting the equivalents of the reagents to take into account the difference in the number of branches originating from the tetravalent "methane" carbon atom of the tris(hydroxymethyl)aminomethane and the bis(hydroxymethyl)aminomethane. The dibranched analog of 5 produced in this manner may be used in place of 5 in the reaction schemes shown in FIGS. 6, 7, 9, 10, 13A, and 14.

Figure 5:
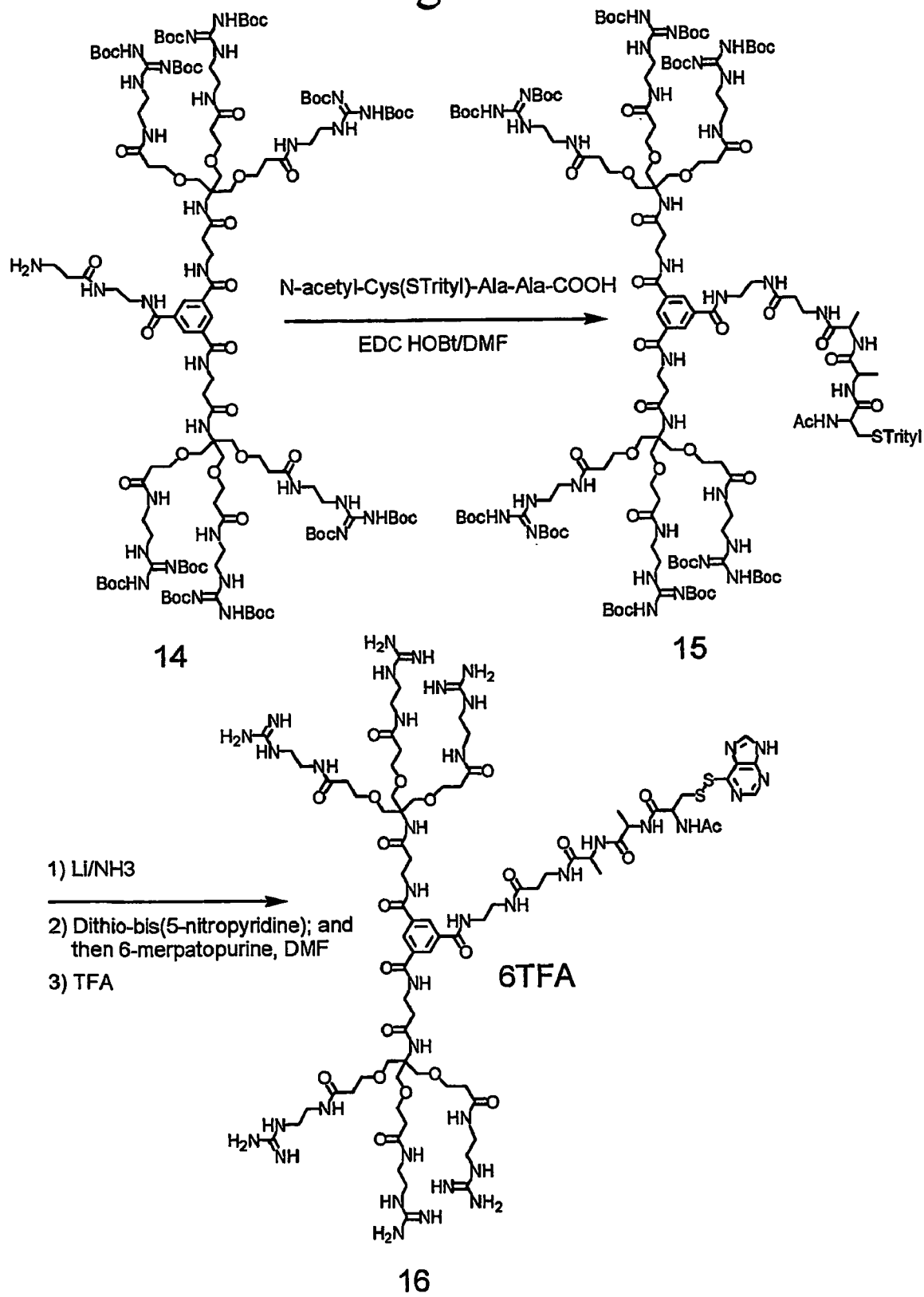
FIG. 5 depicts a reaction scheme for the synthesis of a dendritic oligo-guanidine transport molecule that includes 6-mercaptopurine, a peptide linker moiety, and a dendrimer with six guanidine groups in identical chemical environments.

Inspection of the various reaction schemes shown in the figures and the reaction transformations described in the examples shows that, in many embodiments, the dendrimers of the invention include amide bonds, but do not include any peptide linkages. They may also include ester bonds in some embodiments, and may further include both amide and ester bonds. The flexibility of the synthetic procedures is such that peptide linkages may be incorporated into the dendrimers if desired. For example, as shown in FIG. 5, although dendrimer 14 does not include any peptide bonds, reaction with N-acetyl-Cys(STrityl))-Ala-Ala-COOH produces a dendrimer 15 which includes a linking group that has peptide linkages and a protected sulfhydryl (SH) group that may be deprotected and used to form a disulfide linkage to biologically active molecules that include a sulfhydryl group such as, but not limited to, 6-mercaptopurine.

Dendrimers of the invention may include one or more detection molecules that are bonded to the dendrimer. Such dendrimers may be prepared using the same procedures used to produce transport molecules of the invention. For example, dendrimers with detection molecules include compounds 10, 11, 12, 13, 17, 22, 26, and 34 in which a detection molecule, fluorescein, is bonded to the dendrimer through a thiourea group. Examples of other dendrimers that include detection molecules include those formed with Green Fluorescent Protein (GFP). Such detection molecules may include molecules with isotopes for use in NMR or MRI analysis. Other suitable detection molecules include those with groups that fluoresce such as, but not limited to fluorescein, those which enzymatic conversion (e.g. chloramphenicol transferase), those capable of colorimetric determination (e.g. β-galactosidase). Dendrimers with detection molecules allow the uptake of a dendrimer in a human or animal cell to be analyzed as shown in FIGS. 16A-16N, 17A-17C, 18A-18C, 19A-19C, 20, 21, 22A-22C, 23A-23C, 24A-24C, 25A-25C, 26A-26C, 37A-37B, 38A-38A 39A-39B, 40A-40C, 41A-41E, and in Table 1. A typical method for determining cellular uptake with such dendrimers includes administering a dendrimer that includes a detection molecule to a human, an animal, or a plant, and imaging the detection molecule using any of several known imaging procedures that are known to those skilled in the art.

The invention also provides dendrimers that act as transport molecules. Such transport molecules include any dendrimer of the invention and a biologically active molecule. The dendrimer of the transport molecule includes at least one guanidine group, a salt of at least one guanidine group, at least one protected guanidine group, at least one amidine group, a salt of at least one amidine group, at least one protected amidine group, at least one ureido group, a salt of at least one ureido group, at least one protected ureido group, and at least one thioureido group, a salt of at least one thioureido group, at least one protected thioureido group and the biologically active molecule is bonded to the dendrimer. With respect to the dendrimers of the transport molecules, the definition of the "dendrimer" is expanded for convenience to include compounds such as compounds 40 and 41 which include one guanidine group at the terminal end of one branch that, in some embodiments does not include any peptide linkages, however, as will be readily observed by one of skill in the art, the dendrimers of the majority of embodiments of the transport molecules of the invention include at least two branches and at least two guanidine groups, protonated guanidine groups, or protected guanidine groups; at least two amidine groups, protonated amidine groups, or protected amidine groups; or at least two ureido groups, protonated ureido groups, or protected ureido groups, or at least two thioureido groups, protonated thioureido groups, or protected thioureido groups generally at the terminal end of the at least two branches. In various embodiments, the dendrimer of the transport molecule does not include arginine or lysine units or residues and in some embodiments does not include any peptide linkages.

In some embodiments, the dendrimer of the transport molecule includes at least one tetravalent atom bonded to at least two groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In other embodiments, the dendrimer of the transport molecule includes at least one tetravalent atom bonded to at least three groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In still other embodiments, the dendrimer of the transport molecule includes a first tetravalent atom and a second tetravalent atom, wherein the first tetravalent atom and the second tetravalent atom are each bonded to at least three groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In yet other embodiments, the dendrimer of the transport molecule includes a first tetravalent atom, a second tetravalent atom, and a third tetravalent atom, wherein the first tetravalent atom, the second tetravalent atom, and the third tetravalent atom are each bonded to at least three groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups. In still other embodiments, the dendrimer of the transport molecule includes a first tetravalent atom, a second tetravalent atom, a third tetravalent atom, and a fourth tetravalent atom, wherein the first tetravalent atom, the second tetravalent atom, the third tetravalent atom, and the fourth tetravalent atom are each bonded to at least three groups bearing terminal guanidine groups, terminal protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups.

In still other embodiments, the dendrimer of the transport molecule includes at least two guanidine groups, protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups, and the transport molecule possesses a degree of symmetry such that the at least two guanidine groups, protonated guanidine, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups are in identical chemical environments when all the guanidine groups, protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups of the dendrimer are either neutrally charged or are protonated. In still other embodiments, the dendrimer of the transport molecule includes three or more guanidine groups, protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups, and the transport molecule possesses a degree of symmetry such that each of the three or more guanidine groups, protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups is in an identical chemical environment when each of the three or more guanidine groups, protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups is either neutrally charged or is protonated. In still other embodiments, the dendrimer of the transport molecule possesses $C_{2V}$ symmetry whereas in other embodiments, the dendrimer of the transport molecule possesses $C_{3V}$ symmetry or other symmetry. In still other embodiments, the dendrimer of the transport molecule includes 3, 6, 9, or 12 guanidine groups, protonated guanidine groups, terminal protected guanidine groups, terminal amidine groups, terminal protonated amidine groups, terminal protected amidine groups, terminal ureido groups, terminal protonated ureido groups, terminal protected ureido groups, terminal thioureido groups, terminal protonated thioureido groups, or terminal protected thioureido groups.

In yet other embodiments, the dendrimer of the transport molecule includes a group of formula I a group of formula II or a protonated or a protected form of the group of formula II, a group of formula III a group of formula IV, a group of formula V or a protonated or protected form of the group of formula V, a group of formula VI or a protonated or protected form of the group of formula VI a group of formula VII or a protonated or protected form of the group of formula VII a group of formula VIII or a protonated or protected form of the group of formula VIII or a group of formula IX or a protonated or protected form of the group of formula IX. In some embodiments, the dendrimer of the transport molecule includes one, two, three, or four groups of formula I or formula II or protonated or protected forms of the group of formula II. The dendrimers of the transport molecule may also include a group of formula IX or a protonated or protected form of the group of formula IX.

In other embodiments, the invention provides dendrimers that include at least one group having a structure analogous to that of formula II, formula V, formula VI, formula VII, formula VIII, or formula IX wherein the guanidine groups are replaced with amidine, ureido, or thioureido groups or a protected form of such groups. In some embodiments, the dendrimer of the transport molecule includes one, two, three, or four groups analogous to formula II, wherein the guanidine groups are replaced with amidine, ureido, or thioureido groups or protonated or protected forms of such groups.

The biologically active molecule may be attached to the dendrimer using a wide variety of methodologies. In one embodiment, the biologically active molecule is directly bonded to the dendrimer by reaction of a group on the biologically active molecule with a complimentary reactive group on the dendrimer. In other embodiments, the biologically active molecule is attached to the dendrimer through a linking group that may be formed by reaction of a linking molecule with the dendrimer. In such methods, a reactive group on a peptide or non-peptide-containing linking group that is bonded to the dendrimer is typically reacted with a reactive group on the biologically active molecule to produce the transport molecule. In some embodiments, the dendrimer of the transport molecule includes amide bonds but does not include any peptide linkages. In other embodiments, the transport molecule includes a disulfide linkage, an ether linkage, or a thioether linkage, and the biologically active molecule is bonded to the dendrimer through the disulfide linkage, the ether linkage, or the thioether linkage. For example, in transport molecule 16, a dendrimer with 6 guanidine groups in identical chemical environments is bonded to a biologically active molecule, 6-mercaptopurine, with a peptide-containing linking group through a disulfide linkage. In other embodiments, the biologically active molecule is bonded to the dendrimer through an amide or ester linkage. In other embodiments, the biologically active molecule is bonded to the dendrimer through a thiourea group. In yet other embodiments, the biologically active molecule is bonded to the dendrimer by reaction of a maleimide on the dendrimer with a reactive group on the biologically active molecule. An example of a dendrimer with a reactive maleimide group is compound 44. In still other embodiments, the biologically active molecule is bonded to the dendrimer through a carbon-carbon single bond. In still other embodiments, the biologically active molecule is bonded to the dendrimer through a covalent bond using various methods that will be readily apparent to those skilled in the art.

A wide variety of biologically active molecules are suitable for use in the transport molecules of the invention. Therefore, the tranport molecules of the present invention may be used to treat a wide variety of diseases and conditions in humans. Mammals, and other animals. Diseases and conditions contemplated for treatment in accordance with the present invention include inflammatory and infectious diseases, such as, for example, septic shock, hemorrhagic shock, anaphylactic shock, toxic shock syndrome, ischemia, cerebral ischemia, administration of cytokines, overexpression of cytokines, ulcers, inflammatory bowel disease (e.g., ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, inflammation (e.g., liver inflammation, renal inflammation, and the like), burn, infection (including bacterial, viral, fungal and parasitic infections), hemodialysis, chronic fatigue syndrome, stroke, cancers (e.g., breast, melanoma, carcinoma, and the like), cardiopulmonary bypass, ischemic/reperfusion injury, gastritis, adult respiratory distress syndrome, cachexia, myocarditis, autoimmune disorders, eczema, psoriasis, heart failure, heart disease, atherosclerosis, dermatitis, urticaria, systemic lupus erythematosus, AIDA, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, neurodegenerative disorders, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), myasthenia gravis (MG), ophthalmic diseases, post-angioplasty, restenosis, angina, coronary artery disease, and the like.

Biologically active molecules contemplated for use in the synthesis of transport molecules and for use in pharmaceutical formulation and medicaments of the present invention include, but are not limited to the following:

NSAIDS, such as acetaminophen (Tylenol, Datril, etc.), aspirin, ibuprofen (Motrin, Advil, Rufen, others), choline magnesium salicylate (Triasate), choline salicylate (Anthropan), diclofenac (voltaren, cataflam), diflunisal (dolobid), etodolac (lodine), fenoprofen calcium (nalfon), flurobiprofen (ansaid), indomethacin (indocin, indometh, others), ketoprofen (orudis, oruvail), ketorolac tromethamine (toradol), magnesium salicylate (Doan's, magan, mobidin, others), meclofenamate sodium (meclomen), mefenamic acid (relafan), oxaprozin (daypro), piroxicam (feldene), sodium salicylate, sulindac (clinoril), tolmetin (tolectin), meloxicam, nabumetone, naproxen, lornoxicam, nimesulide, indoprofen, remifenzone, salsalate, tiaprofenic acid, flosulide, and the like;

analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

sedatives/hypnotics (e.g., barbiturates (e.g., pentobarbital, pentobarbital sodium, secobarbital sodium), benzodiazapines (e.g., flurazepam hydrochloride, triazolam, tomazeparm, midazolam hydrochloride, and the like);

antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like));

antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, and the like);

antidepressants (e.g., doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like); antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

antimanic agents (e.g., lithium carbonate), antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

antihypertensive drugs, such as diuretics (hydrochlorothiazide, chlorthalidone, metolazone, indapamide, furosemide, bumetamide, torsemide, triamterene, amiloride, spronolactone), beta-adrenergic blocking agents (acebutolol, atenolol, betaxolol, cartelol, labetalol, metoprolol, nadolol, penbutolol, pindolol, propranolol, timolol), angiotensin converting enzyme inhibitors (benazepril, captopril, enalapril, fosinopril, quinoapril, ramimpril, losartan), calcium channel-blocking agents (diltiazem, verapamil, amlodipine, felodipine, isradipine, nicardipine, nifedipine), aplha-adrenoceptor blocking agents, sympatholytics, and vasodilators (such as prazosin, terazosin, doxazosin, clonidine, guanabenz, guanfacine, methylodopa, guanethidine, guanethidine monosulfate, reserpine, hydralazine, minoxidil, and the like), as well as agents such as trimethaphan camsylate, phenoxybenzamine hydrochloride, pargyline hydrochloride, deserpidine, diazoxide, rescinnamine, sodium nitroprusside, rauwolfia serpentina, alseroxylon, phentolamine mesylate, and the like;

antihistamine/antipruritic drugs, such as ethanolamines (e.g., diphenhydramine, diphenhydramine hydrochloride, clemastine, clemastine fumarate, and the like), ethylenediamines (e.g., brompheniramine, brompheniramine maleate, chlorpheniramine, chlorpheniramine maleate, dexchlorpheniramine maleate, triprolidine, triprolidine hydrochloride, and the like), phenothiazines (e.g., promethazine), piperidines (e.g., hydroxzine, hydroxyzine hydrochloride, terfenadine, astemizole, azatadine, azatadine maleate, and the like), cyproheptadine, cyproheptadine hydrochloride, loratidine, carbinoxamine maleate, diphenylpyraline hydrochloride, phenindamine tartrate, tripelennamine hydrochloride, methdilazine hydrochloride, trimprazine tartrate, and the like;

immunosuppressants, such as glucocorticoids (methylprednisolone), myelin basic protein (e.g., 7-capaxone), anti-Fc receptor monoclonal antibodies, hydroorotate dehydrogenase inhibitor, anti-IL2 monoclonal antibodies (e.g., CHI-621 and dacliximab), buspirone, castanospermine, CD-59 (complement factor inhibitor), 5-lipoxygenase inhibitor (e.g., CMI-392), phosphatidic acid synthesis antagonists, ebselen, edelfosine, enlimomab, galaptin, platelet activating factor antagonists, selectin antagonists (e.g., ICAM-4), interleukin-10 agonist, macrocyclic lactone, methoxatone, mizoribine, OX-19, peptigen agents, PG-27, protein kinase C inhibitors, phosphodiesterase IV inhibitor, single chain antigen binding proteins, complement factor inhibitor, sialophorin, sirolimus, spirocyclic lactams, 5-hydroxytryptamine antagonist, anti-TCR monoclonal antibodies, CD5 gelonin and TOK-8801, and the like;

antimetabolite cytotoxics (azathioprine, cyclophosphamide), C5a release inhibitor, benzydamine, peldesine, pentostatin, SDZ-ASM-981, thalidomide, benzoporphyrin derivatives, arachidonate antagonists (e.g., halometasone, halobetasol propionate), corticosteriod (clobetasol propionate), growth hormone antagonists (octapeptide somatostatin analogue, lanreotide, angiopeptin and dermopeptin), thymopentin, and the like;

neuroprotective agents, such as α-adrenoreceptor antagonist (i.e, α-dihydroergocryptine), NMDA antagonists (e.g., 5,6,7-tichloro-THQTQ, remacemide, 2-piperazinecarboxylic acid, N-indologlycinamide derivatives, spiro[benzo(b)] thiophen-4(5H) derivatives, CP-101606, eliprodil, dexanabinol, GV-150526, L-695902, L-701324, amantadine derivatives, dizocilpine, benzomorphan derivatives, aptiganel, (S)-α-phenyl-2-pyridine ethanamide dihyrochloride and 1-amino-cyclopentanecarboxylic acid), sodium channel antagonists (e.g., 619C89), glycine antagonists (e.g., glystasins), calcium channel antagonists (e.g., 3,5-pyridinedicarboxylic acid derivatives, conopeptides, 1-piperazineethanol, thieno[2,3-b]pyridine-5-carboxylic acid derivatives, NS-3034, nilvadipine, nisoldipine, tirilazad mesylate, 2H-1-enzopyran-6-ol, nitrone spin traps, iacidipine, iomeerzine hydrochloride, lemildipine, lifarizine, CPC-304, efonidipine, F-0401, piperazine derivatives), calpain inhibitors, fibrinogen antagonists (e.g., ancrod), integrin antagonists (e.g., antegren), thromboxane $A_2$ antagonist (e.g., 9H-carbazole-9-propanoic acid derivatives, 5-Heptenoic acid derivatives and 1-azulenesulfonic acid derivatives), brain-derived neurotropic factor, adrenergic transmitter uptake inhibitor (e.g., 1-butanamine), endothelin A receptor antagonists (e.g., benzenesulfonamide derivatives, GABA A receptor antagonists (e.g., triazolopyrimidine derivatives and cyclohexaneacetic acid derivatives), GPIIb IIIa receptor antagonists (e.g., C68-22), platelet aggregation antagonist (e.g., 2(1H)-quinolinone derivatives, 1H-pyrrole-1-acetic acid derivatives and coumadin), Factor Xa inhibitor, CPC-211, corticotropin releasing factor agonist, thrombin inhibitor (e.g., cothrombins, fraxiparine, dermatan sulfate and heparinoid), dotarizine, intracellular calcium chelators (e.g., BAPTA derivatives), radical formation antagonists (EPC-K1, 3-pyridinecarboxamide derivatives, superoxide dismutase, raxofelast, lubeluzole, 3H-pyrazol-3-one derivatives, kynurenic acid derivatives, homopiperazine derivatives, and polynitroxyl albumin), protein kinase inhibitors (e.g., 1H-1,4-diazepine), nerve growth agonist (e.g., floor plate factor-5), glutamate antagonist (e.g., cyclohexanepropanoic acid, riluzole, NS-409 and acetamide derivatives), lipid peroxidase inhibitor (e.g., 2,5-cyclohexadiene-1,4-dione derivatives), sigma receptor agonist (e.g., cyclopropanemethanamine derivatives and SA-4503), thyrotropin releasing hormone agonist (e.g., JTP-2942, L-prolinamide and posatirelin), prolyl endopeptidase inhibitor, monosialoganglioside GM1, proteolytic enzyme inhibitor (e.g., nafamostat), neutrophil inhibitory factor, platelet activating factor antagonist (e.g., nupafant), monoamine oxidase B inhibitor (e.g., parafluoroselegiline and benzonitrile derivatives), PARS inhibitors, Angiotensin I converting enzyme inhibitor (e.g., perindopril and ramipril), acetylcholine agonist (e.g., pramiracetam), protein synthesis antagonist (e.g., procysteine), phosphodiesterase inhibitor (e.g., propentofylline), opioid kappa receptor agonist (e.g., 10H-phenothiazine-2-carboxamine derivatives), complement factor inhibitor (sCRI fragments), somatomedin-1, carnitine acetyltransferase stimulant (e.g., acetylcarnitine), and the like;

T cell inhibitors such as synthetic leucocyte antigen derived peptides, interleukin-1 receptor antagonist, MG/AnergiX, anti-CD3 monoclonal antibodies, anti-CD23 monoclonal antibodies, anti-CD28 antibodies, anti-CD2 monoclonal antibodies, CD4 antagonists, anti-E selectin antibodies, MHC inhibitors, monogens, mycophenolate mofetil, LRA-1 inhibitors, selectin inhibitors, and the like;

antimigraine agents, such as MK-462, 324C91, Phytomedicine, (S)-fluoxetine, calcium channel antagonists (e.g., nimodipine/Nimotop, flunarizine, dotarizine/FI-6026, iomerizine HCL/KB-2796, CPC-304, and CPC-317), α-dihydroergocryptine, 5-HT1 agonists, (e.g., Sumatriptan/Imitrex, Imigran, GR-85548, 311C, and GR-127607), 5-HT1D agonists, 5-HT1A antagonists, 5-HT1B antagonists (e.g., CP-93129), 5-HT1D antagonists (e.g., 1H-indole-5-ethanesulfonide derivatives and 1H-indole-5-methanesulfonamide), 5-HT1D receptor cloned (e.g., 5-HT1D agents), 2-thiophenecarboxamide, 3-piperidinamine, diclofenac potassium, dihydroergotamine (e.g., DHE 45®), ergotamine tartrate, dolasetron mesilate, dotarizine, flupirtine, histamine-H3 receptor agonist, indobufen, 1-azulenesulfonic acid derivatives, cholinesterase inhibitors, (e.g., S-9977), bradykinin antagonists, nitric oxide reductase inhibitors (e.g., BN-52296), nitric oxide receptor antagonists, substance P antagonists (e.g., Capsaicin/Nasocap), endopeptidase inhibitors (e.g., neutral endopeptidase, cloned), piperazine derivatives, neurokinin 1 antagonists, metergoline, dopamine D2 antagonist (e.g., metoclopramide+lysine acetyl), enkephalinase inhibitors (e.g., neutral endopeptidase), 5-HT2 antagonists (e.g., LY-053857), 5-HT3 antagonists (e.g., Dolasetron mesilate/MDL-73147, and 4H-carbazol-4-one derivatives), tenosal, tolfenamic acid, cyclooxygenase inhibitors (e.g., carbasalate/carbaspirin calcium, and tenosal/MR-Y134), alpha adrenoreceptor antagonists (e.g., arotinolol, and dihydroergocryptine), opioid agonists (e.g., flupirtine/D-9998), beta adrenergic antagonists (e.g., propranolol), valproate semisodium, propanolol hydrochloride, isometheptene mucate, dichloralphenazone, and the like;

antiarthritic agents, such as anti-CD4 monoclonal antibodies, phospholipase A1 inhibitor, loteprednol, tobramycin, combinations of loteprednol and tobramycin, salnacedin, amiprilose, anakinra, anergix, anti-B7 antibody, anti-CD3K anti-gp39, anti-MHC MAbs, antirheumatic peptides, anti-Tac(Fv)-PE40, AP-1 inhibitors, AR-324, purine nucleotide phosphorylase inhibitors (e.g., BCX-5), bindarit, CD2 antagonist (e.g., BTI-322), campath-1H, CD4 antagonist (e.g., CE9.1 and SB-210396), tumor necrosis factor antagonist (e.g., p80 TNFR, rhTNFbp, peptide T, CenTNF, thalidomide, CDP-571 and TBP-1), cobra venom factor, interleukin 1a agonist (e.g., cytogenin), interleukin 2 receptor antagonist (e.g., dacliximab), ICAM 1 antagonist (e.g., enlimomab), interleukin 1 beta converting enzyme inhibitors (e.g., ICE-inhibitors), interferons (e.g., thymocartin), interleukin-10, interleukin-13, interleukin 1 antagonist (e.g., SR-31747 and TJ-114), interleukin-2 antagonist (e.g., sirolimus), phospholipase C inhibitor, neurokinin 1 antagonist (e.g., L-733060), laflunimus, leflunomide, leucotriene antagonists, levamisole, LFA3TIP, macrocyclic lactone, MHC class II inhibitors, mizoribine, mycophenolate mofetil, NfkB inhibitors, oncolysin CD6, peldesine, pidotimod, PKC-RACK inhibitors, PNP inhibitors, reumacon, CD28 antagonist, roquinimex, RWJ-50271, subreum, T7 vector, tacrolimus, VLA antagonist (e.g., TBC-772), transforming growth factor beta agonist, methionine synthase inhibitors (e.g., vitamin B12 antagonist), adenosine A2 receptor agonist (e.g., YT-146), CD5 antagonist (e.g., zolimomab), 5-lipoxygenase inhibitor (e.g., zileuton, tenidap, and ABT-761), cyclooxygenase inhibitor (e.g., tenoxicam, talmetacin, piroxicam, piroxicam cinnamate, oxaprozin, NXTHIO, ML-3000, mofezolac, nabumetone, flurbiprofen, aceclofenac, diclofenac, and dexibuprofen), metalloproteinase inhibitor (e.g., XR-168, TNF convertase inhibitors, GI-155704A, AG-3340 and BB-2983), nitric oxide synthase inhibitors (i.e, ARL-16556), phospholipase A2 inhibitor (e.g., ARL-67974), selectin antagonist (e.g., CAM inhibitors), leucotriene B4 antagonist (e.g., CGS-25019C), collagenase inhibitor (e.g., GR-129574A), cyclooxygenase 2 inhibitor (e.g., meloxicam), thromboxane synthase inhibitor (e.g., curcumin), cysteine protease inhibitor (e.g., GR-373), metalloproteinase inhibitor (D-5410), lipocortins synthesis agonist (e.g., rimexolone, prednisolone 21-farnesylate, HYC-141, and deflazacort), chelating agent (diacerein), elastase inhibitors, DNA directed RNA polymerase inhibitor (e.g., estrogens), oxygen radical formation antagonist (e.g., glucosamine sulfate), thrombin inhibitors (e.g., GS-522), collagen inhibitors (e.g., halofuguinone), hyaluronic acid agonist (e.g., NRD-101, hylan, Dispasan, and Hyalart), nitric oxide antagonists (e.g., hydroxocobalamin), stromelysin inhibitors (e.g., L-758354), prostaglandin E1 agonist (e.g., misoprostol, and misoprostol+diclofenac), dihydrofolate reductase inhibitor (e.g., trimetrexate, and M-68), opioid antagonist (e.g., nalmefene), corticotropin releasing factor antagonist (e.g., NBI-103, and NBI-104), proteolytic enzyme inhibitor (e.g., protease nexin-1, and NCY-2010), bradykinin antagonist (e.g., tachykinin antagonists, and NPC-17731), growth hormone antagonist (e.g., octreotide), phosphodiesterase IV inhibitor (e.g., PDEIV inhibitors), gelatinase inhibitor (e.g., REGA-3G12), free radical scavengers (e.g., SIDR-1026), prostaglandin synthase inhibitors (e.g., sulfasalazine), phenylbutazone, penicillamine, salsalate, azathioprine, indomethacin, meclofenamate sodium, gold sodium thiomalate, ketoprofen, auranofin, aurothioglucose, tolmetin sodium, and the like;

antigout agents (e.g., colchicine, allopurinol, and the like);

anticoagulants (e.g., heparin, heparin sodium, warfarin sodium, and the like);

thrombolytic agents (e.g., urokinase, streptokinase, altoplase, and the like);

antifibrinolytic agents (e.g., aminocaproic acid);

hemorheologic agents (e.g., pentoxifylline);

antiplatelet agents (e.g., aspirin, empirin, ascriptin, and the like);

anticonvulsants (e.g., valproic acid, divalproate sodium, phenyloin, phenyloin sodium, clonazepam, primidone, phenobarbitol, phenobarbitol sodium, carbamazepine, amobarbital sodium, methsuximide, metharbital, mephobarbital, mephenyloin, phensuximide, paramethadione, ethotoin, phenacemide, secobarbitol sodium, clorazepate dipotassium, trimethadione, and the like);

agents useful for calcium regulation (e.g., calcitonin, parathyroid hormone, and the like);

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antifungal agents (e.g., griseofulvin, keloconazole, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

antioxidants (e.g., N-acetylcsysteine, Vitamin A, Vitamin C, Vitamin E, β-carotene, EUK-8, flavonoids, glutathione, α-lipoic acid, melatonin, retinols, and the like);

anti-infectives (e.g., miconazole, vidarabine, inosine, pranobex, vidarabine, inosine prabonex, cefpimizole sodium), fradiomycin, and the like);

bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like), and the like;

hypoglycemic agents (e.g., human insulin, purified beef insulin, purified pork insulin, glyburide, chlorpropamide, glipizide, tolbutamide, tolazamide, and the like);

hypolipidemic agents (e.g., clofibrate, dextrothyroxine sodium, probucol, lovastatin, niacin, and the like);

proteins (e.g., DNase, alginase, superoxide dismutase, lipase, and the like);

nucleic acids (e.g., sense or anti-sense nucleic acids encoding any therapeutically active protein, including the proteins described herein, and the like);

agents useful for erythropoiesis stimulation (e.g., erythropoietin);

antiulcer/antireflux agents (e.g., famotidine, cimetidine, ranitidine hydrochloride, and the like);

antinauseants/antiemetics (e.g., meclizine hydrochloride, nabilone, prochlorperazine, dimenhydrinate, promethazine hydrochloride, thiethylperazine, scopolamine, and the like);

septic shock agents, such as angiogenesis inhibitors (OLX-514), bradykinin antagonists (e.g., CP-0502, and NPC-17731), complement factor inhibitors (e.g., C3 convertase inhibitor), C5a release inhibitors (e.g., CAB-2.1), dopamine agonists (e.g., dopexamine), elastase inhibitors (e.g., ONO-5046), E selectin antagonists (e.g., CY-1787), farnesyltransferase inhibitors (RBE limonene), immunostimulants (e.g., CGP-19835A, lipid A vaccine, edobacomab, nebacumab, StaphGAM, and diabodies), immunosuppressants (e.g., CytoTAB, and transcyclopentanyl purine analogues), interleukin 1 antagonists (e.g., interleukin 1 receptors), interleukin 1 receptor antagonists (e.g., anakinra), interleukin 1b antagonists (e.g., interleukin-1β), interleukin 1 beta converting enzyme inhibitors (e.g., ICE-inhibitors), interleukin 8 antagonists (e.g., IL-8 receptor), interleukin 13 agonists (e.g., intereleukin-13), ITF-1697, lipase clearing factor inhibitors (e.g., SC-59735), membrane permeability enhancers (e.g., Bactericidal Permeability Increasing protein/BPI), nitric oxide antagonists (e.g., hydroxocobalamin), nitric oxide synthase inhibitors (e.g., L-NMMA, and α-methyl-N-delta-iminoethyl-ornithine), P2 receptor stimulants (e.g., ATP analogues), phosphatidic acid synthesis antagonists (e.g., lisofylline), phospholipase A2 inhibitors (e.g., S448, acylpyrrole-alkanoic acid derivatives, and indoleacetic acid derivatives), platelet activating factor antagonists (e.g., ABT-299, TCV-309, SM-12502, (2RS,4R)-3-(2-(3-pyridinyl)thiazolidin-4-oyl)indoles, UR-12670, and E-5880), prostacyclin agonists (e.g., taprostene), prostaglandin E1 agonists (e.g., TLC C-53), protein kinase inhibitors (e.g., SB-203580), protein kinase C inhibitors, protein synthesis antagonists (e.g., procysteine), proteolytic enzyme inhibitors (e.g., nafamostat), SDZ-PMX-622, selectin antagonists (e.g., sulfated glycolipid cell adhesion inhibitors), thrombin inhibitors (e.g., GS-522), TNF receptor-Ig, tumor necrosis factor antagonists (e.g., anti-TNF MAbs, MAK-195F, TBP-I, Yeda, rhTNFbp, and CDP-571), tumor necrosis factor alpha antagonists (e.g., E-5531), and the like;

multiple sclerosis agents, such as 4-aminopyridine, 15±deoxyspergualin, ACTH, amantadine, antibody adjuvants (e.g., poly-ICLC, and poly-IC+poly-L-lysine+carboxymethylcellulose), anti-cytokine MAb (CDP-835), anti-inflammatory (e.g., CY-1787, and CY-1503), anti-selectin MAb (e.g., CY-1787), anti-TCR MAb (e.g., NBI-114, NBI-115, and NBI-116), bacloten, bethanechol chloride, carbamazepine, carbohydrate drugs (e.g., CY-1503), clonazepam, CNS and immune system function modulators (e.g., NBI-106, and NBI-107), cyclophosphamide, cyclosporine A, cytokines (e.g., IFN-α, alfaferone, IFN-β, 1b, betaseron, TGF-β2, PEG-TGF-β2, betakine, IFN-β/Rebif, frone, interferon-β, and IFN-β), CD4+T cell inhibitors (e.g., AnergiX), CD28 antagonists (e.g., B7-1, B7-2, and CD28), direct cytotoxicity therapies (e.g., benzoporphyrin derivative (BPD)), FK-506, growth factors (e.g., glial growth factor, GGF, nerve growth factors, TGF-β2, PEG-TGF-β2, and betakine), humanized MAb (e.g., anti-IFN-γMAb, smart anti-IFN-γMAb, anti-Tac antibody, and smart anti-Tac antibody), humanized anti-CD4 MAb (e.g., anti-CD4 MAb, centara), hydrolase stimulants (e.g., castanospermine), IFN-α, IFN-γ antagonist (e.g., anti-IFN-γ MAb, and smart anti-IFN-γ MAb), IL-2 antagonists (e.g., tacrolimus, FK-506, FR-900506, Fujimycin, Prograf, IL-2 fusion toxin, and DAB$_{389}$ IL-2), IL-4 antagonists (e.g., IL-4 fusion toxin, and DAB$_{389}$ IL-4), immune-mediated neuronal damage inhibitors (e.g., NBI-114, NBI-115, and NBI-116), immunoglobins, immunostimulants (e.g., poly-ICLC, edelfosine, ALP, ET-18-OCH3, ET-18-OME, NSC-24, and poly-IC+poly-L-lysine+carboxymethylcellulose), immunosuppressants (e.g., azathioprine, AI-100 animal protein, rDNA human protein AI-101, peptide, AI-102, castanospermine, tacrolimus, FK-506, FR-900506, Fujimycin, Prograf, anti-leukointegrin MAb, Hu23F2G, primatized anti-CD4 antibody, CE9.1, Galaptin 14-1, GL14-1, Lectin-1, recombinant IML-1, linomide, roquinimex, LS-2616, transcyclopentanyl purine analogs, MS-6044, spanidin, 15-deoxyspergualin, deoxyspurgiline, gusperimus HCL, NSC-356894, NKT-01, TCR, CD3/Ti, cyclosporine, OL-27-400, SandImmune, Human IL-10, monogens, anti-TCR MAbs, TCAR MAbs, Monogen TM19, Monogen TM27, Monogen TM29, Monogen TM31, peptigen TP12, anti-CD4 MAb, cantara, immunophilins, VX-10367, VX-10393, VX-10428, synthetic basic copolymer of amino acids, copolymer-1, COP-1, T lymphocyte immunofusion (TIF) protein, and cyclophosphamide), integrin antagonists (e.g., anti-integrin (cell adhesion molecule α4β1 integrin) MAbs, AN-100225, and AN-100226), interferon agonists (e.g., poly-ICLC, and poly-IC+poly-L-lysine+carboxymethylcellulose), interferon-β-1b, isoprinosine, IV methylprednisolone, macrolides (e.g., tacrolimus, FK-506, FR-900506, Fujimycin, and Prograf), MAO B inhibitors (e.g., selegiline, and Parkinyl), methotrexate, mitoxantrone, muscle relaxants (e.g., RGH-5002), muscarinic antagonists (e.g., RGH-5002), neurosteroids (e.g., NBI-106, and NBI-107), octapeptides (e.g., peptide T), oxybutinin chloride, oxygen free radical antagonists (e.g., tetrandrine, biobenzylisoquinoline alkaloid), peptide agonists (e.g., peptide T), phenoxybenzamine, phospholipase C inhibitors (e.g., edelfosine, ALP, ET-18-OCH3, ET-18-OME, NSC-24), photodynamic therapies (e.g., benzoporphyrin derivative (BPD)), plasmapheresis, platelet activating factor antagonists (e.g., ginkgolide B, and BN-52021), potassium channel antagonists (e.g., aminodiaquine, and EL-970), propranolol, prostaglandin synthase inhibitors (e.g., sulfasalazine, salazosulfapyridine, PJ-306, SI-88, azulfidine, salazopyrin), protease antagonists (e.g., ginkgolide B, and BN-52021), recombinant soluble IL-1 receptors, spergualin analogs (e.g., spanidin, 15-deoxyspergualin, deoxyspurgiline, gusperimus HCl, NSC-356894, NKT-01), TCR peptide decoys (e.g., NBI-114, NBI-115, and NBI-116), TCR peptidomimetic decoys (e.g., NBI-114, NBI-115, and NBI-116), TCR peptide vaccines (e.g., AI-208 (Vβ6.2/6.5 phenotype)), selectin antagonists (e.g., lectin-1, and recombinant IML-1), soluble TNF receptor I, TCARs (e.g., TCR, CD3/Ti and peptigen TP12), TNF antagonists (e.g., thalidomide, and TNF inhibitors), tricyclic antidepressants, and the like;

organ transplantation agents, such as anti-CD25 MAbs, anti-Tac antibodies, anti-TNF MAb (e.g., CDP571), apoptosin, azathioprines (e.g., imuran), BCX-34, CA3, CD28, complement inhibiting factors (e.g., CD59), CTLA4Ig, cyclosporines (e.g., CsA), FK-506/rapamycin binding proteins (FKBP), glucocorticoids, humanized version of OKT3 (e.g., huOKT3-185), mycophenolate mofetil, hydroorotate dehydrogenase inhibitors (e.g., Brequinar), orthoclone OKT3 (e.g., IgG2a anti-T cell murine monoclonal antibody, and muromonab-CD3), rapamycins (e.g., AY-22989), and *streptomyces* isolates (e.g., FR-900520, and FR-900523), and the like.

Also encompassed within the scope of the invention are systemic lupus erythematosus (SLE) agents, such as androgen-derived steriods (e.g., Org-4094), anti-CD4 humanized antibodies, anti-DNA/V-88, anti-idiotypic murine MAb (e.g., anti-idiotypic antibody to 3E10/MAb1C7), CD2 antagonists (e.g., CD2), complement inhibitors (e.g., recombinant MCP-based complement inhibitors), cyclosporines (e.g., Sandimmune, cyclosporine analog, OG-37325, cyclosporin-G, and NVal-CyA), cytokines (e.g., IL-4 fusion toxin), cytokine receptor antagonists (e.g., immunomodulatory cytokines), E-selectin antagonists (e.g., anti-ELAM and CY-1787), FK506/tacrolimus (e.g., Prograf), hypercalcemic agents (e.g., KH-1060), IFN-γ antagonists (e.g., anti-IFN-γ MAb, and smart anti-IFN-γ MAb), IL-1β converting enzyme inhibitors (ICE), IL-2 produced by *E. coli* (e.g., celmoleukin, IL-2, TGP-3, and Celeuk), immunoglobulins (e.g., anti-ELAM, CY-1788, and humanized CY-1787), immunostimulants (e.g., thymotrinan, RGH-0205, and TP3), immunosuppressants (e.g., Rapamycin, AY-22989, NSC-226080, NSC-606698, anti-CD4, T-cell inhibitor, anti-tac MAb, smart anti-tac MAb, Migis™ (membrane immunoglobulin-isotype specific) antibodies, SM-8849, immunophilins, VX-10367, VX-10393, VX-10428, mycophenolate mofetil, ME-MPA, RS-61444, OL-27400, Sandimmune, IL-4 fusion toxin, trypanosomal inhibitory factor (TIF), T-cell receptor, CD3/Ti, Org-4094, anti-TBM, CP 17193, Leflunomide/A-77-1726, ELAM-1, AnergiX, Spanidin, 15-deoxyspergualin, deoxyspurgiline, gusperimus hydrochloride, NSC-356894, NKT-01, Roquinimex, LS-2616, linomide, LJP-394, and CD-59 antigen), immunotoxins (e.g., Zolimomab aritox, xmmly-h65-rta, xomazyme-lym/CD5-Plus, OrthoZyme-CD5+, XomaZyme-H65-rta, Xomazyme-CD5 Plus), intravenous immunoglobulins (e.g., IVIG), integrin antagonists (e.g., integrin blockers), murine MAb (e.g., anti-SLE vaccine, and MAb 3E10), primatized anti-CD4 antibodies (e.g., CE9.1), protease inhibitors (e.g., matrix metalloprotease (MMP) inhibitors, and stromelysin), protein synthesis antagonists (e.g., anti-CD6-bR, anti-T12-bR, and oncolysin CD6), purine nucleoside phosphorylase inhibitors (e.g., BCX-25, and BCX-14), selectin antagonists (e.g., CY1503, and Cylexin), spergualin analogues (e.g., Spanidin, 15-deoxyspergualin, deoxyspurgiline, gusperimus hydrochloride, NSC-356894, and NKT-01), T cell inhibitors (e.g., AnergiX), tumor necrosis factor (TNF) antagonists, and the like;

Also encompassed within the scope of the invention are Alzheimer's disease agents, such as ACh release enhancers (e.g., T-588 (benzothiophene derivative)), acetylcholine release stimulants (e.g., DUP-996 and analogues), AMPA agonists (e.g., AMAlex, and Isoxazole compound series), AMPA GluR agonist (e.g., IDRA-21 [7-chloro-3-methyl-3, 4-dihydro-2H-1,2,4-benzothiadiazinine]), AMPA GluR antagonists (e.g., S-18986, and related quinolone derivatives), anticholinesterases (e.g., E-2020), Ca-antagonists (e.g., NS-649, spider venom-derived ICM peptides and analogues, and substituted 2-aminoindanes compound series), combined anticholinesterase and muscarinic AChR antagonists (e.g., PD142676), K-channel blockers (e.g., Trans-R-4-(4-methoxyphenyl-methyl) cyclohexylanine and analogues, and margatoxin-based functional and/or structural analogues), MI muscarinic receptor agonists (e.g., Xanomeline), NMDA antagonists (e.g., certain indole derivatives, and (R—($R^1,S^1$))-α-(4-hydroxyphenyl)-beta-methyl-4-(phenylmenthyl)-1-piperidinepropanol and analogues), nicotinic AChR agonists (e.g., ABT-418 [isoxazole, 3-meth-5-(1-meth-2-pyrrolidinyl)]), and the like;

antiparkinson agents (e.g., ethosuximide, and the like);

psoriasis agents, such as 5-LO inhibitors (e.g., Wy-50295, Wy-49232, Lonapalene, RS-43179, M-886, L-663536, ETH-615, DUP-654, Zileuton, epocarbazolin-A, and A-64077), 5-LO/CO inhibitors (e.g., BF-397, Tenidap, CP-309, and CP-66248), angiogenesis inhibitors (e.g., platelet factor 4), anticancer antibiotic (e.g., AGM-1470, and TNP-470), antiinflammatory cytochrome P450 oxidoreductase inhibitors (e.g., DuP-630, and DuP-983), antiproliferative compounds (e.g., Zyn-Linker), arachidonic acid analogues (e.g., CD581, and CD554), arachidonic acid antagonists (e.g., Lonopalene, RS-43179, triamcinolone acetonide with penetration enhancer Azone, betamethasone dipropionate steroid wipe, G-202, Halobetasol propionate, ultravate, Halometasone, C-48401-Ba, and Sicorten), beta-glucan receptor antagonists, betamethasone steroid wipes, calcium metabolic moderators (e.g., Tacalcitol, Bonealfa, TV-02 ointment, Ro-23-6474, KH-1060, Calcipotriol, BMS-181161, BMY-30434, Dovonex, and Divonex), CD4 binding inhibitors (e.g., PIC 060), cell adhesion compounds (e.g., CY-726, VCAM-1, ELAM-1, and ICAM), cell adhesion inhibitors (e.g., selectin inhibitor, GM-1930), cellular aging inhibitors (e.g., Factor X), corticosteroids (e.g., Halobetasol propionate, ultravate, Halometasone, C-48401-Ba, and Sicorten), cyclosporin analogues (e.g., IMM-125), dihydrofolate reductase inhibitors (e.g., G-301, dichlorobenzoprim, methotrexate, and methotrexate in microsponge delivery system), E-selectin inhibitors (e.g., ISIS 4730), endogenous active form of vitamin $D_3$ (e.g., Calcitriol, and Du-026325), fibroblast growth factor antagonists (e.g., Saporin mitotoxin, and Steno-Stat), fumagillin analogues (e.g., AGM-1470, and TNP-470), G-proteins and signal transduction compounds (e.g., CPC-A), gel formulations for acne (e.g., nicotinamide, N-547, and Papulex), growth hormone antagonists (e.g., Octreotide, Sandostatin, Lanreotide, angiopeptin, BIM-23014, and Somatuline), humanized antibodies (e.g., anti-CD4 antibody), hydroorotate dehydrogenase inhibitors (e.g., Brequinar sodium bipenquinate, and DuP-785), ICAM-1 inhibitors (e.g., ISIS 939), IL-1 and other cytokine inhibitors (e.g., Septanil), IL-1 converting ezyme inhibitors, IL-1 receptor antagonists (e.g., Antril), IL-2 antagonists (e.g., Tacrolimus, Prograf, and FK-506), IL-2 receptor-targeted fusion toxins (DAB389IL-2), IL-8 receptors, immunostimulants (e.g., Thymopentin, and Timunox), immunosuppressants (e.g., XomaZyme-CD5 Plus, cyclosporine, Sandimmune, SR-31747, anti-CD11, 18 MAb, Tacrolimus, Prograf, FK-506, and FK-507), immunosuppressive agents targeting FK506 (e.g., immunophilins, VX-10367, and VX-10428), immunotoxins MAb directed against CD antigen (e.g., XomaZyme-CD5 Plus), leukotriene antagonists (e.g., Sch-40120, Wy-50295, and Wy-49232), leukotriene B4 antagonists (e.g., SC-41930, SC-50605, SC-48928, ONO-4057, LB-457, LY-255283, LY-177455, LY-223982, LY-223980, and LY-255253), leukotriene synthesis inhibitors (MK-886, and L-663536), lipase clearing factor inhibitors (e.g., 1-docosanol, and lidakol), lipid encapsulated reducing agent (e.g., Dithranol), liposomal gel (e.g., Dithranol), LO inhibitors (e.g., CD581, CD554, Masoprocol, and Actinex), lithium succinate ointments (e.g., lithium salts, and Efalith), LO/CO inhibitors (e.g., P-8892, P-8977, CHX-108, and FPL-62064), membrane integrity agonists (e.g., lithium salts, and Efalith), microtubule inhibitors (e.g., Posophyliotoxin-containing compound, and Psorex), octapeptide somatostatin analogues (e.g., Lanreotide, angiopeptin, BIM-23014, and Somatuline), oligonucleotides (e.g., ISIS 4730, ISIS 3801, ISIS 1939, and IL-1 inhibitors), peptide agonists (e.g., octapeptide, and peptide T), PKC inhibitors, phospholipase A2 compounds, pospholipase D compounds, photodynamic anticancer agents (e.g., 5-aminolevulinic acid, and 5-ALA), photodynamic therapies (e.g., benzoporphyrin derivative, synthetic chlorins, synthetic porphyrins, and EF-9), photosensitizer (e.g., Porfirmer sodium), PKC inhibitors (e.g., Safingol, and Kynac), platelet activating factor antagonists (e.g., TCV-309), platelet aggregation inhibitors (e.g., CPC-A), prodrug NSAIDs (e.g., G-201), prostaglandin agonist (e.g., eicosapentaenoic acid+gamma-linolenic acid combination, and Efamol Marine), protein inhibitors (e.g., SPC-103600, and SPC-101210), protein kinase C (PKC) inhibitors (e.g., Ro-31-7549, Ro-31-8161, and Ro-31-8220), protein synthesis antagonists (e.g., Calcitriol, Du-026325, LG-1069, LG-1064, AGN-190168, Namirotene, and CBS-211A), purine nucleoside phosphorylase inhibitors (e.g., BCX-34), radical formation agonists (e.g., benzoporphyrin derivative), recombinant antileukoproteinases (e.g., ALP-242), retinoids (e.g., BMY-30123, LG-1069, and LG-1064), retinoid derivatives (e.g., AGN-190168), rapamycin binding proteins (FKBP) (e.g., immunophilins, VX-10367, and VX-10428), second generation monoaromatic retinoids (e.g., Acitretin, and Neotigason), soluble IL-1, IL-4 and IL-7 receptors, somatostatin and somatostatin analogues (e.g., Octreotide, and Sandostatin), steroids, (e.g., AGN-191743), *streptomyces anulatus* isolates (e.g., epocarbazolin-A), superoxide dismutase (e.g., EC-SOD-B), thymidylate synthase inhibitors (e.g., AG-85, MPI-5002, 5-FU in biodegradable gel-like matrix, 5-FU and epinephrine in biodegradable gel-like matrix, and AccuSite), topical formulations (e.g., P-0751, and P-0802), transglutaminase inhibitors, tyrphostin EGF receptor kinase blockers (e.g., AG-18, and AG-555), VCAM-1 inhibitors (e.g., ISIS 3801), vitamin D analogues (e.g., Ro-23-6474, KH-1060, Calcipotriol BMS-181161, BMY-30434, Dovonex, and Divonex), vitamin $D_3$ analogues (e.g., Tacalcitol, Bonealfa, TV-02 ointment), and vitamin $D_3$ derivatives (e.g., 1,2-diOH-vitamin $D_3$), and the like;

diabetes agents, such as ACE inhibitors (e.g., captopril), amylin, amylin agonists and antagonists (e.g., Normylin™, AC137, GC747, AC253, and AC625), autoimmune compounds (e.g., AI-401), capsaicins (e.g., Zostrix-HP), cell regulators (e.g., protein kinase C inhibitors, and Balanol), domperidones (e.g., Motilium®), fluvastatins (e.g., Lescol), FOX 988, fusion toxins (e.g., $DAB_{389}$ IL-2, and $DAB_{486}$ IL-2), gene therapies (e.g., Transkaryotic Therapies), glucagons (e.g., recombinant yeast glucagon), IL-10 compounds, iloprost, immunosuppressives (e.g., tacrolimus, Prograf, and FK-506), proinsulin, insulin and insulin analogs (e.g., AI-401, Nu-Insulin compounds, Humulin, Iletin, Humalog™, LYs-Pro, and Amaryl), insulin-like growth factors (e.g., Chiron/Ciba-Geigy compounds, Fujisawa compounds, and Genetech compounds), insulinotropins (e.g., Pfizer/Scios Nova compounds), nerve growth factors (e.g., Genentech compounds), oral hypoglycemics (e.g., AS-6, glimepiride, Amaryl, CL 316,243, acarbose, miglitol, recombinant yeast glucagon, GlucaGen™, NovoNorm™, glipizide, insulinotropin, and CI-991/CS-045), platelet-derived growth factors (e.g., Zymo Genetics/Novo Nordisk compounds), sulfonylureas (e.g., tolbutamide, acetohexamide, tolazamide, and chlorpropramide), T cell approaches (e.g., anergize, AnergiX™, Procept compounds, and T cell Sciences compounds), and tolrestats (e.g., Alredase®, and ARI-509), activin, somatostatin, and the like;

stroke agents, such as 5-HT antagonists (e.g., piperazine derivative), 5-HT reuptake inhibitors (e.g., Milnacipran, and Dalcipran), 5-HT 1A agonists (e.g., SR-57746A, and SR-57746), 5-HT 3 agonists (e.g., SR-57227), 5-HT 4 antagonists, 5-lipoxygenase inhibitors (e.g., low NM dual 5-lipoxygenase and PAF inhibitor CMI-392), ACh agonists (e.g., Pramiracetam, Choline-L-alfoscerate, L-alpha-glycerylphosphoryl-choline, and Delecit), adenosine agonists (e.g., GP-1-4683, ARA-100, and arasine analogs), adenosine A1 receptor agonists (e.g., Azaisotere, 2-chloro-N-[4 (phenylthio)-1-piperidinyl]adenosine, and 2120136), adenosine reuptake inhibitors (e.g., Diphenyloxazole derivatives), adrenergic transmitter re-uptake inhibitors (e.g., Bifemelane, E-0687, MCI-2016, Alnert, and Celeport), aldose reductase inhibitors (e.g., Spiro-3' pyrroline derivatives), alpha antagonists (e.g., Drotaverine acephyllinate, and Depogen), alpha 2 agonists (e.g., SNAP-5083, SNAP-5608, and SNAP-5682), AMPA receptor agonists (e.g., heterocyclic compound SYM-1207, and heterocyclic compound SYM-1252), AMPA receptor antagonists (e.g., LY-293558, and LY-215490), Ancrod/Arvin, aspirin, benzothiazoles (e.g., Lubeluzole, and R87926), benzodiazepine receptor antagonists (e.g., 3-oxa-diazolyl-1,6-naphthyridine derivatives, Tetracyclic imidazo-diazepineseries imidazenil, FID-02-023, and Ro-23-1412), blood substitutes, bradykinin antagonists (e.g., CP-0127, Bradycor, and Septicor), C5a release inhibitors (e.g., protein derivative CMI-46000), calcium antagonists (e.g., Lemildipine, NB-818, NPK-1886, Trimetazidine derivative, Iomerizine KP-2796, Diltiazem analog clentiazem maleate, and TA-3090), calcium channel antagonists (e.g., nitrendipine-like compound diperdipine, YS-201, U-92032, Diltiazem derivative, 1058, SM-6586, KP-840, F-0401, D-31-D, Tetrahydronaphthalene derivatives, fasudil, AT-877, H-7, HA-1044, HA-1077, Eril, darodipine, dazodipine, PY-108-068, Plimo, Dihydropy-ridine, AE 0047, GJ-0956, Lacidipine, GR-43659, GR-43659X, GX-1048, S-312-d, S-312, S-830312, Nilvadipine, and FK-235), calpain inhibitors (e.g., AK-275, and CX-275), carnitine palmitoyl-transferase inhibitors, carvedilol, cerebral calcium antagonist vasodilators (e.g., Nimodipine, and Nimotop), cholinesterase inhibitors (e.g., indole and indazole derivatives, and Tacrine analog), complement factor inhibitors (e.g., TK9C, protein derivative TP16, compinact A, compinact C, Factor D inhibitors, and soluble, recombinant MCP-based complement inhibitors), complement inhibitors (e.g., sCRI/BRL-55730, and YM-203), coronary vasodilators (e.g., Nicorandil, RP-46417, SG-75, and Adancor), CPC-111, cytidyl diphosphocholine/citicholines, cytokines (e.g., NBI-117), Dexanabiol, dopamine agonists, EAA receptors, endothelin antagonists (e.g., SB 209670), endothelin receptor antagonists, excitatory amino acid agonists (e.g., acylated polyamine analogs, and N-(4-hydroxyphenylpropanonyl)-spermine analog), excitatory amino acid antagonists (e.g., Tryptophan, 4,6-disubstituted stroke & kynurenine derivatives, NPC-17742, CPC-701, and CPC-702), glutamate antagonists (e.g., Kainate quisqualate NNC-07-9202, NPC-17742, small molecule CNS-1237, NS-257, NS-072, BW-619C, CGS 19755, Riluzole, PK-26124, and RP 54274), glutamate receptor antagonists (e.g., Araxin compounds, Quinoxaline derivative, YM-90K, and YM-900), glycine antagonists, glycine NMDA agonists (e.g., 3-hydroxy-2,5-dioxo-1H-benz[b]azepines), glycine NMDA associated antagonists (e.g., 5,6-dihydro-1H-pyrrolo[1,2,3-de]quinoxaline-2,3-diones, Strychnine-insensitive glycine binding site of NMDA receptor L-687414, Glystasins, ACEA-2011, ACEA-3031, AC-1021, ACPC, and eliprodil), growth factor antagonists (e.g., non-peptide indolocarbazole neutrophic molecules, and CEP-075), GPIIb/IIIa antagonists (e.g., Peptide C68-22), hemorheological agents (e.g., Drotaverine acephyllinate, and Depogen), heparin, hydroxyl radical formation inhibitors (e.g., homopiperazine derivative K-7259), hypocalcemic agents (e.g., calcitonin peptide, related to hCGRP peptide), hypothermic agents/BMY-20862, ICAM-1 compounds (e.g., Enlimomab), immunosuppressants (e.g., small molecule compounds, and NBI-117), integrin general antagonists (e.g., monoclonal antibody AN-100225, and monoclonal antibody AN-100226), Interleukin-1 antagonists (e.g., cyclic nitrones), iron-dependent lipid peroxidation inhibitors (e.g., 2-(amino-methyl) chromans), lactic acid accumulation/inhibitors (e.g., small molecule CPC-211), Leukotriene B4 antagonists (e.g., Ebselen, DR-3305, PZ-25, PZ-51, RP 60931, and RP 61605), lipid peroxidase inhibitors (e.g., Idebenone, and Avan), low molecular weight small molecules, methyltransferase stimulants (e.g., 4-methyl benzenesulfonate, ademetionine sulfate tosilate, FO-156, and Ceritan), monoamine oxidase B inhibitors (e.g., MD-280040, MD-200243, MD-280080, Lazabemide, and Ro-19-6327), MS-153, MS-424, /$Na^+$/$H^+$ $Na^+$/$Li^+$ exchange inhibitors (e.g., Pyrazine derivatives), nadroparin (e.g., Fraxiparin), nafronyl/naftidrofuryl (e.g., Praxilene), nerve growth factor agonists (e.g., small molecule compounds, CNTF, BDNF, 2.5S NGF, monosialoganglioside GM1, and Sigen/Sygen), neuronal calcium channel blockers (e.g., CPC-304, and CPC-317), neuronal differentiation compounds (e.g., F-spondin), neuropeptide agonists (e.g., Neurotrophic Peptide Trofexin), neutrophil inhibitory factors (e.g., small molecule compounds), nitric oxide agonists (e.g., hydroxy derivative N-3393, hydroxy derivative N-3398, nicorandil, and Therapicon), nitric oxide antagonists, NMDA antagonists (e.g., Spiroisoindoles/dizocilpine derivatives, Oxindole compound, CP-112116, LY-104658, LY-235959, FR-115427, Sialic acid derivative, N-palmitoyl-Betaethylglycoside neuraminic acid, ND-37, Ro-01-6794, 706, Dextrorphan, Ifenprodil analogue eliprodil, SL-82.0715, Lipophilic molecules, HU-211, Remacemide, 934-423, 12495, 12859, 12942AA, Selfotel, CGS-19755, SDZ-EAA494, CGP-40116, CGP-37849, CGP-39551, and CGP-43487), NMDA antagonist-partial agonists (e.g., Conantokin G peptide SYM-1010), NMDA channel blockers (e.g., Aptiganel CERBSTAT, and CNS 1102), NMDA receptor antagonists, NMDA receptor subtypes (e.g., Kainate quisqua-late NNC-07-9202), non-competitive NMDA antagonists (e.g., FPL-15896), non-ionic copolymer RheotbRx, nootropic/acetylcholine agonists (e.g., Oxiracetam, CT-848, and Neuractiv), norepinephrine inhibitors (e.g., Midalci-pran), N-type calcium channel antagonists (e.g., NS-626, and NS-638), opioid antagonists (e.g., Nalmefene, nalmetrene, JF-1, ORF-11676, Cervene, and Incystene), opioid kappa receptor agonists (e.g., acrylacetamide enadoline, and CI-997), organoselenims (e.g., Ebselen, DR-3305, PZ-25, PZ-51, RP 60931, and RP 61605), oxygen scavengers (e.g., Tirilazad mesylate, Lazaroids, and Freedox), PA2 inhibitors (e.g., phospholipase A2 inhibitor), PAF antagonists (e.g., nupafant, and BB-2113), partial glycine NMDA agonists (e.g., ACPC), peptide/GPIIb/IIIa antagonists (e.g., Integrelin), peptidic neuron-specific calcium channel antagonists (e.g., SNX-111), phosphodiesterase inhibitors (e.g., Xanthine derivatives, propentofylline, Hoe-285, and Hextol), phospholipase A2 inhibitors (e.g., small organic molecule CEP-217), plasminogen activators (e.g., r-ProUK (recombinant pro-urokinase), platelet-activating factor antagonists (e.g., UK-74505), platelet adhesion inhibitors (e.g., Peptide), platelet aggregation antagonists (e.g., cilostazol, peptide agents, GPHb-IIIA inhibitor, and TP-9201), platelet aggregation inhibitors (e.g., Diaminoalkanioic acid derivatives), potassium channel agonists (e.g., Nicorandil, RP-46417, SG-75, and Adancor), prolyl endopeptidase (PEP) inhibitors (e.g., JTP-4819), protein kinase C inhibitors (e.g., monosialoganglioside derivative Liga-20), proteolytic enzyme inhibitors (e.g., Protease nexin-1, Incyte, PN-1, PN-2, Nafamostat, FUT-175, Duthan, and Futhan), pyrimidine derivatives, Quinolizine derivatives (e.g., KF-17329, and KF-19863), radical formation antagonists (e.g., EPC-K1), recombinant tissue plasminogen activators (e.g., alteplase, and Activase), Schwann cell derived molecules/promoters, sigma antagonists (e.g., Sigma ligand), sigma receptor antagonists (e.g., tetrahyropyridinylisoxazolines and isoxazoles PD-144418), sodium/calcium channel modulators (e.g., Lifarizine, and RS-87476), sodium channel antagonists, streptokinase (e.g., Streptase), substituted guanadine (e.g., small molecule CNS-1237), superoxide dismutase stimulants (e.g., PEG conjugated enzyme superoxide dismutase/Dismutec, and PEG-SOD), thrombin inhibitors, (e.g., non-peptide), thromboxane synthase inhibitors (e.g., Linotroban, and HN-11500), thyrotropin-releasing hormone agonists (e.g., TRH agonists, Protirelin analogthymoliberin, and RX-77368), ticlopidine (e.g., Ticlid), TJ-8007, TRH agonists (e.g., Thyrotropin releasing hormones, and JTP-2942), trilazard, urokinase (e.g., Abbokinase), w-conopeptide (e.g., SNX-111), and warfarin (e.g., Coumadin), and the like.

Other biologically active molecules contemplated for use in the invention include agents useful for the treatment of carcinomas (e.g., adriamycin, taxol, interleukin-1, interleukin-2 (especially useful for treatment of renal carcinoma), and the like, as well as leuprolide acetate, LHRH analogs (such as nafarelin acetate), and the like, which are especially useful for the treatment of prostatic carcinoma);

agents useful for the treatment of endometriosis (e.g., LHRH analogs);

agents useful for the treatment of uterine contraction (e.g., oxytocin);

agents useful for the treatment of diuresis (e.g., vasopressin);

agents useful for the treatment of cystic fibrosis (e.g., Dnase (i.e., deoxyribonuclease), SLPI, and the like);

agents useful for the treatment of neutropenia (e.g., GCSF);

agents useful for the treatment of lung cancer (e.g., beta 1-interferon);

agents useful for the treatment of respiratory disorders (e.g., superoxide dismutase);

agents useful for the treatment of ischemia/reperfusion injury (e.g., selectin inhibitors, Irf1, and the like);

nitric oxide synthase inhibitors (e.g., $N^4$-methyl-L-arginine, aminoguanidine, $N^4$-(iminoethyl)-L-ornithine, thiocitrulline and other citrulline derivatives, $N^4$-nitro-L-arginine, $N^4$-nitro-L-arginine methyl ester, $N^4$-amino-L-arginine, and other arginine derivatives, isothiourea and its derivatives, and the like;

as well as a variety of other agents, such as acyclovir, alendronate sodium, amlodipine, ampicillin, azelaic acid, azithromycin, beclomethasone, betamethasone, bicalutamide, buspirone, carisoprodol carvedilol, cefaclor, cefadroxil cefixime, cefprozil, ceftibuten, cefuroxime axetil cephalexin, cetirizine hydrochloride, cimetidine, ciprofloxacin, cisapride, clarithromycin, clavulanate, clonazepam, clotrimazole, codeine, conjugated estrogens, cyclobenzaprine, desogestrel, dexrazoxane, diazepam, dicyclomine HCl, digoxin, diltiazem, dirithromycin, doxazosin, doxycycline, enalapril, erythromycin, erythromycin base, erythromycin stearate, estradiol, ethinyl estradiol, ethynodiol diacetate, etodolac, famotidine, fluconazole, fluoxetine, fluvastatin, furosemide, gemfibrozil, glipizide, glyburide, guaifenesin, hydrochlorothiazide, hydrocodone, hydrocortisone, ibuprofen, ibutilide fumarate, indapamide, insulin, ipratropium bromide, ketoconazole, ketoprofen, ketorolac tromethamine, lamivudine, lansoprazole, levonorgestrel, levothyroxine, lisinopril, loracarbef, loratidine, lorazepam, losartan potassium, lovastatin, medroxyprogestrone, methylphenidate, methylprednisolone, metoprolol, metoprolol tartrate, moexipril hydrochloride, mometasone furoate, mupirocin, mycophenolate mofetil, nabumetone, nalmefene hydrochloride, naproxen, neomycin, nifedipine, nisoldipine, nitrofurantoin, nizatidine, norethindrone, norgestrel, nortriptyline, ofloxacin, omeprazole, oxaprozin, oxycodone, paroxetine, penicillin, pentoxifylline, phenylpropanolamine, phenyloin, polymyxin, porfimer sodium, potassium chloride, pravastatin, prednisone, promethazine, propoxyphene, pseudoephedrine, quinapril, ramipril, ranitidine, riluzole, salmeterol, saquinavir mesylate, sertraline, sevoflurane, simvastatin, sucralfate, sulfamethoxasole, sumatriptan, temazepam, terazosin, terconazole, terfenadine, tetracycline, theophylline, timolol, tramadol, tramadol hydrochloride, tretinoin, triamcinolone acetonide, triamterene, trimethoprim, valproic acid, venlafaxine, verapamil, wafarin, zolpidem, and the like.

In some embodiments, as shown in FIG. 15, the biologically active molecule bonded to the dendrimer is selected from the group consisting of methotrexate, 6-mercaptopurine, 5-fluorouracil, paclitaxel, cyclosporin A, and ganciclovir. In some embodiments, the biologically active molecule is selected from methotrexate, 5-fluorouracil, paclitaxel, cyclosporin A, or ganciclovir. In other embodiments, the biologically active molecule is selected from 6-mercaptopurine.

As described, a wide variety of biologically active molecules may be included in the transport molecules of the present invention. Therefore, the transport molecules of the invention may be used to treat an extremely wide variety of medical conditions in humans, mammals, and other animals. In some embodiments, the biologically active molecule bonded to the dendrimer is a drug suitable for the treatment of a mammalian condition. Because the dendrimers of the present invention may greatly increase the bioavailability of a biologically active molecule, drug candidates with high in vitro activity or assay activity that have been or will be rejected due to low availability may find successful employment as useful therapeutics when they are included in a transport molecule of the invention. Pharmaceutical formulations and medicaments that include any of the transport molecules of the present invention in combination with a pharmaceutically acceptable carrier are thus provided as are methods and uses of increasing the effectiveness of a drug. Such methods and uses includes administering a pharmaceutical formulation or a medicament of the invention to a human or an animal such as a mammal.

The invention also provides a method of increasing transport of a biologically active compound across a biological membrane. The method includes contacting a biological membrane with any transport molecule of the present invention. The transport molecule that includes the biologically active compound is transported across the biological membrane at a rate greater than the biologically active compound is transported across the biological membrane when the biologically active compound is not bonded to the dendrimer of the transport molecule.

The invention further provides a method of administering a pharmaceutical agent to a subject. The method includes coadministering the pharmaceutical agent and any of the dendrimers of the present invention to the subject. In some such embodiments, the dendrimer is bonded to the pharmaceutical agent. In some such embodiments, the subject is a human, a mammal, or an animal. In other such embodiments, the subject is a cell. In yet other such embodiments, the pharmaceutical agent is selected from any drug or pharmaceutical agent described herein.

The instant invention also provides for compositions which may be prepared by mixing one or more transport molecules or dendrimers of the instant invention, or pharmaceutically acceptable salts or tautomers thereof, with pharmaceutically acceptable carriers, excipients, binders, diluents or the like, to treat or ameliorate a variety of disorders such as, but not limited to cancer. One of ordinary skill in the art will recognize that the dendrimers of the invention may be bonded to an almost limitless number and type of drugs to treat any known human or animal condition which is treated with a drug. A therapeutically effective dose further refers to that amount of one or more composition of the instant invention sufficient to result in amelioration of symptoms of the disorder.

The pharmaceutical formulations and medicaments of the instant invention can be manufactured by methods well known in the art such as conventional granulating, mixing, dissolving, encapsulating, lyophilizing, emulsifying or levigating processes, among others. The composition can be in the form of a solid, a solution, an emulsion, a dispersion, a micelle, a liposome, and the like, wherein the resulting composition contains one or more of the transport molecules or dendrimers of the present invention in admixture with an organic or inorganic carrier or excipient suitable for enteral or parenteral administration.

The compositions can be in the form of, for example, granules, powders, tablets, pellets, capsules, syrup, suppositories, injections, emulsions, elixirs, suspensions, solutions or any other form suitable for use. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compositions of the instant invention can also be administered in a local rather than a systemic fashion, such as injection as a sustained release formulation. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention transport molecules and dendrimers are included in the pharmaceutical formulations in an amount sufficient to produce the desired effect upon the pathological condition. The following dosage forms are given by way of example and should not be construed as limiting the instant invention.

For oral, buccal, and sublingual administration, powders, suspensions, granules, tablets, troches, lozenges, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification Tablets containing transport molecules or dendrimers in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the transport molecules are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

Liquid dosage forms for oral administration may be in the form of pharmaceutically acceptable emulsions, syrups, gel capsules, elixirs, suspensions, slurries, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Suspensions suitable for injection may be formulated according to known methods using suitable dispersing or wetting agents and suspending agents. The sterile injectable preparation can also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- di-, or tri-glycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

For injection, pharmaceutical formulations and medicaments may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, pharmaceutical formulations and medicaments may also be formulated for controlled release or for slow release.

The instant compositions may also comprise, for example, micelles or liposomes, or some other encapsulated form, or may be administered in an extended release form to provide a prolonged storage and/or delivery effect. Therefore, pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form Preferred pharmaceutical formulations, medicaments, and transport molecules of the instant invention include formulations that exhibit a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. Typical doses typically range from nanaograms to milligrams, or more typically from micrograms to milligrams. Concentrations of liquid pharmaceutical formulations and medicaments generally range from nM to M or more generally range from nanomolar to micromolar.

"Treating" within the context of the instant invention, means an alleviation of symptoms associated with a disorder or disease, or halt of further progression or worsening of those symptoms, or prevention or prophylaxis of the disease or disorder. For example, within the context of treating patients in need of an anti-cancer drug, successful treatment may include a reduction in the size of the tumor mass, a reduction in the rate of growth of the tumor, an alleviation of symptoms related to a cancerous growth or tumor, or a halting in the progression of a disease such as cancer or in the growth of cancerous cells. Treatment may also include administering the pharmaceutical formulations, medicaments, transport molecules, and/or dendrimers of the present invention in combination with other therapies. For example, the transport molecules, medicaments, and pharmaceutical formulations of the present invention may be administered before, during, or after surgical procedure and/or radiation therapy. The transport molecules and pharmaceutical formulations of the present invention may also be administered in conjunction with other pharmaceutical agents or biologically active molecules including those used in antisense and gene therapy.

The bioavailability of a drug or pharmaceutical agent may be increased using the dendrimers of the present invention. Methods for increasing the bioavailability of a drug include bonding the drug to any of the dendrimers of the present invention. In some such methods, the dendrimer is bonded to the dendrimer through reaction with a peptide linking group on the dendrimer whereas in other such methods, the drug is bonded to the dendrimer through reaction with a non-peptide linking group on the dendrimer.

The dendrimers of the invention may be synthesized utilizing a variety of methods. One such method includes:

(a) reacting a bis(hydroxyalkyl)aminoalkane or a tris(hydroxyalkyl)aminoalkane with a reactant selected from the group consisting of acrylonitrile, acrylic esters, α haloesters, or cyclic anhydrides, such as succinic anhydride, and then esterifying to produce a diester comprising two ester groups and an amine group or a triester comprising three ester groups and an amine group;

(b) protecting the amine group of the diester or the triester to produce a protected diester comprising two ester groups and a protected amine group or a protected triester comprising three ester groups and a protected amine group;

(c) saponifying the two ester groups of the protected diester or the three ester groups of the protected triester to produce a dicarboxylic acid comprising two carboxylic acid groups and the protected amine group or a tricarboxylic acid comprising three tricarboxylic acid groups and the protected amine group;

(d) reacting
  (i) each of the carboxylic acid groups of the dicarboxylic acid or the tricarboxylic acid with a diaminoalkane, a diaminoalkene, a diaminocycloalkane, or a diaminocycloalkene to produce a product that comprises two or three amide-containing branches, wherein each of the amide-containing branches produced by the reaction of the carboxylic acid groups with the diaminoalkane, the diaminoalkene, the diaminocycloalkane, or the diaminocycloalkene comprises a protected amino group, wherein one of the amino groups of the diaminoalkane, the diaminoalkene, the diaminocycloalkane, or the diaminocycloalkene is protected; or
  (ii) each of the carboxylic acid groups of the dicarboxylic acid or the tricarboxylic acid with a hydroxyaminoalkane, a hydroxyaminoalkene, a hydroxyaminocycloalkane, or a hydroxyaminocycloalkene to produce a product that comprises two or three ester-containing branches, wherein each of the ester-containing branches produced by the reaction of the carboxylic acid groups with the hydroxyaminoalkane, the hydroxyaminoalkene, the hydroxyaminocycloalkane, or the hydroxyaminocycloalkene comprises a protected amino group, wherein the amino group of the hydroxyaminoalkane, the hydroxyaminoalkene, the hydroxyaminocycloalkane, or the hydroxyaminocycloalkene is protected;

(e) selectively deprotecting the protected amino groups at the end of the amide-containing or ester-containing branches introduced in (d) to produce a product with deprotected amine groups; and (f) guanidinylating, amidinylating, ureidolating or thioureidolating the product with deprotected amine groups produced after selectively deprotecting in (e) to produce the dendrimer.

By way of non-limiting example, FIG. 1 shows a method for synthesizing a compound according to the present invention. As shown in FIG. 1, the reaction of a tris(hydroxyalkyl) alkane with a Michael addition agent such as, but not limited to, acrylonitrile, followed by esterification, produces compound 1, a triester having three ester groups and an amine group. The amine group of compound 1 is protected with a Cbz protecting group. Subsequent saponification of the three ester groups of the Cbz-protected amine compound may be used to prepare tricarboxylic acid compound 2 which include three carboxylic acid groups and a protected amine. Reaction of the three carboxylic acid groups of the Cbz-protected amine compound 2 with a diaminoalkane such as, but not limited to, mono-Boc protected 1,2-diaminoethane followed by selective deprotection by removal of the Boc groups and then guanidylation with $(Boc)_2$TfGuan (N,N'-di(t-butoxycarbonyl)-N"-triflylguanidine) affords dendrimer 3. Notably, one of skill in the art will immediately recognize that Cbz-protected amine compound 2 may also be reacted with a hydroxyaminoalkane in which the amino group is protected such as, but not limited to, 2-(t-butoxycarbonylamino)-1-ethanol, 3-(t-butoxycarbonylamino)-1-propanol, or 4(t-butoxycarbonylamino)-1-butanol to produce a product having three ester-containing branches. The product with ester-containing branches may then be selectively deprotected and guanidinylated to produce an ester-containing analog of dendrimer 3.

In some methods for synthesizing a dendrimer, (a) includes reacting the tris(hydroxyalkyl)aminoalkane with acrylonitrile. In some such methods the tris(hydroxyalkyl)aminoalkane is a tris(hydroxyalkyl)aminomethane such as tris(hydroxymethyl)aminomethane. In other methods for synthesizing a dendrimer, (a) includes reacting the bis(hydroxyalkyl)aminoalkane with acrylonitrile. In some such methods, the bis(hydroxyalkyl)aminoalkane is a bis(hydroxymethyl)aminomethane such as bis(hydroxymethyl)aminomethane.

In still other methods for synthesizing a dendrimer, the amine group of the diester or the triester is protected in (b) with a benzyloxycarbonyl (Cbz) group.

In yet other methods for synthesizing a dendrimer, (d) further includes reacting each of the two carboxylic acid groups of the dicarboxylic acid or each of the three carboxylic acid groups of the tricarboxylic acid with a mono-protected 1,2-diaminoethane. In some such methods, the mono-protected 1,2-diaminoethane is protected with a t-butoxycarbonyl group.

In yet other methods for synthesizing a dendrimer, (f) further includes guanidinylating the product produced after selectively deprotecting in (e) using N,N'-di(t-butoxycarbonyl)-N"-triflylguanidine. Other guanidinylating agents include, but are not limited to, cyanamide, N,N'-dialkylcarbodiimide, N,N'-bis(tert-butoxycarbonyl)-thiourea, N,N'-bis(tert-butoxycarbonyl)-S-methyl-isothiourea, S-methyl-isothiourea, 1H-benzotriazole-1-carboxamine, N,N'-bis(tert-butoxycarbonyl)-1H-benzotriazole-1-carboxamine, N,N'-bis(tert-butoxycarbonyl)-5-chloro-1H-benzotriazole-1-carboxamidine, N,N'-bis(tert-butoxycarbonyl)-6-nitro-1H-benzotriazole-1-carboxamidine, 1H-pyrazole-1-carboxamidine, N,N'-bis(tert-butoxycarbonyl)-1H-pyrazole-1-carboxamidine, N,N'-bis(tert-butoxycarbonyl)-4-nitro-1H-pyrazole-1-carboxamidine, N,N'-bis(tert-butoxycarbonyl)-N"-trifluoromethylsolfonyl guanidine, and N,N'-bis(benzyloxycarbonyl-N"-trifluoromethylsulfonyl guanidine.

In yet other methods for synthesizing a dendrimer, the method further includes (g) deprotecting the amine group that was protected in (b). In some such embodiments, the method further includes (h) coupling the product of (g) with a compound comprising a carboxylic acid and a protected amine group to produce a dendrimer with a protected amine group. By way of nonlimiting example, as shown in FIG. 1, the Cbz group of dendrimer 3 may be removed using catalytic hydrogenation and the resulting product may then be coupled with Cbz-β-alanine using standard coupling reagents such as, but not limited to, 1-ethyl-3-(3-dimethylamino-propylcarbodiimide (EDC)/1-hydrobenzotriazole (HOBt) chemistry to afford Cbz-protected dendrimer 4. In some such methods, the compound comprising a carboxylic acid and a protected amine group of (h) is a benzyloxycarbonyl protected β-alanine. In other such methods, the method for synthesizing the dendrimer further includes (i) removing the protecting group from the protected amine group introduced in step (h). In some such embodiments, removing the protecting group in (i) includes hydrogenating the dendrimer with the protected amine group produced in step (h). For example, the Cbz protecting group of dendrimer 4 may be removed using catalytic hydrogenation to produce a dendrimer 5 that includes a free amine group.

Transport molecules and dendrimers with detection molecules of the invention may also be synthesized using a variety of methods. One such method includes:

(j) following (a), (b), (c), (d), (e), (f), (g), (h), and (i) for the method for synthesizing a dendrimer;

(k) optionally reacting the dendrimer with one or more linking molecule to produce a dendrimer comprising a linking group;

(l) reacting a first reactive group of a biologically active molecule or a first reactive group of a detection molecule with the dendrimer of (j) or the linking group of the dendrimer of (k) to produce a transport molecule comprising at least two protected guanidine groups, amidine groups, ureido groups, or thioureido groups or a dendrimer comprising a detection molecule and at least two protected guanidine groups, amidine groups, ureido groups, or thioureido groups; and (m) removing the protecting groups from the protected guanidine groups, amidine groups, ureido groups, or thioureido groups.

Figure 6:
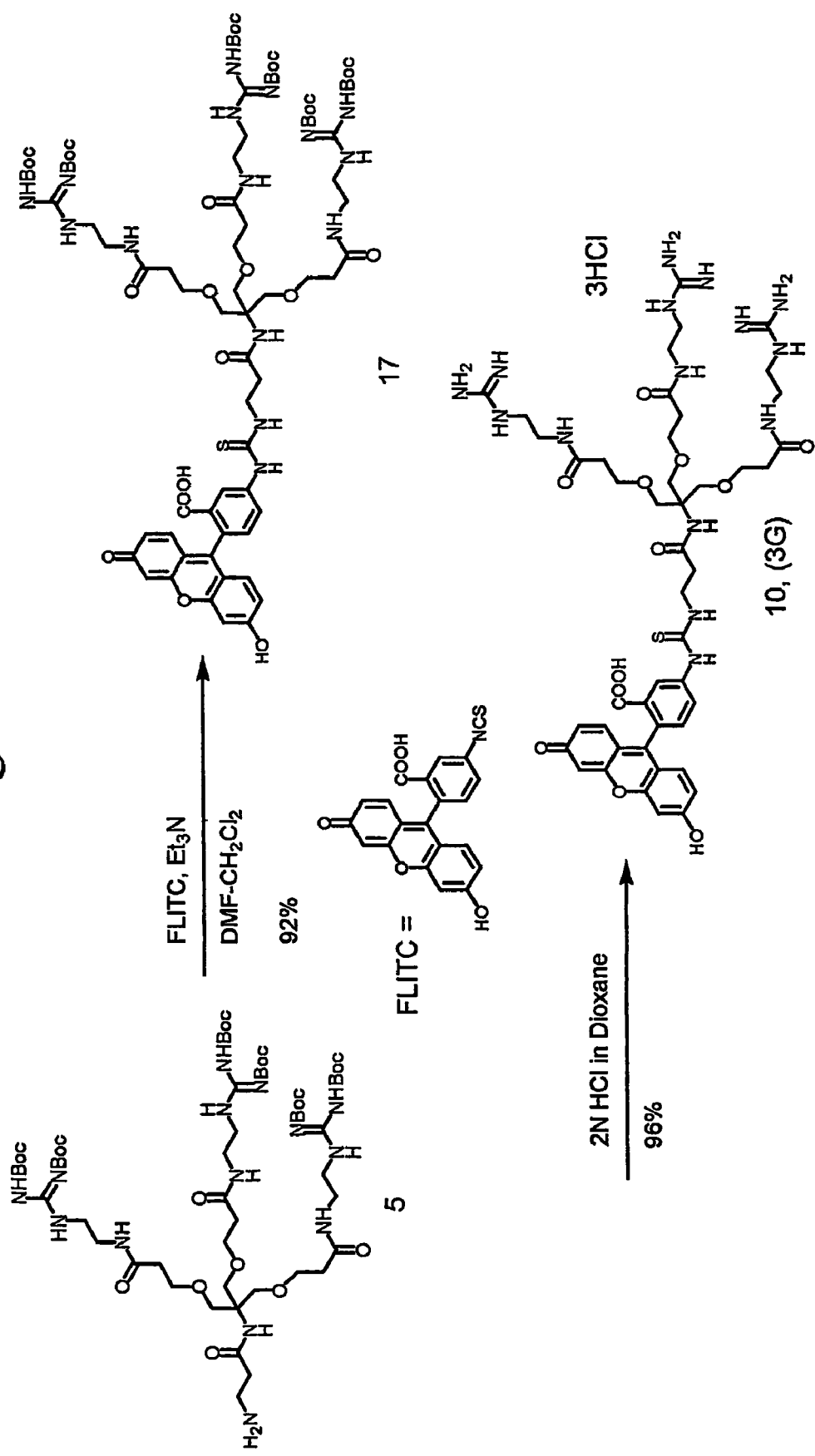
FIG. 6 depicts a reaction scheme for the synthesis of a dendritic oligo-guanidines that includes three guanidine groups in identical chemical environments and a fluorescein detection molecule linked to the dendrimer by a thiourea group.

By way of nonlimiting example, a method for synthesizing a dendrimer that includes a detection molecule is shown in FIG. 6. As shown in FIG. 6, dendrimer 5 may be reacted with an isothiocyanate group on a detection molecule such as fluorescein to produce a dendrimer (17) with three Boc-protected guanidine groups. Removal of the Boc protecting groups affords dendrimer 10.

Another method for synthesizing a dendrimer of the present invention includes guanidinylating, amidinylating, ureidolating, or thioureidolating at least two branches of a core molecule that includes at least two branches and two free amine groups to produce a dendrimer with at least two guanidine groups, at least two amidine groups, at least two ureido groups, or at least two ureido groups wherein each of the at least two branches of the core molecule comprises at least one of the at least two free amine groups prior to being guanidinylated, amidinylated, ureidolated, or thioureidolated. By way of nonlimiting example, FIG. 1 shows that a core molecule (such as the triamine produced by reaction of mono-Boc protected 1,2-diaminoethane with tricarboxylic acid 2 followed by removal of the Boc groups) may be guanidinylated with a guanidinylating agent such as, but not limited to, N,N'-di(t-butoxycarbonyl)-N"-trifiylguanidine, to produce a dendrimer (3) that includes three branches and three guanidine groups. In some such methods, the core molecule further includes at least one protected amine group prior to being guanidinylated, amidinylated, ureidolated, or thioureidolated. In other methods, the core molecule includes at least three branches and at least three free amine groups, wherein each of the at least three branches of the core molecule includes at least one of the at least three free amine groups prior to being guanidinylated, amidinylated, ureidolated, or thiouridolated, and each of the at least three branches is guanidinylated during guanidinylation, is amidinylated during amidinylation, is ureidolated during ureidolation, or is thioureidolated during thioureidolation. In yet other such methods, each of the at least two or the at least three branches of the core molecule has the same structure. In still other methods, each of the at least two or the at least three branches of the core molecule is in an identical chemical environment. In yet other methods of synthesizing a dendrimer, the core molecule is guanidinylated to produce the dendrimer, wherein the dendrimer includes protected guanidine groups. In other methods, one of the at least two free amine groups is bonded to a terminal carbon atom of one of the at least two branches of the core molecule and a second of the at least two free amine groups is bonded to a terminal carbon atom of a second of the at least two branches of the core molecule. In some such methods, each of the at least two branches of the core molecule includes an amide bond and the amide is formed by reacting a carboxylic acid group on a precursor of the core molecule with a compound that includes a free amine group and a protected amine group. In other methods of synthesizing a dendrimer, one of the at least three free amine groups is bonded to a terminal carbon atom of one of the at least three branches of the core molecule, a second of the at least three free amine groups is bonded to a terminal carbon atom of a second of the at least three branches of the core molecule, and a third of the at least three free amine groups is bonded to a terminal carbon atom of a third of the at least three branches of the core molecule. In some such methods, each of the at least three branches of the core molecule includes an amide bond and the amide is formed by reacting a carboxylic acid group on a precursor of the core molecule with a compound that includes a free amine group and a protected amine group. In some methods for synthesizing a dendrimer, the core molecule includes a group of formula I, a group of formula III, or a group of formula IV.

The invention further provides a transport molecule produced by any of the methods for synthesizing a transport molecule and a dendrimer molecule produced by any of the methods for synthesizing a dendrimer.

The invention further provides kits that include at least two of any of the dendrimers of the present invention or at least one dendrimer of the present invention and a linking molecule. In some embodiments, the kit includes at least two dendrimers and at least one linking molecule for linking the dendrimer to a biologically active molecule or a detection molecule. In still other embodiments, the kit includes instructions for attaching a biologically active molecule to the dendrimer using the linking molecule.

The invention further provides a library that includes a plurality of dendrimers or a library that includes a plurality of transport molecules. In some embodiments, the library includes a plurality of both dendrimers and transport molecules. The libraries of the invention can be employed for determining the best dendrimers for use with a specific biologically active molecule. More generally, the libraries may be used to screen a large number of dendrimers and transport molecules to determine which exhibit desirable properties.

A method of preparing pharmaceutical formulations includes mixing any of the above-described transport molecules and/or dendrimers with a pharmaceutically acceptable carrier and water or an aqueous solution.

The present invention, thus generally described, will be understood more readily by reference to the following examples, which are provided by way of illustration and are not intended to limit the present invention.

EXAMPLES

Introduction

New non-peptidic, scaffold-based structures that include multiple guanidine groups have been synthesized and characterized. The synthesis and characterization of dendrimers with and without fluorescent tag detection molecules was accomplished. The fluorescent detection molecules were useful in evaluating cellular uptake of the dendrimers. The syntheses of target dendritic molecules was accomplished using a convergent coupling of a core molecule and guanidine-containing structures with and without a fluorescent tag. This approach allows for the preparation of a wide array of molecule transporters and the development of a library of compounds for clinical investigations. A guanidine-containing key template dendrimer (5) was readily synthesized according to the reaction scheme shown in FIG. 1. A tris(hydroxyalkyl)amino-methane such as tris(hydroxymethyl)aminomethane was converted to the corresponding tri-nitrile compound by Michel-type addition to acrylonitrile. The three nitrile groups were transformed to ethyl esters under anhydrous acidic conditions to produce amino tri-ester (1) with three ester groups in identical chemical environments. The amino group of compound 1 was then protected with a benzyloxycarbonyl (Cbz) group. Basic hydrolysis of the resulting Cbz-protected amine provided the tri-acid (2). Coupling of tri-acid (2) with a mono-Boc-protected diaminoalkane or diaminocycloalkane (Doc t-butoxycarbonyl) such as, mono-Boc-protected 1,2-diaminoethane, 1,3-diaminopropane, 1,4-diaminobutane, 1,5-diaminopentane, 1,6-diaminohexane, cis and trams 1,2-diaminocyclohexane, cis and trans 1,4-diaminocyclohexane, and others or a mono-Boc protected diaminoalkene or diaminocycloalkene such as mono-Boc protected 1,6-diamino-3-hexene, 1,2-cis diaminocyclohex-4-ene, and others, followed by removal of the Boc protecting group with HCl in dioxane and guanidylation with N,N'-diBoc-N"-triflylguanidine (see Feichtinger, L. et al. *J. Org. Chem.*, 63, p. 8432 (1998)) yielded the Cbz-protected dendrimer (3) that includes three Boc-protected guanidine groups in identical chemical environments. Removal of the Cbz group by hydrogenation over Pd—C in ethanol followed by reaction with N-Cbz-β-alanine using standard 1-ethyl-3-(3-dimethylamino-propylcarbodiimide (EDC)/1-hydrobenzotriazole (HOBt) chemistry afforded the Cbz-protected chain-extended dendrimer (4) with three Boc-protected guanidine groups in identical chemical environments. Removal of the Cbz protecting group by hydrogenation over Pd—C in ethanol afforded the template dendrimer (5). The coupling of various core structures such as compounds 6, 7, 8, and 9 shown in FIG. 2 with template dendrimer (5) was straightforward and involved amide bond formation using appropriate activation reagents such as, but not limited to, HOBt, EDC, and thionyl chloride. Fluorescent detection molecules were readily attached to the dendrimers after removal of the Cbz protecting groups by reaction with fluorescein isothiocyanate (FLITC). Subsequent deprotection of the Boc groups provided dendritic molecule containing various numbers of guanidine groups and a fluorescein label for use in analyzing cellular uptake.

Figure 13B:
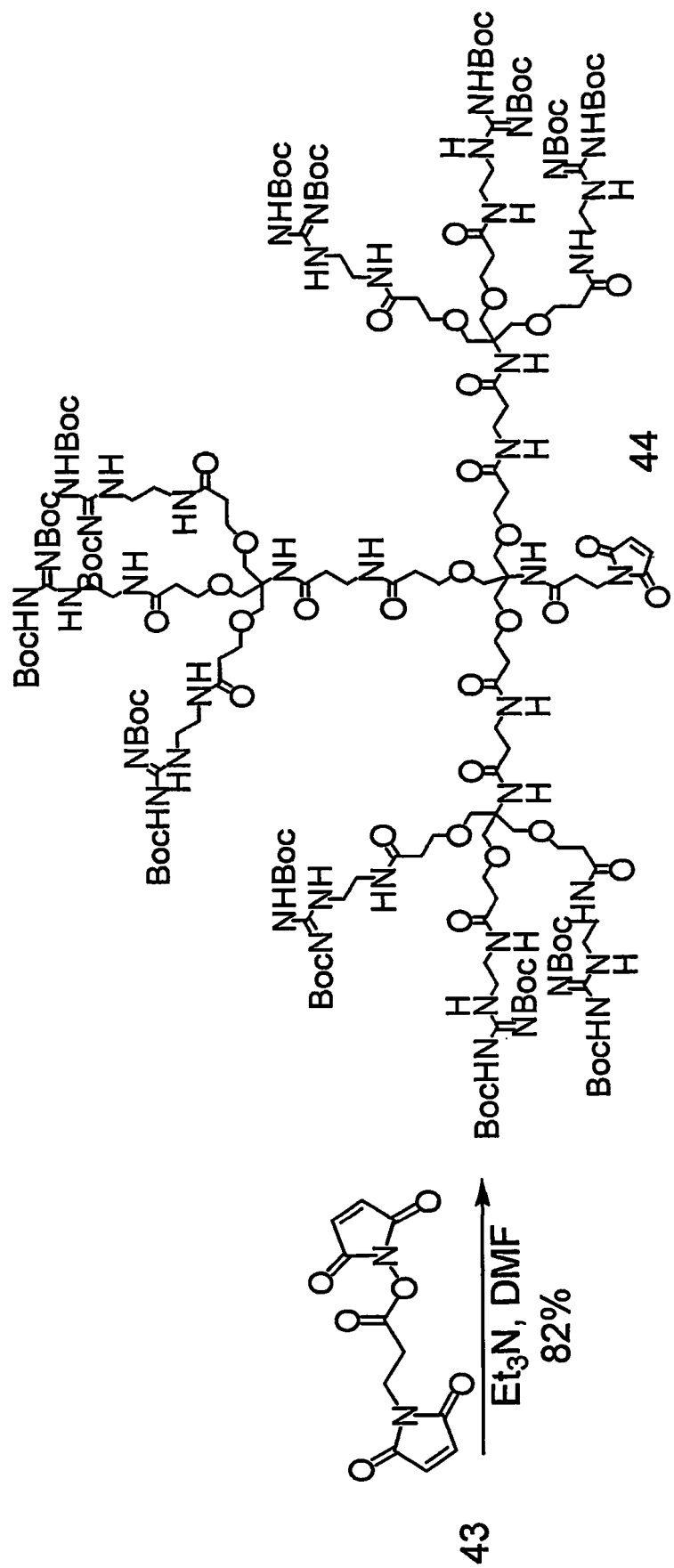

The synthesis of a Boc-protected dendrimer (44) with a maleimide group is shown in FIG. 13B. The reactive maleimide functional group serves as a site for linking a biologically active molecule to the dendrimer. The Cbz-protected tricarboxylic acid (2) was converted to a dendrimer with nine Boc-protected guanidine groups (42) in identical chemical environments by reaction with the template dendrimer (5) in 93% yield by the typical coupling reaction using EDC and HOBt. Subsequent hydrogenation with Pd—C afforded the free amine Boc-protected dendrimer (43). Treatment of the Cbz-deprotected dendrimer (43) with N-succinimidyl 3-maleimidopropionate in DMF afforded the desired dendritic maleimido guanidine with nine Boc-protected guanidine groups (44) in high yield. Various other linkers may be used to bond biologically active molecules to the dendrimers of the present invention Examples of just some of the linkers and biologically active molecules are shown in FIG. 15. An array of linkers may be used to link biologically active cargo molecules to the dendrimers of the present invention. After transport into the cell of a mammal, human, or plant, the cargo molecules are released by enzymatic cleavage such as by proteases, esterases, or phosphatases, by pH-specific hydrolysis, or by reduction within the cell. Although the dendrimers of the invention do not include peptide bonds, linkers containing peptides may be used to secure biologically active molecules to the dendrimers of the present invention as shown in 5 where a biologically active molecule, 5-mercaptopurine, is secured to a dendrimer with six guanidine groups in identical chemical environments through a linker that includes a peptide formed from cysteine and two alanines. Formation of a disulfide bond between the sulfhydryl group (—SH) of the cysteine residue and the sulfhydryl group of the 5-mercaptopurine affords the desired molecule transporter (16).

The starting materials for the syntheses described below may be obtained from Aldrich Chemical, Milwaukee, Wis., Bachem Calif., Inc., Torrance, Calif., Calbiochem-Novabiochem Corp., San Diego, Calif., and Acros Organics/Fisher Scientific, Pittsburgh, Pa. The solvents required for the reactions can be obtained from VWR Scientific, Pittsburgh, Pa.

Synthesis and Characterization of Dendrimers

Example 1

Synthesis and Characterization of a Template Dendrimer (5) with Three Protected Guanidine Groups The synthesis of dendrimer (5) with three Boc-protected guanidine groups is illustrated in FIG. 1 and is set forth in greater detail below.

Step 1: Synthesis of 3-[2-Amino-3-(2-cyanoethoxy)-2-(2-cyanoethoxymethyl)-propoxy]propionitrile To a suspension of tris(hydroxymethyl)aminomethane (5.0 g, 41.25 mmol) in 1,4-dioxane (10 mL) was added aqueous 40% KOH (0.63 mL, 4.13 mmol), and the mixture was stirred for 10 minutes. The reaction solution was cooled to 0° C., and acrylonitrile (9.0 mL, 136.2 mmol) was added using a syringe. The reaction was then warmed to room temperature, stirred overnight, and concentrated under reduced pressure.

The residue was diluted with CH$_2$Cl$_2$ (120 mL) and washed with saturated aqueous NaHCO$_3$ (2×70 mL) and (H$_2$O(2×70 mL). The organic phase was dried over anhydrous MgSO$_4$, and the solvent was removed under reduced pressure. The resulting residue was purified by a flash column chromatography (on silica gel, MeOH:CH$_2$Cl$_2$=1:10) to afford 11.08 g (96%) of the desired tri-nitrile as a slightly yellow liquid. $^1$H NMR (CDCl$_3$): δ 3.68 (t, J=6.2 Hz, 6H, CH$_2$O), 3.44 (s, 6H, CH$_2$O), 2.60 (t, J=6.2 Hz, 6H, CH$_2$CN).

Step 2: Synthesis of 3-[2-Amino-3-(2-ethoxycarbonylethoxy)-2-(2-ethoxycarbonylethoxymethyl)-propoxy]-propionic acid ethyl ester (1)

The tri-nitrile prepared above (10.0 g, 35.67 mmol) was dissolved in EtOH (50 mL). The solution was saturated with anhydrous HCl gas until it became opaque (about 40 minutes), then refluxed for 6 hours. After the reaction was complete, the solvent was removed under reduced pressure. The residue was diluted with CH$_2$Cl$_2$ (200 mL) and washed with saturated aqueous Na$_2$CO$_3$ (2×150 mL) and (H$_2$O(2×200 mL). The organic phase was dried over anhydrous MgSO$_4$, and the solvent was removed under reduced pressure. The resulting residue was purified by a flash column chromatography (on silica gel, MeOH:CH$_2$Cl$_2$=1:10) to afford 11.18 g (74%) of a tri-ester (1) as a slightly yellow liquid. $^1$H NMR (CDCl$_3$): δ 4.13 (q, J=7.2 Hz, 6H, CH$_2$O), 3.68 (t, J=6.4 Hz, 6H, CH$_2$O), 3.32 (s, 6H, CH$_2$O), 2.53 (t, J=6.4 Hz, 6H, CH$_2$CO), 1.25 (t, J=7.2 Hz, 9H, CH$_3$).

Step 3: Synthesis of 3-[2-Benzyloxycarbonylamino-3-(2-ethoxycarbonylethoxy)-2-(2-ethoxycarbonylethoxymethyl)propoxy]propionic acid ethyl ester To a solution of the tri-ester (1) (11.0 g, 26.09 mmol) in 1,4-dioxane (110 mL) was added aqueous K$_2$CO$_3$ (3.97 g, 28.72 mmol in 11.0 mL of H$_2$O). Benzyl chloroformate (6.0 g, 35.16 mmol) was added dropwise at 0° C., and the reaction was warmed to room temperature stirred for 3 hours. The resulting mixture was cooled in an ice bath, acidified to a pH of about 3 to avoid the hydrolysis of the ester, and concentrated under reduced pressure. The residue was diluted with EtOAc (200 mL) and washed with 1N NaHCO$_3$ (150 mL) and H$_2$O (2×200 mL). The organic phase was dried over anhydrous MgSO$_4$, and the solvent was removed under reduced pressure. The resulting residue was purified by flash column chromatography (on silica gel, EtOAc:n-hexanes=1:3) to afford 11.88 g (82%) of the Cbz-protected tri-ester of (1) as a colorless syrup. $^1$H NMR (CDCl$_3$): δ 7.33 (m, 5H, ArH), 5.26 (s, 1H, NH), 5.03 (s, 2H, OCH$_2$Ar), 4.12 (q, J=7.2 Hz, 6H, CH$_2$O), 3.67 (t, J=6.4 Hz, 6H, CH$_2$O), 3.65 (s, 6H, CH$_2$O), 2.52 (t, J=6.4 Hz, 6H, CH$_2$CO), 1.25 (t, J=7.2 Hz, 9H, CH$_3$).

Step 4: General Procedure A: Basic Hydrolysis of Esters

Synthesis of 3-[2-Benzyloxycarbonylamino-3-(2-carboxyethoxy)-2-(2-carboxyethoxymethyl)propoxy]-propionic acid (2)

A solution of the tri-ester prepared above in Step 3 (20.00 g, 36.00 mmol) in MeOH (200 mL) was treated with aqueous NaOH solution (17.28 g, 432.0 mmol in 200 mL of H$_2$O) for 4 hours at room temperature. The mixture was then concentrated to total volume of 150 mL. The resulting mixture was poured into H$_2$O (200 mL), and washed with Et$_2$O (250 mL). The aqueous phase was acidified with 2N HCl to a pH of about 3 and extracted with EtOAc (2×300 mL). The combined organic phase was washed with a brine (300 mL) and H$_2$O (2×300 mL), and dried over anhydrous Na$_2$SO$_4$. After evaporation, the desired tri-carboxylic acid (2) was obtained in 98% yield (16.65 g) as a white solid. $^1$H NMR (CDCl$_3$): δ 9.62 (br, s, 3H, COOH), 7.33 (m, 5H, ArH), 5.26 (s, 1H, NH), 5.03 (s, 2H, OCH$_2$Ar), 3.65 (s, 6H, CH$_2$O), 3.64 (t, J=6.2 Hz, 6H, CH$_2$O), 2.55 (t, J=6.2 Hz, CH$_2$CO).

Step 5: General Procedure B: Amide Bond Formation Using HOBt-EDC

Synthesis of {2-[2-(2-tert-Butoxycarbonylaminoethylcarbamoyl)-ethoxy]-1,1-bis-[2-(2-tert-butoxycarbonylamino-ethylcarbamoyl)-ethoxymethyl]-ethyl}-carbamic acid benzyl ester Tri-carboxylic acid compound (2) may be used as a precursor core molecule to produce a core molecule ready for guanidinylation (See Step 6). To a solution of the tri-carboxylic acid (2) (15.88 g, 0.034 mol) and t-butoxycarbonylaminoethylamine (19.39 g, 0.121 mol) in CH$_2$Cl$_2$ (300 mL) was added 1-hydroxybenzotriazole (HOBt) (16.37 g, 0.121 mol) and then 1-ethyl-3-(3-dimethylaminopropyl)-carbodiimide (EDC) (23.22 g, 0.121 mol) at ice-bath temperature. The mixture was stirred overnight and poured into 300 mL of H$_2$O. The resulting mixture was extracted with CH$_2$Cl$_2$ (2×300 mL), washed with 1N HCl (2×300 mL) saturated NaHCO$_3$ (2×300 mL), and H$_2$O (2×300 mL). The organic phase was dried over anhydrous Na$_2$SO$_4$ and concentrated in vacuo. Purification of the resulting residue by a flash column chromatography (on silica gel, MeOH:CH$_2$Cl$_2$=1:10) afforded 25.98 g (86%) of the desired product as a colorless foam-shaped solid. $^1$H NMR (CDCl$_3$): δ 7.36 (m, 5H, ArH), 6.91 (br s, 3H, NH), 5.56 (s, 1H, NH), 5.34 (br s, 3H, NH), 5.03 (s, 2H, OCH$_2$Ar), 3.68 (t, J=6.0 Hz, 6H, CH$_2$O), 3.64 (s, 6H, CH$_2$O), 3.32 (m, 6H, CH$_2$NH), 3.23 (m, 6H, CH$_2$NHCO), 2.42 (t, J=6.0 Hz, 6H, CH$_2$CO), 1.42 (s, 27H, t-Bu); ESI-MS m/z 933 [M+Cl]$^-$; 921 [M+Na]$^+$, 899 [M+H]$^+$, 619.6[M–H]$^-$.

Step 6: General Procedure C: Deprotection of Boc and Guanidylation Using N,N'-diBoc-N''-triflylguanidine]

Synthesis of [2-(2-{2-[(Bis-tert-butoxycarbonylaminomethyl)-amino]-ethylcarbamoyl}-ethoxy)-1,1-bis-(2-{2-[(bis-tert-butoxycarbonylamino-methyl)-amino]-ethylcarbamoyl}-ethoxymethyl)-ethyl]-carbamic acid benzyl ester (3)

To a solution of the Boc-protected compound prepared above in Step 5 (13.45 g, 14.97 mmol) in 1,4-dioxane (75 mL) was added 4N HCl in dioxane (75 mL) by syringe under a nitrogen atmosphere at ice bath temperature. The resulting mixture was then vigorously stirred for 1 hour. The resulting mixture was then concentrated on the rotary evaporator and dried in vacuo to afford a white solid. The solid was dissolved in 30 mL of H$_2$O and insoluble precipitate was filtered off. The filtrate was lyophilized to provide a colorless foam-shaped solid as the deprotected HCl salt. The resulting HCl salt was dissolved in MeOH (30 mL) and diluted with CHCl$_3$ (300 mL). To the resulting clear solution was added Et$_3$N (17.45 mL, 125.2 mmol). Next, N,N'-diBoc-N''-triflylguanidine (24.47 g, 62.57 mmol) was added at 0° C. The mixture was stirred overnight, poured into 500 mL of H$_2$O, and extracted with CH$_2$Cl$_2$ (3×500 mL). The organic phase was washed with 1N HCl (2×500 mL), saturated NaHCO$_3$ (500 mL) and H$_2$O (2×500 mL), and then dried over anhydrous Na$_2$SO$_4$. After removal of the solvent under reduced pressure, the resulting crude produce was purified by flash column chromatography (on silica gel, MeOH:CH$_2$Cl$_2$=1:10). The desired Boc-protected tri-guanidine (3) was obtained in 86% yield (16.97 g) as a foam-shaped solid, m.p. 86~88° C. $^1$H NMR (CDCl$_3$): δ 11.40 (s, 3H, NH), 8.56 (t, J=5.6 Hz, 3H, NH), 7.76 (t, J=5.6 Hz, 3H, NH), 7.31 (m, 5H, ArH), 5.44 (s, 1H, NH), 4.99 (s, 2H, OCH$_2$Ar), 3.66 (t, J=5.6 Hz, 6H, CH$_2$O), 3.60 (s, 6H, CH$_2$O), 3.50 (dt, J=5.6, 11.2 Hz, 6H, CH$_2$NHCO), 3.37 (dt, J=5.6, 11.2 Hz, CH$_2$NH), 2.40 (t, J=5.6 Hz, CH$_2$CO), 1.48 (s, 27H, t-Bu), 1.46 (s, 27H, t-Bu); ESI-MS m/z 1359[M+Cl]$^-$; 1347[M+Na]$^+$, 1325[M+H]$^+$, 1323 [M−]$^-$.

Step 7: General Procedure D: Deprotection of Cbz Group by Catalytic Hydrogenation on Pd—C A suspension of the Cbz-protected compound (3) prepared in Step 6 (9.12 g, 6.88 mmol) and 10% Pd—C (1.0 g) in EtOH (250 mL) was stirred overnight under a hydrogen atmosphere (using a balloon). After the reactant disappeared on TLC (thin layer chromatography), the mixture was filtered through a Celite pad. The filtrate was concentrated under reduced pressure affording an amino-trisguanidine (7.74 g, 94%) as a foam-shaped solid. $^1$H NMR (CDCl$_3$): δ 11.39 (s, 3H, NH), 8.58 (t, J=5.4 Hz, 3H, NM), 8.04 (s, 3H, NH), 3.70 (t, J=5.8 Hz, 6H, CH$_2$O), 3.53 (dt, J=5.6, 11.2 Hz, 6H, CH$_2$O), 3.40 (m, 12H, CH$_2$NH and CH$_2$NHCO), 2.45 (t, J=5.8 Hz, 6H, CH$_2$CO), 1.47 (s, 27H, t-Bu), 1.45 (s, 27H, t-Bu); ESI-MS m/z 1225[M+Cl]$^-$, 1191[M+H]$^+$, 1189[M−H]$^-$.

Step 8: Synthesis of Compound 4

To a solution of the amino-tris-guanidine prepared as above in Step 7 (6.20 g, 5.18 mmol) and Cbz-β-alanine (1.38 g, 6.21 mmol) in CH$_2$Cl$_2$ (200 mL), was added 1-hydrobenzotriazole (HOBt) (0.84 g, 6.21 mmol), and then 1-ethyl-3-(3-dimethylaminopropyl)-carbodiimide(EDC) (1.19 g, 6.21 mmol) at ice-bath temperature. The mixture was stirred overnight and poured into 200 mL of H$_2$O. The resulting mixture was extracted with CH$_2$Cl$_2$ (2×200 mL), washed with 1N HCl (2×300 mL), saturated NaHCO$_3$ (2×300 mL) and H$_2$O (2×300 mL). The organic phase was dried over anhydrous Na$_2$SO$_4$ and concentrated in vacuo. Purification of the resulting residue by flash column chromatography (on silica gel, MeOH:CH$_2$Cl$_2$=1:10) afforded 6.72 g (93%) of the desired product (4) as a colorless foam-shaped solid. $^1$H NMR (CDCl$_3$): δ 11.40 (s, 3H, NH), 8.62 (s, 3H, NH), 7.75 (s, 3H, NH), 7.34 (m, 5H, ArH), 6.70 (s, 1H, NH), 5.89 (s, 1H, NH), 5.07 (s, 2H, OCH$_2$Ar), 3.66 (m, 12H, CH$_2$O), 3.52 (m, 6H, CH$_2$NHCO), 3.45 (m, 2H, CH$_2$NHCO), 3.38 (m, 6H, CH$_2$NH), 2.44 (t, J=5.6 Hz, 2H, CH$_2$CO), 2.40 (t, J=5.6 Hz, 6H, CH$_2$CO), 1.48 (s, 27H, t-Bu), 1.47 (s, 27H, t-Bu); ESI-MS m/z 1417[M+Na]$^+$, 1395[M+H]$^+$.

Step 9: Synthesis of Dendrimer 5

A suspension of the Cbz-protected compound (4) prepared in Step 8 above (2.40 g, 1.72 mmol) and 10% Pd—C (0.2 g) in EtOH (100 mL) was stirred overnight under a hydrogen atmosphere (using a balloon). After the reactant disappeared on TLC (thin layer chromatography), the mixture was filtered through a Celite pad. The filtrate was concentrated under reduced pressure to afford a β-alanine-tris guanidine compound (5) (2.13 g, 98%) as a colorless solid. $^1$H NMR (CDCl$_3$): δ 11.42 (s, 3H, NH), 8.60 (s, 3H, NH), 7.82 (s, 3H, NH), 7.02 (s, 1H, NH), 3.68 (t, J=5.6 Hz, 6H, CH$_2$O), 3.66 (s, 6H, CH$_2$O), 3.54 (dt, J=5.6, 10.8 Hz, 6H, CH$_2$NHCO), 3.40 (dt, J=5.6, 10.8 Hz, 6H, CH$_2$NHCO), 2.95 (t, J=6.0 Hz, 6H, CH$_2$NH$_2$), 2.41 (t, J=5.6 Hz, 6H, CH$_2$CO), 2.33 (t, J=5.6 Hz, 2H, CH$_2$CO), 1.48 (s, 27H, t-Bu), 1.46 (s, 27H, t-Bu); ESI-MS m/z 1296[M+Cl]$^-$, 1284[M+Na]$^+$, 1262[M+H]$^+$, 1260 [M−H]$^-$.

Example 2

Synthesis and Characterization of a Fluorescein-Labeled Dendrimer (10)

The synthesis of fluorescein-labeled dendrimer (10) from dendrimer (5) is illustrated in FIG. 6 and is set forth in greater detail below.

Step 1: General Procedure E: Coupling Reaction with Fluorescein Isothiocyanate (FLITC)

Synthesis of Compound 17
The starting amine (5) (0.15 g, 0.12 mmol) and fluorescein isothiocyanate (FLITC) (0.056 g, 0.14 mmol) were dissolved in a mixture of DMF and CH$_2$Cl$_2$ (6 mL, 1:5 ratio) at room temperature. The reaction was cooled to 0° C., and then an excess amount of Et$_3$N (66 μL, 0.48 mmol) was added dropwise. An orange colored precipitate was immediately formed and remained during the entire period of the reaction. After completion of the reaction, the insoluble precipitate was filtered off; and the solvent was removed under reduced pressure. The residue was diluted with CH$_2$Cl$_2$ (15 mL), washed with 1N HCl (2×15 mL) and H$_2$O (2×15 mL). The organic phase was dried over anhydrous Na$_2$SO$_4$ and evaporated under reduced pressure to afford 0.18 g (92%) of fluorescein-labeled guanidine (17) as an orange colored foam-shaped solid. $^1$H NMR (CD$_3$OD): δ 8.20 (s, 1H, ArH), 7.86 (m, 1H, ArH), 7.22 (m, 2H, ArH), 6.64 (m, 3H, ArH), 6.56 (m, 2H, ArH), 3.86 (m, 2H, CH$_2$NHCS), 3.66 (m, 12H, CH$_2$O), 3.46 (m, 6H, CH$_2$NHCO), 3.38 (m, 6H, CH$_2$NH), 2.58 (m, 2H, CH$_2$CO), 2.42 (m, 6H, CH$_2$CO), 1.48 (s, 27H, t-Bu), 1.46 (s, 27H, t-Bu).

Step 2: General Procedure F: Deprotection of Boc-Protected Guanidine Groups in Fluorescein-Labeled Transport Molecules Synthesis of Compound 10
To a solution of Boc-protected compound prepared in Step 1 above (17) (0.15 g, 0.098 mmol) in dioxane (5 mL) was added 4N HCl in dioxane (5 mL) by syringe under a nitrogen atmosphere at ice bath temperature. Insoluble bright yellow precipitates were immediately formed. The reaction was warmed to room temperature and vigorously stirred for 2 hours. The insoluble precipitate was carefully collected by filtration under a nitrogen gas flow and dried in vacuo to afford a yellow solid. The solid was dissolved in 5 mL of H$_2$O and insoluble precipitate was filtered off. The filtrate was lyophilized to provide 0.10 g (96%) of deprotected HCl salt (10) as a bright yellow foam-shaped solid. $^1$H NMR (D2O): δ 7.98 (s, 1H, ArH), 7.60 (s, 1H, ArH), 7.18 (m, 3H, ArH), 6.82 (m, 4H, ArH), 3.82 (m, 2H, CH$_2$NHCS), 3.54 (m, 12H, CH$_2$O), 3.38-3.18 (m, 12H, CH$_2$NHCO and CH$_2$NH), 2.34 (m, 8H, CH$_2$CO); MALDI-FTMS m/z: 1049.4394 calculated for C$_{46}$H$_{63}$N$_{15}$O$_{12}$S (free guanidine)+Na$^+$. found 1072.4406; ESI-MS m/z 1051 [free guanidine M$^+$+1], 1049 [free guanidine M$^+$−1].

Example 3

Figure 7:
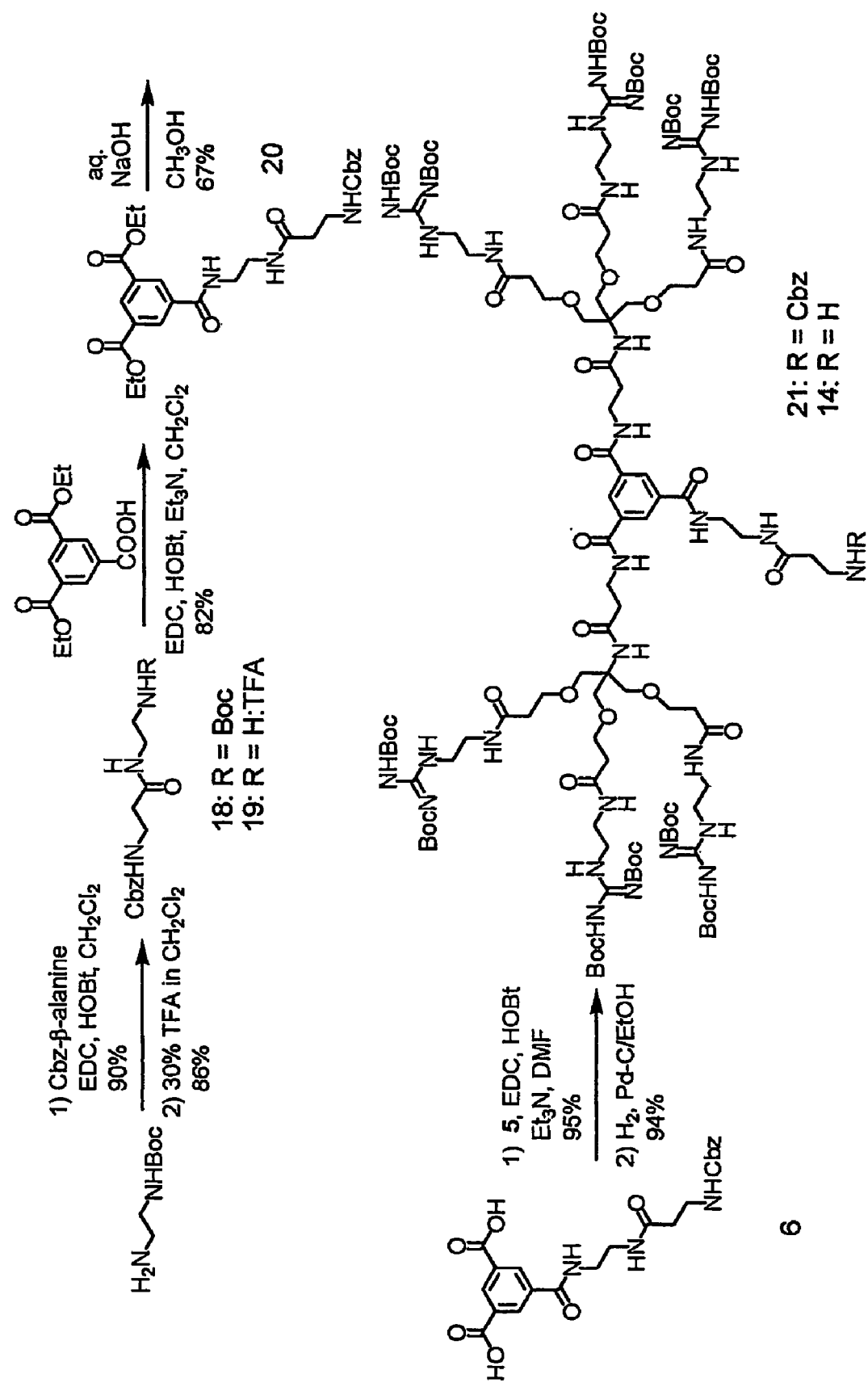
FIG. 7 depicts a reaction scheme for the synthesis of a dendritic oligo-guanidine that includes six protected guanidine groups in identical chemical environments.

Synthesis and Characterization of a Dendrimer (14) with Six Protected Guanidine Groups The synthesis of dendrimer (14) with six Boc-protected guanidine groups is illustrated in FIG. 7 and is set forth in greater detail below.

Step 1: Synthesis of [2-(3-Benzyloxycarbonylamino-propionylamino)-ethyl]-carbamic acid tert-butyl ester (18)

To a solution of mono-Boc protected ethylene diamine (2.0 g, 12.5 mmol) and Cbz-β-alanine (3.35 g, 14.99 mmol) in $CH_2Cl_2$ (40 mL) was added HOBt (2.03 g, 14.99 mmol) and EDC (2.87 g, 14.99 mmol) at ice bath temperature. The mixture was stirred for 4 hours at room temperature and poured into ice water (50 mL). The resulting mixture was extracted with $CH_2Cl_2$ (2×80 mL). The organic phase was washed with 1N HCl (2×80 mL), saturated $NaHCO_3$ (2×80 mL), brine (2×80 mL) and $H_2O$ (2×80 mL), and evaporated under reduced pressure. The residue was recrystallized from methanol to afford the desired product (18) (4.12 g, 90%) as a white solid. $^1H$ NMR ($CDCl_3$): δ 7.32 (m, 5H, ArH), 6.26 (s, 1H, NH), 5.52 (s, 1H, NH), 5.32 (s, 1H, NM), 5.06 (s, 2H, $OCH_2Ar$), 3.45 (t, J=6.0 Hz, 2H, $CH_2NHCO$), 3.32 (t, J=5.6 Hz, 2H, $CH_2NHCO$), 3.23 (t, J=5.6 Hz, 2H, $CH_2NHCO$), 2.28 (t, J=6.0 Hz, 2H, $CH_2CO$), 1.42 (s, 9H, t-Bu).

Step 2: Synthesis of [2-(2-Amino-ethylcarbamoyl)-ethyl]-carbamic acid benzyl ester trifluoroacetic acid salt (19); 5-[2-(3 Benzyloxycarbonylamino-propionylamino)-ethylcarbamoyl]-isophthalic acid diethyl ester (20); and 5-[2-3-Benzyloxycarbonylamino-propionylamino)-ethylcarbamoyl]-isophthalic acid (6)

Boc-protected compound (18) prepared as described in Step 1 above (3.0 g, 8.21 mmol) was treated with 30% trifluoroacetic acid (TFA) in $CH_2Cl_2$ (20 mL) for 30 minutes at room temperature. The resulting mixture was evaporated under reduced pressure. The residue was diluted with dry toluene (5 mL), and then the mixture was evaporated under reduced pressure to afford a crude product (19). Without further purification, the crude compound (19) was used for the subsequent coupling reaction with 3,5-diethoxycarbonyl-benzoic acid (2.18 g, 8.21 mmol) using HOBt (1.33 g, 9.85 mmol) and EDC (1.89 g, 9.85 mmol) in $CH_2Cl_2$ (60 mL). The reaction was conducted under the same condition as described in General Procedure B. After normal workup and removal of the solvent, the resulting residue was recrystallized from methanol to afford the desired diester (20). The subsequent basic hydrolysis of the compound (20) was performed in a mixture of NaOH solution (1.31 g in 20 mL of $H_2O$) and methanol (20 mL) at room temperature for 6 hours. The resulting mixture was poured into ice water (40 mL) and washed with $Et_2O$ (40 mL). The aqueous phase was acidified with 2N HCl until a pH of about 3 was reached. The resulting insoluble precipitate was collected by filtration and dried in vacuo to afford the desired diacid (6) (1.94 g, 67%) as white solid. $^1H$ NMR ($CD_3OD$): δ 8.73 (s, 1H, ArH), 8.68 (s, 2H, ArH), 5.00 (s, 2H, $OCH_2Ar$), 3.48 (m, 2H, $CH_2NHCO$), 3.39 (m, 4H, $CH_2NHCO$), 2.38 (t, J=6.4 Hz, 2H, $CH_2CO$); ESI-MS m/z 492$[M+Cl]^-$; 480$[M+Na]^+$, 458 $[M+H]^+$, 456$[M-H]^-$.

Step 3: Synthesis of Compound 21

Compound 21 was prepared using General Procedure B with diacid 6 (0.11 g, 0.31 mmol), dendrimer 5 (0.94 g, 0.74 mmol), 1-hydrobenzotriazole (HOBt) (0.10 g, 0.74 mmol), and 1-ethyl-3-(3-dimethylaminopropyl)carbodiimide (EDC) (0.15 g, 0.74 mmol) in DMF (10 mL). Purification by flash column chromatography (on silica gel, MeOH:$CH_2Cl_2$=1:15) afforded 0.87 g (95%) of the desired product (21) as a colorless foam-shaped solid. $^1H$ NMR ($CD_3OD$): δ 8.42 (s, 3H, ArH), 7.26 (m, 5H, ArH), 5.04 (s, 2H, $OCH_2Ar$), 3.62 (m, 28H, $CH_2O$ and $CH_2NHCO$), 3.48 (m, 14H, $CH_2NHCO$), 3.38 (m, 16H, $CH_2NHCO$ and $CH_2NH$), 3.23 (m, 6H, $CH_2NHCO$), 2.56 (t, J=6.0 Hz, 4H, $CH_2CO$), 2.42 (m, 14H, $CH_2CO$), 1.48 (s, 54H, t-Bu), 1.45 (s, 54H, t-Bu).

Step 4: Synthesis of Dendrimer 14

The compound 14 was prepared using General Procedure D, using Cbz-protected compound 21 (0.70 g, 0.24 mmol) and Pd—C (0.1 g) in EtOH (150 mL). After filtering off the used Pd—C, removal of the solvent afforded 0.64 g (94%) of the desired amine (14) as a colorless foam-shaped solid. $^1H$ NMR ($CD_3OD$): δ 8.44 (s, 3H, ArH), 3.62 (m, 28H, $CH_2O$ and $CH_2NHCO$), 3.48 (m, 12H, $CH_2NHCO$), 3.40 (m, 16H, $CH_2NHCO$ and $CH_2NH$), 3.22 (t, J=6.2 Hz, 2H, $CH_2NH_2$), 2.64 (t, J=6.2 Hz, 2H, $CH_2CO$), 2.58 (t, J=6.0 Hz, 4H, $CH_2CO$), 2.42 (m, 12H, $CH_2CO$), 1.48 (s, 54H, t-Bu), 1.45 (s, 54H, t-Bu); ESI-MS m/z 2844$[M+Cl]^-$; 2832$[M+Na]^+$, 2810 $[M-H]^-$.

Example 4

Synthesis and Characterization of a Fluorescein-Labeled Dendrimer (11)

Figure 8:
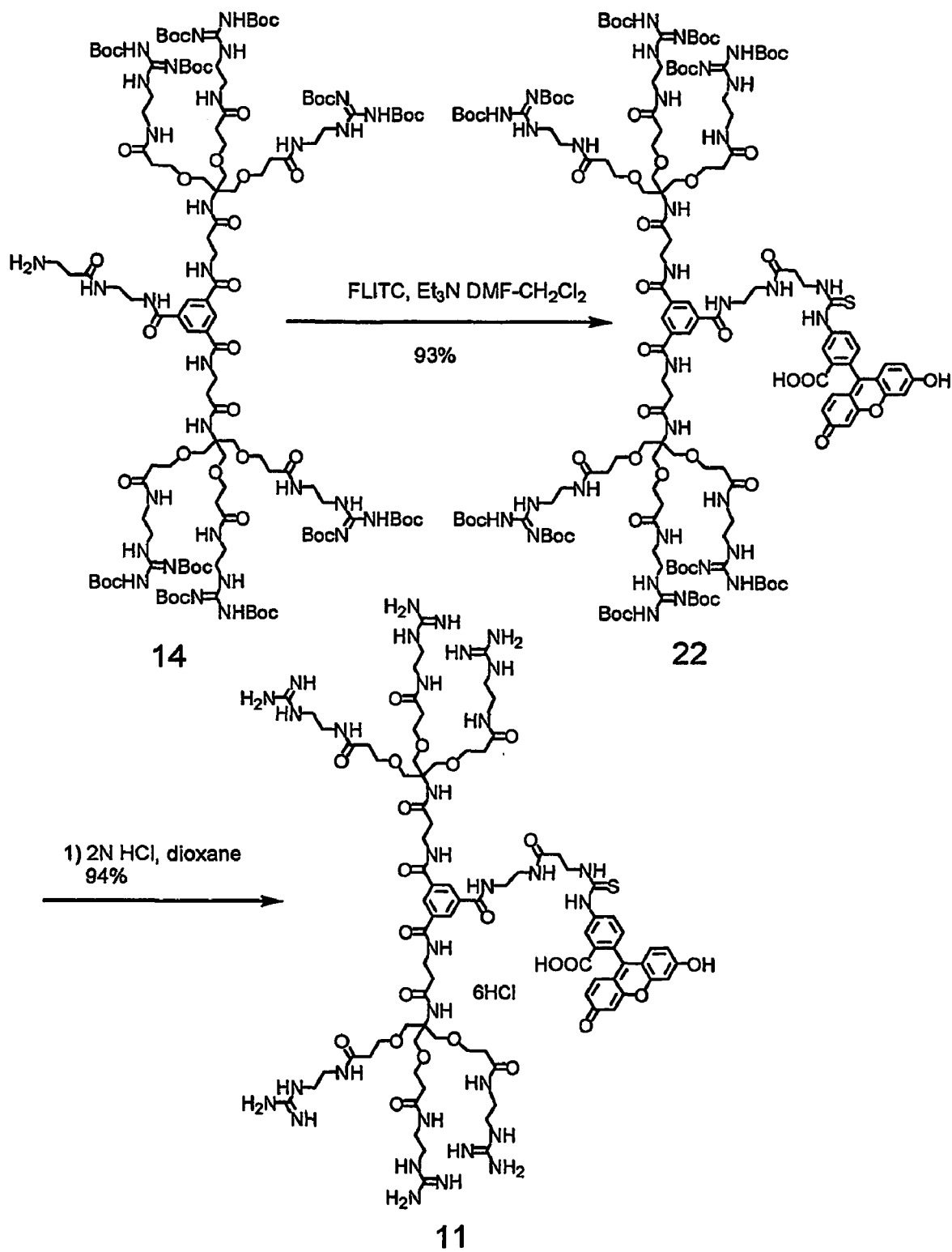
FIG. 8 depicts a reaction scheme for the synthesis of a dendritic oligo-guanidine that includes six guanidine groups in identical chemical environments and a fluorescein detection molecule linked to the dendrimer by a thiourea group.

The synthesis of fluorescein-labeled dendrimer (11) from dendrimer (14) is illustrated in FIG. 8 and is set forth in greater detail below.

Step 1: Synthesis of Compound 22

The compound 22 was prepared using General Procedure E with the dendrimer amine 14 (0.30 g, 0.11 mmol), fluorescein isothiocyanate (FLITC) (0.083 g, 0.21 mmol), and $Et_3N$ (89 mL, 0.64 mmol) in a mixture of DMF and $CH_2Cl_2$ (12 mL, 1:5 ratio). The fluorescein-labeled Boc-protected guanidine (22) was obtained as 0.37 g (93%) of an orange foam-shaped solid. $^1H$ NMR ($CD_3OD$): δ 8.22 (s, 3H, ArH), 7.82 (m, 2H, ArH), 7.02 (m, 2H, ArH), 6.56 (m, 3H, ArH), 6.40 (m, 2H, ArH), 3.78 (m, 2H, $CH_2NHCS$), 3.48 (m, 28H, $CH_2O$ and $CH_2NHCO$), 3.36 (m, 14H, $CH_2NHCO$), 3.22 (m, 16H, $CH_2NHCO$ and $CH_2NH$), 2.44 (t, J=6.2 Hz, 2H, $CH_2CO$), 2.38 (m, 4H, $CH_2CO$), 2.24 (m, 12H, $CH_2CO$), 1.48 (s, 54H, t-Bu), 1.45 (s, 54H, t-Bu).

Step 2: Synthesis of Compound 11

The compound 11 was prepared using General Procedure F with the Boc-protected guanidine 22 (0.18 g, 0.056 mmol) and 2N HCl in dioxane (10 mL). The fluorescein-labeled guanidinium HCl salt (11) was obtained as 0.12 g (94%) of an orange hygroscopic solid. $^1H$ NMR ($CD_3OD$): δ 8.18 (s, 3H, ArH), 7.94 (m, 1H, ArH), 7.62 (m, 1H, ArH), 7.22 (m, 2H, ArH), 7.02-6.68 (m, 5H, ArH), 3.68 (m, 2H, CH$_2$NHCS), 3.52 (m, 28H, CH$_2$O and CH$_2$NHCO), 3.24 (m, 30H, CH$_2$NHCO and CH$_2$NH$_3^+$), 2.42 (m, 2H, CH$_2$CO), 2.32 (m, 14H, CH$_2$CO).

Example 5

Synthesis and Characterization of Transport Molecule (16) with 6-Mercantopurine Bonded to Nonaguanidine Dendrimer The synthesis of transport molecule (16) with nine guanidine groups is illustrated in FIG. 5 and is set forth in greater detail below.

Step 1: Synthesis of Compound 15

The compound 15 is prepared from Boc-protected dendrimer 14 by reacting it with N-acetyl-Cys(S-trityl)-Ala-Ala-COOH using HOBt and EDC to afford Compound 15.

Step 2: Synthesis of Compound 16

The transport molecule 16 is prepared from Boc-protected 15 by reacting it with Li/NH$_3$ to deprotect the S-trityl group. Next, the resulting product is treated with dilithio-bis(5-nitropyridine)(DTNP) to activate the resulting thiol. Treatment of the resulting product with 6-mercaptopurine forms the Boc-protected transport molecule in which the 6-mercaptopurine is bonded to the dendrimer by a disulfide linkage through the N-acetyl-Cys-Ala-Ala linker where the alanine residues are included as additional spacers to render the disulfide more accessible to thiols and reducing agent for cleavage within the cell. Subsequent treatment with trifluoroacetic acid removes the Boc protecting groups to afford the transport molecule (16).

Example 6

Figure 9:
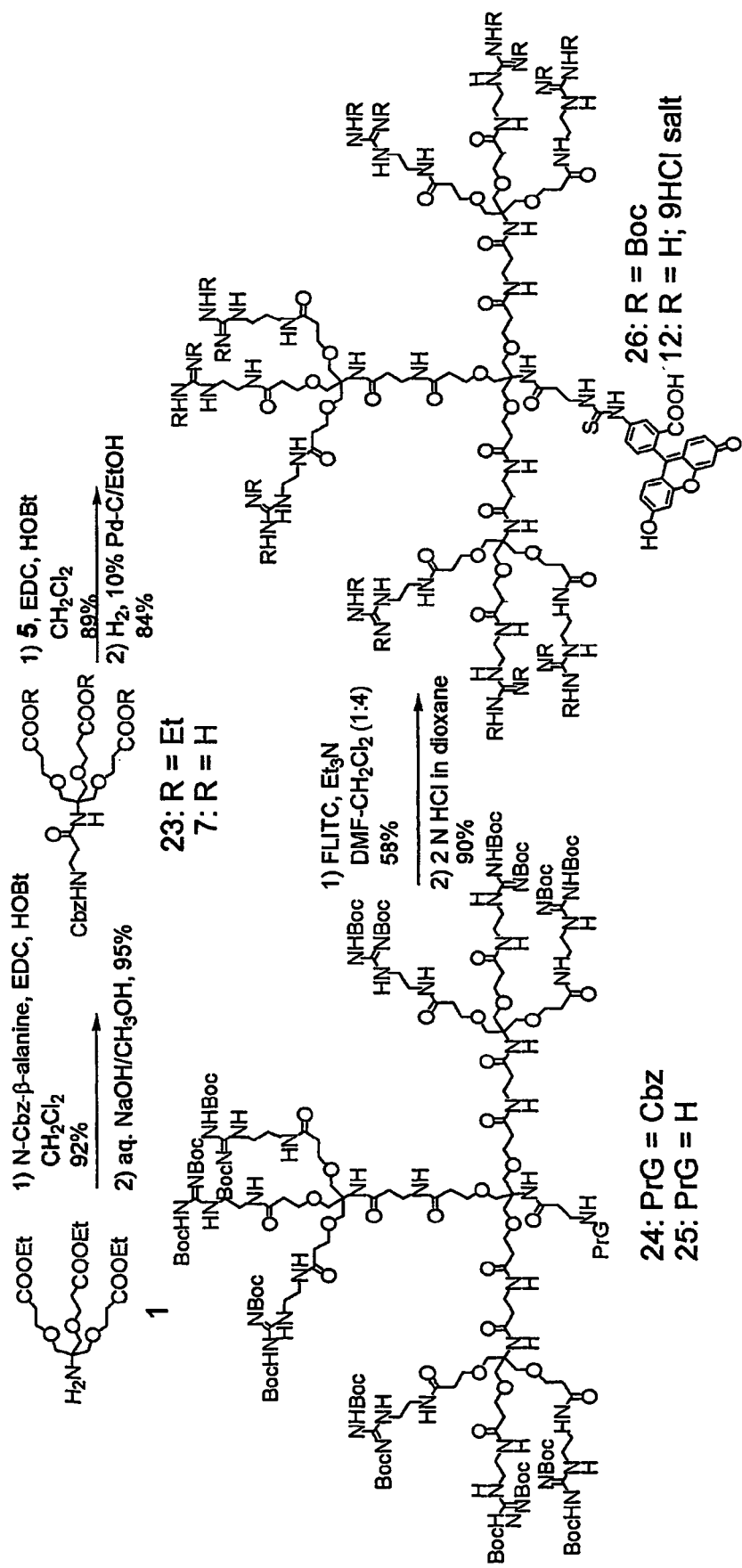
FIG. 9 depicts a reaction scheme for the preparation of dendritic oligo-guanidines that includes nine guanidine groups in identical chemical environments and a dendrimer with a fluorescein detection molecule linked to the dendrimer by a thiourea group.

Synthesis and Characterization of a Dendrimer (25) with Nine Protected Guanidine Groups The synthesis of dendrimer (25) with nine Boc-protected guanidine groups is illustrated in FIG. 9 and is set forth in greater detail below.

Step 1: Synthesis of 3-[2-(3-Benzyloxycarbonylamino-propionylamino)-3-(2-ethoxycarbonylethoxy)-2-(2-ethoxycarbonylethoxymethyl)-propoxy]-propionic acid ethyl ester (23)

The compound 23 was prepared using General Procedure B with amine 1 (4.0 g, 9.49 mmol), N-Cbz-β-alanine (2.54 g, 11.39 mmol), 1-hydrobenzotriazole (HOBt) (1.53 g, 11.39 mmol), and 1-ethyl-3-(3-dimethylaminopropyl)carbodiimide (EDC) (2.18 g, 11.39 mmol) in CH$_2$Cl$_2$ (50 mL). Purification by flash column chromatography (on silica gel, EtOAc:n-hexane=1:3) afforded 5.36 g (90%) of the desired product 23 as a colorless syrup. $^1$H NMR (CDCl$_3$): δ 7.31 (m, 5H, ArH), 6.16 (s, 1H, NH), 5.66 (s, 1H, NH), 5.08 (s, 2H, OCH$_2$Ar), 4.12 (q, J=6.4 Hz, 6H, OCH$_2$), 3.67 (m, 12H, CH$_2$O), 3.45 (dt, J=7.4, 15.0 Hz, 2H, CH$_2$NHCO), 2.51 (t, J=8.4 Hz, 6H, CH$_2$CO), 2.37 (dt, J=7.4, 8.6 Hz, 2H CH$_2$CO), 1.24 (t, J=6.4 Hz, 9H, CH$_3$).

Step 2: Synthesis of 3-[2-(3-Benzyloxycarbonylamino-propionylamino)-3-(2-carboxyethoxy)-2-(2-carhoxyethoxymethyl)-propoxy]-propionic acid (7)

The compound 7 was prepared using General Procedure A with the ester (23) (3.93 g 6.27 mmol) and an aqueous NaOH solution (3.01 g, 72.25 mmol in 50 mL of H$_2$O) in methanol (50 mL). The desired tri-acid (7) was obtained as 3.23 g (95%) of a colorless syrup. $^1$H NMR (CDCl$_3$): δ 7.32 (m, 5H, ArH), 6.38 (s, 1H, NM), 5.81 (s, 1H, NH), 5.08 (s, 2H, OCH$_2$Ar), 3.68 (m, 12H, CH$_2$O), 3.40 (m, 2H, CH$_2$NHCO), 2.54 (m, 6H, CH$_2$CO), 2.40 (m, 2H, CH$_2$CO); MALDI-FTMS m/z 649.2943 calculated for C$_{30}$H$_{46}$N$_2$O$_{12}$, (free guanidine)+Na$^+$. found 649.2949.

Step 3: Synthesis of Compound 24

The compound 24 was prepared using General Procedure B with the amine 5 (4.0 g, 1.59 mmol), N-Cbz-β-alanine-tri-acid 7 (0.22 g, 0.39 mmol), 1-hydrobenzotriazole (HOBt) (0.21 g, 1.59 mmol), and 1-ethyl-3-(3-dimethylaminopropyl) carbodiimide (EDC) (0.30 g, 1.59 mmol) in CH$_2$Cl$_2$ (25 mL). Purification by flash column chromatography (on silica gel, CH$_2$Cl$_2$:methanol=10:1) afforded 1.45 g (86%) of the desired product (24) as a colorless foam-shaped solid. $^1$H NMR (CDCl$_3$): δ 11.40 (s, 9H, NH), 8.61 (s, 9H, NH), 7.87 (s, 9H, NH), 7.32 (m, 5H, ArH), 7.18 (s, 3H, NH), 6.80 (s, 1H, NH), 6.62 (s, 3H, NM, 6.14 (s, 1H, NH), 5.04 (s, 2H, OCH$_2$Ar), 3.64 (m, 48H, CH$_2$O), 3.53 (m, 18H, CH$_2$NH), 3.39 (m, 26H, CH$_2$NHCO), 2.48 (m, 8H, CH$_2$CO), 2.41 (m, 24H, CH$_2$CO), 1.49 (s, 81H, t-Bu), 1.47 (s, 81H, t-Bu); ESI-MS m/z 4272 [M$_{avg}$].

Step 4: Synthesis of Compound 25

The compound 25 was prepared using General Procedure D with Cbz-protected dendrimer 24 (0.95 g, 0.22 mmol) and Pd—C (0.1 g) in EtOH (30 mL). After filtering off the used Pd—C, removal of the solvent was followed by flash column chromatography (on silica gel, CH$_2$Cl$_2$:methanol=10:1) to afford the desired amine 25 in 44% (0.77 g) yield as a colorless foam-shaped solid. $^1$H NMR (CD$_3$OD): δ 3.68 (m, 48H, CH$_2$O), 3.62 (m, 18H, CH$_2$NH), 3.42 (m, 24H, CH$_2$NHCO), 3.26 (m, 2H, CH$_2$NH$_2$), 2.58 (m, 8H, CH$_2$CO), 2.47 (m, 24H, CH$_2$CO), 1.48 (s, 81H, t-Bu), 1.46 (s, 81H, t-Bu).

Example 7

Synthesis and Characterization of a Fluorescein-Labeled Dendrimer (12)

The synthesis of fluorescein-labeled dendrimer (12) from dendrimer (25) is illustrated in FIG. 9 and is set forth in greater detail below.

Step 1: Synthesis of Compound 26

The compound 26 was prepared using General Procedure E with the amine 25 (0.40 g, 0.01 mmol) fluorescein isothiocyanate (FLITC) (0.076 g, 0.02 mmol), and Et$_3$N (135 μL, 0.04 mmol) in a mixture of DMF and CH$_2$Cl$_2$ (10 mL, 1:4 ratio). After short path column chromatography (on silica gel, CH$_2$Cl$_2$:methanol=10:1), the fluorescein-labeled Boc-protected guanidine 26 was obtained in 58% (0.26 g) yield as an orange foam-shaped solid. $^1$H NMR (10% CD$_3$OD in CDCl$_3$): δ 7.98 (m, 1H, ArH), 7.64 (m, 1H, ArH), 7.18 (m, 3H, ArH), 6.48 (m, 4H, ArH), 3.80 (m, 50H, CH$_2$O and CH$_2$NHCS), 3.38 (18H, CH$_2$NH), 3.26 (m, 24H, CH$_2$NHCO), 2.58 (m, 6H, CH$_2$CO), 2.47 (m, 26H, CH$_2$CO), 1.38 (s, 81H, t-Bu), 1.37 (s, 81H, t-Bu).

Step 2: Synthesis of Compound 12

The compound 12 was prepared using General Procedure F with the Boc-protected guanidine 26 (198 mg, 0.04 mmol) in 2N HCl in dioxane (14 mL). The fluorescein-labeled guanidinium HCl salt (12) was obtained in 90% (121 mg) yield as an orange hygroscopic solid. $^1$H NMR (D$_2$O): δ 7.95 (m, 1H, ArH), 7.61 (m, 1H, ArH), 7.24 (m. 2H, ArH), 7.02-6.64 (m, 5H, ArH), 3.70 (m, 2H, CH$_2$NHCS), 3.50 (m, 48H, CH$_2$O), 3.26-3.12 (m, 44H, CH$_2$NHCO and CH$_2$NH, 2.48 (m, 6H, CH$_2$CO), 2.33 (m, 26H, CH$_2$CO).

Example 8

Figure 10:
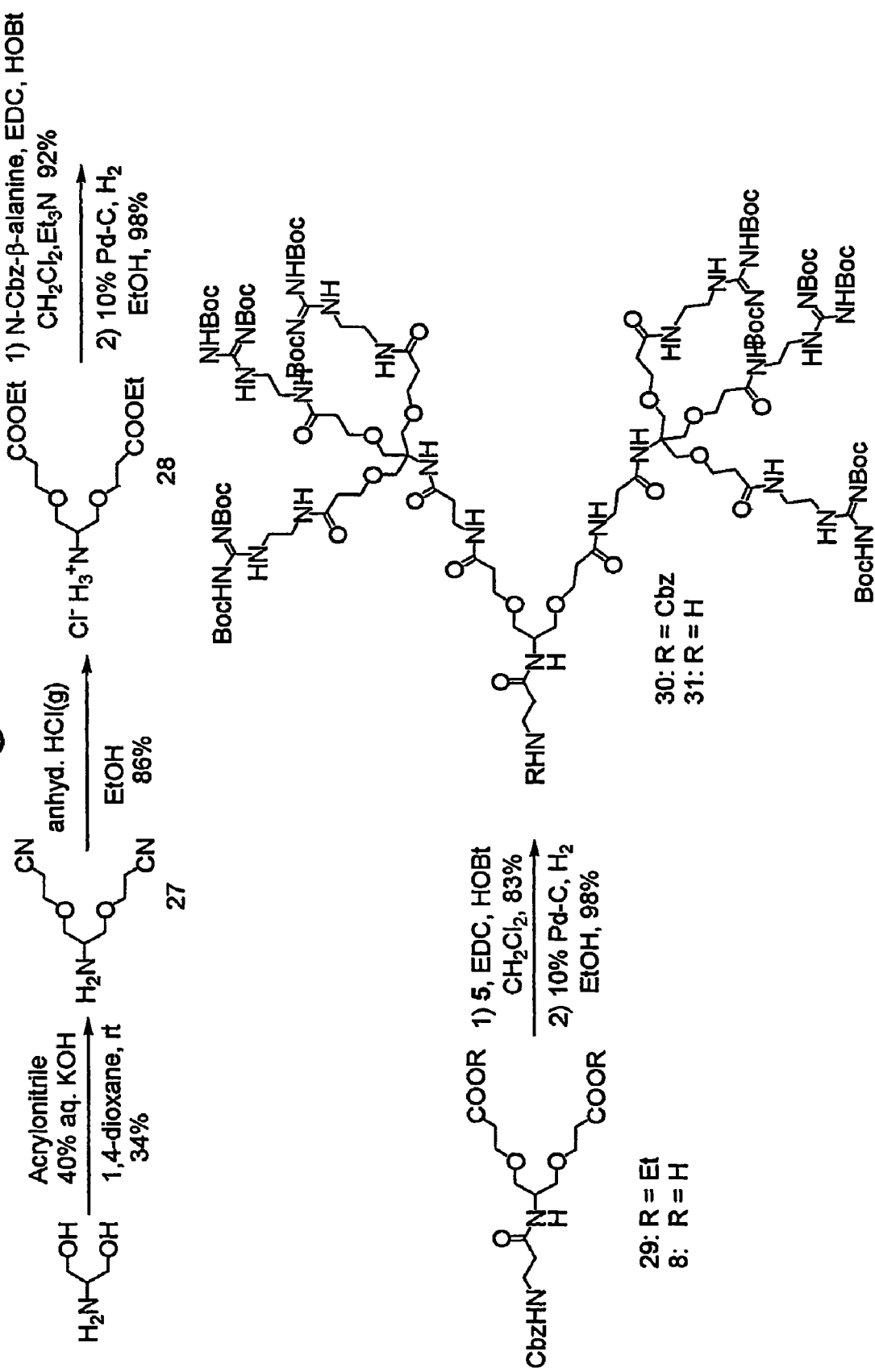
FIG. 10 depicts a reaction scheme for the synthesis of a dendritic oligo-guanidines that includes six guanidine groups in identical chemical environments.

Synthesis and Characterization of a Dendrimer (31) with Six Protected Guanidine Groups The synthesis of dendrimer (31) with six Boc-protected guanidine groups is illustrated in FIG. 10 and is set forth in greater detail below.

Step 1: Synthesis of 3-[2-Amino-3-(2-cyanoethoxy)propoxy]-propionitrile (27)

To a suspension of 2-amino-1,3-propandiol (3.0 g, 0.033 mol) in 1,4-dioxane (8 mL) was added aqueous 40% KOH (0.46 mL, 0.003 mol), and the mixture was stirred for 10 minutes. The reaction solution was cooled to 0° C., and acrylonitrile (5.20 mL, 0.079 mol) was added with a syringe. The reaction was then warmed to room temperature, stirred overnight, and concentrated under reduced pressure. The residue was diluted with CH$_2$Cl$_2$ (120 mL) and washed with saturated aqueous NaHCO$_3$ (2×70 mL) and H$_2$O (2×70 mL). The organic phase was dried over anhydrous MgSO$_4$, and the solvent was removed under reduced pressure. The resulting residue was purified by flash column chromatography (on silica gel, MeOH:CH$_2$Cl$_2$=1:10 affording 1.62 g (34%) of the desired dinitrile (27) as a slightly yellow liquid. $^1$H NMR (CDCl$_3$): δ 3.68 (t, J=6.4 Hz, 4H, CH$_2$O), 3.48 (m, 4H, CH$_2$O), 3.15 (m, 1H, CH), 2.61 (t, J=6.4 Hz, 1H, CH$_2$CN).

Step 2: Synthesis of 3-[2-Amino-3-(2-ethoxycarbonylethoxy)propoxy]-propionic acid ethyl ester HCl salt (28)

A solution of the dinitrile (27) (1.60 g, 11.10 mmol) in anhydrous ethanolic HCl [freshly made by the reaction of acetyl chloride (5.0 mL) and EtOH (20 mL) at 0° C.] was heated at reflux temperature for 2 hours. After completion of the reaction, the solvent was removed under reduced pressure to afford hydrochloride salt (28) in a 86% (3.14 g) yield as a slightly yellow solid. $^1$H NMR (CDCl$_3$): δ 4.14 (q, J=7.2 Hz, 4H, CH$_2$O), 3.70 (m, 4H, CH$_2$O), 3.38 (m, 4H, CH$_2$O), 3.13 (m, 1H, CH), 2.55 (t, J=6.3 Hz, 4H, CH$_2$CO), 1.25 (t, J=7.2 Hz, 6H, CH$_3$).

Step 3: Synthesis of 3-[2-(3-Benzyloxycarbonylaminopropionylamino)-3-(2-ethoxycarbonylethoxy)-propoxy]-propionic acid ethyl ester (29)

The compound 29 was prepared using General Procedure B with the ester hydrochloride salt (28) (1.53 g, 5.26 mmol), N-Cbz-β-alanine (1.41 g, 6.31 mmol), 1-hydrobenzotriazole (HOBt) (0.99 g, 7.36 mmol), 1-ethyl-3-(3-dimethylaminopropyl)carbodiimide (EDC) (1.41 g, 7.36 mmol) and Et$_3$N (1.02 mL, 7.36 mmol) in CH$_2$Cl$_2$ (30 mL). Purification by flash column chromatography (on silica gel, EtOAc:n-hexane=3:1) afforded 2.39 g (92%) of the desired product (29) as a colorless liquid. $^1$H NMR (CDCl$_3$): δ 7.33 (m, 5H, ArH), 6.33 (d, J=8.0 Hz, 1H, NH), 5.57 (s, 1H, NM, 5.08 (s, 2H, OCH$_2$Ar), 4.18 (m, 1H, CH), 4.13 (q, J=7.2 Hz, 4H, CH$_2$O), 3.70 (m, 4H, CH$_2$O), 3.56 (m, 2H, CH$_2$O), 3.48 (d, J=6.0, 12.0 Hz, 2H, CH$_2$NHCO), 3.40 (m, 2H, CH$_2$O), 2.53 (m, 4H, CH$_2$CO), 2.42 (t, J=6.0 Hz, 2H, CH$_2$CO), 1.25 (t, J=7.2 Hz, 6H, CH$_3$).

Step 4: Synthesis of 3-[2-(3-Benzyloxycarbonylaminopropionylamino)-3-(2-carboxy-ethoxy)propoxy]-propionic acid (8)

The compound 8 was prepared using General Procedure A with diester 29 (1.32 g, 2.66 mmol) and an aqueous NaOH solution (0.85 g, 21.29 mmol in 10 mL of H$_2$O) in methanol (10 mL). The desired diacid (8) was obtained in 96% (1.12 g) yield as a colorless syrup. $^1$H NMR (CDCl$_3$): δ 7.32 (m, 5H, ArH), 6.59 (s, 1H, NH), 5.54 (s, 1H, NH), 5.08 (s, 2H, OCH$_2$Ar), 4.18 (m, 1H, CH), 3.69 (m, 4H, CH$_2$O), 3.56 (m, 2H, CH$_2$O), 3.45 (m, 4H, CH$_2$NHCO and CH$_2$O), 2.55 (m, 4H, CH$_2$O), 2.43 (m, 2H, CH$_2$CO); ESI-MS m/z 475[M+Cl]$^-$; 463[M+Na]$^+$, 441 [M+H]$^+$, 439[M−H]$^-$.

Step 5: Synthesis of Compound 30

The compound 30 was prepared using General Procedure B with the diacid (8) (0.2 g, 0.45 mmol), dendrimer amine 5 (1.37 g, 1.09 mmol), 1-hydrobenzotriazole (HOBt) (0.15 g, 1.09 mmol), 1-ethyl-3-(3-dimethylaminopropyl)carbodiimide (EDC) (0.21 g, 1.09 mmol) in CH$_2$Cl$_2$ (30 mL). Purification by flash column chromatography (on silica gel, MeOH:CH$_2$Cl$_2$=1:15) afforded 1.10 g (83%) of the desired product (30) as a colorless foam-shaped solid. $^1$H NMR (CDCl$_3$): δ 11.40 (s, 6H, NH), 8.59 (s, 6H, NH), 7.86 (s, 6H, NH), 7.80 (s, 2H, NH), 7.31 (m, 5H, ArH), 6.68 (s, 2H, NH), 6.52 (s, 1H, NM, 6.04 (s, 1H, NH), 5.06 (s, 2H, OCH$_2$Ar), 4.18 (m, 1H, CH), 3.67 (m, 32H, CH$_2$O), 3.54 (m, 16H, CH$_2$NHCO), 3.47 (m, 2H, CH$_2$NHCO), 3.39 (m, 12H, CH$_2$NH), 2.41 (m, 22H, CH$_2$CO), 1.48 (s, 54H, t-Bu), 1.46 (s. 54H, t-Bu).

Step 6: Synthesis of Compound 31

The compound 31 was prepared using General Procedure D with Cbz-protected compound 30 (0.99 g, 0.34 mmol) and Pd—C (0.1 g) in EtOH (50 mL). After filtering off the used Pd—C, removal of the solvent gave the desired amine (31) in 98% (0.93 g) yield as a colorless foam-shaped solid. $^1$H NMR (CDCl$_3$): δ 11.40 (s, 6H, NH), 8.59 (s, 6H, NH), 7.92 (s, 6H, NH), 7.80 (s, 2H, NH), 6.76 (s, 2H, NH), 6.54 (s, 1H, NH), 4.18 (m, 1H, CH), 3.67 (m, 32H, CH$_2$O), 3.52 (m, 16H, CH$_2$NHCO), 3.42 (m, 12H, CH$_2$NH), 3.36 (m, 2H, CH$_2$NH:), 2.41 (m, 22H, CH$_2$CO) 1.48 (s, 54H, t-Bu), 1.46 (s, 54H, t-Bu); ESI-MS m/z 2821[M+H]$^+$.

Example 9

Figure 11:
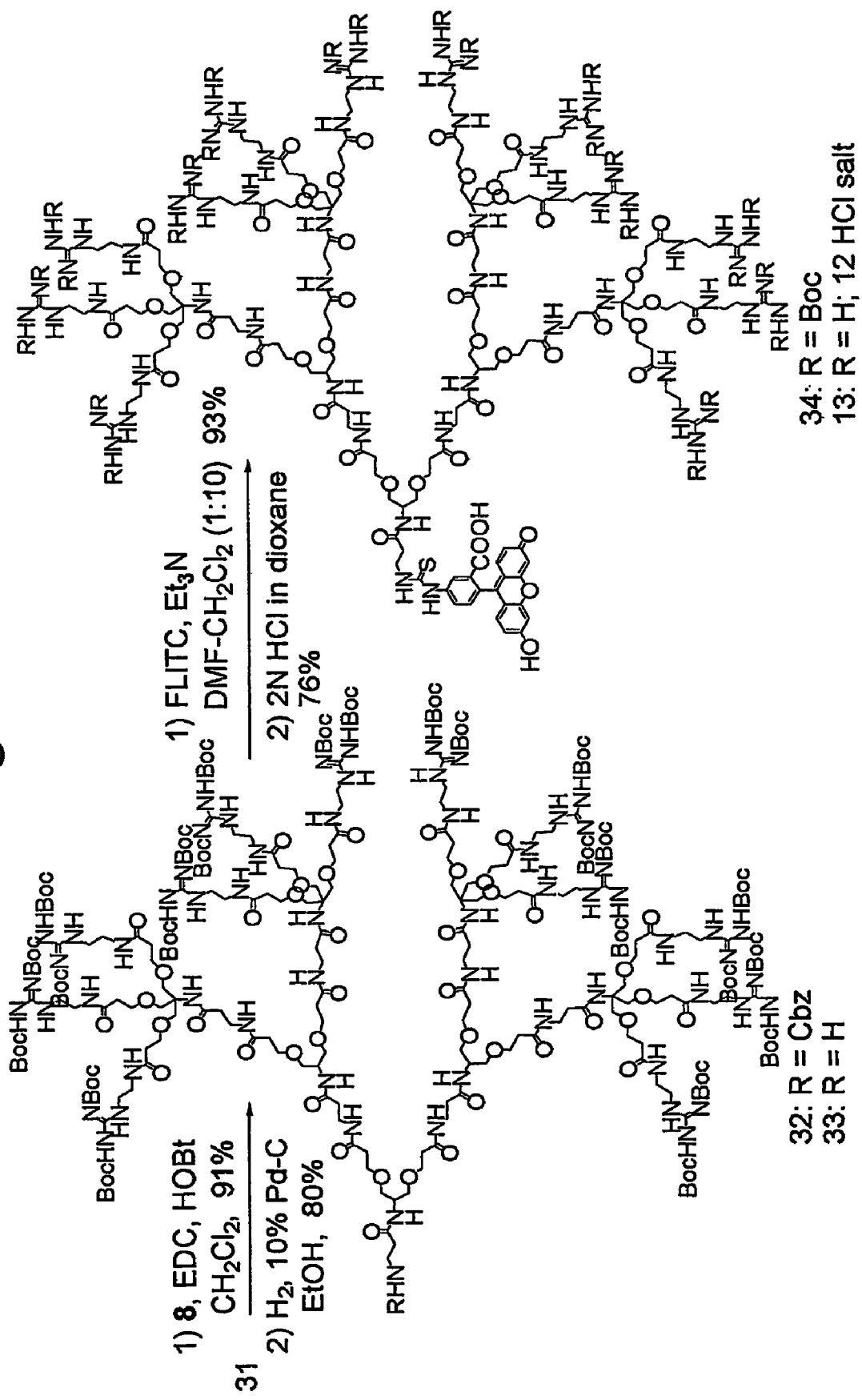
FIG. 11 depicts a reaction scheme for the synthesis of dendritic oligo-guanidines that includes twelve guanidine groups in identical chemical environments and a dendrimer having a fluorescein detection molecule linked to the dendrimer by a thiourea group.

Synthesis and Characterization of a Dendrimer (33) with Twelve Protected Guanidine Groups The synthesis of dendrimer (33) with twelve Boc-protected guanidine groups is illustrated in FIG. 11 and is set forth in greater detail below.

Step 1: Synthesis of Compound 32

The compound 32 was prepared using General Procedure B with diacid (8) (0.06 g, 0.14 mmol), dendrimer amine 31 (0.90 g, 0.32 mmol), 1-hydrobenzotriazole (HOBt) (0.06 g, 0.41 mmol), 1-ethyl-3-(3-dimethylaminopropyl)-carbodiimide (EDC) (0.08 g, 0.41 mmol) in $CH_2Cl_2$ (10 mL). Purification by flash column chromatography (on silica gel, MeOH:$CH_2Cl_2$=1:10) afforded 0.76 g (91%) of the desired product 32 as a colorless foam-shaped solid. $^1H$ NMR ($CDCl_3$): δ 11.40 (s, 12H, NH), 8.62 (s, 12H, NH), 7.89 (s, 12H, NH), 7.80 (s, 4H, NH), 7.32 (m, 5H, ArH), 6.98 (s, 2H, NH), 6.82 (s, 1H, NH), 6.64 (s, 4H, NH), 6.48 (s, 2H, NM), 5.94 (s, 1H, NH), 5.06 (s, 2H, $OCH_2Ar$), 4.14 (m, 3H, CH), 3.68 (m, 72H, $CH_2O$), 3.56 (m, 36H, $CH_2NHCO$), 3.40 (m, 26H, $CH_2NHCO$ and $CH_2NH$), 2.46 (m, 38H, $CH_2CO$), 1.48 (s, 108H, t-Bu), 1.46 (s, 108H, t-Bu).

Step 2: Synthesis of Compound 33

The compound 33 was prepared using General Procedure D with Cbz-protected compound 32 (0.32 g, 0.05 mmol) and Pd—C (0.05 g) in EtOH (20 mL). After filtering off the used Pd—C, removal of the solvent afforded the desired amine (33) in 80% (0.25 g) yield as a colorless foam-shaped solid. $^1H$ NMR ($CDCl_3$): δ 11.40 (s, 12H, NH), 8.64 (s, 12H, NH), 7.90 (s, 12H, NH), 7.80 (s, 4H, NH) 2H, NH), 6.64 (s, 4H, NH), 6.48 (s, 2H, NH), 4.08 (m, 3H, CH), 3.68 (m, 72H, $CH_2O$), 3.54 (m, 36H, $CH_2NHCO$), 3.38 (m, 24H, $CH_2NH$), 2.88 (m, 2H, $CH_2NH_2$), 2.44 (m, 38H, $CH_2CO$), 1.48 (s, 108H, t-Bu), 1.46 (s, 108H, t-Bu).

Example 10

Synthesis and Characterization of a Fluorescein-Labeled Dendrimer (13)

The synthesis of fluorescein-labeled dendrimer (13) from dendrimer (33) is illustrated in FIG. 11 and is set forth in greater detail below.

Step 1: Synthesis of Compound 34

The compound 34 was prepared using General Procedure E with the amine 33 (0.15 g, 0.025 mmol), fluorescein isothiocyanate (FLITC) (23 mg, 0.05 mmol) and $Et_3N$ (14 μL, 0.10 mmol) in a mixture of DMF and $CH_2Cl_2$ (11 mL, 1:10 ratio). After short path column chromatography (on silica gel, $CH_2Cl_2$:MeOH=10:1), the fluorescein-labeled guanidine (34) was obtained in 93% (0.148 g) yield as an orange foam-shaped solid. $^1H$ NMR ($CD_3OD$): δ 8.13 (s, 1H, ArH), 7.72 (m, 2H, ArH), 7.26 (m, 2H, ArH), 6.65 (m, 4H, ArH), 4.14 (m, 3H, CH), 3.86 (m, 2H, $CH_2NHCS$), 3.66 (m, 72H, $CH_2O$), 3.49 (m, 36H, $CH_2NHCO$), 3.38 (m, 24H, $CH_2NH$), 2.66 (m, 2H, $CH_2CO$), 2.60 (m, 2H, $CH_2CO$), 2.44 (m, 36H, $CH_2CO$), 1.48 (s, 108H, t-Bu), 1.46 (s, 108H, t-Bu).

Step 2: Synthesis of Compound 13

The compound 13 was prepared using General Procedure F with Boc-protected guanidine dendrimer (34) (70 mg, 0.01 mmol) in 2N HCl in dioxane (6 mL). After the reaction was complete, the resulting orange precipitate was collected and dried in vacuo. The solid was then washed with $CH_2Cl_2$ and cold $H_2O$. The fluorescein-labeled guanidinium HCl salt (13) was obtained in 76% (36 mg) yield as an orange solid which is barely soluble in $H_2O$. $^1H$ NMR ($CD_3OD$): δ 8.21 (s, 1H, ArH), 7.81 (m, 1H, ArH), 7.51 (m, 3H, ArH), 7.34 (m, 2H, ArH), 7.20 (m, 2H, ArH), 4.10 (m, 3H, CH), 3.92 (m, 2H, $CH_2NHCS$), 3.66 (m, 72H, $CH_2O$), 3.34 (m, 24H, $CH_2NH_3^+$), 3.32 (m, 36H, $CH_2NHCO$), 2.72 (m, 2H, $CH_2CO$), 2.62 (m, 2H, $CH_2CO$), 2.44 (m, 36H, $CH_2CO$).

Example 11

Synthesis and Characterization of a Fluorescein-Labeled Monoguanidine Compound (41)

Figure 12:
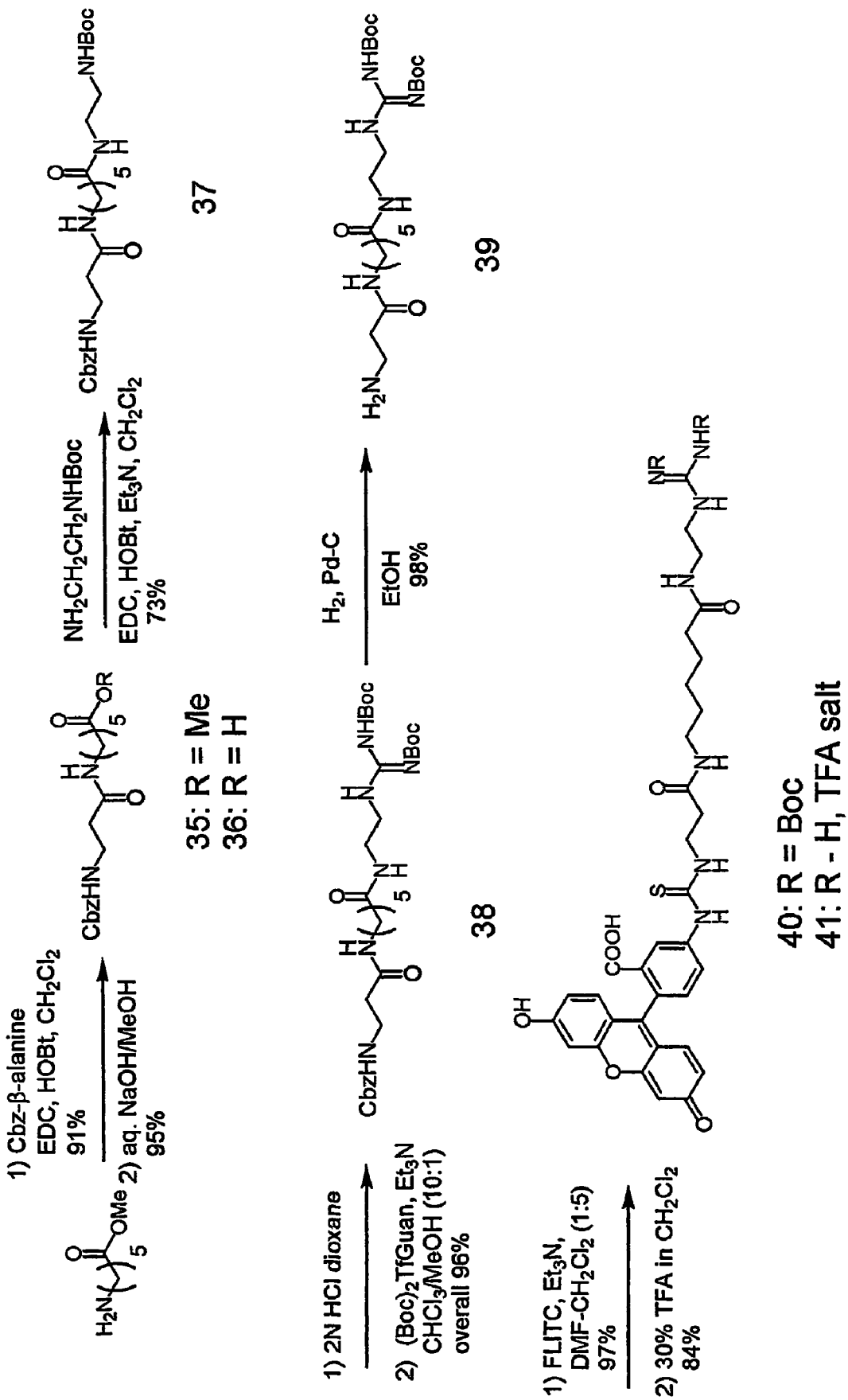
FIG. 12 depicts a reaction scheme for the synthesis of a molecule that includes one guanidine group and a fluorescein detection molecule.

The synthesis of fluorescein-labeled monoguanidine compound (41) with is illustrated in FIG. 12 and is set forth in greater detail below.

Step 1: Synthesis of 6-(3-Benzyloxycarbonylamino-propionylamino)-hexanoic acid methyl ester (35)

The compound 35 was prepared using General Procedure B with 6-aminohexanoic acid methyl ester hydrochloride salt (3.0 g, 16.5 mmol), N-Cbz-β-alanine (3.68 g, 16.5 mmol), 1-hydrobenzotriazole (HOBt) (2.68 g, 19.8 mmol), 1-ethyl-3-(3-dimethylamino-propyl)carbodiimide (EDC) (3.80 g, 19.8 mmol) and $Et_3N$ (5.52 mL, 39.6 mmol) in $CH_2Cl_2$, (100 mL). Recrystallization of the crude product from a mixture of MeOH and $H_2O$ (10:1 ratio) afforded 5.28 g (91%) of the desired product (35) as a white solid. $^1H$ NMR ($CDCl_3$): 7.32 (m, 5H, ArH), 5.82 (s, 1H, NH), 5.54 (s, 1H, NH), 5.07 (s, 2H, $OCH_2Ar$), 3.64 (s, 3H, $OCH_3$), 3.45 (dt, J=6.1, 12.0 Hz, 2H, $CH_2NHCO$), 3.21 (dt, J=6.4, 12.8 Hz, 2H, $CH_2NHCO$), 2.38 (dt, J=6.1, 6.8 Hz, 2H, $CH_2CO$), 2.29 (t, J=7.2 Hz, 2H, $CH_2CO$), 1.61 (m, 2H, $CH_2$), 1.48 (m, 2H, $CH_2$), 1.33 (m, 2H, $CH_2$).

Step 2: Synthesis of 6-(3-Benzyloxycarbonylamino-propionylamino)-hexanoic acid (36)

The compound 36 was prepared using General Procedure A with ester 35 (3.20 g, 9.13 mmol) and an aqueous NaOH solution (1.46 g, 36.53 mmol in 40 mL of $H_2O$) in MeOH (40 mL). Recrystallization from MeOH produced the desired acid 36 in 95% (2.92 g) yield as a white solid. $^1H$ NMR ($CDCl_3$): δ 7.32 (m, 5H, ArH), 6.10 (s, 1H, NH), 5.67 (s, 1H, NH), 5.04 (s, 2H, $OCH_2Ar$), 3.45 (dt, J=6.4, 12.0 Hz, 2H, $CH_2NHCO$), 3.21 (dt, J=6.4, 12.8 Hz, 2H, $CH_2NHCO$), 2.40 (dt, J=6.0, 6.4 Hz, 2H, $CH_2CO$), 2.32 (t, J=7.2 Hz, 2H, $CH_2CO$), 1.61 (m, 2H, $CH_2$), 1.48 (m, 2H, $CH_2$), 1.33 (m, 2H, $CH_2$); ESI-MS m/z 371[M+Cl]$^-$, 359[M+Na]$^+$, 337[M+H]$^+$, 335[M−H]$^-$.

Step 3: Synthesis of {2-[5-(2-tert-Butoxycarbony-laminoethylcarbamoyl)-pentylcarbamoyl]ethyl}-carbamic acid benzyl ester (37)

The compound 37 was prepared using General Procedure B with the acid 36 2.23 g, 6.63 mmol), 2-t-butoxycarbony-lamino-ethylamine (1.27 g, 7.95 mmol), 1-hydrobenzotriazole (HOBt) (1.25 g, 9.28 mmol), and 1-ethyl-3-(3-dimethy-laminopropyl)carbodiimide (EDC) (1.79 g, 9.28 mmol) in DMF (20 mL). Recrystallization of the crude product from EtOAc afforded 2.30 g (73%) of the desired product (37) as a white solid. $^1H$ NMR ($CDCl_3$): δ 7.32 (m, 5H, ArH), 6.44 (s, 1H, NH), 6.23 (s, 1H, NH), 5.19 (s, 1H, NH), 5.06 (s, 2H, $OCH_2Ar$), 3.45 (dt, J=6.4, 12.4 Hz, 2H, $CH_2NHCO$), 3.31 (dt, J=5.2, 10.4 Hz, 2H, $CH_2NHCO$), 3.21 (m, 4H, $CH_2NHCO$), 2.39 (dt, J=6.0, 6.4 Hz, 2H, $CH_2CO$), 2.14 (dt, J=7.0, 7.2 Hz, 2H, $CH_2CO$), 1.60 (m, 2H, $CH_2$), 1.47 (m, 2H, $CH_2$), 1.41 (s, 9H, t-Bu), 1.30 (m, 2H, $CH_2$); ESI-MS m/z 513[N+Cl]⁻; 501[M+Na]⁺, 479[M+H]⁺.

Step 4: Synthesis of Compound 38

To a solution of the Boc-protected compound 37 (1.73 g, 3.61 mmol) in 1,4-dioxane (8 mL), was added 4N HCl in dioxane (8 mL) by syringe under a nitrogen atmosphere at ice bath temperature. The resulting mixture was then vigorously stirred for 1 hour. The resulting mixture was concentrated on a rotary evaporator, and dried in vacuo to afford a white solid. The solid was dissolved in 10 mL of $H_2O$ and the insoluble precipitate was filtered off. The filtrate was lyophilized to provide a colorless foam-shaped solid as a deprotected HCl salt. The resulting HCl salt was dissolved in MeOH (3 mL) and diluted with $CHCl_3$ (16 mL). To the resulting clear solution was added $Et_3N$ (2.0 mL, 14.4 mmol) and then a N,N'-diBoc-N"-triflylguanidine (2.83 g, 7.22 mmol) at 0° C. The mixture was stirred overnight, poured into 50 mL of $H_2O$, and extracted with $CH_2Cl_2$ (3×50 mL). The organic phase was washed with 1N HCl (2×50 mL), with saturated $NaHCO_3$ (50 mL), and with $H_2O$ (2×50 mL) and then dried over anhydrous $Na_2SO_4$. After removal of the solvent under reduced pressure, the resulting crude product was purified by recrystallization from EtOAc. The desired guanidine (38) was obtained in 96% (2.15 g) yield as a white solid. ¹H NMR ($CDCl_3$): δ 11.42 (s, 1H, NH), 8.62 (s, 1H, NH), 7.84 (s, 1H, NH), 6.88 (s, 1H, NH), 5.96 (s, 1H, NH), 5.06 (s, 2H, $OCH_2Ar$), 3.52 (m, 2H, $CH_2NH$), 3.45 (dt, J=6.4, 12.4 Hz, 2H, $CH_2NHCO$), 3.38 (m, 2H, $CH_2NHCO$), 3.23 (dt, J=6.4, 12.8 Hz, 2H, $CH_2NHCO$), 2.42 (dt, J=6.0, 6.4 Hz, 2H, $CH_2CO$), 2.18 (dt, J=7.0, 7.2 Hz, 2H, $CH_2CO$), 1.61 (m, 2H, $CH_2$), 1.48 (s, 9H, t-Bu), 1.44 (s, 9H, t-Bu), 1.43 (m, 2H, $CH_2$), 1.31 (m, 2H, $CH_2$); ESI-MS m/z 655.4[M+Cl]⁻, 643.6[M+Na]⁺, 621.6[M+H]⁺, 619.6 [M−H]⁻.

Step 5: Synthesis of Compound 39

The compound 39 was prepared using General Procedure D with Cbz-protected compound 38 (0.52 g, 0.84 mmol) and Pd—C (0.10 g) in EtOH (150 mL). After filtering off the used Pd—C, removal of the solvent afforded the desired amine (39) in 98% (0.40 g) yield as a colorless foam shaped solid. ¹H NMR ($CDCl_3$): δ 11.42 (s, 1H, NH), 8.62 (s, 1H, NH), 7.73 (s, 1H, NH), 7.18 (s, 1H, NH), 3.56 (m, 2H, $CH_2NH$), 3.40 (m, 2H, $CH_2NHCO$), 3.23 (dt, J=6.4, 12.6 Hz, 2H, $CH_2NHCO$), 3.04 (m, 2H, $CH_2NH_2$), 2.38 (dt, J=6.0, 6.4 Hz, 2H, $CH_2CO$), 2.20 (m, 2H, $CH_2CO$), 1.64 (m, 2H, $CH_2$), 1.54 (m, 2H, $CH_2$), 1.52 (s, 9H, t-Bu), 1.48 (s, 9H, t-Bu), 1.34 (m, 2H, $CH_2$); ESI-MS m/z 487[M+H]⁺.

Step 6: Synthesis of Compound 40

The compound 40 was prepared using General Procedure E with the amine 39 (0.24 g, 0.49 mmol), fluorescein isothiocyanate (FLITC) (0.38 g, 0.98 mmol), and $Et_3N$ (0.41 mL, 2.96 mmol) in a mixture of DMF and $CH_2Cl_2$ (12 mL, 1:5 ratio). The fluorescein-labeled Boc-protected guanidine (40) was obtained in 97% (0.42 g) yield as an orange foam-shaped solid. ¹H NMR ($CD_3OD$): δ 8.13 (s, 1H, ArH), 7.72 (m, 2H, ArH), 7.12 (m, 2H, ArH), 6.65 (m, 4H, ArH), 3.85 (m, 2H. $CH_2NHCS$), 3.43 (m, 2H, $CH_2N$), 3.30 (m, 4H, $CH_2NHCO$), 3.17 (m, 2H, $CH_2NHCO$), 2.56 (dt, J=6.0, 6.4 Hz, 2H, $CH_2CO$), 2.16 (dt, J=6.2, 7.2 Hz, 2H, $CH_2CO$), 1.59 (m, 2H, $CH_2$), 1.49 (m, 2H, $CH_2$), 1.48 (s, 9H, t-Bu), 1.43 (s, 9H, t-Bu), 1.31 (m, 2H, $CH_2$); MALDI-FTMS m/z 898.3416 calculated for $C_{43}H_{53}N_7O_{11}S+Na^+$. found 898.3434.

Step 7: Synthesis of 5-(3-{2-[5-(2-Guanidinoethyl-carbamoyl)-pentylcarbamoyl]-ethyl}-thioureido)-2-(6-hydroxy-3-oxo-3H-xanthen-9-yl)-benzoic acid (41)

Boc-protected guanidine 40 (0.24 g, 0.27 mmol) was treated with 30% trifluoroacetic acid in $CH_2Cl_2$ at room temperature for 1 hour. After the reaction was completed, the resulting mixture were evaporated and dried in vacuo. Next, the residue was decanted with $CH_2Cl_2$ and $H_2O$. After drying in vacuo, the fluorescein labeled guanidinium TFA salt (41) was obtained in 84% (0.18 g) yield as an orange solid, which is barely soluble in $H_2O$. ¹H NMR ($CD_3OD$); δ 8.13 (s, 1H, ArH), 7.81 (m, 2H, ArH), 7.16 (m, 2H, ArH), 6.82 (m, 4H, ArH), 3.83 m, 2H, $CH_2NHCS$), 3.26 (m, 4H, $CH_2NHCO$ and $CH_2NH$), 3.16 (t, J=6.9 Hz, 2H, $CH_2NHCO$), 2.54 (dt, J=6.0, 6.4 Hz, 2H, $CH_2CO$), 2.16 (dt, J=6.2, 7.2 Hz, 2H, $CH_2CO$), 1.56 (m, 2H, $CH_2$), 1.47 (m, 2H, $CH_2$), 1.31 (m, 2H, $CH_2$); MALDI-FTMS m/z 676.2475 calculated for $C_{33}H_{37}N_7O_7S$ (free base)+H⁺. found 676.2545.

Example 12

Synthesis and Characterization of a Dendrimer (43) with Nine Protected Guanidine Groups The synthesis of dendrimer (43) with nine Boc-protected guanidine groups is illustrated in FIG. 13A and is set forth in greater detail below.

Step 1: Synthesis of Compound 42

The compound 42 was prepared using General Procedure B with the acid (4) (0.22 g, 0.46 mmol), the dendrimer amine (5) (2.34 g, 1.85 mmol), 1-hydrobenzotriazole (HOBt) (0.25 g, 1.85 mmol), and 1-ethyl-3-(3-dimethylaminopropyl)carbodiimide (EDC) (0.36 g, 1.85 mmol) in DMF (20 mL). Purification by flash column chromatography (on silica gel, MeOH:$CH_2Cl_2$=1:10) afforded 1.79 g (93%) of the desired product (42) as a colorless foam-shaped solid. ¹H NMR ($CDCl_3$): δ 11.39 (s, 9H, NH), 8.62 (s, 9H, NH), 7.83 (s, 9H, NH), 7.32 (m, 5H, ArH), 6.88 (s, 3H, NH), 6.58 (s, 1H, NH), 5.06 (s, 2H, $OCH_2Ar$), 3.52 (m, 2H, $CH_2NH$), 3.67 (m, 48H, $CH_2O$), 3.47 (m, 18H, $CH_2NH$), 3.38 (m, 24H, $CH_2NHCO$), 2.40 (m, 30H, $CH_2CO$), 1.48 (s, 81H, t-Bu), 1.46 (s, 81H, t-Bu).

Step 2: Synthesis of Compound 43

The compound 43 was prepared using General Procedure D with Cbz-protected compound (42) (1.46 g, 0.34 mmol) and Pd—C (0.20 g) in EtOH (120 mL). After filtering off the used Pd—C, removal of the solvent gave the desired dendrimer amine (43) in 90% (1.27 g) yield as a colorless foam-shaped solid. ¹H NMR ($CD_3OD$): δ 3.66 (m, 48H, $CH_2O$), 3.49 (m, 18H, $CH_2NH$), 3.38 (m, 24H, $CH_2NHCO$), 2.43 (m, 24H, $CH_2CO$), 1.51 (s, 81H, t-Bu), 1.46 (s, 81H, t-Bu).

Example 13

Synthesis and Characterization of a Dendrimer with a Reactive Maleimide Group (44)

The synthesis of a dendrimer with a reactive maleimide group and nine Boc-protected guanidines (44) is illustrated in FIG. 13B and is set forth in greater detail below.

Step 1: Synthesis of Compound 44

To a solution of dendritic amine 43 (0.4 g, 0098 mmol) and N-succinimidyl 3-maleimidopropionate (0.10 g, 0.40 mmol) in dry DMF (2 mL), was added an excess of $Et_3N$ (0.11 mL, 0.79 mmol) at room temperature. The resulting mixture was stirred for 4 hours at 50° C., then for 6 hours at room temperature. After the reaction was complete, the solvent was removed under reduced pressure. The residue was diluted with $CH_2Cl_2$ (40 mL) and washed with 1N HCl (40 mL) and $H_2O$ (2×40 mL). The organic phase was dried over anhydrous $Na_2SO_4$, and the solvent was removed under reduced pressure. The resulting residue was purified by flash column chromatography (on silica gel, MEOH:$CH_2Cl_2$=1:10) affording 0.34 g (82%) of the desired maleimido compound (44) as a colorless foam-shaped solid. $^1H$ NMR ($CD_3OD$): δ 6.83 (s, 2H, vinyl CH), 3.72 (t, J=7.2 Hz, 2H, $CH_2N$), 3.65 (m, 48H, $CH_2O$), 3.49 (m, 18H, $CH_2NH$), 3.37 (m, 24H, $CH_2NHCO$), 2.64 (m, 2H. $CH_2CO$), 2.43 (m, 30H, $CH_2CO$), 1.51 (s, 81H, t-Bu), 1.46 (s, 81H, t-Bu); ESI-MS m/z 1428.9 $[M+3Na]^{3+}$, 1077.3$[M+4Na]^{4+}$.

Example 14

Synthesis and Characterization of a Dendrimer (46) with Nine Guanidine Groups The synthesis of dendrimer (46) with nine guanidine groups is illustrated in FIG. 14 and is set forth in greater detail below.

Step 1: Synthesis of Compound 45

To a solution of dendrimer amine 5 (1.0 g, 0.79 mmol) and $Et_3N$ (0.13 mL, 0.95 mmol) in 10 mL of $CH_2Cl_2$, was added dropwise a solution of 1,3,5-benzenecarbonyl trichloride (55 mg, 0.21 mmol) in $CH_2Cl_2$ at room temperature. The mixture was stirred overnight and poured into ice water (50 mL). The resulting mixture was extracted with $CH_2Cl_2$ (2×50 mL). The organic phase was washed with 1N HCl (2×50 mL), saturated $NaHCO_3$ (50 mL), brine (50 mL) and $H_2O$ (2×50 mL), and evaporated under reduced pressure. The resulting residue was purified by flash column chromatography (on silica gel, MeOH:$CH_2Cl_2$=1:10) affording 0.73 g (89%) of the desired Boc-protected nonaguanidine compound (45) as a colorless foam-shaped solid. $^1H$ NMR ($CDCl_3$): δ 11.40 (s, 9H, NH), 8.64 (s, 9H, NH), 8.49 (s, 3H, ArH), 8.01 (s, 3H, NH), 7.92 (s, 9H, NH), 6.72 (s, 3H, NH), 3.65 (m, 36H, $CH_2O$), 3.56 (m, 24H, $CH_2NHCO$), 3.38 (m, 18H, $CH_2NH$), 2.54 (m, 6H, $CH_2CO$), 2.40 (m, 18H, $CH_2CO$), 1.47 (s, 81H, t-Bu), 1.46 (s, 81H, t-Bu); $^{13}C$ NMR ($CDCl_3$): δ 171.88, 171.71, 171.63, 166.36, 163.01, 157.13, 157.07, 152.96, 135.37, 128.84, 83.63, 83.56, 79.64, 69.59, 67.60, 59.96, 40.71, 37.34, 36.73, 28.60, 28.36; ESI-MS m/z 3936 $[M_{avg}]$.

Step 2: Synthesis of Compound 46

The compound 46 was prepared using General Procedure F, using the Boc-protected dendrimer guanidine 45 (0.31 g, 78.6 mmol) in 2N HCl in dioxane (10 mL). The nona-guanidinium HCl salt (46) was obtained in 91% (0.18 g) yield as a colorless hygroscopic solid. $^1H$ NMR ($CD_3OD$): δ 8.62 (s, 1H, ArH), 8.54 (s, 2H, ArH), 3.65 (m, 42H, $CH_2O$ and $CH_2NHCO$), 3.33 (m, 36H, $CH_2NHCO$ and $CH_2NH$), 2.60 (m, 6H, $CH_2CO$), 2.44 (m, 26H, $CH_2CO$); $^{13}C$ NMR ($CD_3OD$): δ 174.62, 173.65, 168.00, 158.55, 136.12, 131.74, 130.20, 70.00, 68.45, 61.56, 41.94, 39.57, 38.11, 37.39, 34.79: ESI-MS m/z 2138 $[M+H]^+$, 2172 $[M-Cl]^+$.

Example 15

Synthesis and Characterization of a Dendrimer with Amidine Groups

The synthesis of a dendrimer with amidine groups is described below.

Figure 27A:
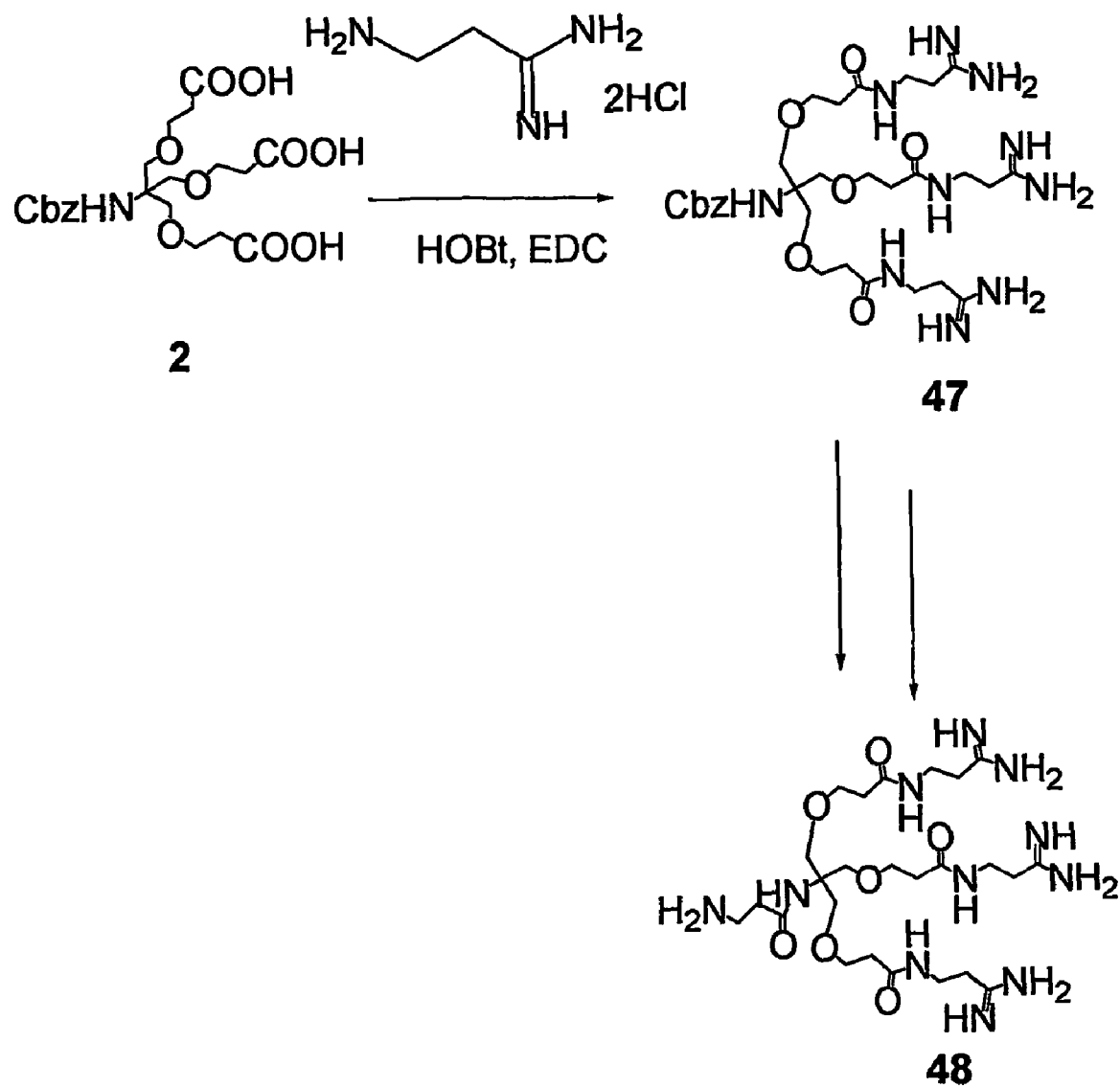
FIGS. 27A-27C depict reaction schemes for the synthesis of dendritic oligo-amidines that include six and nine amidine groups in identical chemical environments.
Figure 27B:
Figure 27B:
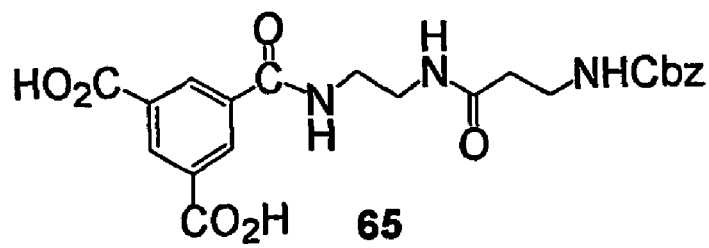
Figure 27B:
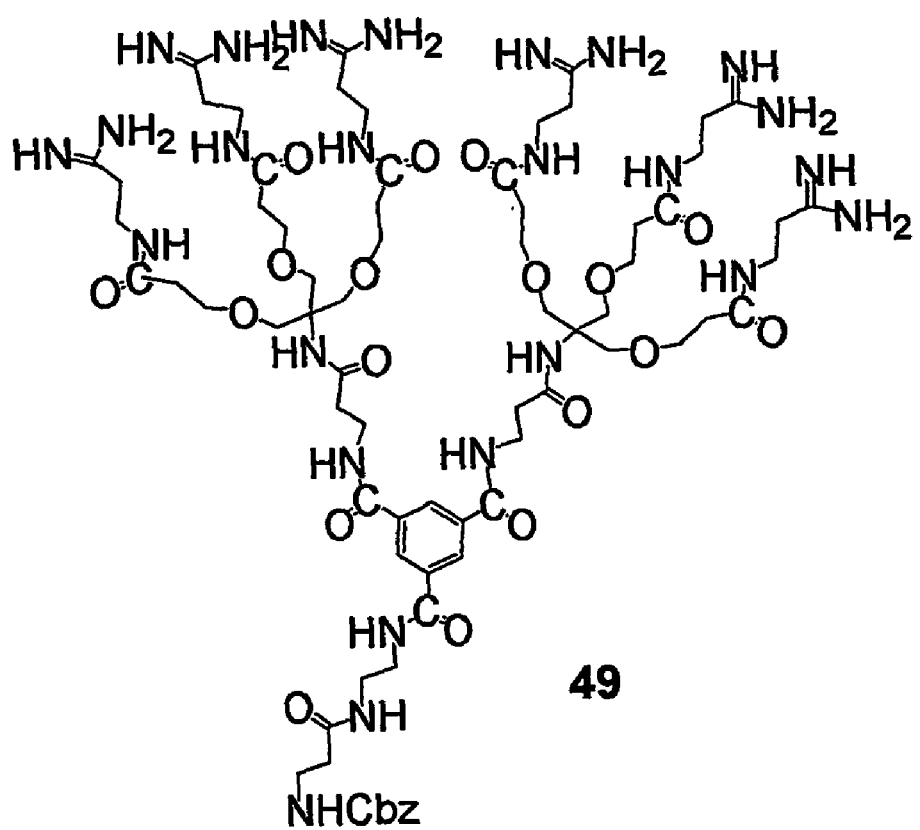
Figure 27C:
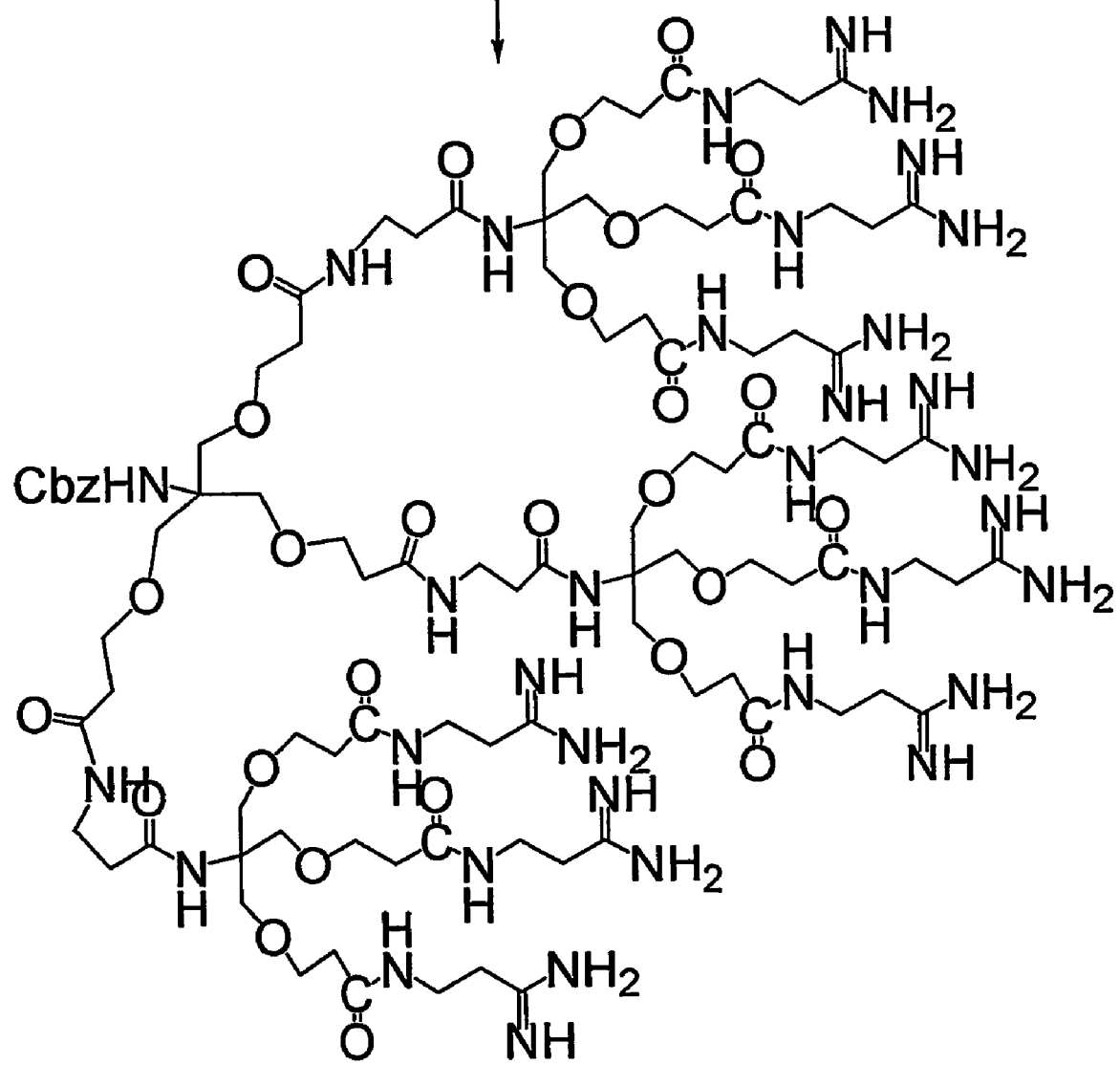
Figure 28A:
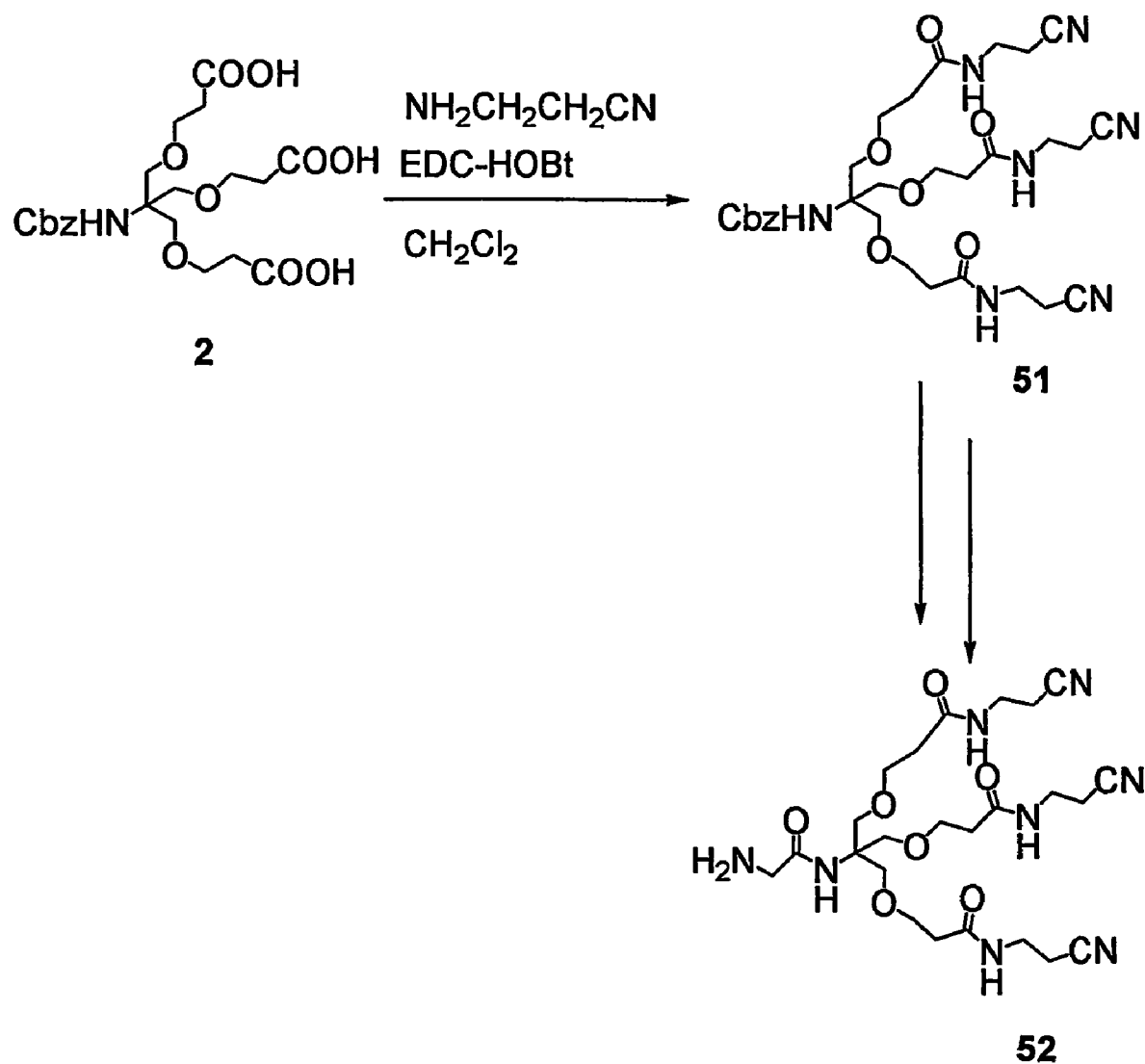
FIGS. 28A-28C depict reaction schemes for the synthesis of dendritic oligo-amidines that include six and nine amidine groups in identical chemical environments.
Figure 28B:
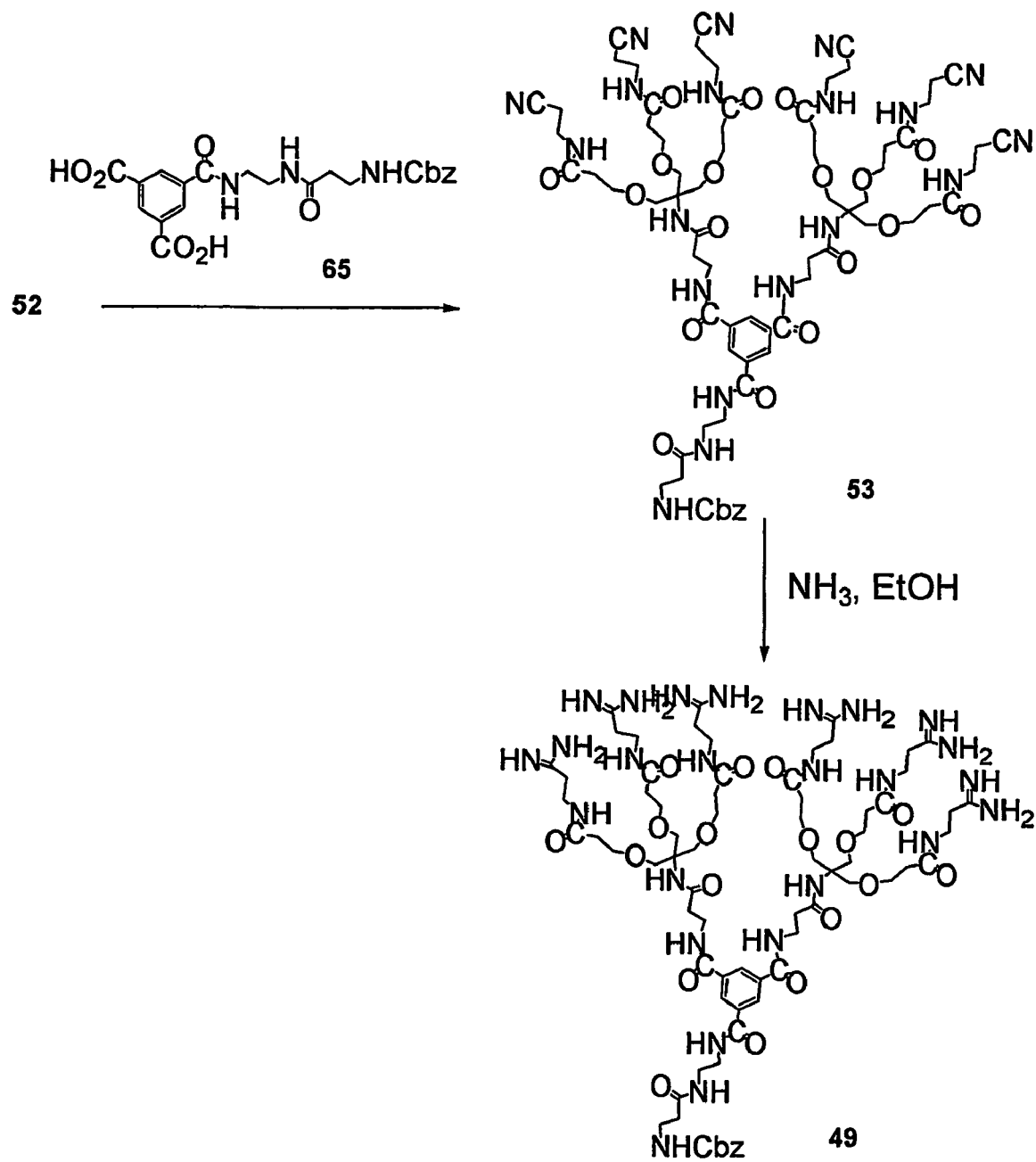
Figure 28C:
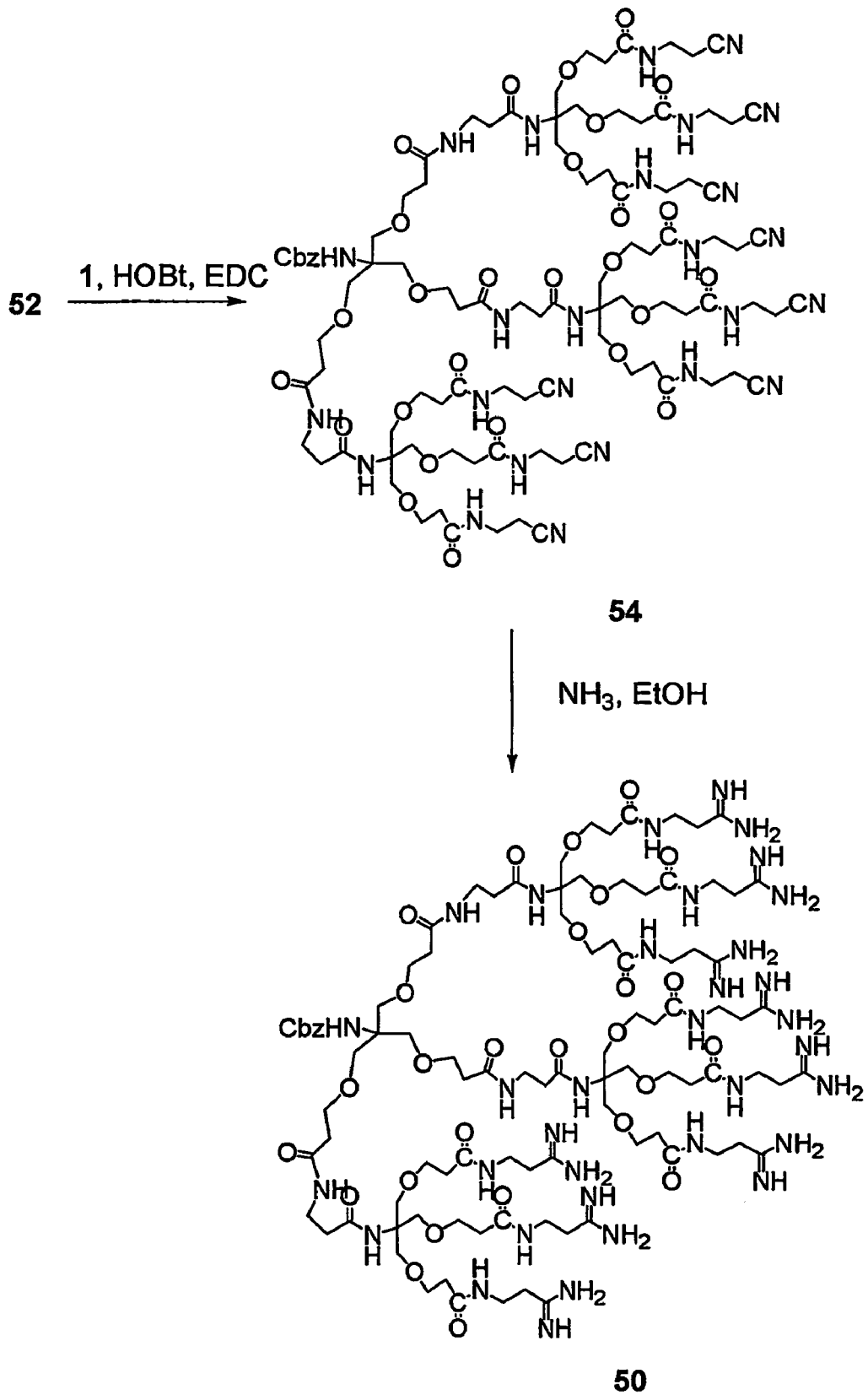

Starting from triacid 2 in FIG. 27A, it is either possible to attach an unprotected amidine directly to the acid moiety, as illustrated in FIG. 27A, or to carry out the synthesis via a nitrile functionality which is converted to the amidine in the last step of the synthesis, as shown in FIGS. 28B and 28C.

Example 16

Synthesis and Characterization of a Dendrimer with Thioureido Groups

The synthesis of a dendrimer with thioureido groups is described below.

Figure 29:
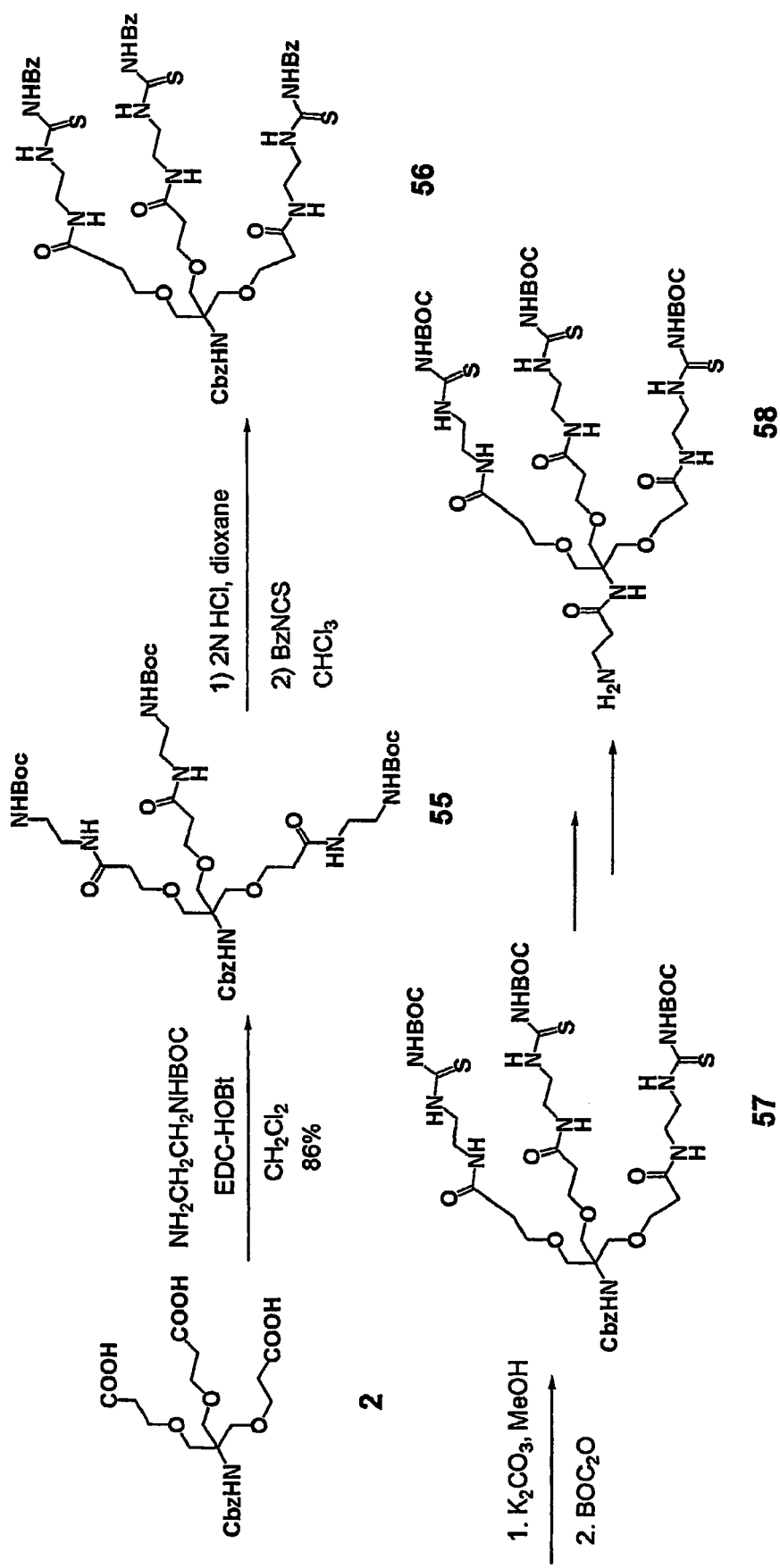
FIG. 29 depicts a reaction scheme for the synthesis of a dendrimer with three protected thiourea groups.
Figure 30:
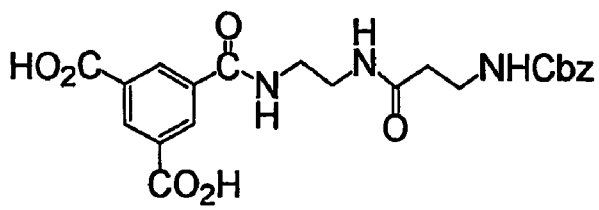
FIG. 30 depicts a reaction scheme for the synthesis of a dendrimer with six protected thiourea groups.
Figure 30:
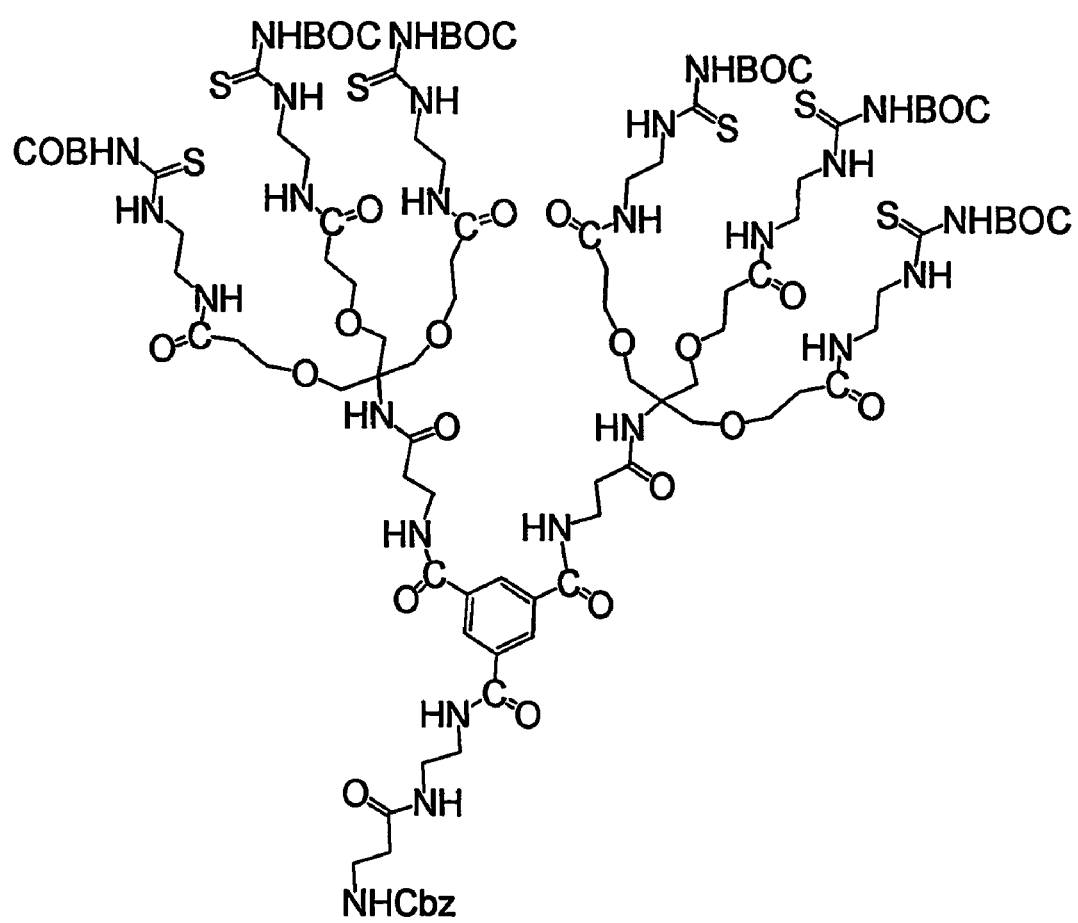
Figure 31:
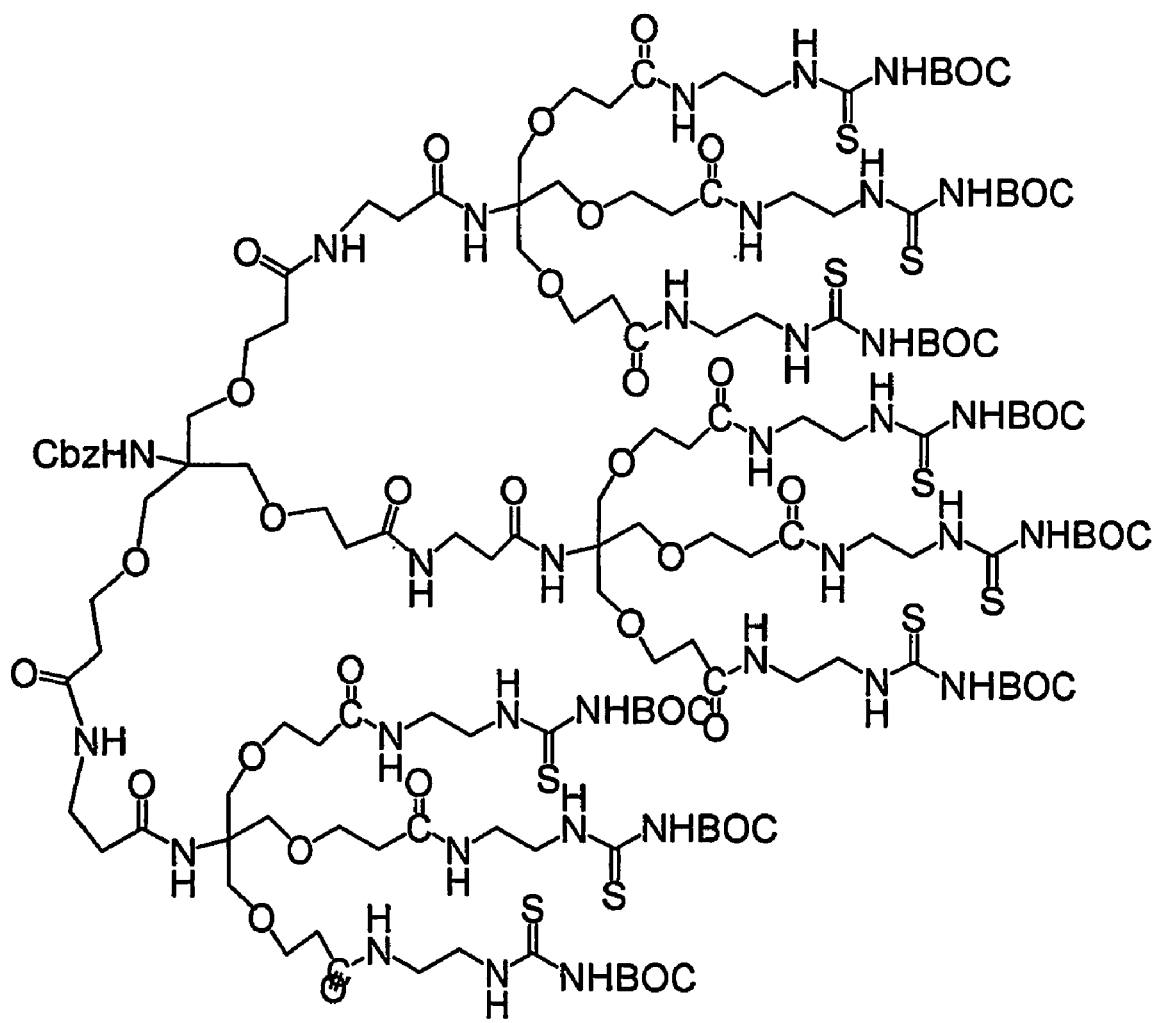
FIG. 31 depicts a reaction scheme for the synthesis of a dendrimer with nine protected thiourea groups.

The synthesis of the thioureido containing dendrimer structures is illustrated in FIGS. 29 through 31. The synthesis starts from the readily available triacid core structure 2. This triacid is converted to the Boc protected tris amine 55. Deprotection of the amines and subsequent reaction with benzoylisothiocyanate provides the benzoyl protected thioureido 56, that is deprotected under basic conditions and protected as a tert butyl carbamate without purification of the free thioureido to obtain the Boc protected compound 57. This is illustrated in FIG. 29. Incorporation of a β-alanine structure via deprotection, coupling and deprotonation leads to the scaffold 58 that is allowed to react with a core structure either leading to six or nine thioureido containing transport molecules 59 and 60, respectively. This is illustrated in FIGS. 30 and 31.

Example 17

Synthesis and Characterization of a Dendrimer with Uredio Groups

The synthesis of a dendrimer with ureido or thioureido groups is described below.

Figure 32:
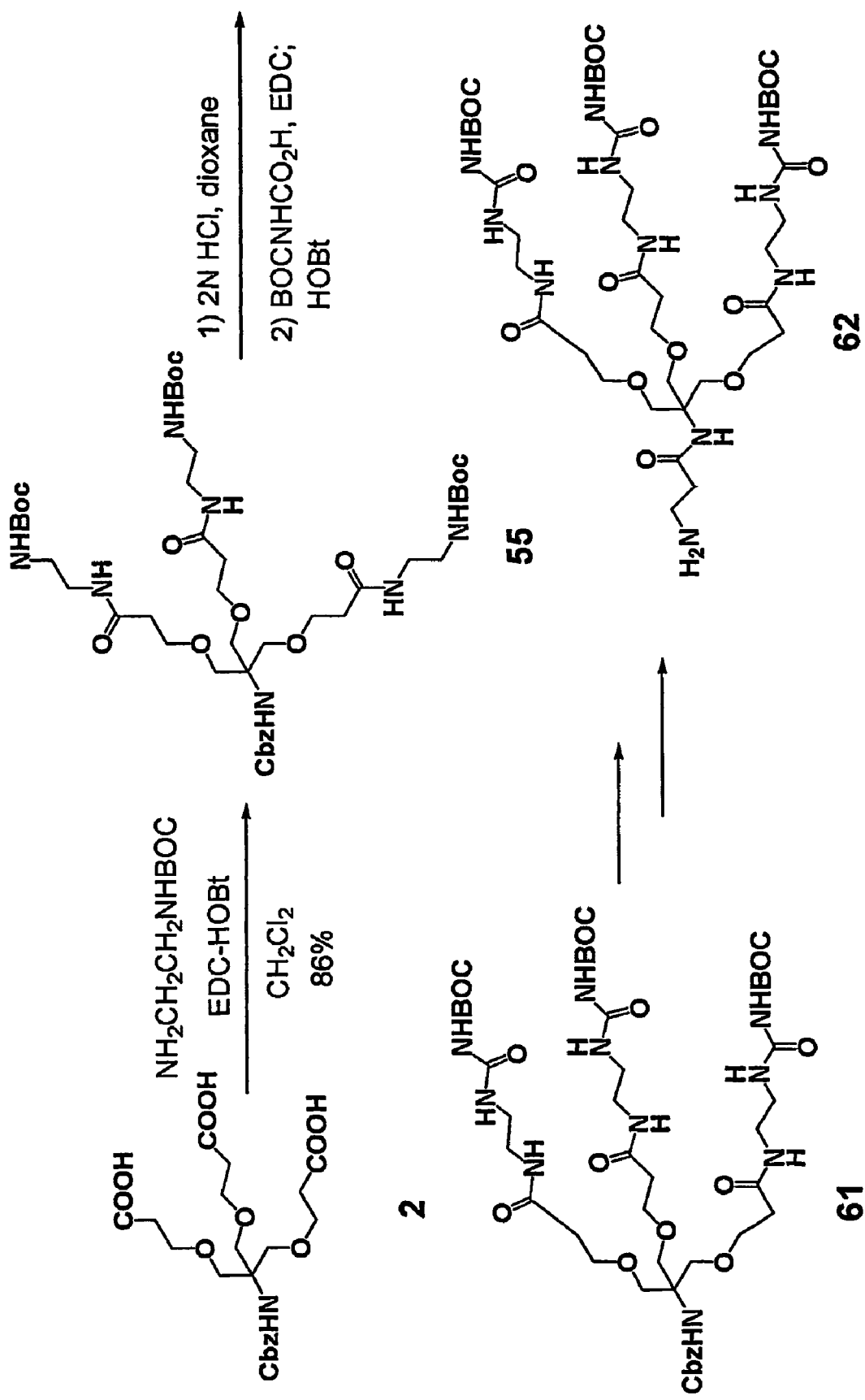
FIG. 32 depicts a reaction scheme for the synthesis of a dendrimer with three protected urea groups.
Figure 33:
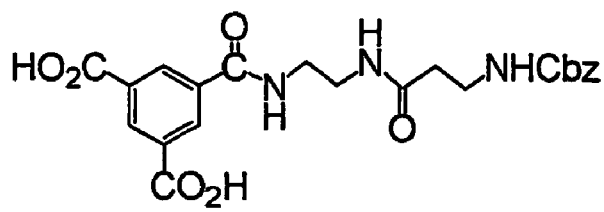
FIG. 33 depicts a reaction scheme for the synthesis of a dendrimer with six protected urea groups.
Figure 33:
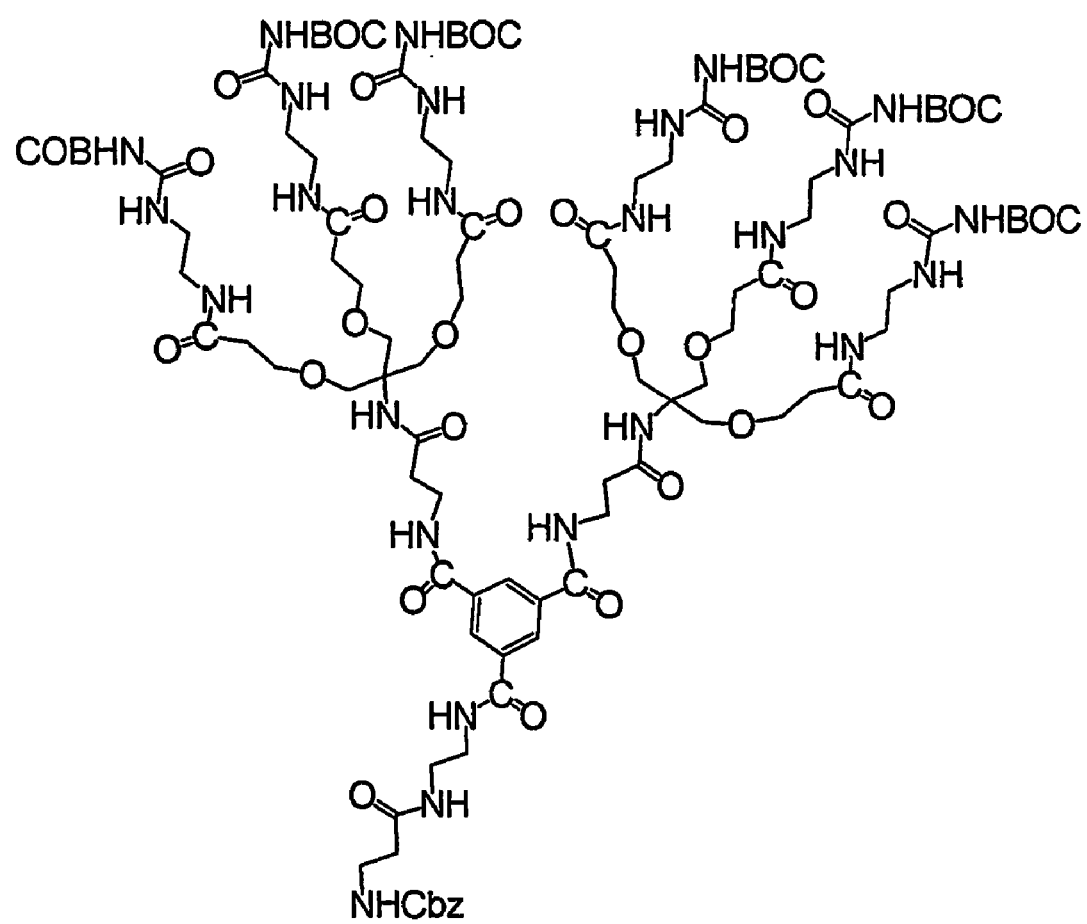
Figure 34:
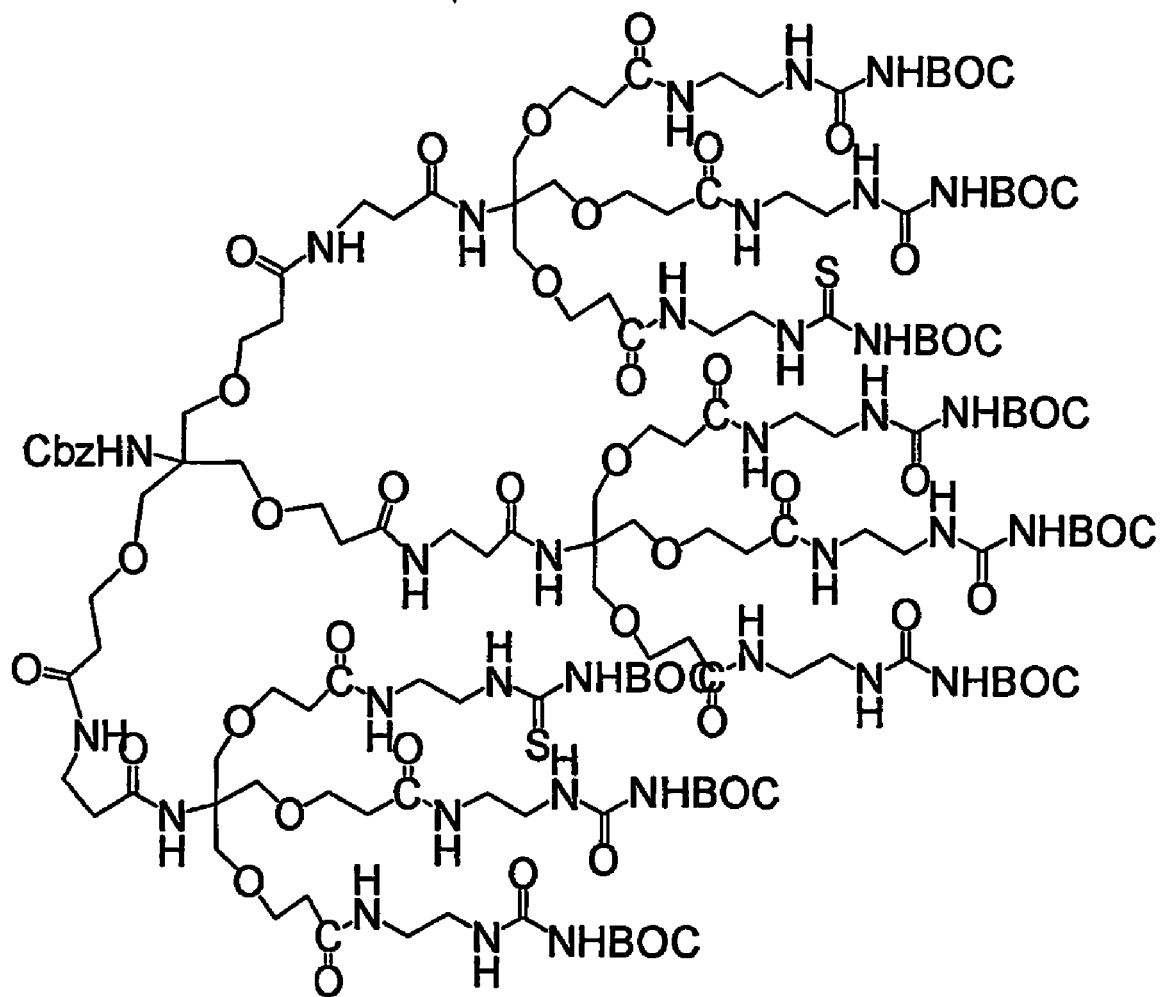
FIG. 34 depicts a reaction scheme for the synthesis of a dendrimer with nine protected urea groups.

The synthesis of the ureido containing dendrimer structures is illustrated in FIGS. 32 and 33. The synthesis commences with triacid 2 which is converted to the triamine 55. Deprotection of the Boc groups and subsequent reaction with Boc protected carbamic acid provides the Boc protected scaffold 62, containing three urea groups. This is illustrated in FIG. 32. Analogous reactions with core structures 2 and 65 leads to six and nine ureido containing structures. This is illustrated in FIG. 33.

Example 18

Synthesis of Transporters with Activated Disulfide Bonds

Figure 35:
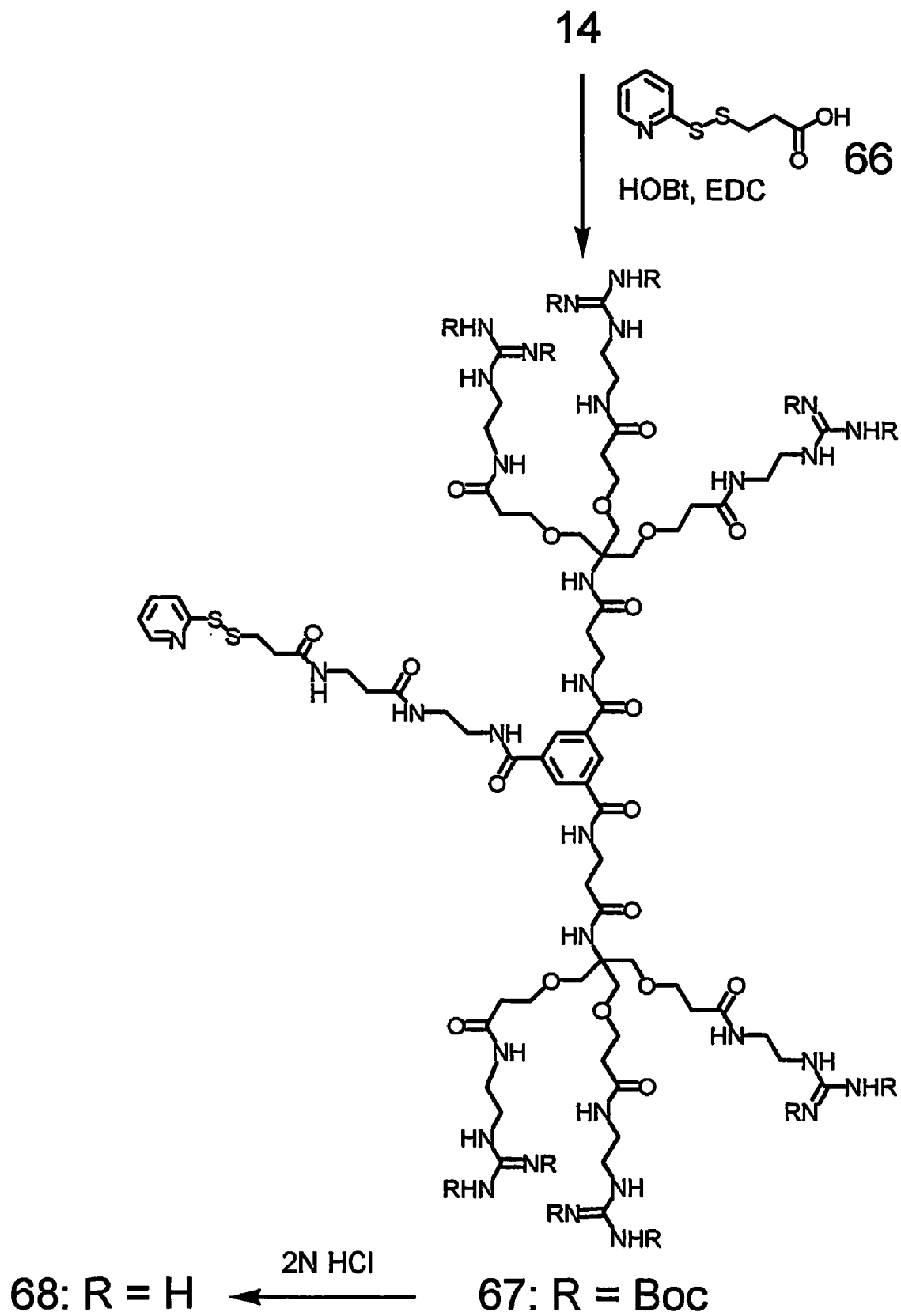
FIG. 35 depicts a reaction scheme for the synthesis of a dendrimer with six guanidine groups and a disulfide group.

For the synthesis of a disulfide dendrimer with six guanidine groups (68), the activated disulfide was attached via peptide coupling prior to deprotection of the guanidines as shown in FIG. 35.

To a solution of 14 (400 mg, 142 μmol) in dichloromethane (10 mL) was added triethlamine (40 μL, 2 eq.), 66 (60 mg, 2 eq.) and hydroxybenzotriazole (40 mg, 2 eq). The solution was cooled to ice bath temperature and 1-ethyl-3-(3-dimethylamino-propyl)-carbodiimide (EDC) (56 mg, 2 eq.) was added. The solution was allowed to warm to room temperature and stirred for 4 hours. The reaction mixture was diluted with dichloromethane (40 mL) and poured into water (50 mL). The aqueous phase was extracted with dichloromethane (3×50 mL). The combined organic layers were then washed with 1 N aqueous hydrochloric acid (3×100 mL), saturated aqueous bicarbonate solution (1×100 mL), and brine (1×50 mL). The solution was dried over magnesium sulfate and concentrated. Flash column chromatography (DCM/MeOH 10:1) gave the product (67) as a colorless foam shaped solid (330 mg, 72%).

To a solution of 67 (100 mg, 35 μmol) in 1,4-dioxame (3 mL) was added 4 N HCl in 1,4-dioxane (3 mL). After 2.5 hours, the precipitate was filtered off and dried in vacuum. The solid was dissolved in water (I mL) and the aqueous solution was then washed with diethylether (3×1 mL) and lyophylized to give the product (68) as a foam shaped hygroscopic solid (61.4 mg, 85%).

Figure 36:
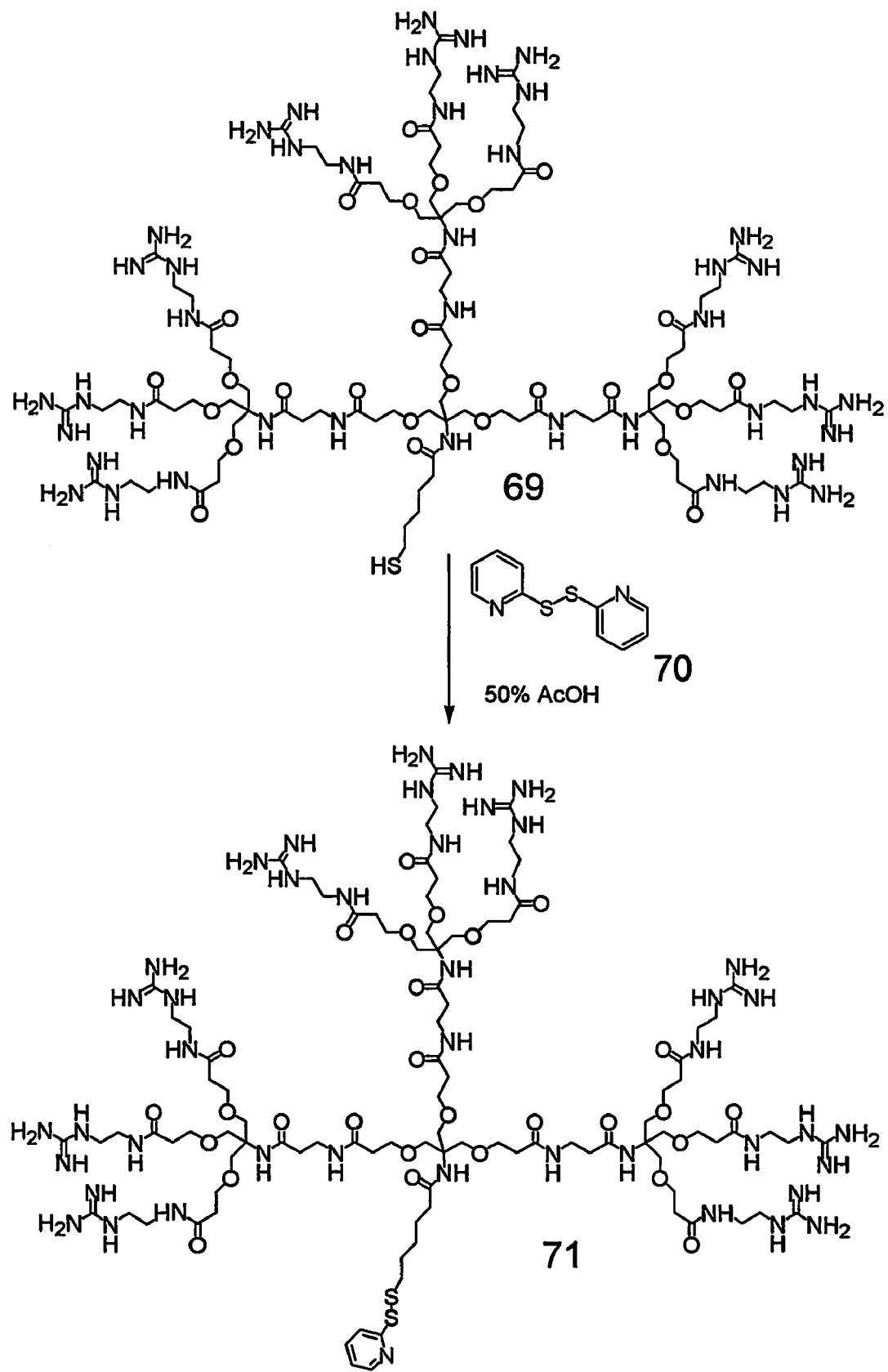
FIG. 36 depicts a reaction scheme for the synthesis of a dendrimer with nine guanidine groups and a disulfide group.

For the synthesis of a disulfide dendrimer with nine guanidine groups (71), the pyridinium disulfide bond was incorporated after deprotection of the guanidines via disulfide formation as shown in FIG. 36.

Compound 69 was synthesized from compound 43 (FIG. 13A). 6-Tritylsulfanyl-hexanoic acid was coupled to 43 via standard EDC/HOBt coupling. To a solution of 43 (140 mg, 34 μmol) and 6-tritylsulfanyl-hexanoic acid (67 mg, 5 equivalents) in dichloromethane (2 mL) was added hydroxybenzotriazole (23 mg, 5 equivalents) and triethlamine (24 μL, 5 equivalents). The solution was cooled to ice bath temperature and 1-ethyl-3-(3-dimethylamino-propyl)-carbodiimide (EDC) (33 mg, 5 equivalents) was added. The solution was allowed to warm to room temperature and stirred at this temperature for 12 hours. The reaction mixture was diluted with dichloromethane (10 mL) and decanted into water (10 mL). The aqueous phase was extracted with dichloromethane (3×20 mL). The combined organic layers were then washed with 1 N aqueous hydrochloric acid (3×30 mL), saturated aqueous bicarbonate solution (1×30 mL) and brine (1×10 mL). The solution was dried over magnesium sulfate and concentrated. Flash column chromatography (DCM/MeOH 10:1) gave the intermediate product as a colorless foam shaped solid. (145 mg, 96%)

To a solution of the intermediate product prepared as described in the preceding paragraph (45 mg, 10 μmol) in 1,4-dioxane (1 mL) was added 4 N HCl in 1,4-dioxane (1 mL). After 4 hours, the precepitate was filtered off and dried under reduced pressure. The solid was dissolved in water (1 mL), and the aqueous solution was then washed with diethylether (3×1 mL) and lyophylized to give the product 69 as a foam shaped hygroscopic solid (30 mg, quantitative).

To a solution of the HCl salt (69) (50 mg) in 50% acetic acid was added 2,2'-pyridinium disulfide (70) (20 mg, 100 μmol), and the solution was stirred for 48 hours. Soon after the addition of 2,2'-pyridinium disulfide (70), the color of the solution turned light yellow. The solution was then extracted with diethylether until the wash was colorless (6×1 mL). Lyophilization of the aqueous layer provided the product (71) as a colorless foam shaped solid (49.7 mg, 96%).

For the evaluation of the dendrimers as molecular transporters, they were coupled to the Green Fluorescent Protein (GFP) and the uptake of the conjugates into HeLa cells was compared to the uptake of a $Tat_{49-57}$-GFP conjugate.

Microscopic images and FACS analysis showed that the transport molecule with nine guanidine groups showed the best results in terms of transportation into cells. While the dose dependency measurements showed similar results, the time dependency showed that the conjugated guanidinylated dendrimers penetrated the cellular membrane more rapidly than the conjugate of the Tat derived peptide. (see FIGS. 39A-39B).

Example 19

Cellular Uptake and Toxicity Studies

Some of the dendritic molecules synthesized and characterized above include fluorescent tags (fluorescein). The fluorescein enables the cellular uptake of these dendrimers to be readily visualized. In this study, the cellular uptake of each molecular fluorescein-labeled dendrimer is visualized and quantified to assess the usability of each molecule in our work Method HeLa S3, human epithelioid cervical carcinoma cells of approximately 50% confluency were treated with concentrations varying from 250 nM to 50 μM of each of the molecular transporters 10, 11, 12, 13, and 41 at 37° C. The molecular transporters were directly added to the media (Dulbecco's modified eagle medium containing 10% fetal bovine serum and 1× antibiotic-antimycotic), and the delivery to the cells was visualized by microscopy.

Quantification of the uptake of the molecular transporter into the cells was performed by flow cytometry 4 hours after treatment. Adherent cells, grown on 6 well plates, were displaced with trypsin, after which the cells were washed with phosphate-buffered saline (PBS). The final cell pellet was collected by centrifugation and resuspended in PBS to a concentration of approximately $1\times10^6$ cells/mL. A minimum of 20,000 cell events were counted and analyzed using the FACSCalibur and CellQuest brand software (BD Biosciences, San Jose, Calif.).

A sulphorhodamine B (SRB) assay was performed to determine whether compound 12 showed cytotoxic effects to HeLa S3 cells. The cells were treated with varying concentrations (250 nM to 50 μM) of compound 12 for 4 hours at 37° C. The cells were fixed with trichloroacetic acid and were then subsequently stained with SRB dye. The cells were washed with water, and the SRB-bound complexes were solubilized in Tris buffer. The absorbance at 572 nm was measured in each sample.

Results

The cellular uptake of five molecular transporters at each concentration was observed by microscopy. Generally, those transporters possessing higher efficiency of uptake into HeLa S3 cells showed brighter and increased number of cell staining (see FIGS. 16A-16N). Furthermore, as cells were treated with increasing transporter concentrations, there was also an increase in the number of stained cells. Preferential localization of the transporter to the nucleus and nucleolus (FIGS. 16A-16N) was observed.

Figure 20:
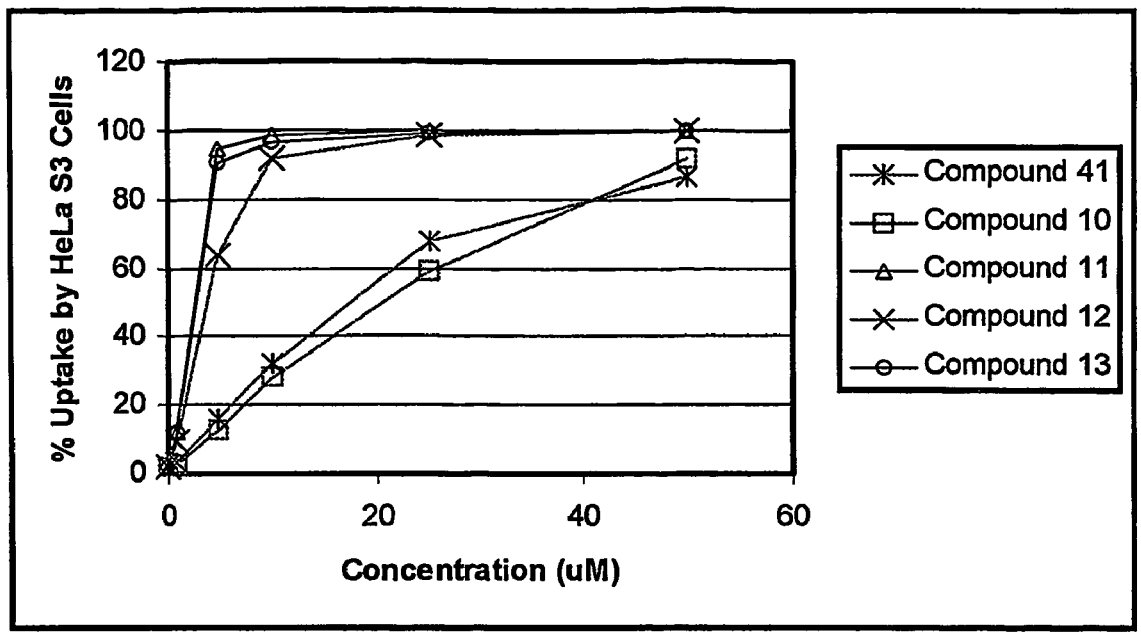
FIG. 20 is a graph of the percentage uptake of compounds 10, 11, 12, 13, and 41 by HeLa S3 human epithelioid cervical cancer cells as a function of concentration in μM.
Figure 21:
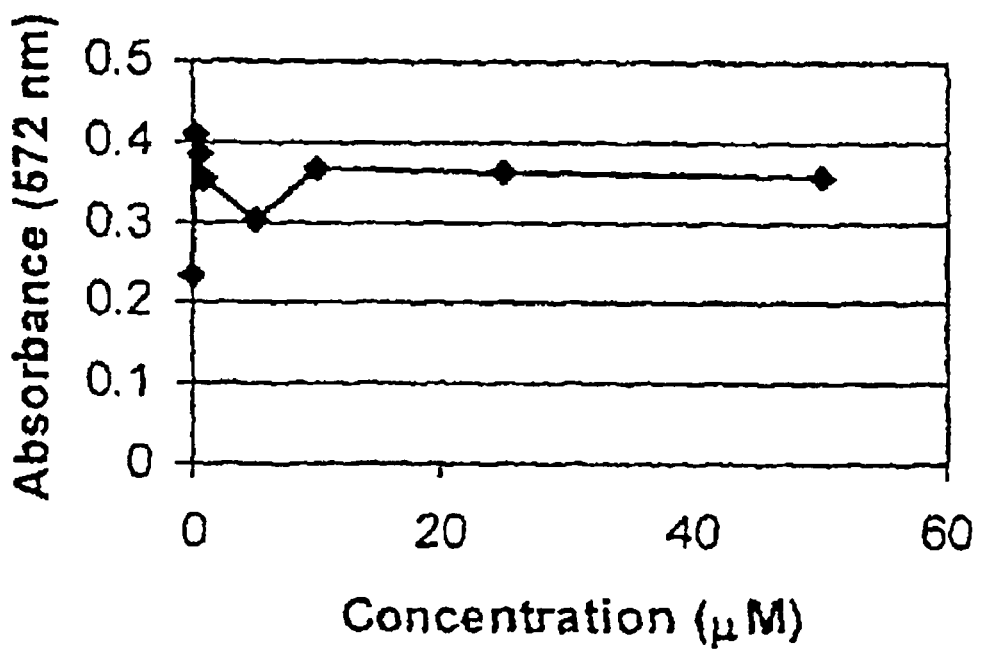
FIG. 21 is a graph of the absorbance at 572 nm as a function of the concentration of compound 12 in a sulphorhodamine B (SRB) assay. The graph shows retention of the absorbance of 572 nm between 0.3 and 0.4 OD indicating that compound 12 exhibited no cytotoxic effect and did not cause cell lysis during the 4 hour treatment at concentrations of up to 50 μM.
Figure 22A:
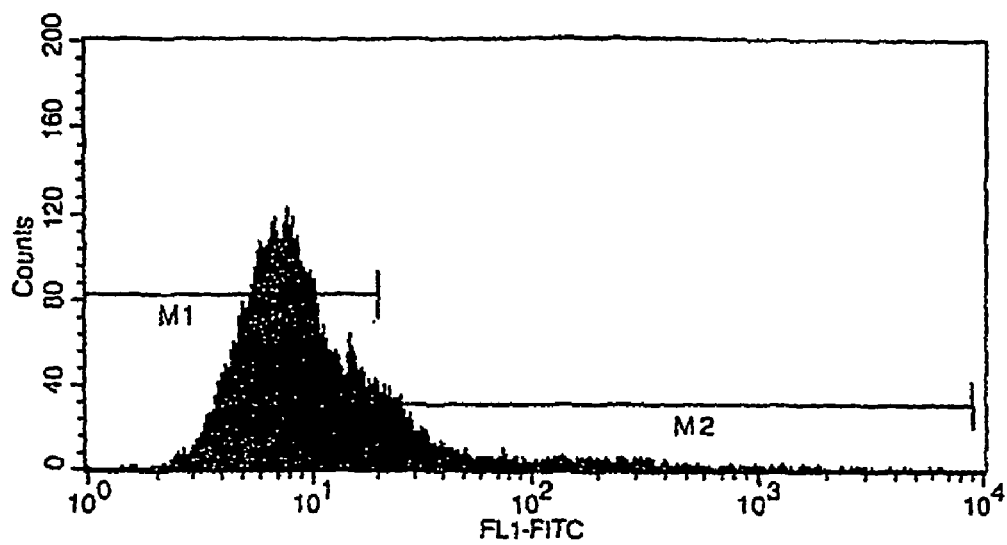
FIGS. 22A-22C depict graphs relating to the cellular uptake of fluorescein-labeled compound (12) at a concentration of 250 nM by HeLa S3 human epithelioid cervical carcinoma cells.
Figure 22B:
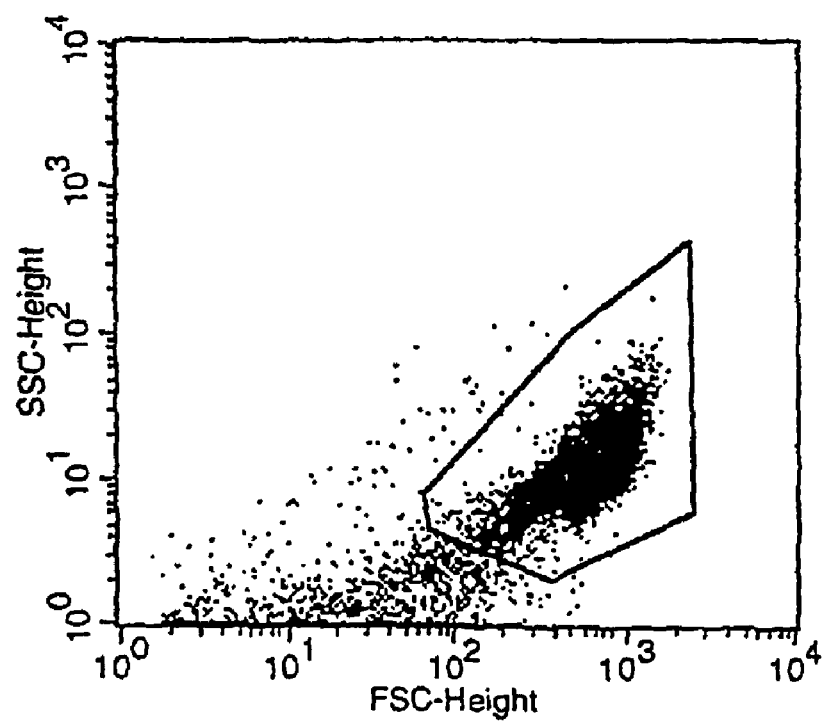
Figure 22C:
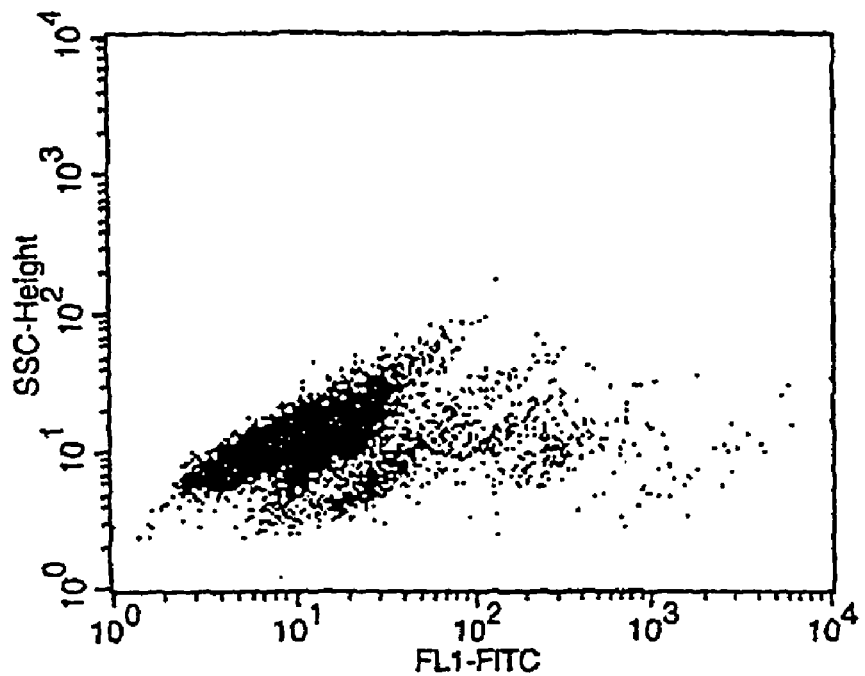
Figure 23A:
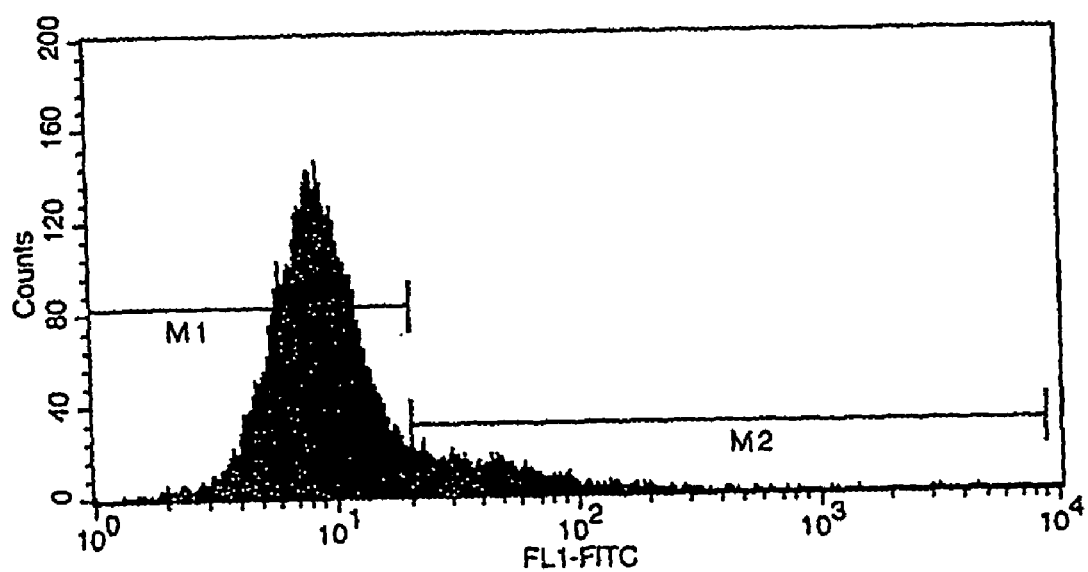
FIGS. 23A-23C depict graphs relating to the cellular uptake of fluorescein-labeled compound (12) at a concentration of 500 nM by HeLa S3 human epithelioid cervical carcinoma cells.
Figure 23B:
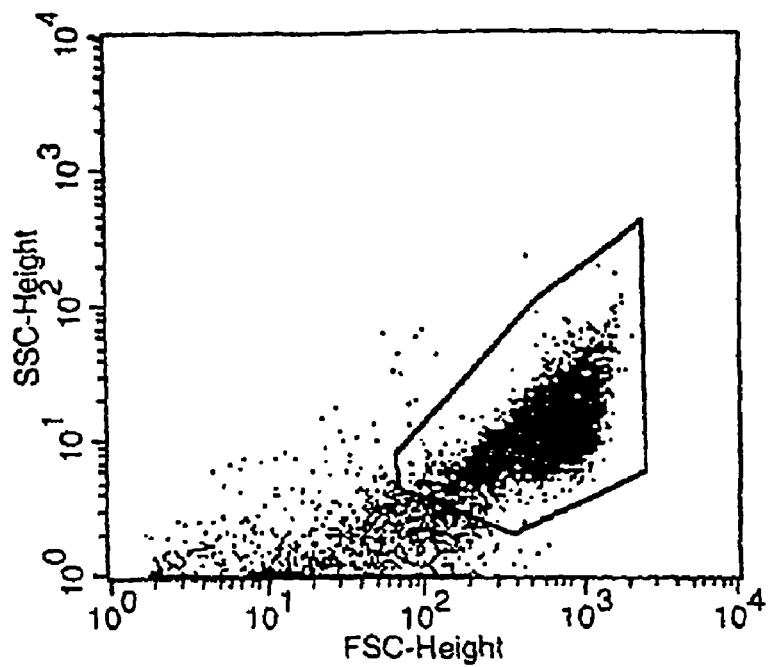
Figure 23C:
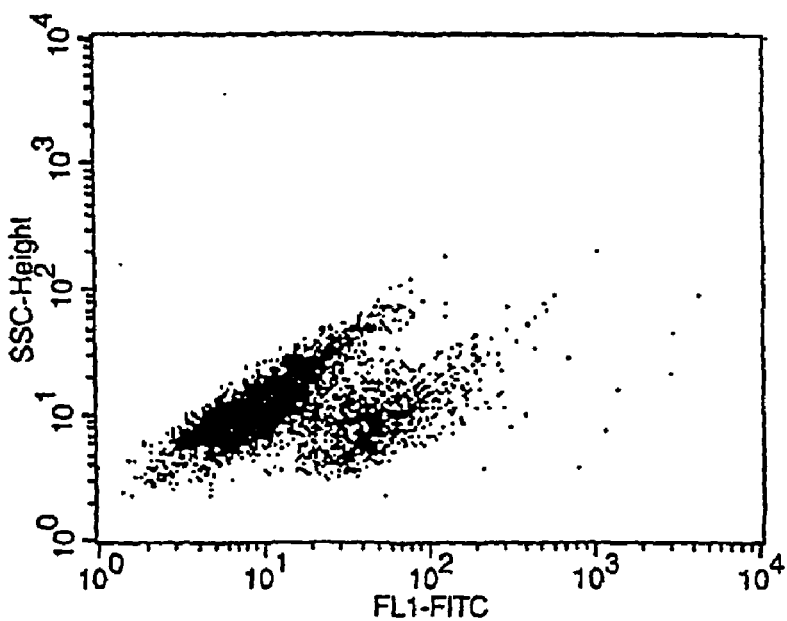
Figure 24A:
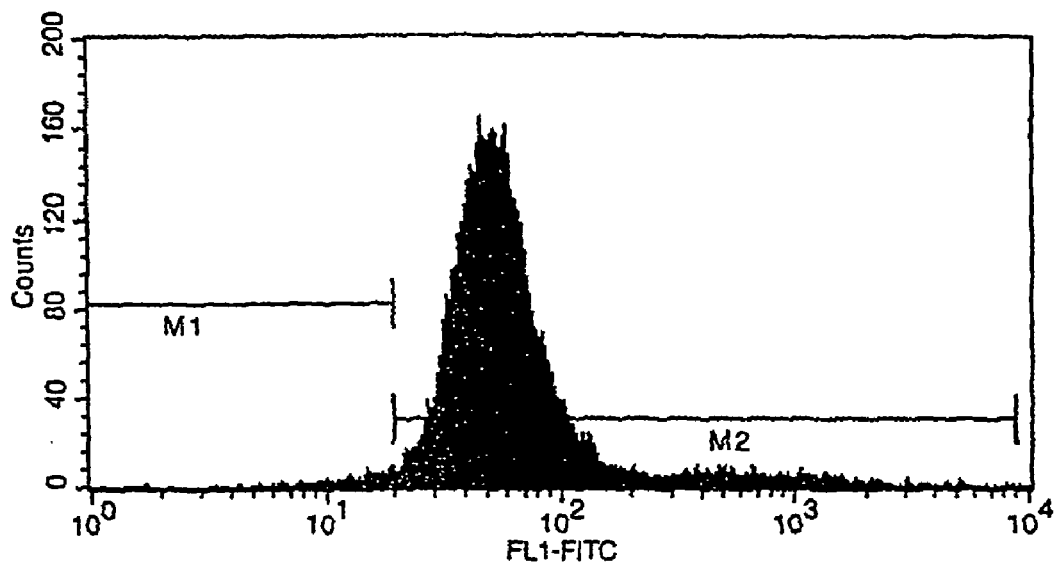
FIGS. 24A-24C depict graphs relating to the cellular uptake of fluorescein-labeled compound (12) at a concentration of 10 μM by HeLa S3 human epithelioid cervical carcinoma cells.
Figure 24B:
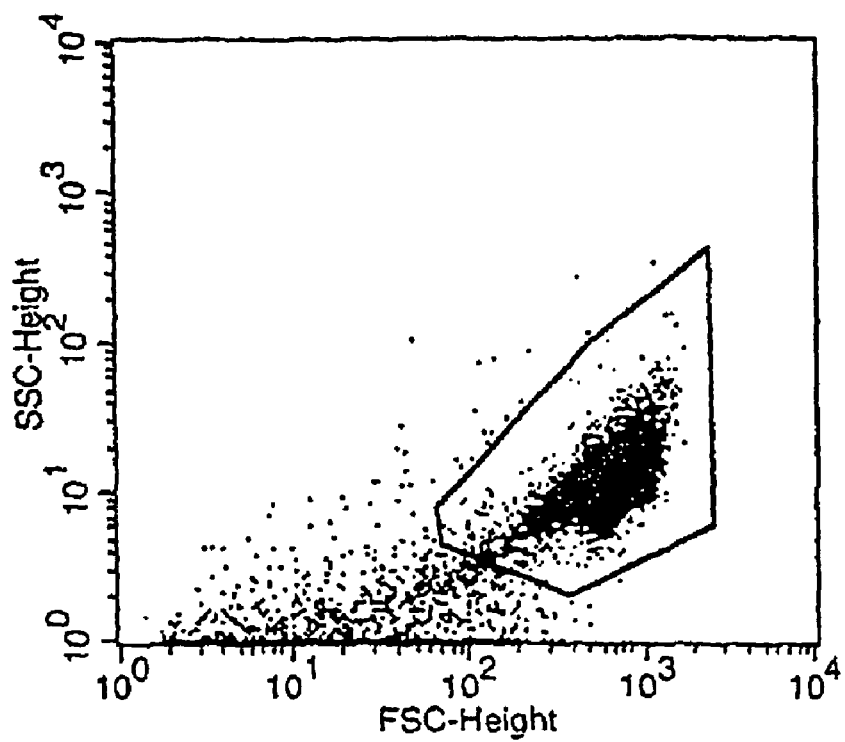
Figure 24C:
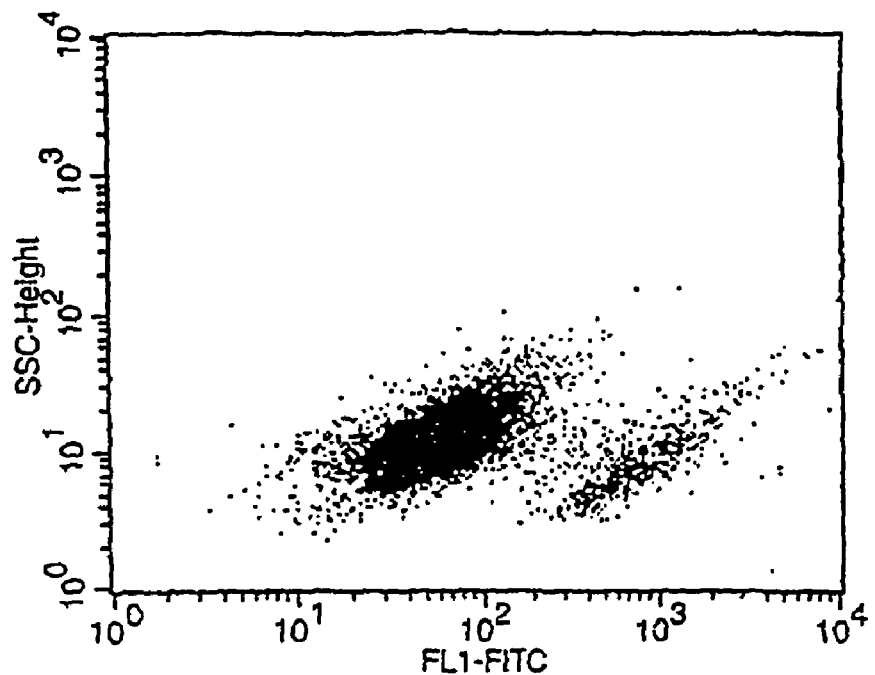
Figure 25A:
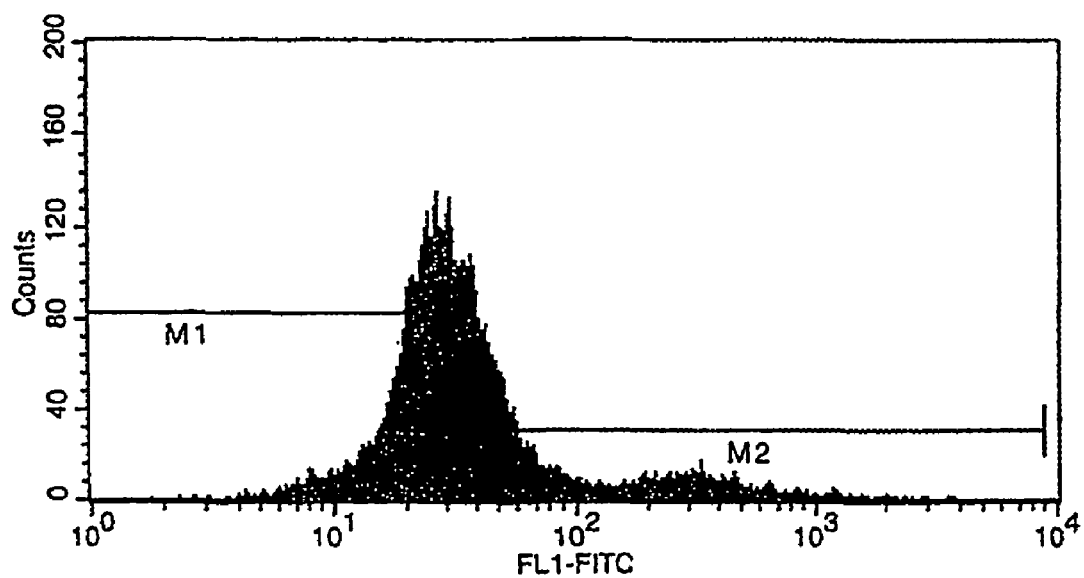
FIGS. 25A-25C depict graphs relating to the cellular uptake of fluorescein-labeled compound (12) at a concentration of 5 μM by HeLa S3 human epithelioid cervical carcinoma cells.
Figure 25B:
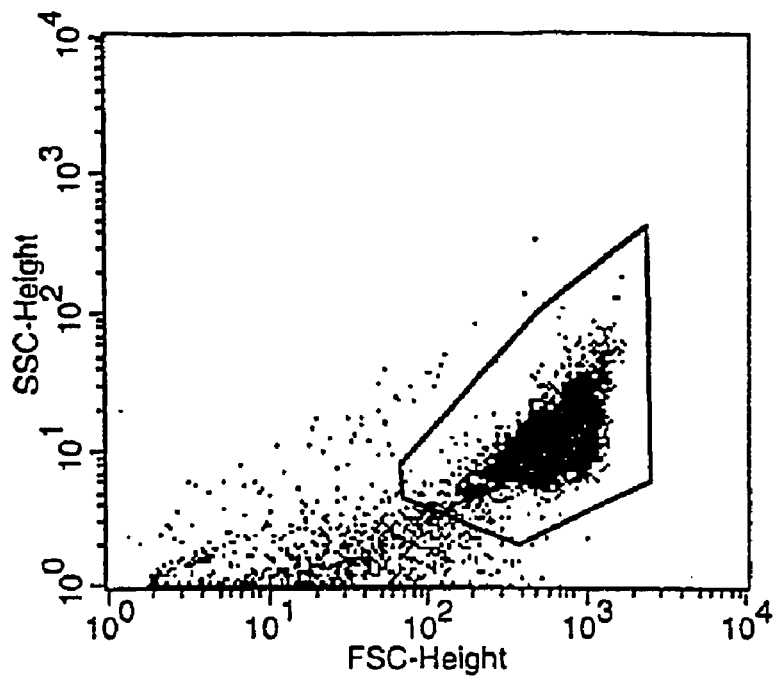
Figure 25C:
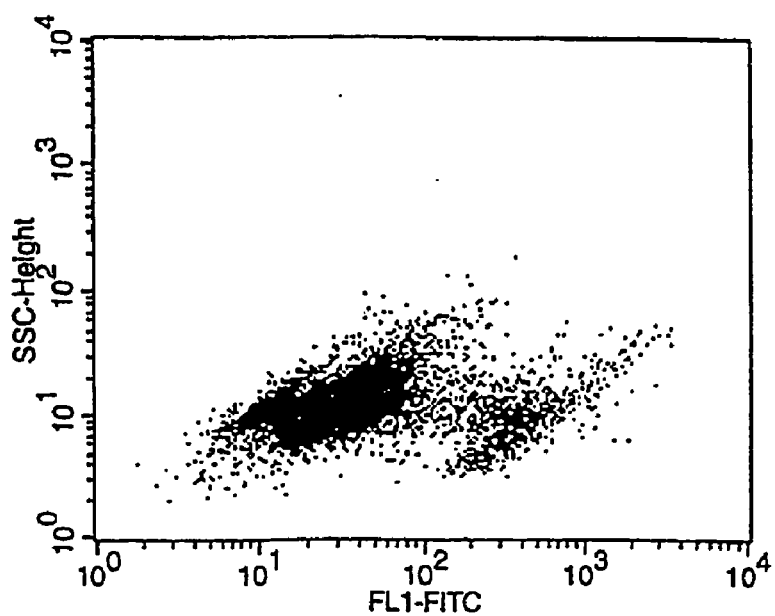
Figure 26A:
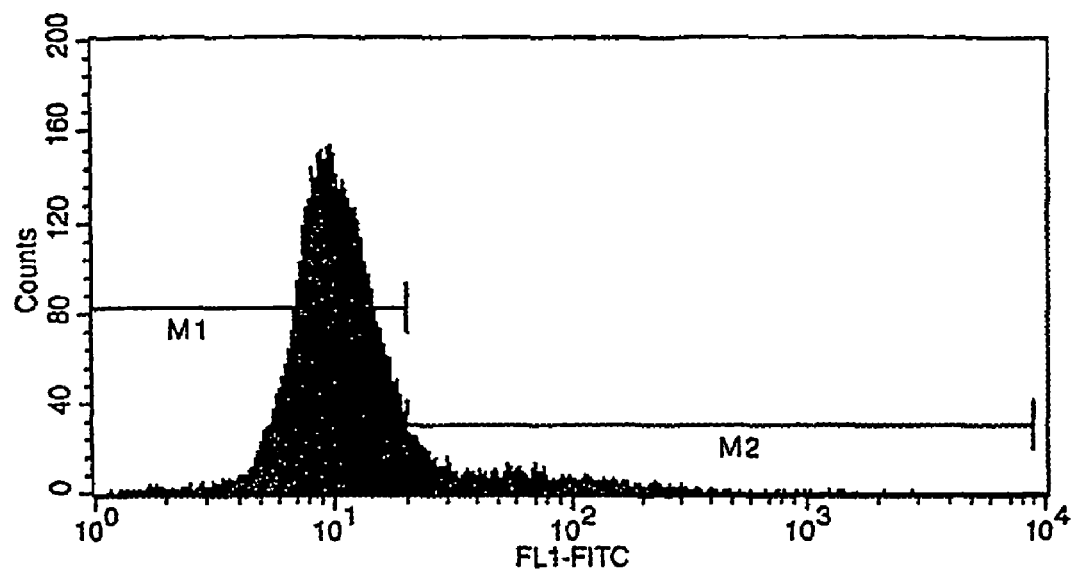
FIGS. 26A-26C depict graphs relating to the cellular uptake of fluorescein-labeled compound (12) at a concentration of 1 μM by HeLa S3 human epithelioid cervical carcinoma cells.
Figure 26B:
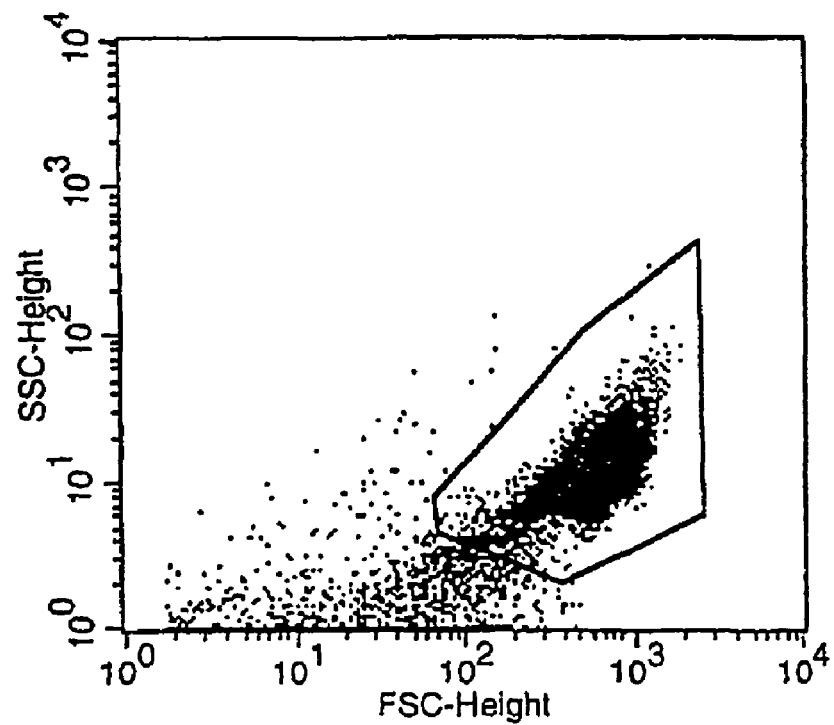
Figure 26C:
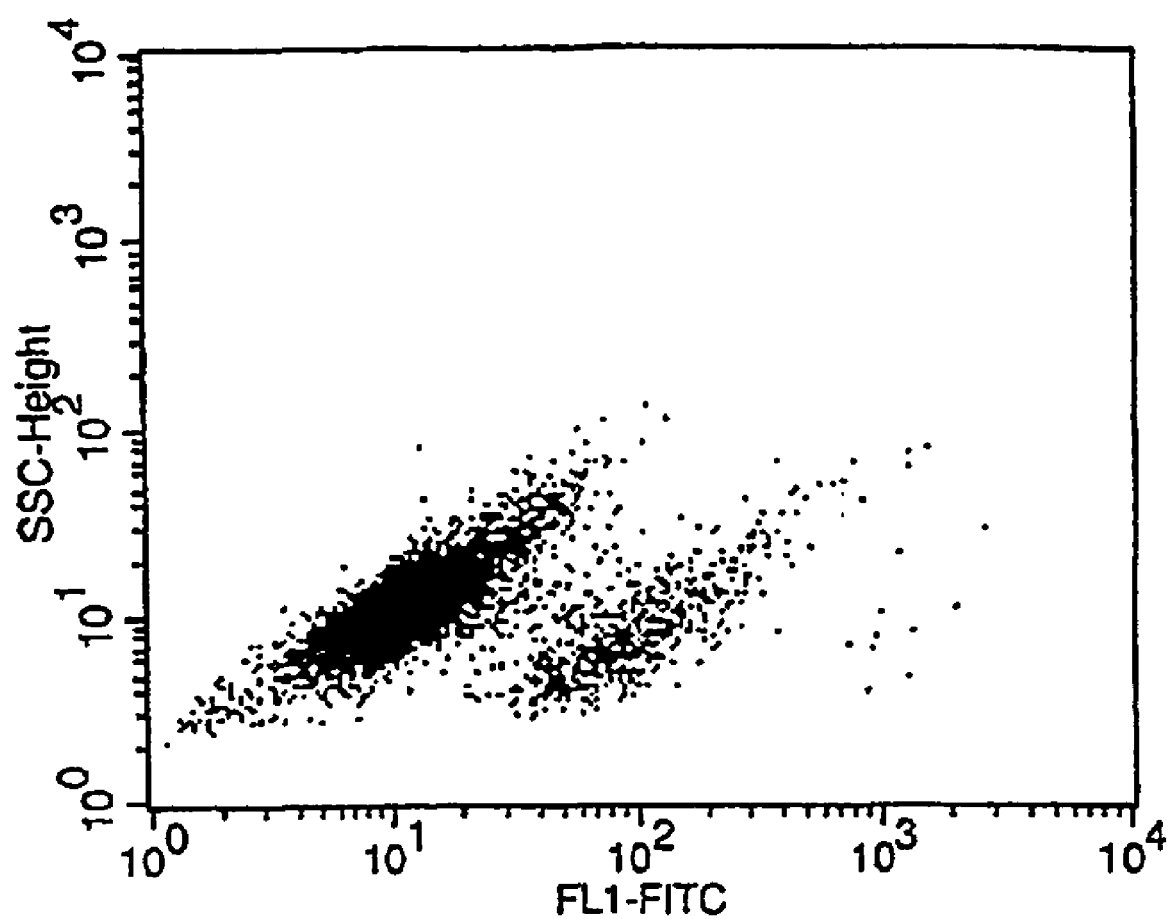

To quantify the number of cells that had taken up the molecular transporter, FACS analyses were performed. Raw data collected by CellQuest acquisition was obtained. An example of one data set illustrating the percentage of uptake of compound 12 at various concentrations is shown in FIGS. 18A-18C, 19A-19C, 22A-22C, 23A-23C, 24A-24C, 25A-25C, and 26A-26C. The fluorescing cells of the gated population are shown in M2. The percentage uptake of compounds 10, 11, 12, 13, and 41 in HeLa S3 cells is shown in Table 1 and FIGS. 18A-18C, 19A-19C, 20, 22A-22C, 23A-23C, 24A-24C, 25A-25C, and 26A-26C. The values presented in Table 1 are an average percentage from two separate experiments. As the concentration of molecular transporter increased, there was a gradual increase of uptake into cells until saturation of approximately 100% of uptake was achieved. This was observed for all 5 of transporters 10, 11, 12, 13, and 41. Transporters 11 (6 guanidines), 12 (9 guanidines), and 13 (12 guanidines) possess an increased number (>6) of guanidine groups and exhibited excellent delivery to HeLa S3 cells. Transporters 11, 12, and 13 exhibit similar dose-dependent percentage uptake curves (FIG. 20).

TABLE 1

Uptake of Fluorescein-Labeled Dendrimers by HeLa S3 Human Epithelioid Cervical Carcinoma Cells

| Compound (Guanidines) | Percentage of Cellular Uptake | | | | | | | |
|---|---|---|---|---|---|---|---|---|
| | Untreated 0 nM | 250 nM | 500 nM | 1 µM | 5 µM | 10 µM | 25 µM | 50 µM |
| 41 (1) | 2.02 | 1.95 | 2.065 | 3.025 | 16.07 | 32.4 | 67.47 | 86.71 |
| 10 (3) | 2.045 | 1.845 | 2.89 | 2.85 | 12.44 | 27.91 | 59.15 | 92.07 |
| 11 (6) | 2.04 | 4.56 | 7.52 | 11.74 | 94.54 | 98.55 | 99.79 | 99.87 |
| 12 (9) | 2.01 | 9.07 | 8.71 | 9.17 | 63.52 | 91.74 | 98.61 | 99.75 |
| 13 (12) | 2.03 | 3.22 | 6.59 | 11.91 | 90.79 | 96.77 | 99.11 | 99.82 |

Cell viability was maintained with each molecular transporter such that cell count remained similar before and after treatment with the transporter. Furthermore, the SRB assay confirmed that compound 12 exhibited no cytotoxic effect and did not cause cell lysis during the 4 hour treatment at concentrations of up to 50 µM (see FIG. 21). This was demonstrated by the retention of the absorbance at 572 nm between 0.3 and 0.4 in each sample.

The results presented herein demonstrate that the molecular transporters of the invention are highly efficient and are effectively taken up into mammalian cells such as human cancer cells. Although the percentage of uptake varies between transporters and may vary at different concentrations, these transporters may be employed to deliver biologically active cargo molecules, such as proteins, nucleic acids, and pharmaceuticals into cells. Based on the preliminary results observed in cellular uptake by HeLa S3 epithelioid cervical carcinoma cells, it is clear that the dendrimers of the present invention may be used to deliver small organic molecules that have poor solubility in aqueous liquids such as serum and aqueous saline. Therefore, bioactive agents with therapeutic efficacies which are limited by low solubility may be administered in greater dosage using the dendrimers of the present invention. Furthermore, linking such drugs to a dendrimer of the present invention results in the production of molecule transporters with drugs that are more efficacious on a molar basis than is the same drug when it is not bonded or tethered to the dendrimer. Consequently, the dendrimers of the invention increase the pharmaceutical acceptability and bioavailability of pre-existing drugs and may be used to create drugs which otherwise would not be used due to poor bioavailability especially with drugs that would otherwise exhibit high activity. Biologically active molecules including, but not limited to, proteins, peptides, nucleic acids, small molecule pharmaceuticals, and other pharmaceuticals may be transformed, by linkage to a dendrimer of the invention, from unacceptable candidates into highly efficient candidates for drug development.

Example 20

Effects of Guanidinium Groups on Transfer in HeLa Cells

Chemical Synthesis of Synthetic Transporters of the Branched Guanidinium Groups

Dendrimers with multiple branched guanidinium groups (nine, six, and three guanidinium groups) were prepared as described above. The G6-GFP and the G9-GFP GFP conjugated compounds were produced by respectively reacting compounds 68 and 71 (See FIG. 35 and FIG. 36) with GFP.

Preparation of Green Fluorescent Protein (GFP)

The coding region of GFP was inserted in the BamHI/SalI sites of pET21b vector (Novagen, Inc.) for the expression of GFP as a fusion with C-terminal 6 histidine residues (6×His) in *E. coli*. A cysteine residue was added at the N-terminus of GFP (pET/Cys-GFP) for conjugating GFP-6×His with the branched structure of guanidinium groups using a disulfide bond formation. The basic domain of HIV Tat$_{49-57}$ (RKKRRQRRR) was also fused to the N-terminus of GFP (pET/Tat$_{49-57}$-GFP) as a control. A BL21 (DE3) bacterial strain was used for the expression of these proteins. Soluble proteins with a bright green color were highly expressed when they were induced with 0.5 µM IPTG at 25° C. overnight. The proteins were first affinity-purified using Ni-NTA agarose (Qiagen, Inc.) and then imidazole and salts were removed using a PD10 desalting column (Amersham Bioscience, Corp.) according to the instructions.

Conjugation of Cys-GFP with Branched Guanidinium Groups

Purified Cys-GFP protein (20 µM final in PBS) was incubated with a 20-fold molar excess of the branched guanidinium groups with a cleavable disulfide linker (200 µM) in the presence of a 10-fold molar excess of DTT (100 µM) at room temperature for 4 hours. The conjugated proteins were first purified in His-affinity column (Ni-NTA) to remove the un-reacted guanidinium groups. Then they were further purified in CM ion exchange column to remove the un-reacted GFP using the basic charge of the guanidinium groups. The purified proteins were finally desalted on a PD10 column and quantified using BCA assay (Pierce Biotechnology, Inc.).

Treatment of the GFP-Conjugated Transporters to Animal Cells

Human cervical carcinoma cell lines, HeLa and HeLa S3 cells were maintained in Dulbeco's Modified Eagle's Medium (DMEM) supplemented with 10% FBS and antibiotics. Cells were plated in 12-well plates the day before treatment. The cells were treated with GFP-conjugated guanidinium groups and Tat$_{49-57}$-GFP in 500 μL of DMEM without serum. The concentration of the transporters and treatment time were as indicated in each set of experiments.

FACS and Microscopic Analyses for Assessing Transduction

After treatment, transporters were removed and cells were washed with 1 mL PBS at least four times. Uptake of the transporters into the cells was analyzed by FACS analysis or by microscopic observation of GFP fluorescence using a FITC wavelength channel. For confocal image analysis, cells were plated on the cover glass in 12-well plates and treated with 8 μM of each transporter for 4 hours. After washing as above, cells were fixed with 3.7% para-formaldehyde for 10 minutes, counter-stained for actin and nucleus with Texas Red-X phalloidin (Molecular Probes, Inc.) and DAPI (Pierce Biotechnology, Inc.), respectively. Each process was performed at room temperature according to the manufacturer's instruction and followed by extensive washing with PBS. Finally, cover glasses were mounted on the slides and left in a dark environment to dry. Fluorescence images were obtained at the magnification of 1000× in the confocal microscope using wavelengths of 617 nm (actin), 528 nm (GFP) and 457 nm (nucleus).

Results

Conjugation of the Branched Guanidinium Groups with Green Fluorescent Protein (GFP)

Figure 37B:
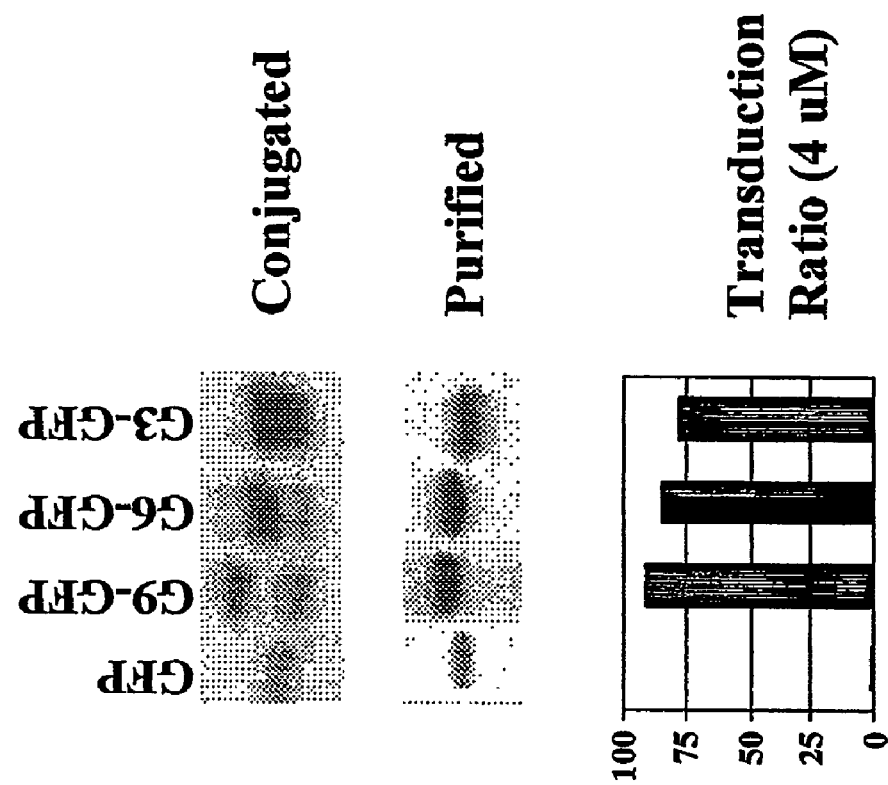
FIGS. 37A-37B depict the G3, G6, and G9 conjugated with Green Fluorescent Protein (GFP) and their transduction efficiency. G9 refers to compound 71 of FIG. 36.
Figure 37A:
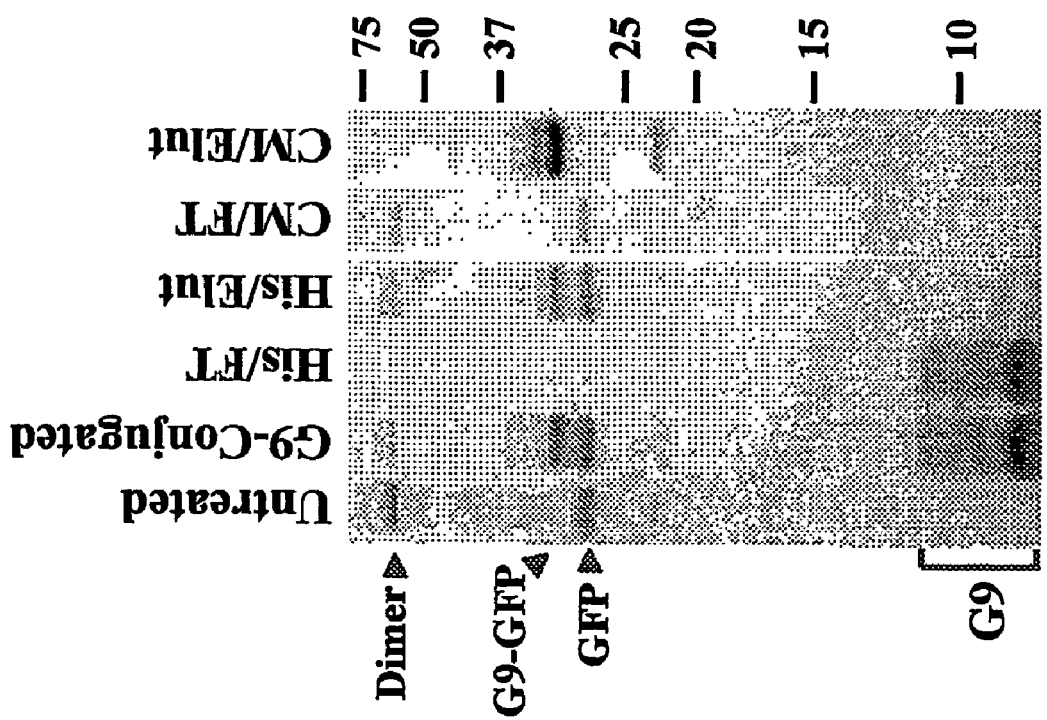

The Green Fluorescent Protein (GFP) was used as a cargo to evaluate the synthetic transporters. Their transduction was measured by microscopic images and statistically quantifiable FACS. GFP for conjugation and Tat$_{49-57}$-GFP as a control were prepared as described above. Reaction conditions for conjugation were tested and it was found that a molar excess of 20 fold for the guanidinium groups and 10 fold for DTT to the amount of GFP provided the best result. An increase in reaction time generally resulted in an increase in conjugation efficiency, but the incubation for 4 hours showed comparable efficiency to that of 24 hour-incubation (data not shown). Un-conjugated guanidinium groups and GFP were removed sequentially using His-affinity and carboxymethyl (CM) cation exchange columns, respectively (FIG. 37A). GFP conjugates of nine (G9-GFP), six (G6-GFP) and three (G3-GFP) guanidinium groups were successfully obtained in high quality (FIG. 37B, top).

Transduction of the Branched Guanidinium Groups into Animal Cells

Figure 39B:
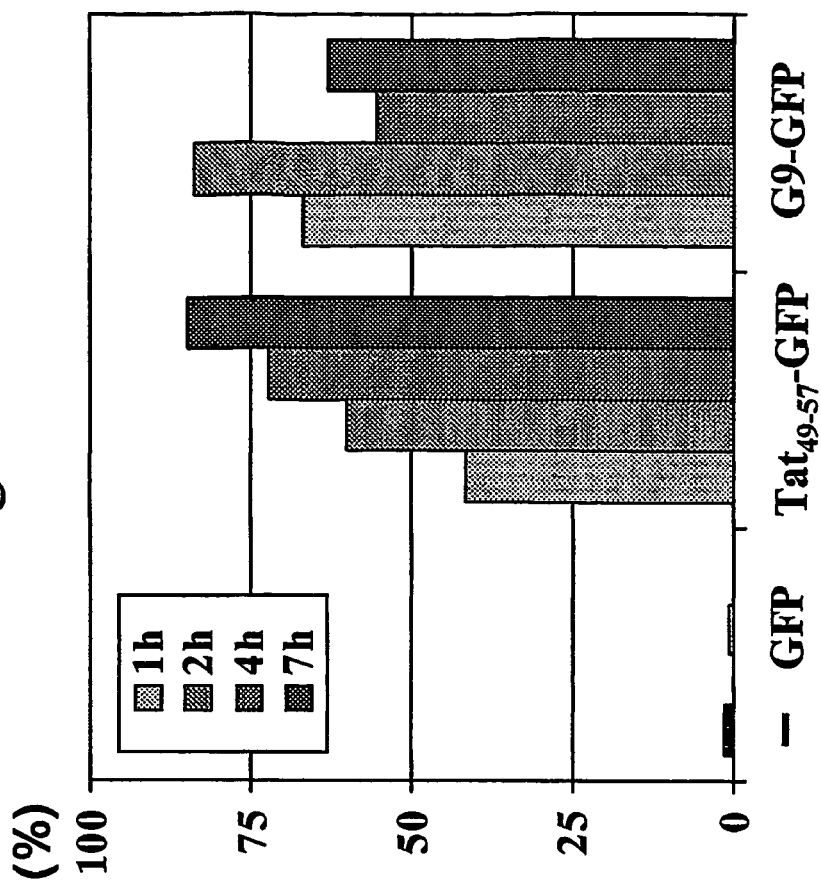
FIGS. 39A-39B are graphs of the dose-dependency (FIG. 39A) and time-dependency (FIG. 39B) of transduction of 71-GFP). For dose-dependency, HeLa cells were treated with 1, 2, or 4 μM each of $Tat_{49-57}$-GFP, or 71-GFP for 4 hours at 37° C. without serum. G9 at the bottom of the graphs represents compound 71. For time-dependency, cells were treated with 2 μM with each of the proteins and harvested at 1, 2, 4 and 7 hour time points for analysis. Transduction efficiencies were measured using FACS analysis.
Figure 39A:
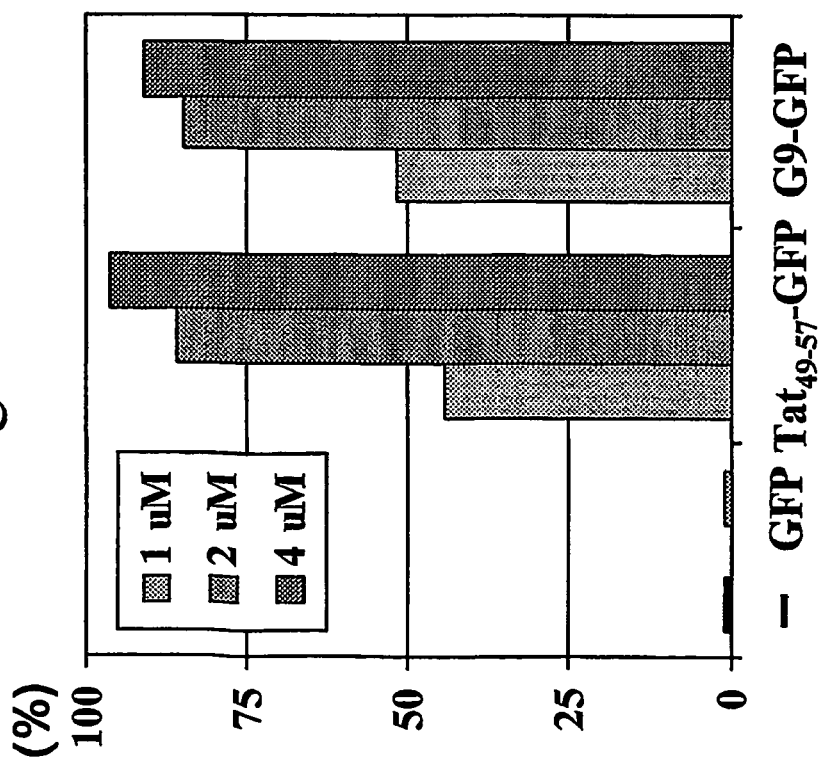

Transducing activity of the three synthetic transporters with GFP was first assessed in HeLa cells, which is known to be well-transduced by the molecular transporters in several previous reports. When tested with 4 μM concentrations of the transporters for 4 hours, the highest transduction efficiency corresponded to nine guanidinium groups (FIG. 37B, bottom). The transduction efficiency peaked at the 4 hour time-point within 2-4 μM concentration range of these transporters, and the test in HeLa S3 cells showed similar results (FIGS. 39A-39B).

Tat basic domain (aa 49-57) is a well-known molecular transporter and contains six arginine residues. When compared in HeLa cells, the transduction of the nine guanidinium groups (G9-GFP) was as efficient as that of the Tat basic domain (Tat$_{49-57}$-GFP) both by microscopic observation (FIGS. 38A-38R) and in the FACS analysis for the dose- and time-dependency of transduction (FIGS. 39A-39B). The transduction efficiency of about 50% was seen at 1 μM and reached near saturation at 2-4 μM for both transporters in 4 hour treatments (FIG. 39A). When tested at 2 μM, Tat$_{49-57}$-GFP showed a gradual increase in transduction efficiency depending on the treatment time starting from about 40% transduction at 1 hour and reaching near saturation at 7 hour treatments. The transduction of G9-GFP was faster than that of Tat$_{49-57}$-GFP showing about 70% transduction at 1 hour and near saturation at 2-4 hours after treatment (FIG. 39B). Therefore, the nine guanidinium groups with a branched structure proved to be a potent transporter for the delivery of bio-molecules into cells.

Cellular Localization of the Branched Guanidinium Groups in HeLa Cells

Figure 38A:
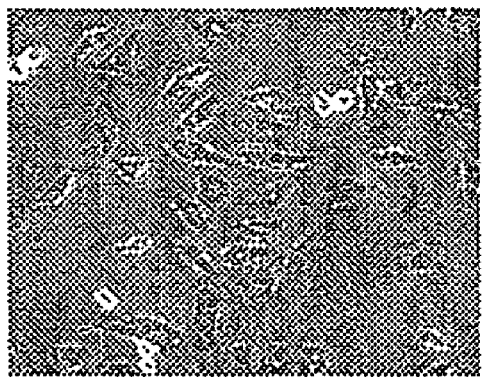
FIGS. 38A-38H depict comparisons of the transduction efficiencies of $Tat_{49-57}$-GFP (See FIG. 4A) and 71-GFP. HeLa cells were treated with 4 μM each of Tat basic domain (aa 49-57) conjugated with GFP or 71-GFP for 4 hrs at 37° C. without serum. After washing four times with PBS, the fluorescence image of GFP was taken. Same concentration of GFP alone was used as a negative control.
Figure 38B:
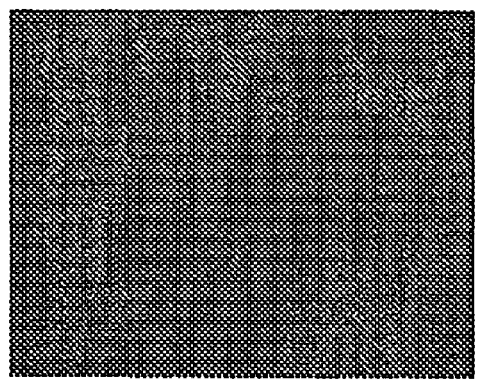
Figure 38C:
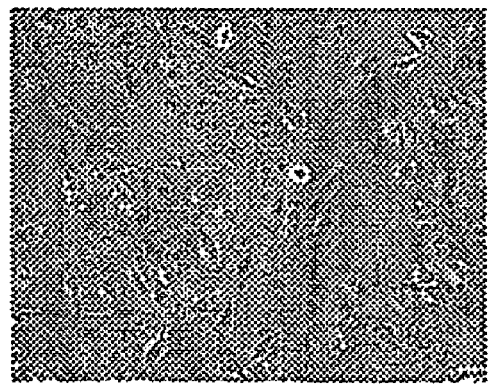
Figure 38D:
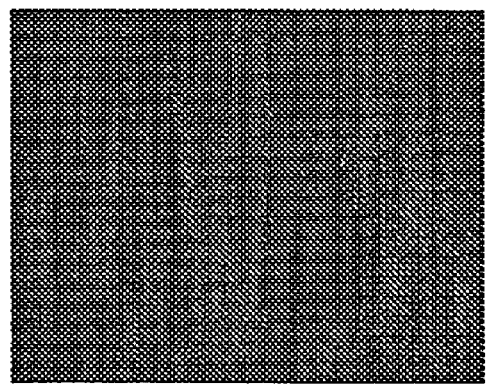
Figure 38E:
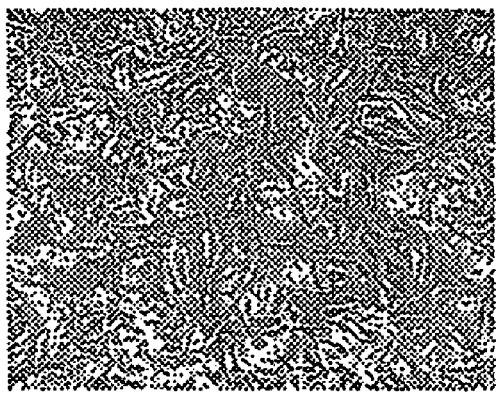
Figure 38F:
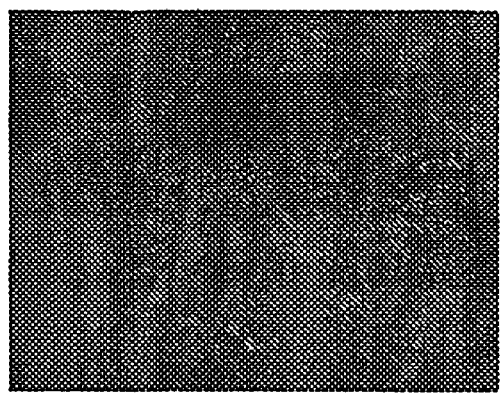
Figure 38G:
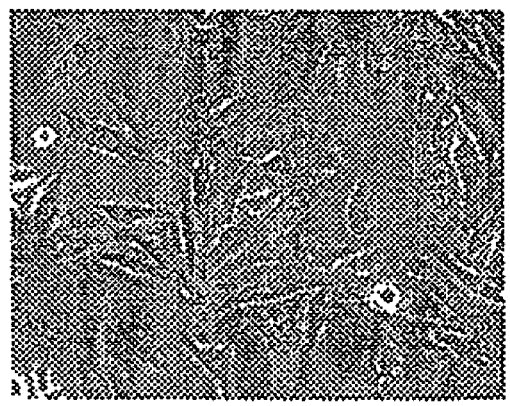
Figure 38H:
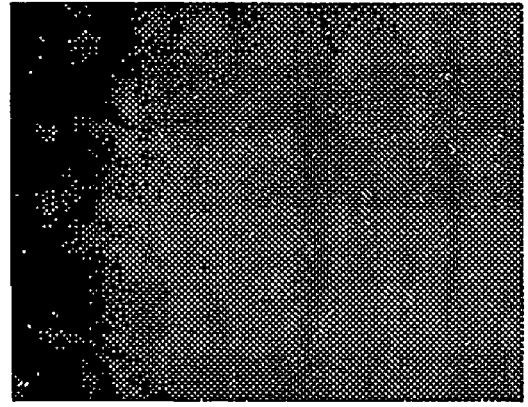
Figure 40A:
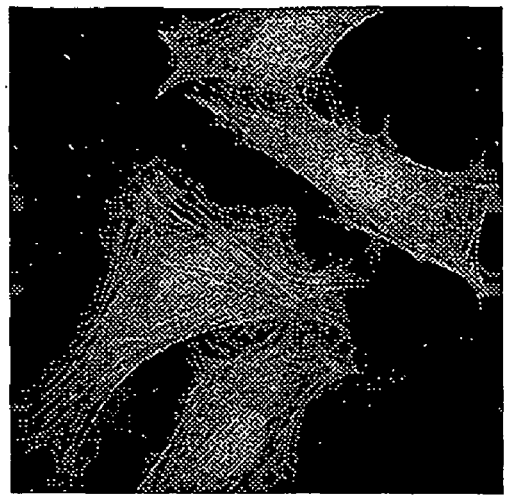
FIGS. 40A-40C compare cellular uptake in HeLa cells.
Figure 40B:
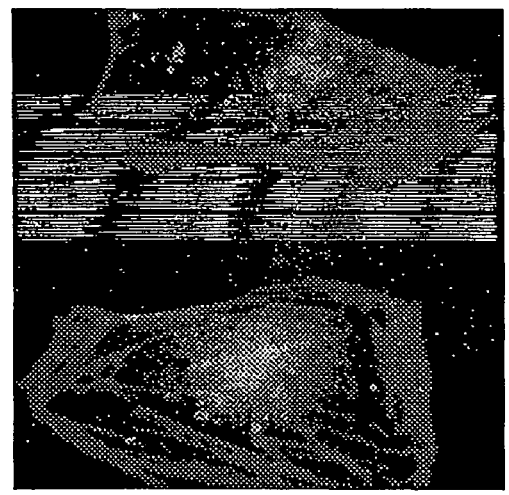
Figure 40C:
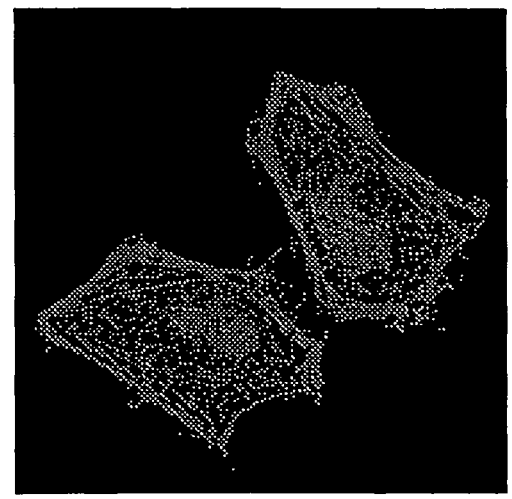
Figure 41C:
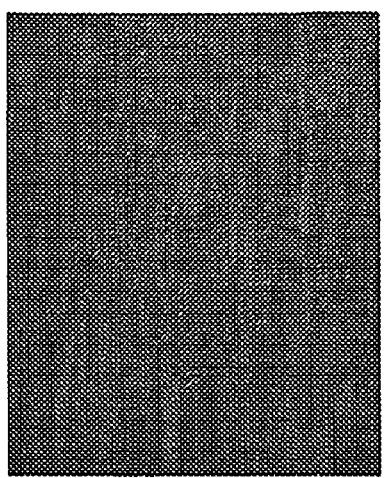
FIGS. 41A-41E depict time dependent localization of 71-GFP in HeLa cells upon treating with a 2 μM solution for 0 hours (FIG. 41A), for 1 hour (FIG. 41B), for 2 hours (FIG. 41C), for 4 hours (FIG. 41D), and for 7 hours (FIG. 41E).
Figure 41B:
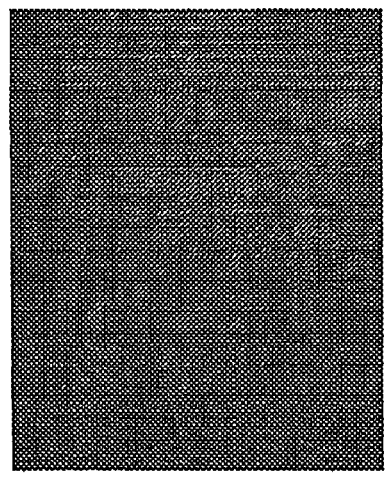
Figure 41E:
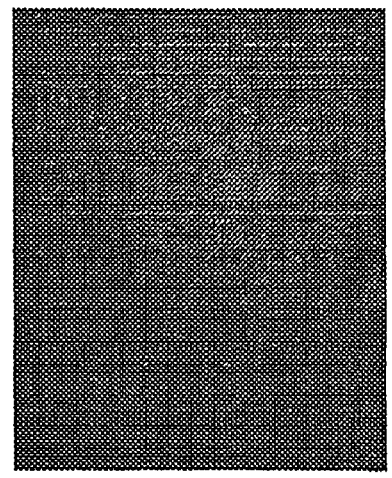
Figure 41A:
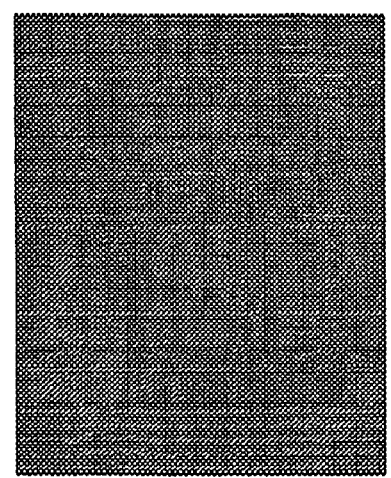
Figure 41D:
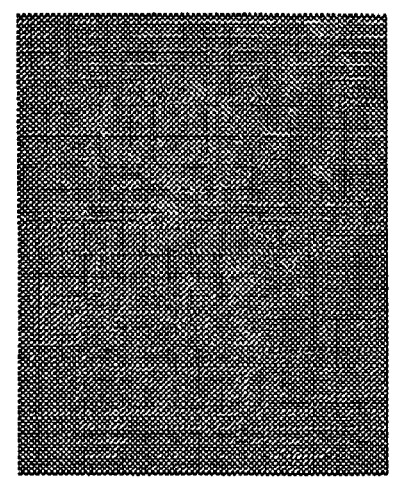

To determine whether the transporters were really inside the cells and their sub-cellular localization, confocal microscopic observation of the GFP fluorescence was performed in HeLa cells as described (FIGS. 40A-40C). Cells were treated with high concentrations (8 μM) for each transporter for 4 hours to obtain a high intensity of GFP fluorescence. After treatment, cells were counter-stained for actin (red) and for the nucleus (blue). Tat$_{49-57}$-GFP mainly localized in the nucleus with an intense speckled pattern (FIG. 40B). However this might occur only with high concentrations of the transporter, because a relatively even distribution of Tat$_{49-57}$-GFP both in the nucleus and cytoplasm was observed at concentrations lower than 4 μM (FIGS. 38E-38F). G9-GFP was relatively well spread throughout the cell body with a large proportion in the nucleus (FIG. 40C). Interestingly, G9-GFP showed changes in the localization patterns in the time-course experiment at 2 μM in HeLa cells (FIGS. 41A-41E). G9-GFP localized in the cell membrane until 2 hours, then stained the whole cell body at 4 hours, and showed irregular localization inside of the cells after 7 hours of treatments. This was not observed with Tat$_{49-57}$-GFP under the same conditions, which showed an even distribution in the whole cell body from the early time points of 1 hour after treatment. This pattern of G9-GFP localization is not likely to mean the slow or low transduction activity of G9-GFP in the initial uptake process, because it was very rapid and efficient in the FACS analysis (FIG. 39B). Rather, there might be an interaction between G9-GFP and cell membrane holding the transporter in the cell membrane for awhile until some threshold concentration level is reached.

While the invention has been described in detail with reference to certain preferred embodiments thereof it will be understood that modifications and variations are within the spirit and scope of that which is described. It is also understood that the invention is not limited to the embodiments set forth herein for illustration, but embraces all such forms thereof as come within the scope of the following claims.

What is claimed is:

1. A transport molecule comprising a dendrimer and a biologically active molecule, wherein the dendrimer comprises a group of formula V or a protonated or a protected form of the group of formula V

V

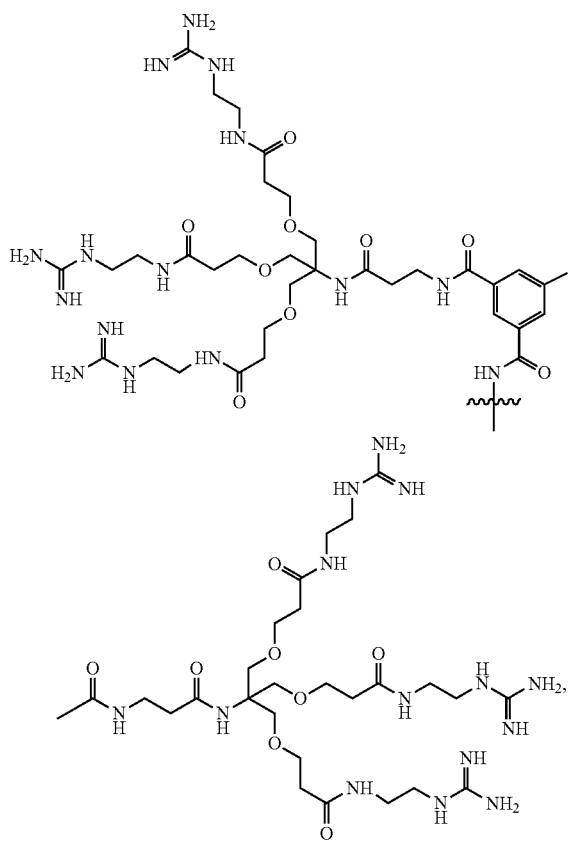

and further wherein the biologically active molecule is covalently bonded to the dendrimer.

2. The transport molecule of claim 1, wherein the biologically active molecule bonded to the dendrimer is selected from the group consisting of methotrexate, 5-fluorouracil, paclitaxel, cyclosporin A, and ganciclovir.

3. The transport molecule of claim 1, wherein the biologically active molecule bonded to the dendrimer comprises a protein.

4. The transport molecule of claim 3, wherein the protein has a size of less than 10 kDalton.

5. The transport molecule of claim 3, wherein the protein has a size of more than 10 kDalton.

6. The transport molecule of claim 1, wherein the biologically active molecule bonded to the dendrimer is a drug for the treatment of a mammalian condition.

7. A pharmaceutical formulation, comprising the transport molecule of claim 6 in combination with a pharmaceutically acceptable carrier.

8. A method of increasing the effectiveness of a drug, comprising administering the pharmaceutical formulation of claim 7 to a human or an animal.

9. A method of increasing transport of a biologically active molecule across a biological membrane, comprising: contacting a biological membrane with a transport molecule according to claim 1, wherein the transport molecule comprising the biologically active molecule bonded to the dendrimer is transported across the biological membrane at a rate greater than the biologically active molecule is transported across the biological membrane when the biologically active molecule is not bonded to the dendrimer of the transport molecule.

10. The method of claim 9, wherein the biologically active molecule comprises a protein.

11. The method of claim 10, wherein the protein has a size of less than 10 kDalton.

12. The method of claim 10, wherein the protein has a size of more than 10 kDalton.

* * * * *